(12) United States Patent
Apelian et al.

(10) Patent No.: US 9,254,320 B2
(45) Date of Patent: Feb. 9, 2016

(54) COMPOSITIONS AND METHODS FOR THE TREATMENT OR PREVENTION OF HUMAN ADENOVIRUS-36 INFECTION

(75) Inventors: David Apelian, Boonton Township, NJ (US); Thomas King, Denver, CO (US); Claire Coeshott, Denver, CO (US); Yingnian Lu, Denver, CO (US)

(73) Assignee: GlobeImmune, Inc., Louisville, CO (US)

( * ) Notice: Subject to any disclaimer, the term of this patent is extended or adjusted under 35 U.S.C. 154(b) by 0 days.

(21) Appl. No.: 13/994,881

(22) PCT Filed: Dec. 19, 2011

(86) PCT No.: PCT/US2011/065868
§ 371 (c)(1),
(2), (4) Date: Oct. 28, 2013

(87) PCT Pub. No.: WO2012/083302
PCT Pub. Date: Jun. 21, 2012

(65) Prior Publication Data
US 2014/0072590 A1    Mar. 13, 2014

Related U.S. Application Data

(60) Provisional application No. 61/424,472, filed on Dec. 17, 2010.

(51) Int. Cl.
A61K 39/00    (2006.01)
A61K 39/235   (2006.01)
A61K 39/12    (2006.01)

(52) U.S. Cl.
CPC .............. *A61K 39/235* (2013.01); *A61K 39/12* (2013.01); *A61K 2039/523* (2013.01); *C12N 2710/10334* (2013.01)

(58) Field of Classification Search
None
See application file for complete search history.

(56) References Cited

U.S. PATENT DOCUMENTS

| | | | |
|---|---|---|---|
| 4,775,622 | A | 10/1988 | Hitzeman et al. |
| 5,234,830 | A | 8/1993 | Oshima et al. |
| 5,310,654 | A | 5/1994 | Isberg et al. |
| 5,413,914 | A | 5/1995 | Franzusoff |
| 5,830,463 | A | 11/1998 | Duke et al. |
| 5,858,378 | A | 1/1999 | Bostwick |
| 5,919,651 | A | 7/1999 | Hitzeman et al. |

(Continued)

FOREIGN PATENT DOCUMENTS

| | | |
|---|---|---|
| EP | 0414404 | 2/1991 |
| FR | 2486400 | 1/1982 |

(Continued)

OTHER PUBLICATIONS

Atkinson et al., "Human adenovirus-36 is associated with increased body weight and paradoxical reduction of serum lipids," International Journal of Obesity, 29: 281-286 (2005).*

(Continued)

*Primary Examiner* — Benjamin P Blumel
*Assistant Examiner* — M. Franco Salvoza
(74) *Attorney, Agent, or Firm* — Sheridan Ross P.C.

(57) ABSTRACT

Disclosed are fusion proteins, recombinant nucleic acid molecules, and therapeutic compositions, including yeast-based immunotherapy compositions, for use in the diagnosis, prevention and treatment of adenovirus-36 (Ad-36) infection and sequela thereof.

20 Claims, 15 Drawing Sheets

(56) References Cited

U.S. PATENT DOCUMENTS

| | | | |
|---|---|---|---|
| 7,083,787 | B2 | 8/2006 | Duke et al. |
| 7,439,042 | B2 | 10/2008 | Duke et al. |
| 7,465,454 | B2 | 12/2008 | Franzusoff et al. |
| 2002/0044948 | A1 | 4/2002 | Khleif et al. |
| 2003/0035810 | A1 | 2/2003 | Caplan |
| 2004/0166122 | A1* | 8/2004 | Evans et al. ............... 424/204.1 |
| 2007/0172503 | A1 | 7/2007 | Selitrennikoff et al. |
| 2007/0224208 | A1 | 9/2007 | Guo et al. |
| 2008/0003239 | A1* | 1/2008 | Duke et al. ................ 424/206.1 |
| 2009/0142367 | A1 | 6/2009 | Franzusoff et al. |
| 2010/0034840 | A1 | 2/2010 | Apelian et al. |
| 2010/0111912 | A1 | 5/2010 | Apelian et al. |
| 2010/0189749 | A1 | 7/2010 | Franzusoff et al. |
| 2011/0008295 | A1* | 1/2011 | Roy et al. ..................... 424/93.6 |
| 2011/0256098 | A1 | 10/2011 | Apelian et al. |
| 2012/0321664 | A1 | 12/2012 | Bellgrau et al. |

FOREIGN PATENT DOCUMENTS

| | | |
|---|---|---|
| JP | 2010-254721 | 11/2010 |
| WO | WO 2006/044923 | 4/2006 |
| WO | WO 2007/092792 | 8/2007 |
| WO | WO 2009/073104 | 6/2009 |
| WO | WO 2010/011440 | 1/2010 |
| WO | WO 2010/065626 | 6/2010 |
| WO | WO 2011/115914 | 9/2011 |
| WO | WO 2012/019127 | 2/2012 |
| WO | WO 2012/083302 | 6/2012 |
| WO | WO 2012/109404 | 8/2012 |
| WO | WO 2012/125998 | 9/2012 |
| WO | WO 2012/174220 | 12/2012 |
| WO | WO 2013/025972 | 2/2013 |

OTHER PUBLICATIONS

Liu et al., "Expression, purification, and characterization of hepatitis B virus surface antigens (HBsAg) in yeast Pichia Pastoris," Appl. Biochem. Biotechnol. 158(2): 432-44 (2009).*

Rock et al., "Natural endogenous adjuvants," Springer Semin Immun 26:231-246 (2005).*

Toth et al., "Adenovirus immunoregulatory E3 proteins prolong transplants of human cells in immunocompetent mice," Virus Research 108 149-159 (2005).*

Sharma et al., "Adenovirus E3 proteins help tumors to evade innate and adaptive immune responses," Cancer Biology & Therapy 8:12: 1133-1135 (2009).*

Arnold et al. "Genomic characterization of human adenovirus 36, a putative obesity agent," Virus Research, May 2010, vol. 149, No. 2, pp. 152-161.

Bizzini et al. "Use of live *Saccharomyces cerevisiae* cells as a biological response modifier in experimental infections," FEMS Microbiology Immunology, 1990, vol. 64, pp. 155-168.

Brake et al. "alpha-Factor-directed synthesis and secretion of mature foreign proteins in *Saccharomyces cerevisiae*," Proceedings of the National Academy of Sciences USA, Aug. 1984, vol. 81, pp. 4642-4646.

Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.

Franzusoff, A. et al. "Yeasts Encoding Tumour Antigens in Cancer Immunotherapy," Expert Opinion on Biological Therapy, Apr. 2005, vol. 5, No. 4, pp. 565-575.

Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.

Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.

Lu, et al., "Mutation-Selective Tumor Remission with Ras-Targeted, Whole Yeast-Based Immunotherapy," Cancer Research, 2004, vol. 64, pp. 5084-5088.

Klepfer et al. "Characterization of rabies glycoprotein expressed in yeast," Archives of Virology, 1993, vol. 128, pp. 269-286.

Krishnapuram et al. "Infectivity period of mice inoculated with human adenoviruses." Lab Anim., Apr. 2011, vol. 45, No. 2, pp. 103-108 (Abstract Only).

Moore et al., "Novel yeast-based vaccine 1-40, against HIV-SF2 gp160 promotes a cytotoxic 43-62 cell response." FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USSA; Jun. 2-6, 1996.

Na et al. "Infectobesity: a New Area for Microbiological and Virological Research," Journal of Bacteriology and Virology, Jun. 2011, vol. 41, No. 2, pp. 65-76.

Robinson et al. "The E3 CR1-gamma gene in human adenoviruses associated with epidemic keratoconjunctivitis," Virus Research, Sep. 2011, vol. 160, No. 1-2, pp. 120-127.

Schreuder et al. "Yeast expressing hepatitis B virus surface antigen determinants on its surface: implications for a possible oral vaccine," Vaccine, Apr. 1996, vol. 14, No. 5, pp. 383-388.

Sinai et al. "Enhancement of Resistance to Infectious Diseases by Oral Administration of Brewers Yeast," Infection and Immunity, May 1974, vol. 9, No. 5, pp. 781-787.

Stubbs, et al., "Whole Recombinant Yeast Vaccine Activates Dendritic Cells and Elicits Protective Cell-Mediated Immunity," National Medicine, May 2001, vol. 7, No. 5, pp. 1-5.

Torres et al. "The Revolution in Viral Genomics as Exemplified by the Bioinformatic Analysis of Human Adenoviruses," Viruses, Jul. 2010, vol. 2, No. 7, pp. 1367-1381.

UNiProt Direct Submission D4N3K1_9ADEN. [Retrieved from the Internet Jul. 21, 2012: <www.uniprot.org/uniprot/D4N3K1.txt?version+1>] 1 page.

Valenzuela et al. "Antigen engineering in yeast: Synthesis and assembly of hybrid hepatitis B surface antigen—Herpes simplex 1 gD particles", Bio/Technology, Apr. 1985, vol. 3, 323-326.

International Search Report and Written Opinion for International (PCT) Patent Application No. PCT/US11/65868, mailed Aug. 3, 2012 13 pages.

International Preliminary Report on Patentability for International (PCT) Patent Application No. PCT/US2011/065868, mailed Jun. 27, 2013 9 pages.

Extended European Search Report and Search Opinion for European Patent Application No. 11848223.1, dated Sep. 4, 2014, 11 pages.

* cited by examiner

SEQUENCE LISTING

```
<160> NUMBER OF SEQ ID NOS: 58

<210> SEQ ID NO 1
<211> LENGTH: 36604
<212> TYPE: DNA
<213> ORGANISM: Adenovirus type 36
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (805)..(805)
<223> OTHER INFORMATION: n is a, c, g, or t
<220> FEATURE:
<221> NAME/KEY: misc_feature
<222> LOCATION: (813)..(814)
<223> OTHER INFORMATION: n is a, c, g, or t
<220> FEATURE:
<221> NAME/KEY: misc_feature
<222> LOCATION: (1402)..(1402)
<223> OTHER INFORMATION: n is a, c, g, or t
<220> FEATURE:
<221> NAME/KEY: misc_feature
<222> LOCATION: (1407)..(1407)
<223> OTHER INFORMATION: n is a, c, g, or t
<220> FEATURE:
<221> NAME/KEY: misc_feature
<222> LOCATION: (1415)..(1415)
<223> OTHER INFORMATION: n is a, c, g, or t
<220> FEATURE:
<221> NAME/KEY: misc_feature
<222> LOCATION: (1976)..(1976)
<223> OTHER INFORMATION: n is a, c, g, or t
<220> FEATURE:
<221> NAME/KEY: misc_feature
<222> LOCATION: (1981)..(1981)
<223> OTHER INFORMATION: n is a, c, g, or t
```

-continued

```
<220> FEATURE:
<221> NAME/KEY: misc_feature
<222> LOCATION: (1989)..(1989)
<223> OTHER INFORMATION: n is a, c, g, or t
<220> FEATURE:
<221> NAME/KEY: misc_feature
<222> LOCATION: (3489)..(3489)
<223> OTHER INFORMATION: n is a, c, g, or t
<220> FEATURE:
<221> NAME/KEY: misc_feature
<222> LOCATION: (3492)..(3492)
<223> OTHER INFORMATION: n is a, c, g, or t
<220> FEATURE:
<221> NAME/KEY: misc_feature
<222> LOCATION: (3500)..(3500)
<223> OTHER INFORMATION: n is a, c, g, or t
<220> FEATURE:
<221> NAME/KEY: misc_feature
<222> LOCATION: (3917)..(3917)
<223> OTHER INFORMATION: n is a, c, g, or t
<220> FEATURE:
<221> NAME/KEY: misc_feature
<222> LOCATION: (3922)..(3922)
<223> OTHER INFORMATION: n is a, c, g, or t
<220> FEATURE:
<221> NAME/KEY: misc_feature
<222> LOCATION: (3930)..(3930)
<223> OTHER INFORMATION: n is a, c, g, or t
<220> FEATURE:
<221> NAME/KEY: misc_feature
<222> LOCATION: (3934)..(3934)
<223> OTHER INFORMATION: n is a, c, g, or t
<220> FEATURE:
<221> NAME/KEY: misc_feature
<222> LOCATION: (3936)..(3936)
<223> OTHER INFORMATION: n is a, c, g, or t
<220> FEATURE:
<221> NAME/KEY: misc_feature
<222> LOCATION: (5294)..(5294)
<223> OTHER INFORMATION: n is a, c, g, or t
<220> FEATURE:
<221> NAME/KEY: misc_feature
<222> LOCATION: (5297)..(5297)
<223> OTHER INFORMATION: n is a, c, g, or t
<220> FEATURE:
<221> NAME/KEY: misc_feature
<222> LOCATION: (5300)..(5300)
<223> OTHER INFORMATION: n is a, c, g, or t
<220> FEATURE:
<221> NAME/KEY: misc_feature
<222> LOCATION: (5303)..(5303)
<223> OTHER INFORMATION: n is a, c, g, or t
<220> FEATURE:
<221> NAME/KEY: misc_feature
<222> LOCATION: (5311)..(5311)
<223> OTHER INFORMATION: n is a, c, g, or t
<220> FEATURE:
<221> NAME/KEY: misc_feature
<222> LOCATION: (5315)..(5315)
<223> OTHER INFORMATION: n is a, c, g, or t
<220> FEATURE:
<221> NAME/KEY: misc_feature
<222> LOCATION: (5317)..(5317)
<223> OTHER INFORMATION: n is a, c, g, or t
<220> FEATURE:
<221> NAME/KEY: misc_feature
<222> LOCATION: (8860)..(8860)
<223> OTHER INFORMATION: n is a, c, g, or t
<220> FEATURE:
<221> NAME/KEY: misc_feature
<222> LOCATION: (8864)..(8864)
<223> OTHER INFORMATION: n is a, c, g, or t
<220> FEATURE:
<221> NAME/KEY: misc_feature
<222> LOCATION: (8872)..(8873)
<223> OTHER INFORMATION: n is a, c, g, or t
<220> FEATURE:
<221> NAME/KEY: misc_feature
<222> LOCATION: (9274)..(9274)
```

<223> OTHER INFORMATION: n is a, c, g, or t
<220> FEATURE:
<221> NAME/KEY: misc_feature
<222> LOCATION: (9277)..(9277)
<223> OTHER INFORMATION: n is a, c, g, or t
<220> FEATURE:
<221> NAME/KEY: misc_feature
<222> LOCATION: (9281)..(9281)
<223> OTHER INFORMATION: n is a, c, g, or t
<220> FEATURE:
<221> NAME/KEY: misc_feature
<222> LOCATION: (9289)..(9289)
<223> OTHER INFORMATION: n is a, c, g, or t
<220> FEATURE:
<221> NAME/KEY: misc_feature
<222> LOCATION: (9293)..(9293)
<223> OTHER INFORMATION: n is a, c, g, or t
<220> FEATURE:
<221> NAME/KEY: misc_feature
<222> LOCATION: (9295)..(9295)
<223> OTHER INFORMATION: n is a, c, g, or t
<220> FEATURE:
<221> NAME/KEY: misc_feature
<222> LOCATION: (11215)..(11215)
<223> OTHER INFORMATION: n is a, c, g, or t
<220> FEATURE:
<221> NAME/KEY: misc_feature
<222> LOCATION: (11219)..(11219)
<223> OTHER INFORMATION: n is a, c, g, or t
<220> FEATURE:
<221> NAME/KEY: misc_feature
<222> LOCATION: (11227)..(11227)
<223> OTHER INFORMATION: n is a, c, g, or t
<220> FEATURE:
<221> NAME/KEY: misc_feature
<222> LOCATION: (12358)..(12358)
<223> OTHER INFORMATION: n is a, c, g, or t
<220> FEATURE:
<221> NAME/KEY: misc_feature
<222> LOCATION: (12362)..(12362)
<223> OTHER INFORMATION: n is a, c, g, or t
<220> FEATURE:
<221> NAME/KEY: misc_feature
<222> LOCATION: (12370)..(12370)
<223> OTHER INFORMATION: n is a, c, g, or t
<220> FEATURE:
<221> NAME/KEY: misc_feature
<222> LOCATION: (14068)..(14068)
<223> OTHER INFORMATION: n is a, c, g, or t
<220> FEATURE:
<221> NAME/KEY: misc_feature
<222> LOCATION: (14071)..(14071)
<223> OTHER INFORMATION: n is a, c, g, or t
<220> FEATURE:
<221> NAME/KEY: misc_feature
<222> LOCATION: (14079)..(14079)
<223> OTHER INFORMATION: n is a, c, g, or t
<220> FEATURE:
<221> NAME/KEY: misc_feature
<222> LOCATION: (15654)..(15654)
<223> OTHER INFORMATION: n is a, c, g, or t
<220> FEATURE:
<221> NAME/KEY: misc_feature
<222> LOCATION: (15658)..(15658)
<223> OTHER INFORMATION: n is a, c, g, or t
<220> FEATURE:
<221> NAME/KEY: misc_feature
<222> LOCATION: (15666)..(15666)
<223> OTHER INFORMATION: n is a, c, g, or t
<220> FEATURE:
<221> NAME/KEY: misc_feature
<222> LOCATION: (16266)..(16266)
<223> OTHER INFORMATION: n is a, c, g, or t
<220> FEATURE:
<221> NAME/KEY: misc_feature
<222> LOCATION: (16270)..(16270)
<223> OTHER INFORMATION: n is a, c, g, or t
<220> FEATURE:
<221> NAME/KEY: misc_feature

```
<222> LOCATION: (16278)..(16278)
<223> OTHER INFORMATION: n is a, c, g, or t
<220> FEATURE:
<221> NAME/KEY: misc_feature
<222> LOCATION: (17289)..(17289)
<223> OTHER INFORMATION: n is a, c, g, or t
<220> FEATURE:
<221> NAME/KEY: misc_feature
<222> LOCATION: (17292)..(17292)
<223> OTHER INFORMATION: n is a, c, g, or t
<220> FEATURE:
<221> NAME/KEY: misc_feature
<222> LOCATION: (17300)..(17300)
<223> OTHER INFORMATION: n is a, c, g, or t
<220> FEATURE:
<221> NAME/KEY: misc_feature
<222> LOCATION: (17537)..(17537)
<223> OTHER INFORMATION: n is a, c, g, or t
<220> FEATURE:
<221> NAME/KEY: misc_feature
<222> LOCATION: (17541)..(17541)
<223> OTHER INFORMATION: n is a, c, g, or t
<220> FEATURE:
<221> NAME/KEY: misc_feature
<222> LOCATION: (17549)..(17549)
<223> OTHER INFORMATION: n is a, c, g, or t
<220> FEATURE:
<221> NAME/KEY: misc_feature
<222> LOCATION: (18266)..(18266)
<223> OTHER INFORMATION: n is a, c, g, or t
<220> FEATURE:
<221> NAME/KEY: misc_feature
<222> LOCATION: (18268)..(18268)
<223> OTHER INFORMATION: n is a, c, g, or t
<220> FEATURE:
<221> NAME/KEY: misc_feature
<222> LOCATION: (18271)..(18271)
<223> OTHER INFORMATION: n is a, c, g, or t
<220> FEATURE:
<221> NAME/KEY: misc_feature
<222> LOCATION: (18279)..(18279)
<223> OTHER INFORMATION: n is a, c, g, or t
<220> FEATURE:
<221> NAME/KEY: misc_feature
<222> LOCATION: (21126)..(21126)
<223> OTHER INFORMATION: n is a, c, g, or t
<220> FEATURE:
<221> NAME/KEY: misc_feature
<222> LOCATION: (21133)..(21133)
<223> OTHER INFORMATION: n is a, c, g, or t
<220> FEATURE:
<221> NAME/KEY: misc_feature
<222> LOCATION: (21141)..(21141)
<223> OTHER INFORMATION: n is a, c, g, or t
<220> FEATURE:
<221> NAME/KEY: misc_feature
<222> LOCATION: (21783)..(21783)
<223> OTHER INFORMATION: n is a, c, g, or t
<220> FEATURE:
<221> NAME/KEY: misc_feature
<222> LOCATION: (21788)..(21788)
<223> OTHER INFORMATION: n is a, c, g, or t
<220> FEATURE:
<221> NAME/KEY: misc_feature
<222> LOCATION: (21796)..(21796)
<223> OTHER INFORMATION: n is a, c, g, or t
<220> FEATURE:
<221> NAME/KEY: misc_feature
<222> LOCATION: (21800)..(21800)
<223> OTHER INFORMATION: n is a, c, g, or t
<220> FEATURE:
<221> NAME/KEY: misc_feature
<222> LOCATION: (23283)..(23283)
<223> OTHER INFORMATION: n is a, c, g, or t
<220> FEATURE:
<221> NAME/KEY: misc_feature
<222> LOCATION: (23287)..(23287)
<223> OTHER INFORMATION: n is a, c, g, or t
<220> FEATURE:
```

-continued

```
<221> NAME/KEY: misc_feature
<222> LOCATION: (23295)..(23295)
<223> OTHER INFORMATION: n is a, c, g, or t
<220> FEATURE:
<221> NAME/KEY: misc_feature
<222> LOCATION: (25503)..(25503)
<223> OTHER INFORMATION: n is a, c, g, or t
<220> FEATURE:
<221> NAME/KEY: misc_feature
<222> LOCATION: (25507)..(25507)
<223> OTHER INFORMATION: n is a, c, g, or t
<220> FEATURE:
<221> NAME/KEY: misc_feature
<222> LOCATION: (25515)..(25516)
<223> OTHER INFORMATION: n is a, c, g, or t
<220> FEATURE:
<221> NAME/KEY: misc_feature
<222> LOCATION: (26047)..(26047)
<223> OTHER INFORMATION: n is a, c, g, or t
<220> FEATURE:
<221> NAME/KEY: misc_feature
<222> LOCATION: (26051)..(26051)
<223> OTHER INFORMATION: n is a, c, g, or t
<220> FEATURE:
<221> NAME/KEY: misc_feature
<222> LOCATION: (26059)..(26059)
<223> OTHER INFORMATION: n is a, c, g, or t
<220> FEATURE:
<221> NAME/KEY: misc_feature
<222> LOCATION: (26482)..(26482)
<223> OTHER INFORMATION: n is a, c, g, or t
<220> FEATURE:
<221> NAME/KEY: misc_feature
<222> LOCATION: (26486)..(26486)
<223> OTHER INFORMATION: n is a, c, g, or t
<220> FEATURE:
<221> NAME/KEY: misc_feature
<222> LOCATION: (26494)..(26494)
<223> OTHER INFORMATION: n is a, c, g, or t
<220> FEATURE:
<221> NAME/KEY: misc_feature
<222> LOCATION: (27190)..(27190)
<223> OTHER INFORMATION: n is a, c, g, or t
<220> FEATURE:
<221> NAME/KEY: misc_feature
<222> LOCATION: (27194)..(27194)
<223> OTHER INFORMATION: n is a, c, g, or t
<220> FEATURE:
<221> NAME/KEY: misc_feature
<222> LOCATION: (27202)..(27202)
<223> OTHER INFORMATION: n is a, c, g, or t
<220> FEATURE:
<221> NAME/KEY: misc_feature
<222> LOCATION: (27535)..(27535)
<223> OTHER INFORMATION: n is a, c, g, or t
<220> FEATURE:
<221> NAME/KEY: misc_feature
<222> LOCATION: (27543)..(27543)
<223> OTHER INFORMATION: n is a, c, g, or t
<220> FEATURE:
<221> NAME/KEY: misc_feature
<222> LOCATION: (27551)..(27551)
<223> OTHER INFORMATION: n is a, c, g, or t
<220> FEATURE:
<221> NAME/KEY: misc_feature
<222> LOCATION: (28157)..(28157)
<223> OTHER INFORMATION: n is a, c, g, or t
<220> FEATURE:
<221> NAME/KEY: misc_feature
<222> LOCATION: (28161)..(28161)
<223> OTHER INFORMATION: n is a, c, g, or t
<220> FEATURE:
<221> NAME/KEY: misc_feature
<222> LOCATION: (28169)..(28169)
<223> OTHER INFORMATION: n is a, c, g, or t
<220> FEATURE:
<221> NAME/KEY: misc_feature
<222> LOCATION: (28652)..(28652)
<223> OTHER INFORMATION: n is a, c, g, or t
```

```
<220> FEATURE:
<221> NAME/KEY: misc_feature
<222> LOCATION: (28659)..(28659)
<223> OTHER INFORMATION: n is a, c, g, or t
<220> FEATURE:
<221> NAME/KEY: misc_feature
<222> LOCATION: (28667)..(28667)
<223> OTHER INFORMATION: n is a, c, g, or t
<220> FEATURE:
<221> NAME/KEY: misc_feature
<222> LOCATION: (29936)..(29936)
<223> OTHER INFORMATION: n is a, c, g, or t
<220> FEATURE:
<221> NAME/KEY: misc_feature
<222> LOCATION: (29944)..(29944)
<223> OTHER INFORMATION: n is a, c, g, or t
<220> FEATURE:
<221> NAME/KEY: misc_feature
<222> LOCATION: (29952)..(29952)
<223> OTHER INFORMATION: n is a, c, g, or t
<220> FEATURE:
<221> NAME/KEY: misc_feature
<222> LOCATION: (30819)..(30819)
<223> OTHER INFORMATION: n is a, c, g, or t
<220> FEATURE:
<221> NAME/KEY: misc_feature
<222> LOCATION: (30827)..(30827)
<223> OTHER INFORMATION: n is a, c, g, or t
<220> FEATURE:
<221> NAME/KEY: misc_feature
<222> LOCATION: (30835)..(30835)
<223> OTHER INFORMATION: n is a, c, g, or t
<220> FEATURE:
<221> NAME/KEY: misc_feature
<222> LOCATION: (31123)..(31123)
<223> OTHER INFORMATION: n is a, c, g, or t
<220> FEATURE:
<221> NAME/KEY: misc_feature
<222> LOCATION: (31131)..(31131)
<223> OTHER INFORMATION: n is a, c, g, or t
<220> FEATURE:
<221> NAME/KEY: misc_feature
<222> LOCATION: (31139)..(31139)
<223> OTHER INFORMATION: n is a, c, g, or t
<220> FEATURE:
<221> NAME/KEY: misc_feature
<222> LOCATION: (31526)..(31526)
<223> OTHER INFORMATION: n is a, c, g, or t
<220> FEATURE:
<221> NAME/KEY: misc_feature
<222> LOCATION: (31531)..(31531)
<223> OTHER INFORMATION: n is a, c, g, or t
<220> FEATURE:
<221> NAME/KEY: misc_feature
<222> LOCATION: (31539)..(31539)
<223> OTHER INFORMATION: n is a, c, g, or t
<220> FEATURE:
<221> NAME/KEY: misc_feature
<222> LOCATION: (31943)..(31943)
<223> OTHER INFORMATION: n is a, c, g, or t
<220> FEATURE:
<221> NAME/KEY: misc_feature
<222> LOCATION: (31946)..(31946)
<223> OTHER INFORMATION: n is a, c, g, or t
<220> FEATURE:
<221> NAME/KEY: misc_feature
<222> LOCATION: (31949)..(31949)
<223> OTHER INFORMATION: n is a, c, g, or t
<220> FEATURE:
<221> NAME/KEY: misc_feature
<222> LOCATION: (31952)..(31952)
<223> OTHER INFORMATION: n is a, c, g, or t
<220> FEATURE:
<221> NAME/KEY: misc_feature
<222> LOCATION: (31960)..(31960)
<223> OTHER INFORMATION: n is a, c, g, or t
<220> FEATURE:
<221> NAME/KEY: misc_feature
<222> LOCATION: (31964)..(31964)
```

```
<223> OTHER INFORMATION: n is a, c, g, or t
<220> FEATURE:
<221> NAME/KEY: misc_feature
<222> LOCATION: (32127)..(32127)
<223> OTHER INFORMATION: n is a, c, g, or t
<220> FEATURE:
<221> NAME/KEY: misc_feature
<222> LOCATION: (32132)..(32132)
<223> OTHER INFORMATION: n is a, c, g, or t
<220> FEATURE:
<221> NAME/KEY: misc_feature
<222> LOCATION: (32140)..(32140)
<223> OTHER INFORMATION: n is a, c, g, or t
<220> FEATURE:
<221> NAME/KEY: misc_feature
<222> LOCATION: (33268)..(33268)
<223> OTHER INFORMATION: n is a, c, g, or t
<220> FEATURE:
<221> NAME/KEY: misc_feature
<222> LOCATION: (33272)..(33272)
<223> OTHER INFORMATION: n is a, c, g, or t
<220> FEATURE:
<221> NAME/KEY: misc_feature
<222> LOCATION: (33280)..(33280)
<223> OTHER INFORMATION: n is a, c, g, or t
<220> FEATURE:
<221> NAME/KEY: misc_feature
<222> LOCATION: (33284)..(33284)
<223> OTHER INFORMATION: n is a, c, g, or t
<220> FEATURE:
<221> NAME/KEY: misc_feature
<222> LOCATION: (33286)..(33286)
<223> OTHER INFORMATION: n is a, c, g, or t
<220> FEATURE:
<221> NAME/KEY: misc_feature
<222> LOCATION: (33691)..(33691)
<223> OTHER INFORMATION: n is a, c, g, or t
<220> FEATURE:
<221> NAME/KEY: misc_feature
<222> LOCATION: (33695)..(33695)
<223> OTHER INFORMATION: n is a, c, g, or t
<220> FEATURE:
<221> NAME/KEY: misc_feature
<222> LOCATION: (33703)..(33703)
<223> OTHER INFORMATION: n is a, c, g, or t
<220> FEATURE:
<221> NAME/KEY: misc_feature
<222> LOCATION: (33707)..(33707)
<223> OTHER INFORMATION: n is a, c, g, or t
<220> FEATURE:
<221> NAME/KEY: misc_feature
<222> LOCATION: (34599)..(34599)
<223> OTHER INFORMATION: n is a, c, g, or t
<220> FEATURE:
<221> NAME/KEY: misc_feature
<222> LOCATION: (34603)..(34603)
<223> OTHER INFORMATION: n is a, c, g, or t
<220> FEATURE:
<221> NAME/KEY: misc_feature
<222> LOCATION: (34611)..(34611)
<223> OTHER INFORMATION: n is a, c, g, or t
<220> FEATURE:
<221> NAME/KEY: misc_feature
<222> LOCATION: (34615)..(34615)
<223> OTHER INFORMATION: n is a, c, g, or t
<220> FEATURE:
<221> NAME/KEY: misc_feature
<222> LOCATION: (35012)..(35012)
<223> OTHER INFORMATION: n is a, c, g, or t
<220> FEATURE:
<221> NAME/KEY: misc_feature
<222> LOCATION: (35016)..(35016)
<223> OTHER INFORMATION: n is a, c, g, or t
<220> FEATURE:
<221> NAME/KEY: misc_feature
<222> LOCATION: (35024)..(35024)
<223> OTHER INFORMATION: n is a, c, g, or t
<220> FEATURE:
<221> NAME/KEY: misc_feature
```

```
<222> LOCATION: (35028)..(35028)
<223> OTHER INFORMATION: n is a, c, g, or t
<220> FEATURE:
<221> NAME/KEY: misc_feature
<222> LOCATION: (35404)..(35404)
<223> OTHER INFORMATION: n is a, c, g, or t
<220> FEATURE:
<221> NAME/KEY: misc_feature
<222> LOCATION: (35408)..(35408)
<223> OTHER INFORMATION: n is a, c, g, or t
<220> FEATURE:
<221> NAME/KEY: misc_feature
<222> LOCATION: (35416)..(35416)
<223> OTHER INFORMATION: n is a, c, g, or t
<220> FEATURE:
<221> NAME/KEY: misc_feature
<222> LOCATION: (35420)..(35420)
<223> OTHER INFORMATION: n is a, c, g, or t
<220> FEATURE:
<221> NAME/KEY: misc_feature
<222> LOCATION: (35787)..(35787)
<223> OTHER INFORMATION: n is a, c, g, or t
<220> FEATURE:
<221> NAME/KEY: misc_feature
<222> LOCATION: (35791)..(35791)
<223> OTHER INFORMATION: n is a, c, g, or t
<220> FEATURE:
<221> NAME/KEY: misc_feature
<222> LOCATION: (35799)..(35799)
<223> OTHER INFORMATION: n is a, c, g, or t
<220> FEATURE:
<221> NAME/KEY: misc_feature
<222> LOCATION: (35803)..(35803)
<223> OTHER INFORMATION: n is a, c, g, or t
<220> FEATURE:
<221> NAME/KEY: misc_feature
<222> LOCATION: (36209)..(36209)
<223> OTHER INFORMATION: n is a, c, g, or t
<220> FEATURE:
<221> NAME/KEY: misc_feature
<222> LOCATION: (36213)..(36213)
<223> OTHER INFORMATION: n is a, c, g, or t
<220> FEATURE:
<221> NAME/KEY: misc_feature
<222> LOCATION: (36221)..(36221)
<223> OTHER INFORMATION: n is a, c, g, or t
<220> FEATURE:
<221> NAME/KEY: misc_feature
<222> LOCATION: (36225)..(36225)
<223> OTHER INFORMATION: n is a, c, g, or t

<400> SEQUENCE: 1
cgcdsdacyr tnakrtndac ycatnnatga gacacctgcg ccttctacct tcaactgtgc      60
ccggcgacct ggctgtgatt atgctggagg actttgtgaa tacagttctg gaggacgaac     120
tgcatccaga gccatttgag ctgggaccta cacttcagga cctctatgat ctggaggtag     180
atgcccatga tgacgaccct aacgaagagg ctgtgaattt aatatttcca gaatctatga     240
ttcttcaggc tgacatagcc agtgaagcca tagttactcc tctacatact cccactctgc     300
ctcccatacc tgaattggag gaggatgaag aaatagacct ccggtgctac gaggaaggtt     360
ttcctcccag cgattcagag gacgaacagg gtgagcagca gatggctcta atctctgatt     420
tagcttgtgt gattgtggag gaacaagttg tgattgaaaa atctaccgag ccagtacaag     480
gctgtaggaa ctgccagtat caccgggata agtccggaga cccgaacgct tcctgcgctc     540
tgtgttacat gaaatctact ttcagcttta tttacagtcc ggtgtcagag gatgagtcat     600
caccctcaga agaagaccac ccgtctcccc ctgagctgtc aggcgaaacg cccctgcaag     660
tgcacagacc cacccagtc agagccagtg gcgagaggcg agcagctgta gaaaaaattg     720
aggacttgtt acatgacatg ggtggggatg aacctttgga cctgagcttg aaacgcccca     780
```

```
ggaactagcg cdsdacyrtn akrtndacyc atnnatgaga cacctgcgcc ttctaccttc    840
aactgtgccc ggcgacctgg ctgtgattat gctggaggac tttgtgaata cagttctgga    900
ggacgaactg catccagagc catttgagct gggacctaca cttcaggacc tctatgatct    960
ggaggtagat gcccatgatg acgaccctaa cgaagaggct gtgaatttaa tatttccaga   1020
atctatgatt cttcaggctg acatagccag tgaagccata gttactcctc tacatactcc   1080
cactctgcct cccatacctg aattggagga ggatgaagaa atagacctcc ggtgctacga   1140
ggaaggtttt cctcccagcg attcagagga cgaacagggt ccggtgtcag aggatgagtc   1200
atcaccctca gaagaagacc acccgtctcc ccctgagctg tcaggcgaaa cgcccctgca   1260
agtgcacaga cccaccccag tcagagccag tggcgagagg cgagcagctg tagaaaaaat   1320
tgaggacttg ttacatgaca tgggtgggga tgaacctttg gacctgagct gaaacgccc    1380
caggaactag cgcdsdacyr tnbkrtndac ycatnatgga tgtgtggact atccttgcag   1440
actttagcaa gacacgccgg cttgtagagg atagttcaga cgggtgctcc gggttctgga   1500
gacactggtt tggaactcct ctatctcgcc tggtgtatac agttaagaag gattataaag   1560
aggaatttga aaatctttt gctgactgct ctggtctgct agattctctg aatcttggcc   1620
accagtccct tttccaggaa agggtactcc acagccttga tttttccagc ccagggcgca   1680
ctacagccgg ggttgctttt gtggtttttc tggttgacaa atggagccag gacacccaac   1740
tgagcagggg ctacatcctg gacttcgcag ccatgcacct gtggagggcc tggatcaggc   1800
agcggggaca gagaatcttg aactactggc ttctacagcc agcagctccg ggtcttcttc   1860
gtctacacag acaaacatcc atgttggagg aagaaatgag gcaggccatg gacgagaacc   1920
cgaggagcgg cctggaccct ccgtcggaag aggagctgga ttgacgcdsd acyrtnbkrt   1980
ndacycatna tggagccagg acacccaact gagcaggggc tacatcctgg acttcgcagc   2040
catgcacctg tggagggcct ggatcaggca gcggggacag agaatcttga actactggct   2100
tctacagcca gcagctccgg gtcttcttcg tctacacaga caaacatcca tgttggagga   2160
agaaatgagg caggccatgg acgagaaccc gaggagcggc ctggaccctc cgtcggaaga   2220
ggagctggat tgaatcaggt atccagcctg tacccagagc ttagcaaggt gctgacatcc   2280
atggccaggg gagtgaagag ggagaggagc gatgggggta ataccgggat gatgaccgag   2340
ctgactgcca gtctgatgaa tcggaagcgc ccagagcgcc ttacctggta cgagctacag   2400
caggagtgca gggatgagat aggcctgatg caggataaat atggcctgga gcagataaaa   2460
acccattggt tgaacccaga tgaggattgg gaggaggcta ttaagaagta tgccaagata   2520
gccctgcgcc cagattgcaa gtacatagtg accaagaccg tgaatatcag acatgcctgc   2580
tacatctcgg ggaacggggc agaggtggtc atcgataccc tggacaaggc cgccttcagg   2640
tgttgcatga tgggaatgag agcaggagtg atgaatatga attccatgat cttcatgaac   2700
attaagttca atggagagaa gtttaatggg gtgctgttca tggccaacag ccacatgacc   2760
ctgcatggct gcagcttctt cggtttcaac aacatgtgcg ccgaggtctg ggagctgct    2820
aagatcaggg gatgtaagtt ttatggctgc tggatgggcg tggtcggaag acccaagagc   2880
gagatgtctg tgaagcagtg tgtgtttgag aaatgctacc tggagtgtct taccgagggc   2940
aatgctagag tgagacactg ctcttccatg gagacgggct gcttctgcct ggtgaagggc   3000
acggcctctc tgaagcataa tatggtgaag ggctgcacgg atgagcgcat gtacaacatg   3060
ctgcctgcg attcggggggt ctgccatatc ctgaagaaca tccatgtgac ctcccacccc   3120
agaaagaagt ggccagtgtt tgagaataac ctgctgatca agtgccatat gcacctgggt   3180
```

```
gccagaaggg gcaccttcca gccgtaccag tgcaacttta gccagaccaa gctgctgttg   3240
gagaacgatg ccttctccag ggtgaacctg aacggcatct tgacatgga tgtctcggtg    3300 tacaagatcc tgagatacga tgagaccaag tccagggtgc gcgcttgcga gtgcgggggc   3360
agacacacca ggatgcaacc agtggccctg gatgtgacag aggagctgag accagaccac   3420
ctggtgatgg cctgtaccgg gaccgagttc agctccagtg gggaggacac agattagcgc   3480
dsdacyrtnr tndacycatn atgaacggga ccggcggggc cttcgaaggg ggcttttta   3540 gcccttattt gacaacccgc ctgccgggat gggccggagt tcgtcagaat gtgatgggat   3600
ctacggtgga tgggcgccca gtgcttccag caaattcctc gaccatgacc tacgcgaccg   3660
tggggagctc gtcgctcgac agcaccgccg cagccgcggc agccgcagcc gccatgacag   3720
cgacgagact ggcctcgagc tacatgccca gcagcagcag tagcccctct gtgcccagtt   3780
ccatcatcgc cgaggagaaa ctgctggccc tgctggcaga gctggaagcc ctgagccgcc   3840
agctggccgc cctgacccag caggtgtccg agctccgcga gcaacagcag cagcaaaata   3900
aatgacgcds dacyrtnvar tndacycatn cmmntnatgg agacgcgagg gcgaagaccg   3960
tgcccgtttc agcaccagca ggatgagtct caagcgcacc cttgcaagcg cccagcccgg   4020
ggcccacccc ttcaccgtga cggagaccac actcacgcgg accctgagac cctggaagga   4080
catgacgctg gccgcgctgg acgcccatcg tctcgtgccc tacagtcgca gtcgtcccaa   4140
cccccgaaac gaggaagtct gctggatcga gatgccgtag agcacgtcac cgagctctgg   4200
gaccgcctgg agctcctctc gcagaccctc gccaagatgc ccatggccga cggactcaag   4260
cccctgaaaa actttgcttc cctgcaagag ctcctctcgc tgggcgggga ccgcctcctc   4320
ggcgagctcg tccgggaaaa cctccaagtc agagacatgc tcaacgaggt ggccccctc    4380 ctccgggacg acggcagctg catgtccttg aactaccacc tgcaacccgt catcggggtc   4440
atctacggcc cgaccgggtg cggcaagtcc cagctgttga gaaacctgct ctcctcgcag   4500
ctcatcaccc ccgccccgga aaccgttttt ttcatcgccc cgcaggtgga catgatcccc   4560
ccctccgaga tgaaagcctg ggagatgcag atctgtgagg ggaactttgc cccggggccc   4620
gagggaacta tcgtcccca atctggcacc ctccgcccca aattcattaa aatgtcttat    4680
gatgatctca cccaggagca taattacgat gtctctgacc ccagaaacgt ctttgccaaa   4740
gccgcagccc acgggcccat cgccatcatc atggatgagt gcatgaaaa cctgggcggg    4800 cacaagggcg tctccaaatt cttccacgca ttcccttcca agttgcatga taagttcccc   4860
aagtgcacgg gctacaccgt cctggtggtc ctgcacaaca tgaacccag gcgggatctg    4920 ggcggcaaca ttgccaacct caagatccag gccaaactgc acatcatctc cccccgcatg   4980
catccctccc agctcaaccg cttcgccaac acctacacca aggggctccc cgtggccatc   5040
agtctcctcc ttaaggacat catccagcac cacgcccagc gccctgcta tgactggatc    5100 atctacaaca cgaccccaga gcacgaggcc atgcagtggt gctacctcca cccccgggac   5160
gggctcatgc ccatgtacct caacatccaa tcccacctct accgggtcct ggaaaaaatc   5220
caccgcactc tcaatgatcg ggagaggtgg accagggcct accgcgcgcg aaaaaataaa   5280
taacgcdsda cygnrtnrtn rtndacycat ncmmntnatg gccttggttc aaagtcacgg   5340
ggcccgtggt cttcacgcag aggcggcaga tccaggatgt caaccgccgc gtcgtcgcgc   5400
acgccagcgc tctcagggcg cagcaccggg acctgcccga gcgccacgcc gacgtgcctc   5460
tgccgcccct gcccgcgggg ccggaaccgc cgctgccgcc gggagcgcgt ccgcgacacc   5520
```

-continued

```
gcttctaaaa gcgcaccgcg gcacggtcgt ggccccgcgc agctacgggc tcatgcaatg    5580
cgtggacacg gccaccaact cacccgtaga aatcaagtac catctgcatc tcaagcacgc    5640
cctcacccgc ttctacgagg tcaacctcag aaccctgccc ccggacctgg atctccgcga    5700
caccatggac agctcccaac tgcgcgccct cgtcttcgct ctccgccccc gccgcgccga    5760
gatctggacc tggctcccgc gcgggctcgt cagcctctcc gtcctcgagg agccccaggg    5820
tgagtcccac gcaggcgaac atgaaaacca ccagccaggg ccgccactcc tgaagttcct    5880
cctcaaggga cgcgctgtgt atctcgtgga tgaggtacag cccgtgcagc gctgcgagta    5940
ctgcggacgc ttttacaagc atcagcacga gtgctcggtt cgccggcggg atttctactt    6000
tcatcacatc aacagccact cgtccaactg gtggcaggaa atccagttct cccaatcgg    6060 ctctcatcct cgcacggagc ggctctttgt cacctacgat gtagaaacct acacctggat    6120
ggggtccttc ggcaagcagc tcgtcccctt catgctggtc atgaaattct ccggggaccc    6180
cgagctggtc gccctcgctc gcgatctcgc cgtgcgctta cgctgggatc gctgggagcg    6240
ggaccccctc accttctact gcgtcacacc cgaaaagatg gccgtgggcc agcagttccg    6300
tctctttcgc gacgagctcc agaccctcat ggcccgcgag ctctgggctt ccttcatgca    6360
agccaaccca catctccagg agtgggcgct cgagcagcac ggactgcaat gccccgagga    6420
cctcacctac gaggagctca aaaagctgcc gcacatcaaa ggccgcccgc gattcatgga    6480
actctacatc gtcgggcaca acatcaacgg cttcgacgag atcgtgctcg ccgcccaggt    6540
catcaacaac cgagcctccg tcccgggccc tttccgcatc acccgcaatt tcatgccgcg    6600
ggcaggcaag attctcttca atgacgtcac tttcgctctg cctaaccccc tctcgaagaa    6660
gcgcaccgat ttcgagctct gggagcacgg cggctgcgac gactcggatt tcaagtacca    6720
gttcttgaaa gtcatggtca gagacacctt cgccctgacg cacacctcgc tccgcaaggc    6780
cgctcaagct tacgccctcc ccgtggagaa gggctgctgt ccctacaagg ccgtgaacca    6840
tttctacatg ctgggctctt accgtgcgga cgatcgagga ttcccgctcc gggagtactg    6900
gaaggatgac gaggagtacg ccctcaaccg cgagctgtgg gagaagaaag gagaggcggg    6960
ttatgacatc atccgcgaaa cgctggacta ctgtgccatg gacgtcctcg tcaccgccga    7020
gctcgtcgcc aagctgcaag actcctacgc gcacttcatc cgcgactcgg tccgcctgcc    7080
tcacgcccac tttaacatct tccaacggcc caccatctcc tcaaaactcg cacgccatctt   7140 tcgccagatc gtcttccgcg ccgagcagcc ccagcgcacc aatctcggcc ccgccttctt    7200 ggcccctcg cacgagttgt atgactacg gcgcgccagc atccgcgggg ggcgctgtta    7260
tcccacctac atcggcatcc tctcggagcc catctatgtg tatgacatct gcggcatgta    7320
cgcctccgcc ctcacgcatc ccatgccctg gggtccgccc ctcaaccccc acgagcgagc    7380
gctggccgcc cgcgagtggc agatggcctt ggatgatgca tcctcaaaaa tcgattattt    7440
tgacaaggaa ctctgtccgg gcatcttcac catcgatgcg gacccccctg acgagcatct    7500
gcttgatgtg ctgcccccgt tctgctcgcg caagggcggc agactctgct ggaccaacga    7560
gcccctgcgc ggcgaggtgg ccaccagcgt ggacctggtc accctgcata accgcggctg    7620
gcgcgtcagg atcgtgcccg acgagcgcac caccgtcttc cccgaatgga agtgcgtcgc    7680
gcgcgagtat gtccagctaa acatcgcggc caaggagcgc gccgaccgtg acaaaaatca    7740
gaccatgaga tccatcgcca agcttctatc caacgccctc tatggctcct ttgccaccaa    7800
gcttgacaat aaaaaaattg tcttttctga ccagatggat gaaagtctcc taaaaagcat    7860
cgcggcaggg caggccaaca tcaaatcctc ctcgtttcta gaaactgaca acctgagtgc    7920
```

```
cgaggtcatg cccgctctag agagggaata cctaccccaa cagctggcgc tcgtggacag   7980
cgacgcggaa gagagtgagg acgagcacag acccgccccc ttttataccc cccgtcgggg   8040 gaccccggt  cacgtggcct acacctacaa gccaatcacc ttcttggatg cggaggaggg   8100
ggacatgtgt ctgcacacgg tggaaaaggt ggaccccctg gtggacaacg accgctaccc   8160
ctcgcacgtg gcctcctttg tcttggcgtg gacgcgcgcc tttgtctcag agtggtccga   8220
gtttctctac gaggaggacc gcgggacgtc cctgcaggac aggcccatca agtccgtcta   8280
cggggacacc gacagcctgt ttgtcaccga gcgcggacac agactcatgg agacgcgagg   8340
taagaagcgc atcaaaaaga acgggggaaa actggttttt gaccccgagc agcccgagct   8400
cacctggctc gtcgagtgcg agaccgtctg cgcccactgc ggagcggacg ccttcgcccc   8460
cgagtccgtt tttctcgcac ccaagctcta cgccctgcaa tcccttctct gtcccgcctg   8520
cgggcgctct tccaagggca agctccgcgc caagggccac gccgccgagg ccctcaacta   8580
cgagctcatg gtcaactgct atctcgccga gcgcagggc  gaagaccgtg cccgtttcag   8640
caccagcagg atgagtctca agcgcaccct tgcaagcgcc cagcccgggg cccacccctt   8700
caccgtgacg gagaccacac tcacgcggac cctgagaccc tggaaggaca tgacgctggc   8760
cgcgctggac gcccatcgtc tcgtgcccta cagtcgcagt cgtcccaacc cccgaaacga   8820
ggaagtctgc tggatcgaga tgccgtagcg cdsdacyrtn krtndacyca tnnatgagag   8880
ccgattggga agaactggat ttcctgccac cagttggacg agtggctgtt gatgtgatga   8940
aagtagaaat cccgccggcg aaccgagcac tcgtgctgat gcttgtaaaa gcgtccgcag   9000
tactcgcagc gctgcacggg ctgtacctca tccacgagat acacagcgcg tcccttgagg   9060
aggaacttca ggagtggcgg ccctggctgg tggttttcat gttcgcctgc gtgggactca   9120
ccctggggct cctcgaggac ggagaggctg acgagcccgc gcgggagcca ggtccagatc   9180
tcggcgcggc gggggcggag agcgaagacg agggcgcgca gttgggagct gtccatggtg   9240
tcgcggagat ccaggggacg tgacgcdsda cygnrtntrt ndacycatnc mmntnatggc   9300
cttgagcgtc aatgactgcg cgcgtctcac cggccagacc gtgccgacca tggattattt   9360
cctgccgctg cgcaacatct ggaaccgcgt ccgcgagttc ccgcgcgcct ccaccaccgc   9420
cgccggcatc acctggatgt cccgctacct ctacggctac caccgcctca tgctcgagga   9480 cctgccccg  ggcgcgccgg ccacccagcg ctggccgctc taccgccagc cgccgccgca   9540
cttcctagtc ggctaccagt acctcgtgcg cacctgcaac gactacgtct tcgactcgcg   9600
cgccttctcg cggctcaggt actccgaggt cgtgcaaccc ggcctgcaga ccgtcaactg   9660
gtcgctcatg gccaactgca cctacaccat caacaccggg gcctaccacc gcttcgtcga   9720
catggatgac ttccaggaca ccctcacccg cgtgcaacag gccatcctcg ccgagcgcgt   9780
cgtcgccgac ctggcgctcg tgcagccgct caggggcgtc ggggtcaccc gcatggaaga   9840
ctccgcctcc gccagtgatg acattgaaag gctcatgcat gactactaca agaacctgag   9900
ccggtgtcag ggccaggcct ggggcatggc cgagcggctc cgcatccagc aagcgggacc   9960
caaggacctg gtcctcctcg ccaccatccg ccgccttaaa aacgcctact tcaattacat  10020
catcagcaac cgcaattcta acagcgtcca cagggctgct acgtgtttga gcttaccttg  10080
cgactgcgat tggctagacg cttttcctcga aagattctcc gatccggtcg atctcgacgc  10140
gctcacgtcc cctacaccgc aattgataag atgcatcgtc agcgcctat  cgctgcccaa  10200 cggggacccg ccccattacc gggagatgac cggcggcgtc ttcacgctgc gtcctcgcga  10260
```

```
acggggtcgc gccgtcaccg aaaccatgcg tcgccgccgc ggggagatga tcgagcgctt   10320
cgtcgaccgt ctcccggtgc gtcgccgtcg tcgtcgggcc ccgccaccac caccgccccc   10380
agaggaagaa atagaagaag aggtcgtcat ggaagaagag gaagaggagg aggtccccgg   10440
ggatttcgag cgccgaggtgc gcgccaccat cgccgagctc atccggctcc tggaagacga   10500
gctcacggtc tcggcccgca acgcccagtt tttcaacttc gccgtggatt tctacgaggc   10560
catggaaagg ctgcgaggcca tcggcgacat cagcgagatg cccctgcgcc gctggatcat   10620
gtacttcttc gtcaccgagc acatcgccac caccctcaac tacctcttcc agcgcctgcg   10680
caactacgcc gtcttcacgc ggcacgtgga gctcaacctc gcgcaggtgg tcatgcgcgc   10740
gcgcgacgcc gacggggacg tggtctacag ccgcgtctgg aacgagagcg gcctgggcgc   10800
cttctcgcag ctaatgggtc gcatctcgaa tgacctcgcc gccaccgtgg agcgcgcggg   10860
ccgcggcgat ctccaggagg aggagatcga gcagttcatg tccgagatcg cctaccagga   10920
caactcgggc gacgtgcaag agatcctgcg tcaggccgcc gtcaatgacg ccgagattga   10980
ttctgttgaa ctgtctttca ggttcaaagt cacggggccc gtggtcttca cgcagaggcg   11040
gcagatccag gatgtcaacc gccgcgtcgt cgcgcacgcc agcgctctca gggcgcagca   11100
ccgggacctg cccgagcgcc acgccgacgt gcctctgccg cccctgcccg cggggccgga   11160
accgccgctg ccgccgggag cgcgtccgcg acaccgcttc taacgcdsda cyrtnkrtnd   11220
acycatnatg catcccgtcc tgcgccaaat gcgtcccacc cccccggcga ccaccgcgac   11280
cgcggccgta acaggcgccg cgctagcca gccacagaca gagatggact tggaagaggg   11340
cgaagggctg cgcgagactgg gggcgccgtc cccggagcga caccccccgcg tgcagctgca   11400
gaaggacgtg cgcccggcgt acgtgcctgc gcagaacctg ttcagggacc gcagcgggga   11460
ggagcccgag gagatgcgcg actgccggtt tcgggcgggc agggagctgc gcagggcct   11520
ggaccgccag cgcgtgctgc gcgacgagga tttcgagccg aacgagcaga cggggatcag   11580
ccccgcgcgc gcgcacgtgg cggcggccaa cctggtgacg gcctacgagc agacggtgaa   11640
gcaggagcgc aacttccaaa agagtttcaa caaccacgtg cgcacgctga tagcgcgcga   11700
ggaggtggcc ctgggcctga tgcacctgtg ggacctggcg gaggccatcg tgcagaaccc   11760
ggacagcaag cctctgacgg cgcagctgtt cctggtggtg cagcacagca gggacaacga   11820
ggcgttcagg gaggcgctgc tgaacatcgc cgagcccgag ggtcgctggc tgctggagct   11880
gatcaacatc ttgcagagca tcgtagtgca ggagcgcagc ctgagcctgg ccgagaaggt   11940
ggcggcgatc aactactcgg tgctgagcct gggcaagttt tacgcgcgca agatttacaa   12000
gacgccgtac gtgcccatag acaaggaggt gaagatagac agcttttaca tgcgcatggc   12060
gctcaaggtg ctgacgctga gcgacagacct gggcgtgtat cgcaacgacc gcatccacaa   12120
ggccgtgagc acgagccggc ggcgcgagct gagcgaccgc gagctgatgc tgagcctgcg   12180
ccgggcgctg gtaggggcg ccgccggcgg cgaggagtcc tacttcgaca tggggcgga   12240
cctgcattgg cagccgagcc ggcgcgcctt ggaggccgcc tacggtccag aggacttgga   12300
tgaggatgag gaagaggagg aggatgcacc cgttgcgggg tactgacgcd sdacyrtnar   12360
tndacycatn atgtcccagc aagcccccgga ccccgccata agggcggcgc tgcaaagcca   12420
gccgtccggt ctagcatcgg acgactggga ggccgcgatg caacgcatca tggccctgac   12480
gacccgcaac cccgagtcct ttagacaaca gccgcaggcc aacagactct cggccattct   12540
ggaggcggtg gtcccctctc ggaccaaccc cacgcacaga aaggtgctgg cgatcgtgaa   12600
cgcgctggcg gagaacaagg ccatccgtcc cgacgaggcc gggctggtgt acaacgccct   12660
```

```
gctggagcgc gtgggccgct acaacagcac gaacgtgcag tccaacctgg accggctggt   12720 gacgacgtg  cgcgaggccg tggcgcagcg cgagcggttc aagaacgagg gcctgggctc   12780
gctggtggcg ctgaacgcct tcctggcgac gcagccggcg aacgtgccgc gagggcagga   12840
cgattacacc aactttatca gcgcgctgcg gctgatggtg accgaggttc cccagagcga   12900
ggtgtaccag tcgggcccgg actactttt  ccagacaagc cggcagggcc tgcagacggt   12960
gaacctgagt caggctttca agaacctgcg cgggctgtgg ggcgtgcagg cgcccgtggg   13020
cgaccggtcg acggtgagca gcttgctgac gcccaactcg cggctgctgc tgctgctgat   13080
cgcgcccttc accgacagcg gcagcgtgaa ccgcaactcg tacctgggcc acctgctgac   13140
gctgtaccgc gaggccatag gccaggcgca ggtggacgag cagaccttcc aggagatcac   13200
gagcgtgagc cgcgcgctgg ggcagaacga caccgacagt ctgagggcca ccctgaactt   13260
tttgctgaca aatagacagc agaagatccc ggcgcagtac gcactgtcgg ccgaggagga   13320
aaggatcctg agatatgtgc agcagagcgt agggctgttc ctgatgcagg agggtgccac   13380
ccccagcgcc gcgctggaca tgaccgcgcg caacatggaa cctagcatgt acgccgccaa   13440
ccggccgttc atcaataagc tgatggacta cctgcaccgc gcggcggcca tgaacacgga   13500
ctactttaca aacgccatat tgaacccgca ctggcttccg ccgccggggt tctacacggg   13560
cgagtacgac atgcccgacc ccaacgacgg gttcctgtgg gacgacgtgg acagcgcggt   13620
gttctcgccg acctttcaaa agcgccagga ggcgccgccg agcgagggcg cggtggggag   13680 gagcccttt  cctagcttag ggagtttgca tagcttgccg ggctcggtga acagcggcag   13740
ggtgagccgg ccgcgcttgc tgggcgagga cgagtacctg aacgactcgc tgctgcagcc   13800
gccgcgggtc aagaacgcca tggccaataa cgggatagag agtctggtgg acaaactgaa   13860
ccgctggaag acctacgctc aggaccatag ggagcctgcg cccgcgccgc ggcgacagcg   13920
ccacgaccgg cagcggggcc tggtgtggga cgacgaggac tcggccgacg atagcagcgt   13980
gttggacttg ggcgggagcg gtggggccaa cccgttcgcg catctgcagc ccagactggg   14040
gcggcggatg ttttgacgcd sdacyrtnrt ndacycatna tgaggcgtgc ggtggtgtct   14100
tcctctcctc ctccctcgta cgagagcgtg atggcgcagg cgaccctgga ggttccgttt   14160
gtgcctccgc ggtatatggc tcctacggag ggcagaaaca gcattcgtta ctcggagctg   14220
gctccgcagt acgacaccac tcgcgtgtac ttggtggaca caagtcggc  ggacatcgct   14280 tccctgaact accaaaacga ccacagcaac ttcctgacca cggtggtgca gaacaacgat   14340 ttcaccccg  ccgaggccag cacgcagacg ataaattttg acgagcggtc gcggtggggc   14400
ggtgatctga agaccattct gcacaccaac atgcccaatg tgaacgagta catgttcacc   14460
agcaagttta aggcgcgggt gatggtggct agaaagcatc ccaaagatgt agatgccagt   14520
gatttaagca aggatatctt agagtataag tggtttgagt ttaccctgcc cgagggcaac   14580
ttttccgaga ccatgaccat agacctgatg aacaacgcca tcttggaaaa ctacttgcaa   14640
gtggggcggc agaatggcgt gctggagagc gatatcggag tcaagtttga cagcaggaat   14700
ttcagactgg gctgggaccc ggtgaccaag ctggtgatgc caggggtcta cacctacgag   14760
gccttccacc cggacgtggt gctactgccg ggctgcgggg tggacttcac cgagagccgc   14820
ctgagcaacc tcctgggcat tcgcaagaag caacctttc  aagagggctt cagaatcatg   14880
tatgaggatc tagaaggggg taacatcccc gctctcctgg ataccaaaaa atatctggat   14940
agcaagaagg aacttgagga tgctgccaag gaagctgcaa agcaacaggg agatggtgct   15000
```

```
gtcactagag gcgataccca cctcactgta gctcaagaaa aagcagctga aaaggagcta   15060
gtgatcgtac caattgaaaa ggatgagagc aacagaagtt acaacctgat caaggacacc   15120
catgacaccc tgtaccgaag ctggtacctg tcctatacct acggggaccc cgagaagggg   15180
gtgcagtcgt ggacgctgct caccacccg gacgtcacct cgggcgcgga gcaagtctac    15240
tggtcgctgc cggacctcat gcagaccccc gtcaccttcc gctctaccca gcaagtcagc   15300
aactaccccg tggtcggcgc cgagctcatg cccttccgcg ccaagagctt ttacaacgac   15360
ctcgccgtct actcccagct catccgcagc tacacctccc tcacccacgt cttcaaccgc   15420
ttccccgaca accagatcct ctgccgcccc ccgcgccca ccatcaccac cgtcagtgaa     15480
aacgtgcctg ctctcacaga tcacgggacg cttccgctgc gcagcagtat ccgcggagtc   15540
cagcgagtga ccgtcactga cgcccgtcgc cgcacctgtc cctacgtcta caaggccctg   15600
ggcatagtcg cgccgcgcgt gctctccagt cgcaccttct aacgcdsdac yrtnvrtnda   15660
cycatnatgt ctattctcat ctcgcccagc aataacaccg gctggggtct tactaggccc   15720
agcaccatgt acggaggagc caagaagcgc tcccagcagc accccgtccg cgtccgcggt   15780
cacttccgcg ctccctgggg agcttacaag cgggggcgca ctgccaccgc cgccgccgtg   15840
cgcaccaccg tcgacgacgt catcgactcg gtggtcgccg acgcgcgcaa ctacacccc    15900 gcccctcca ccgtggacgc ggtcatcgac agcgtggtgg ccgacgcgcg cgactatgcc    15960
agacgcaaga gccggcggcg acggatcgcc aggcgccacc ggagcacgcc cgccatgcgc   16020
gccgcccggg ctctgctgcg ccgcgccaga cgcacgggcc gccgggccat gatgcgagcc   16080 gcgcgccgc ccgccactgc acccccgca ggcaggactc gcagacgagc ggccgccgcc     16140
gctgccgcgg ccatctctag catgaccaga cccaggcgcg gaaacgtgta ctgggtgcgc   16200
gactccgtca cgggcgtgcg cgtgcccgtg cgcaccccgtc ctcctcgtcc ctgacgcdsd  16260
acyrtnvrtn dacycatnat gtcaaagcgc aaaatcaagg aggagatgct ccaggtcgtc   16320
gccccggaga tttacggacc cccggaccag aaaccccgca aaatcaagcg ggttaaaaaa   16380
aaggatgagg tggacgaggg ggcagtagag tttgtgcgcg agttcgctcc gcggcggcgc   16440
gtaaattgga aggggcgcag ggtgcagcgc gtgttgcggc ccggcacggc ggtggtgttc   16500
acgcccggcg agcggtcctc ggtcaggagc aagcgtagct atgacgaggt gtacggcgac   16560
gacgacatcc tggaccaggc ggcggagcgg gcgggcgagt cgcctacgg gaagcggtcg    16620 cgcgaagagg agctgatctc gctgccgctg gacgaaagca accccacgcc gagcctgaag   16680
cccgtgaccc tgcagcaggt gctgcccag gcggtgctgc tgccgagccg cggggtcaag     16740
cgcgagggcg agagcatgta cccgaccatg cagatcatgg tgcccaagcg ccggcgcgtg   16800
gaggacgtgc tggacaccgt gaaaatggat gtggagcccg aggtcaaggt gcgccccatc   16860
aagcaggtgg cgccgggcct gggcgtgcag accgtggaca ttcagatccc caccgacatg   16920
gatgtcgaca aaaaccctc gaccagcatc gaggtgcaga ccgaccctg gctcccagcc    16980 tccaccgcta ccgtctccac ttttaccgcc gccacggcta ccgagcctcc caggaggcga   17040
agatggggcg ccgccagccg gctgatgccc aactacgtgt tgcatccttc catcatcccg   17100
acgccgggct accgcggcac ccggtactac gccagccgca ggcgcccagc cgccaaacgc   17160
cgccgccgca ctgccacccg ccgccgtctg gccccgcccc gcgtgcgccg cgtaaccacg   17220
cgccggggcc gctcgctcgt tctgcccacc gtgcgctacc accccagcat ccttttaacgc  17280 dsdacyrtnr tndacycatn atggctctca cttgccgcct gcgcatcccc gtcccgaatt   17340
accgaggaag atcccgccgc aggagaggca tggcaggcag cggcctgaac cgccgccggc   17400
```

```
ggcgggccat gcgcaggcgc ctgagtggcg ggtttctgcc cgcgctcatc cccataatcg   17460
ccgcggccat cggcacgatc ccgggcatag cttccgttgc gctgcaggcg tcgcagcgcc   17520
gttgacgcds dacyrtnvrt ndacycatna tggaagacat caattttgcg tccctggctc   17580
cgcggcacga cacgcggccg ttcatgggca cctggaacga gatcggcacc agccagctga   17640 acggggggcgc cttcaattgg agcagtgtct ggagcgggct taaaaatttc ggctcgacgc   17700
tccggaccta tgggaacaag gcctggaata gtagcacggg gcagttgtta agggaaaagc   17760
tcaaagacca gaacttccag cagaaggtgg tggacgggct ggcctcgggc attaacgggg   17820
tggtggacat cgcgaaccag gccgtgcagc gcgagataaa cagccgcctg acccgcggcg   17880
cgcccacggt ggtggagatg aagatgcaa ctcttccgcc gcccaaaggc gagaagcggc   17940
cgcggcccga cgcggaggag acgatcctgc aggtggacga gccgccctcg tacgaggagg   18000
ccgtcaaggc cggcatgccc accacgcgca tcatcgcgcc gctggccacg ggtgtaatga   18060
aacccgccac ccttgacctg cctccaccac ccacgcccgc tccaccgaag gcagctccgg   18120
ttgtgcaggc ccctccggtg gcgaccgccg tgcgccgcgt ccccgcccgc cgccaggccc   18180
agaactggca gagcacgctg cacagtatcg tgggcctggg agtgaaaagt ctgaagcgcc   18240
gccgatgcta ttgacgcdsd acyrtnhnrt ndacycatna tggccacccc ctcgatgatg   18300
ccgcagtggg cgtacatgca catcgccggg caggacgcct cggagtacct gagcccgggt   18360
ctggtgcagt ttgcccgcgc caccgacacg tacttcagcc tgggcaacaa gtttaggaac   18420
cccacggtgg ccccgaccca tgatgtgacc acggaccggt cccagcgtct gacgctgcgc   18480
ttcgtgcccg tggatcgcga ggacaccacg tactcgtaca aggcgcgctt cactctggcc   18540
gtgggcgaca accgggtgct agacatggcc agcacgtact ttgacatccg cggcgtcctg   18600
gaccgcggtc ccagcttcaa accctactcg ggcacggctt acaacagttt ggcccccaag   18660
ggcgccccca actccagtca gtggactgac aaagaacggc aaaatggtgg acaaccaccc   18720
actacaaaag atgttacaaa acattcggga gtagcagcca ggggagggct tcatattact   18780
gataaaggac tacaaatagg agaagatgaa aataacgagg atggtgaaga agagatatat   18840
gcagacaaaa ctttccagcc agaacctcaa gtaggagagg aaaactggca agatactgat   18900
gttttctatg gcggcagagc gcttaaaaag gaaaccaaaa tgaaaccatg ctatggctct   18960
tttgccagac ctaccaatga aaaggaggt caagctaaat ttttaaatgg cgaaaacggt   19020
caaccttcta aagatcaaga tattacatta gctttctttg atcttaaaca aaatgacact   19080
ggaactactc aaaaccagcc agatgttgtc atgtacactg aaaatgtgta tctggaaacc   19140
ccagacaccc atgtggtgta caaacctggc aaggaagata caagctccgc tgctaaccttt   19200 acacaacagt ccatgcccaa caggcccaac tacattggtt tcaggacaa ctttgtgggg   19260 ctcatgtatt acaacagcac tggcaacatg gtgtgctgg ctggtcaggc ctctcagttg   19320
aatgctgtgg ttgacttgca agacagaaac accgagctgt cttatcagct cttgctagat   19380
tctctgggtg acagaaccag atactttagc atgtggaatt ctgcggtgga cagctatgat   19440
ccagatgtca ggatcattga gaatcacggt gttgaagatg agcttccaaa ttattgcttc   19500
ccactggatg gatctggcag caataccgca tatcaaggtg ttaaatatga aaacggagct   19560
ggcaatggaa gctggaaagt agatggcgaa gttgcttctc agaatcagat cgccaagggt   19620
aatctgtatg ccatggagat aaaccttcag gccaacctgt ggaagagttt tctgtactcg   19680
aacgtggcgc tgtatctacc agactcctac aagtacacgc cggccaacat cacgctgccc   19740
```

```
accaacacca acacctacga gtacatgaac ggccgcgtgg tggcaccctc gctggtggat   19800
gcctatgtca acatcggtgc ccgctggtcg ctggacccca tggacaacgt caacccttc    19860 aaccaccacc gcaacgcggg tctgcgctac cgctccatgc ttctgggcaa cggccgctac   19920
gtgcccttcc acatccaagt gccccaaaag ttctttgcca tcaagaacct gctcctgctt   19980
cccggttcct acacctacga gtggaacttc cgcaaggatg tcaacatgat cctgcaaagt   20040
tccctcggca acgacctgcg cgtcgacggc ggcctccgtcc gcttcgacag cgtcaacctc   20100
tatgccacct tcttccccat ggcgcacaac accgcctcca cccttgaagc catgctgcgc   20160
aacgacacca acgaccagtc cttcaacgac tacctctcgg ccgccaacat gctctaccca   20220
atcccggcca aggccaccaa cgtgcccatc tccatcccct cgcgcaactg ggccgccttc   20280
cgcggctgga gtttcacccg gctcaagacc aaggaaactc cctccctcgg ctcgggtttc   20340
gacccctact ttgtctactc gggctccatt ccctacctcg acggaaccctt ctacctcaac   20400 cacaccttca agaaggtctc catcatgttc gactcctcgg tcagctggcc cggcaacgac   20460
cggctgctca cgccgaacga gttcgagatc aagcgcagcg tcgacgggga gggctacaac   20520
gtggcccaat gcaacatgac taaggactgg ttcctcgtcc agatgctctc tcattacaac   20580
attggctacc agggcttcta cgtgcctgag ggttacaagg accgcatgta ctccttcttc   20640
cgcaacttcc agcccatgag caggcaggtg gtcgatgaga tcaactacaa ggactacaag   20700
gccgtcaccc tgcccttcca gcacaacaac tcgggcttca ccggctacct cgcacccacc   20760
atgcgtcagg ggcagccata ccccgccaac ttcccctacc cgctcatcgg ccagacagcc   20820
gtgccctccg tcacccagaa aaagttcctc tgcgacaggg tcatgtggcg catcccctc     20880 tccagcaact tcatgtccat gggcgccctc accgacctgg gtcagaacat gctctacgcc   20940
aactcggccc acgcgctcga catgaccttc gaggtggacc ccatggatga gcccaccctc   21000
ctctatcttc tcttcgaagt tttcgacgtg gtcagagtgc accagccgca ccgcggcgtc    21060
atcgaggccg tctacctgcg cacgcccttc tccgccggaa acgccaccac ataacgcdsd    21120
acyrtnrtas rtndacycat natgagcggc tccagcgaac gagagctcgc ggccatcgtg   21180
cgcgacctgg gctgcggggcc ctacttttg ggaacccacg acaagcgctt ccctggcttc    21240
ctcgccggcg acaagctggc ctgcgccatc gtcaacacgg ccggccgcga accggaggc     21300 gtgcactggc tcgccttcgg ctggaacccg cgctcgcgca cctgctacat gttcgacccc   21360
tttgggttct cggaccgccg gctcaagcag atttacagct tcgagtacga ggccatgctg   21420
cgccgcagcg ccctggcctc ctcgcccgac cgctgtctca gcctcgagca gtccacccag   21480
accgtgcagg ggcccgactc cgccgcctgc ggactttttct gttgcatgtt cttgcatgcc   21540
ttcgtgcact ggcccgaccg acccatggac gggaacccca ccatgaactt gctgacgggg   21600
gtgcccaacg gcatgctaca atcgccacag gtgctgccca ccctccggcg caaccaggag   21660
gagctctacc gcttcctcgc gcgccactcc ccttactttc gatcccaccg cgccgccatc   21720
gaacacgcca ccgcttttga caaaatgaaa caactgcgtg tatctcaata acgcdsdacy   21780
rtndbrtnda cycatncmmn tatggccggc ggcagtcagg acgtgcgccg gttcatggag   21840
cgagaggcca ctccgccccg gggccacggg tcggcgcgct atccgccgga gcaggagagg   21900
agcccctcgc cgccacctcc tctgcccacc aagcgccgaa agtatcagcg ggtgggctcc   21960
gggtcttcgg aggaggacgt ggtcccgtg gacagccctc caaaaaagaa gcaagccaga    22020
aagaccaagc atgtgacaaa ggtagaccca gacgaagaga tgcccagga agacgccgtg    22080 atcgtgggag tgggattcag ccagcctccg gttctgttga aggaaggcaa ggacggaaaa   22140
```

```
cgcatcgtcg agcccgcgac ccccggtgtc ctgaacgtgc gcaaccccct gagtctgcct    22200
ctggtctcgt cctgggagaa gggcatggat accatgaacg tgctgatgga acgctaccgc    22260
gtcgacagcg gcctgcgcga tgcttacaag ctcatgccag agcagaccga gatcttccag    22320
aagatgtgcc agacctggat gaacgaggag gcccgcggtc tgcaactgac cttcaccacc    22380
cagaaagcct ttagcaccgt catgggtcgc ctgttgcaag gttacatctt cagccacagc    22440
gggatcgcgc ataagaactg ggagtgcacc ggatgcgccc tgtgggatca cggctgcacc    22500
gaggtggaag gccagctcaa gtgtctgcat ggaacggtga tgatccacaa agaccacgtg    22560
gtggagatga atgtgaccag cgagaacgga cagcgcgcgc tgaaggagca acccagcaag    22620
gccaaggtga cccagaaccg ctggggacgg agcgtggtgc aactgaccag ccatgacgcg    22680
cgctgctgcg tgcaggatgc cggttgcggg aataaccagt tcagcgggaa gagctgcggg    22740
ctgttttttca gcgagggagc caaggcccag caagcttttca aacagatctc ggcctttgtc    22800
aaggccctct acccgaatat gcagcgcggc gcggggatga tgctaatgcc cattcactgc    22860
gagtgtaacc acaagcctca gagcgtgccc ttcctgggcc gccagctgtg caagatgacc    22920
ccgtttggcc tgagcaacgc cgaggacctt gacaaggatc agatcaccga caagagcgtg    22980
ctggccagtg tgaagtaccc cagtctgatg gtgttccagt gctgcaaccc cgtgtaccgc    23040
aactcgcgcg cgcagagcac cggtcccaac tgcgatttca agatctccgc cccggacatg    23100
ctgggcgccc tgcagatgag ccggcgcatg tggagcgaga ccttccccga gattccggtt    23160
cccaaactgg tgatccccga gttcaagtgg cttcccaagt accagtaccg caacgtggcc    23220
ctccccagcg cggcgcacaa cgacgagcgc gagaacccct tcgacttttta acgcdsdacy    23280
rtnkrtndac ycatnatgga gggagcagcc cgtaagcagg agcaggagga ggacttaacc    23340
acccacgagc aacccaaaat cgagcaggac ctgggcttcg aagagccggc tcgtctagaa    23400
cccccacagg atgaacagga gcacgagcaa gacgcaggcc aggaggagac cgacgctggg    23460
ctcgagcatg gctacctggg aggagaggag gatgtgctgc tgaaacacct gcagcgccag    23520
tccctcatcc tccgggacgc cctggccgac cggagcgaaa ccccctcag cgtcgaggag    23580
ctgtgtcggg cctacgagct caacctcttc tcgccgcgcg tgcccccaa acgccagccc    23640
aacggcacct gcgagcccaa cccgcgtctc aacttctatc ccgtctttgc ggtccccgag    23700
gcccttgcca cctatcacat ctttttcaag aaccaaaaga tccccgtctc ctgccgcgcc    23760
aaccgcaccc gcgccgacgc gctcctcgct ctggggcccg gcgcgcgcat acctgatatc    23820
gcttccctgg aagaggtgcc caagatcttc gaagggctcg gtcgggacga gacgcgcgcg    23880
gcgaacgctc tgaaagaaac agcagaggaa gagggtcaca ctagcgccct ggtagagttg    23940
gaaggcgaca acgccaggct ggtcgtgctc aagcgcagcg tcgagctcac ccacttcgcc    24000
taccccgccg ttaacctccc gcccaaggtc atgcgtcgca tcatggatca gcttatcatg    24060
ccccacatcg aggccatcga tgagacccaa gagcagcgcc ccgaggacgc ccggcccgtg    24120
gtcagcgacg agatgctcgc gcgctggctc gggacccgcg accccaggc tttggaacag    24180
cggcgcaagc tgatgctggc cgtagtcctg gtcaccctcg agctcgaatg catgcgccgc    24240
ttcttctgcg accccgagac cctgcgcaag gtcgaggaga ccctgcacta cactttcaga    24300
cacggtttcg tcaggcaagc ctgcaagatc tccaacgtgg agctgaccaa cctggtctcc    24360
tgcctgggga tcctgcatga gaaccgcctg gggcagacag tgctccactc taccctgaag    24420
ggcgaggcac ggcgggacta tgtccgcgac tgcgtctttc tctttctatg ccacacatgg    24480
```

| | |
|---|---|
| caagcagcca tgggcgtgtg gcagcagtgt ctcgaggacg agaacctgaa ggagctggac | 24540 |
| aagcttcttg ctagaaacct taaaaagttg tggacgggct tcgacgagcg caccgtcgcc | 24600 |
| tcggacctgg ccgagatcgt tttccccgag cgcctgaggc atacgctgaa aggcgggctg | 24660 |
| cccgacttca tgagccagag catgttgcaa aactaccgca ctttcattct cgagcgctcg | 24720 |
| ggtatcctgc ccgccacctg caacgccttc ccctccgact tgtcccgct gagctaccgc | 24780 |
| gagtgtcccc cgccgctgtg gagccactgc tacctcttgc agctggctaa ctacatctcc | 24840 |
| taccactcgg acgtgatcga ggacgtgagc ggcgaggggc tgctcgagtg ccactgccgc | 24900 |
| tgcaacctgt gctccccgca ccgctccctg gtctgcaacc cccagctcct gagcgagacc | 24960 |
| caggtcatcg gtaccttcga gctgcaaggt ccggagaagt ccaccgctcc gctgaaactc | 25020 |
| acgccggggt tgtggacttc cgcgtacctg cgcaaatttg tacccgaaga ctaccacgcc | 25080 |
| catgagataa agttcttcga ggaccaatcg cgtccgcagc acgcggatct cacggcctgc | 25140 |
| gtcatcaccc agggcgcgat cctcgcccaa ttgcatgcca tccaaaaatc ccgccaagag | 25200 |
| tttcttctga aaaagggtag aggggtctac ctggacccc agacgggcga ggtgctcaac | 25260 |
| ccgggtctcc cccagcatgc cgaggaagaa gcaggagccg ctagtggagg agatggaaga | 25320 |
| agaatgggac agccaggcag aggaggacga atgggaggag gagacagagg aggaagaatt | 25380 |
| ggaagaggtg gaagaggagc aggcaacaga gcagcccgtc gccgcaccat ccgcgccggc | 25440 |
| agccccggcg gtcacggata caacctccgc tccggtcaag cctcctcgta gcgcdsdacy | 25500 |
| rtnkrtndac ycatnnatgc cgaggaagaa gcaggagccg ctagtggagg agatggaaga | 25560 |
| agaatgggac agccaggcag aggaggacga atgggaggag gagacagagg aggaagaatt | 25620 |
| ggaagaggtg gaagaggagc aggcaacaga gcagcccgtc gccgcaccat ccgcgccggc | 25680 |
| agccccggcg gtcacggata caacctccgc tccggtcaag cctcctcgta gatgggatcg | 25740 |
| agtgaaggt gacgctaaga aaaagcaagt aagaggagtc gccggaggag gcctgaggat | 25800 |
| cgcggcgaac gagccctcga ccaccaggga gctgaggaac cggatcttcc ccactcttta | 25860 |
| tgccattttt cagcagagtc gaggtcagca gcaagagctc aaagtaaaaa atcggtctct | 25920 |
| gcgctcgctc acccgcagtt gcttgtacca caaaaacgaa gatcagctgc agcgcactct | 25980 |
| cgaagacgcc gaggctctgt tccacaagta ctgcgcgctc actcttaaag actaacgcds | 26040 |
| dacyrtnkrt ndacycatna tgccgaggaa gaagcaggag ccgctagtgg aggagatgga | 26100 |
| agaagaatgg gacagccagg cagaggagga cgaatgggag gaggagacag aggaggaaga | 26160 |
| attggaagag gtgaagagg agcaggcaac agagcagccc gtcgccgcac catccgcgcc | 26220 |
| ggcagccccg gcggtcacgg atacaacctc cgctccggtc aagcctcctc gtagatggga | 26280 |
| tcgagtgaag ggtgacggta agcacgagcg gcagggctac cgatcatgga gggcccacaa | 26340 |
| agccgcgatc atcgcctgct tgcaagactg cgggggggaac atcgctttcg cccgccgcta | 26400 |
| cctgctcttc caccgcgggg tgaacatccc ccgcaacgtg ttgcattact accgtcacct | 26460 |
| tcacagctaa cgcdsdacyr tnvrtndacy catnatgagc aaggagattc ccacccctta | 26520 |
| catgtggagc tatcagcccc agatgggcct ggccgcgggc gcctcccagg actactccac | 26580 |
| ccgcatgaac tggctcagtg ccggcccctc gatgatctca cgggtcaacg gggtccgtaa | 26640 |
| ccatcgaaac cagatattgt tggagcaggc ggcggtcaca tccacgccca gggcaaagct | 26700 |
| caacccgcgt aattggccct ccaccctggt gtatcaggaa atccccgggc cgactaccgt | 26760 |
| actacttccg cgtgacgcac tggccgaagt ccgcatgact aactcaggtg tccagctggc | 26820 |
| cggcggcgct tcccggtgcc cgctccgccc acaatcgggt ataaaaaccc tgatgatccg | 26880 |

```
aggcagaggc acacagctca acgacgagtt ggtgagctct tcgatcggtc tgcgaccgga   26940
cggagtgttc caactagccg gagccgggag atcatccttc actcccaacc aggcctacct   27000
gaccttgcag agcagctctt cggagcctcg ctccggaggc atcggaaccc tccagttcgt   27060
ggaggagttt gtgccctcgg tctacttcaa cccttctcg ggatcgccag gcctctaccc    27120
ggacgagttc ataccgaact tcgatgcagt gagagaagcg gtggacggct acgactgacg   27180
cdsdacyrtn krtndacyca tnatgtccca tggtgactcg gctgagctcg ctcggttgag   27240
gcatctggac cactgccgcc gcctgcgctg cttcgcccgg gagagctgcg gactcatcta   27300
ctttgagctg cccgaggagc accccaacgg ccctgcacac ggagtacgga tcaccgtaga   27360
gggcaccgcc gagtctcacc tggtcaggtt cttcacccag caacccttcc tggtcgagcg   27420
ggaccggggc gccaccacct acaccgtcta ctgcatctgt cctacccaa agttgcatga    27480
gaattttgc tgtactcttt gtggtgagtt taataaaagc tgacgcdsda cyrtncraha    27540
rtndacycat natgagaatt tttgctgtac tctttgtggt gagtttaata aaagctgaac   27600
taagaaccta ctttggaatc ccttgtcgtc atcaaatcca caagaccatc aacttcacct   27660
ttgaggaaca ggtgaacttt acctgcaagc cacacaagaa gtacgtcacc tggttttacc   27720
agaacactac tctagcagta gccaacacct gctcgaacga cggtgttctt cttccaaaca   27780
atctcaccag tggactaact ttctcagtga aaagggcaaa gctaattctt catcgccta    27840
ttgtagaagg aacttaccag tgtcagagcg gaccttgctt ccacagtttc actttggtga   27900
acgttaccgg cagcagcaca gtcgctccag aaactaacct tctttctgat actaacactc   27960
ctaaaaccgg aggtgagctc tgggttccct ctctgacaga gggggtagt catattgaag    28020
cggtcgggta tttgatttta ggggtggtcc tgggtgggtg catagcggtg ctatattacc   28080
ttccttgctg ggtcgaaatc agggtattta tctgctgggt cagacattgt ggggaggaac   28140
catgacgcds dacyrtnkrt ndacycatna tgaaggggct cttgctgatt atcctttccc   28200
tggttggggg tttactggcc tgccacgaac agccacgatg taacatcacc acaggcaatg   28260
agaggaacga ctgctctgta gtgatcaaat gcgagcacca gtgtcctctc aacattacat   28320
tcaagaataa gaccatggga aatgtatggg tgggattctg gcaaccagga gatgagcaga   28380
actacacggt cactatccat ggtagcgatg gaaatcacac tttcggtttc aaattcattt   28440
ttgaagtcat gtgtgatatc acactgcatg tggctagact tcatggcttg tggccccta    28500
ccaaggagaa catggttggg ttttctttgg cttttgtgat catggcctgt gcaatgtcag   28560
gtctgctggt aggggctcta gtgtggttcc tgaagcgcaa gcccaggtac ggaaatgagg   28620
agaaggaaaa attgctataa cgcdsdacyr tnkcrbrtnd acycatnatg aatactttga   28680
ccagtgtcgt gctgctctct cttttagtta ttaatgtgga atgtgccgat cctattctag   28740
ttagtgtaga ttggggaaaa aatcttacat tagagggtcc taaagaaaca ccagttgaat   28800
ggtgggtgg aagaaacata caacaactgt gcatagggaa tcaaaccaaa cataaagagc    28860
taagtcacag atgtaatgtc cagaacataa ctttactgtt tgtaaatact agttttaatg   28920
gagactactt tgggttaaa aatgataaca gcggtatgaa acattataaa gtcacagtta    28980
taccccctaa accctccact cggaaacctc tttctcctcc acactatgta aacgcaacta   29040
tgggcaaaa cctaacatta gtggggcctg caaacattcc agttacttgg cttagtgaat    29100
atggcacgtt gtgtgagggc aaaaaaattt tgcacaaaga attaaatcac acctgtaacg   29160
aacagaacct cacgttactg tttgttaata tgacacacaa cggaccatat tttggctttg   29220
```

```
acaaatacaa cattgataga gagcagtatg aggtttctat tattagtttg tttaaagttg    29280
gcgctggaca gaagaaaatt gggaaaggac agaaaaagga ggaaaagaca aaaccaaact    29340
ctagtgattt gggacaaaga caatccagac caaagaaaaa agatattgtt gaagaggtcc    29400
aaatcaaaac aggagaaaat cgaacccttg ttggtccacc tggaaaagtt gattggatta    29460
aactttccag tggaaacaat aatgttctta agttgtgtaa tggcgacaag tatattaaac    29520
acacatgtga tggtcaaaat ttaacattaa ttaatgtgac tagaatttat gacggaactt    29580
attatggttc tagcaatgat ggctcaagtc attacaaagt taccatctat gaattacaca    29640
aagttaataa aactaaatct atgcttaagc catacactac aaaaagaact acagtgaatg    29700
caacagatga cagtgctcac aaaattgctt tgcagcagga aaataatggg caaacagaaa    29760
atgatcaaga atcaaaaatt ccatctgcta ctgtggcaat cgtggtggga gtgattgcgg    29820
gcttcataac tataatcatt gtcattctgt gctacatctg ctgccgcaag cgtcccaggg    29880
catacaataa tatggtagac ccactactca gcttctctta ctgacgcdsd acyrtnbkcr    29940
grtndacyca tnatgaaggc tttcacagct tgcgttctga ttagcataat tacacttagt    30000
ttagcagcac ctaaaccaga agtatataca caagttaatg tcactagggg tgggaatgct    30060
acactagatg gaccatttaa caataacaca tggacaagat atcatgatga tgggagaaaa    30120
aacggatgga tgaatatttg taaatggtca gacccatcat acacatgtca tagtaatgga    30180
agccttagta ttttttgcttt caacattagt tcaggtaaat ataagttca aagttacact    30240
aacagttata atggattaga tggttatgaa aaacttgaag ttaaaatgtt taatctaaca    30300
gtaattgagc ctccaaccac tagagcaccc accacagtta ggacaactaa ggaaacaaca    30360
cagcctacca ctgtacccac tacacatcca accaccacag tcagtacaac tattgagacc    30420
actactcata ctacacagct agacacaaca gtgcagaata ctactttact gattgaattt    30480
ttactaagag ggaatgaaag tactactgat cagacagagg ctacctcaag tgccttcagc    30540
agtactgcaa atttaacttc gcttgcttgg actaatgaaa ccggagtatc attgatgcat    30600
ggccagcctt actcaggttt ggatattcaa attacttttc tggttgtctg tgggatcttt    30660
attcttgtgg ttcttctgta ctttgtctgc tgcaaagcca gagagaaatc tagtaggccc    30720
atctacaggc cagtaatcgg ggaacctcag cctctccaag tggaagggg tctaaggaat    30780
cttctcttct ctttttcagt atggtgacgc dsdacyrtnb krdartndac ycatnatgat    30840
tcctaggttc ttcctatta acatcctctt ctgtctcttc aacatctgcg ctgccttcgc    30900
ggccgtctcg cacgcctcgc ccgactgtct cgggccctc cccacctacc tcctctttgc    30960
cctgctcacc tgcacctgcg tctgcagcat tgtctgcctg gtcgtcacct tcctgcagct    31020
catcgactgg tgctgcgcgc gttacaatta tctccaccac agtcccgaat acagggacaa    31080
gaacgtagcc agaatcttaa ggctcatctg acgcdsdacy rtnbkrdbrt ndacycatna    31140
tgcagactct gctgatactg ctatccctcc tctcccctgc ccttgctgac tgtaaatttg    31200
cggacatatg gaatttctta gactgttatc aagagaaaat ggatatgcct tcctattact    31260
tggtgattgt gggtgtagtc atggtctgct cctgcacttt ctttgctatc atgatctacc    31320
cctgttttga tctcggctgg aactctgttg aggcattcac atacacacta gaaagcagtt    31380
cactagcctc cacgccgcca cccacaccgc ctccccgcag aaatcagttc ccctgattc    31440
agtacttaga agagcccct cccggcccc cttccactgt tagctacttt cacataaccg    31500
gcggcgatga ctgacgcdsd acyrtnbkrt ndacycatna tgactgacca ccacctggac    31560
ctcgagatgg acggccaggc ctccgagcag cgcatcctgc aactgcgcgt ccgtcagcag    31620
```

```
caggagcggg ccgccaagga gctcctcgat gccatcaaca tccaccagtg caagaagggc   31680
atcttctgcc tggtcaaaca ggcaaagatc acctacgagc tcgtgtccaa cggcaaacag   31740
catcgcctca cctatgagat gccccagcag aagcagaagt tcacctgcat ggtgggcgtc   31800
aaccccatag tcatcaccca gcagtcgggc gagaccagcg gctgcatcca ctgctcctgc   31860 gaaagcccg agtgcatcta ctccctcctc aagaccctt gcggacttcg cgacctcctc    31920
cccatgaact gacgcdsdac ygnrtnrtnr tndacycatn cmmntatgaa aattgtggac   31980
caggaatttg acatcccttt caaggtgtgg aggaagttcg ccgcccgccg gggactggag   32040
taccagagct gggaggaggg taccgaggtg ctgctgaaca actacaccag agacatactt   32100
tcagatttca agtaacgcds dacyrtnbrr tndacycatn atgtcaaaga ggctccgggt   32160
ggaagatgac ttcaacccg tctacccta tggctacgcg cggaatcaga atatcccctt    32220
cctcactccc cccttttgtct cctccgatgg attccaaaac ttccccctg gggtcctgtc    32280 actcaaactg gctgatccaa tcgccatcgc caatgggaat gtctcactca aggtgggagg   32340
gggactcact gtagaacaac agtctggaaa actgagtgtg gatactaagg caccccttgca  32400 agttgcaaat gacaacaaat tggagctatc ttatgatgat ccatttaagg tagagaataa   32460
caaacttgga attaaagctg ccatggttt agcagttgta actaaagaaa acacaagtct    32520
tcctagtcta gttggaacac ttgtagtttt aactggaaaa ggaataggta ctggatcaag   32580
tgcacatgga ggaactattg atgtaagact tggtgaagga ggtgggttat catttgatga   32640
aaaaggagac ttagtagctt gggacaaaaa aaatgataca cgcacccttt ggacaacacc   32700
tgatccttct ccaaattgca agttgaaac agcaagagac tcaaagctaa ccttagcact    32760
tacaaaatgt ggtagtcaaa tttttggccac tgtatcttta cttgttgtta cgggcaaata   32820
tgctattata agtgacacag tcaacccaaa gcagttctct attaagttac tgtttaatga   32880
caagggtgtt ttgttaagtg actcaaatct tgatgggaca tattggaact atagaagcaa   32940
caataacaac ataggcactc cttataaaga ggctgttggt tttatgccaa gcacaacagc   33000
ttatcctaag ccaaccaaca acaccagcac agatccggat aaaaaagtga gtcaaggtaa   33060
aaataaaatt gtaagcaata tttatcttgg aggagaggta tatcaaccag gatttattgt   33120
tgttaaattt aatcaggaaa ctgatgccaa ttgtgcatac tctattacat ttgattttgg   33180
atggggtaag gtgtataagg atcctatacc atatgatacc tcttcttta ctttctcata   33240 tatcgctcaa gaatgacgcd sdacyrtnrr tndacycatn cmmntnatga gcaccgagga   33300
acaatcgacc tcgctccgcc atcatccata ccgcagggcc cgtttaccac gatctgagga   33360
ggagaccagg gcctcactga ctgaacaaca ccccctgctg cccgattgtg atcatgctga   33420
atatcataat actgtgacct ggactgtga ggcccgcttg gaagactttt cagaggacgg    33480
cttcatctca atcaccgatc cccgtttggc tcgccaggaa actgtgtgga ttatagacac   33540
taaatccagt tcccgcacta atcagaacat tccctatttt aaggccaccc gtgctgagag   33600
aattgtttac actgtgaaat gggctggtgg tgggagactg actacccgtg ctggtgtaaa   33660
aatcaataaa gatacatgac gcdsdacyrt nkrtndacyc atncmmntat gagcaccgag   33720
gaacaatcga cctcgctccg ccatcatcca taccgcaggg cccgtttacc acgatctgag   33780
gaggagacca gggcctcact gactgaacaa caccccctgc tgcccgattg tgatcatgct   33840
gaatatcata atgtaagttc tgtccgtgga ttaccatgtg ctgctggctt taccctgctc   33900
caagagtttc cagtcccctg ggatatgatc ctgaccccag aggaaataaa aatttaaaa    33960
```

```
agatgtatgt cagtgtgcct gtgccccgct accctggact tggtgagagc tcagatggtg    34020
agcgggtacg agcgctggat cctgcattgc cactgttcgt ccccgggctc cctgcagtgc    34080
cgggcgggag gcaccctgct ggccgtgtgg ttcaggagag tcatttacgg gtgcatgttc    34140
aaccagcgct tcccctggta ccgccagatt gtgaacagaa acatgcccaa agagatcatg    34200
tatatgggca gtgtgttcat gaggggcagg cacctgatat actgccgcat ttggtatgat    34260
ggtcacgtgg gttccatcat ccccaacatg agctttggct ggagcaccct gaattatggg    34320
ctgctgaata acatggtgat tatgtgctgc acttactgtg agaacatgag cgagatcagg    34380
atgaggtgct gtgcccgacg caccaggaga ctgatgctga aggctgtggg gatcatagtc    34440
agagagactt gcgatcccga tcccatctgc agcagccgca ccgagccccg gcggcagaga    34500
ctgttgaggg cgctgatgga gaggcacaga cccatcctgt tttccgagta tgaatctgtg    34560
cgttcttctc attccaccag actgtgacgc dsdacyrtnk rtndacycat ncmmntatgt    34620
gctgctggct ttaccctgct ccaagagttt ccagtcccct gggatatgat cctgaccccca    34680 gaggaaataa aaattttaaa aagatgtatg tcagtgtgcc tgtgccccgc tacccctggac    34740 ttggtgagag ctcagatggt gagcgggtac gagcgctgga tcctgcattg ccactgttcg    34800
tccccgggct ccctgcagtg ccgggcggga ggcaccctgc tggccgtgtg gttcaggaga    34860
gtcatttacg ggtgcatgtt caaccagcgc ttcccctggt accgccagat tgtgaacaga    34920
aacatgccca aagagatcat gtatatgggc agtgtgttca tgaggggcag gcacctgata    34980
tactgccgca tttggtatga cgcdsdacyr tnrrtndacy catncmmnta tggttcttcc    35040
aatcctgcca ccgcccccctc tgaatgatag acaaggcagc attaactgga tggggatggc    35100
ctacagagtc ctggctgatg tgatgagggg aattcgcatg gacgggcttt tgtttcatc    35160 agatgcagag gaacttctcc agaaccttcg ggaatggatg tacttcagtt ggatgactga    35220
gcggcagcag cgaaaggacg gacggaggag gggtatctgc tgttcccggg ccactttctg    35280
ctggcagaag tacgacaagg tacgcaagag ggtgcactac aatgagcacc gaggaacaat    35340
cgacctcgct ccgccatcat ccataccgca gggcccgttt accacgatct gacgcdsdac    35400
yrtnrrtnda cycatncmmn tatgaaggtc tgcctgctta tgaaggtgga gggggcgctg    35460
tgggagcttt tcaacatgtg tggagtggac ttacaccaac agtttgtagc gataattcaa    35520
ggctggaaaa acgaaaatta cctggggatg gttcaggact gtaatatgat gattgaggag    35580
caggatggcg ggcccgcttt taatgtgctg ttgtttctgg atgtacgtgt ggagcctctg    35640
ctggaagcca cagtagagca ccttgagaat cgcataattt ttgatttggc tgtctgtttc    35700
caccaaaaca gtggaggaga gaggtgccac ctccgtgacc tgaattttat attgctgcgc    35760
gaccgtttgg agtaacgcds dacyrtnrrt ndacycatnc mmntatgctt gagcggcgcg    35820
gtgtcagcta ccacattgtg gtccctgggg ccctagtgac ttatttagag acttttcca    35880 ttactgctat gattaaagag cacctacctc gctttatcac tcacctcttg aaggaatca    35940 ccggtgacac aaagagagct tattccagca tgcagttttt gggggctaat tatgagctc    36000 taagatactc cctcacgctt gccagtccaa cgcttagccc tggctctgac ttggcatctg    36060
tagtggccga ggacttgagt gacttttac agctaacact gagacgcgag ctcagggcag    36120
agggcagaaa ctcattgaat cttgttgttt tgaacacgct gcaggttgtg gagcagccag    36180
atctgttgct attatgacgc dsdacyrtnr rtndacycat ncmmntatgg ctgaatctct    36240
gtatgctttc atagatagcc ctggagggat cgctcccgtc caggaagggg ctagcaatag    36300
atatatcttc ttttgccccg aatctttcca cattcctccg catgggtga tattgcttca    36360
```

```
cctcagagtg agcgtgctgg ttcctactgg atatcagggc agatttatgg ccttgaatga    36420
ctaccatgcc aggggcatac taacccagtc cgatgtgata tttgccggga gaagacatga    36480
tctctctgtg ctgctcttta accacacgga ccgatttttg tatgtccgcg agggccaccc    36540
agtgggaacc ctgctgctgg agagagtgat ttttccttca gtgagaatag ccaccctggt    36600
ttag                                                                  36604
```

<210> SEQ ID NO 2
<211> LENGTH: 253
<212> TYPE: PRT
<213> ORGANISM: Adenovirus type 36

<400> SEQUENCE: 2

```
Met Arg His Leu Arg Leu Leu Pro Ser Thr Val Pro Gly Asp Leu Ala
1               5                   10                  15

Val Ile Met Leu Glu Asp Phe Val Asn Thr Val Leu Glu Asp Glu Leu
            20                  25                  30

His Pro Glu Pro Phe Glu Leu Gly Pro Thr Leu Gln Asp Leu Tyr Asp
        35                  40                  45

Leu Glu Val Asp Ala His Asp Asp Pro Asn Glu Glu Ala Val Asn
    50                  55                  60

Leu Ile Phe Pro Glu Ser Met Ile Leu Gln Ala Asp Ile Ala Ser Glu
65                  70                  75                  80

Ala Ile Val Thr Pro Leu His Thr Pro Thr Leu Pro Pro Ile Pro Glu
                85                  90                  95

Leu Glu Glu Asp Glu Glu Ile Asp Leu Arg Cys Tyr Glu Glu Gly Phe
            100                 105                 110

Pro Pro Ser Asp Ser Glu Asp Glu Gln Gly Glu Gln Gln Met Ala Leu
        115                 120                 125

Ile Ser Asp Leu Ala Cys Val Ile Val Glu Glu Gln Val Val Ile Glu
    130                 135                 140

Lys Ser Thr Glu Pro Val Gln Gly Cys Arg Asn Cys Gln Tyr His Arg
145                 150                 155                 160

Asp Lys Ser Gly Asp Pro Asn Ala Ser Cys Ala Leu Cys Tyr Met Lys
                165                 170                 175

Ser Thr Phe Ser Phe Ile Tyr Ser Pro Val Ser Glu Asp Glu Ser Ser
            180                 185                 190

Pro Ser Glu Glu Asp His Pro Ser Pro Glu Leu Ser Gly Glu Thr
        195                 200                 205

Pro Leu Gln Val His Arg Pro Thr Pro Val Arg Ala Ser Gly Glu Arg
    210                 215                 220

Arg Ala Ala Val Glu Lys Ile Glu Asp Leu Leu His Asp Met Gly Gly
225                 230                 235                 240

Asp Glu Pro Leu Asp Leu Ser Leu Lys Arg Pro Arg Asn
                245                 250
```

<210> SEQ ID NO 3
<211> LENGTH: 191
<212> TYPE: PRT
<213> ORGANISM: Adenovirus type 36

<400> SEQUENCE: 3

```
Met Arg His Leu Arg Leu Leu Pro Ser Thr Val Pro Gly Asp Leu Ala
1               5                   10                  15

Val Ile Met Leu Glu Asp Phe Val Asn Thr Val Leu Glu Asp Glu Leu
```

```
                    20                  25                  30

His Pro Glu Pro Phe Glu Leu Gly Pro Thr Leu Gln Asp Leu Tyr Asp
                35                  40                  45

Leu Glu Val Asp Ala His Asp Asp Pro Asn Glu Glu Ala Val Asn
 50                  55                  60

Leu Ile Phe Pro Glu Ser Met Ile Leu Gln Ala Asp Ile Ala Ser Glu
 65                  70                  75                  80

Ala Ile Val Thr Pro Leu His Thr Pro Thr Leu Pro Pro Ile Pro Glu
                85                  90                  95

Leu Glu Glu Asp Glu Glu Ile Asp Leu Arg Cys Tyr Glu Glu Gly Phe
               100                 105                 110

Pro Pro Ser Asp Ser Glu Asp Glu Gln Gly Pro Val Ser Glu Asp Glu
               115                 120                 125

Ser Ser Pro Ser Glu Glu Asp His Pro Ser Pro Glu Leu Ser Gly
               130                 135                 140

Glu Thr Pro Leu Gln Val His Arg Pro Thr Pro Val Arg Ala Ser Gly
145                 150                 155                 160

Glu Arg Arg Ala Ala Val Glu Lys Ile Glu Asp Leu Leu His Asp Met
                165                 170                 175

Gly Gly Asp Glu Pro Leu Asp Leu Ser Leu Lys Arg Pro Arg Asn
                180                 185                 190

<210> SEQ ID NO 4
<211> LENGTH: 182
<212> TYPE: PRT
<213> ORGANISM: Adenovirus type 36

<400> SEQUENCE: 4

Met Asp Val Trp Thr Ile Leu Ala Asp Phe Ser Lys Thr Arg Arg Leu
  1               5                  10                  15

Val Glu Asp Ser Ser Asp Gly Cys Ser Gly Phe Trp Arg His Trp Phe
                 20                  25                  30

Gly Thr Pro Leu Ser Arg Leu Val Tyr Thr Val Lys Lys Asp Tyr Lys
                 35                  40                  45

Glu Glu Phe Glu Asn Leu Phe Ala Asp Cys Ser Gly Leu Leu Asp Ser
             50                  55                  60

Leu Asn Leu Gly His Gln Ser Leu Phe Gln Glu Arg Val Leu His Ser
 65                  70                  75                  80

Leu Asp Phe Ser Ser Pro Gly Arg Thr Thr Ala Gly Val Ala Phe Val
                 85                  90                  95

Val Phe Leu Val Asp Lys Trp Ser Gln Asp Thr Gln Leu Ser Arg Gly
                100                 105                 110

Tyr Ile Leu Asp Phe Ala Ala Met His Leu Trp Arg Ala Trp Ile Arg
                115                 120                 125

Gln Arg Gly Gln Arg Ile Leu Asn Tyr Trp Leu Leu Gln Pro Ala Ala
            130                 135                 140

Pro Gly Leu Leu Arg Leu His Arg Gln Thr Ser Met Leu Glu Glu
145                 150                 155                 160

Met Arg Gln Ala Met Asp Glu Asn Pro Arg Ser Gly Leu Asp Pro Pro
                165                 170                 175

Ser Glu Glu Glu Leu Asp
            180

<210> SEQ ID NO 5
<211> LENGTH: 495
```

```
<212> TYPE: PRT
<213> ORGANISM: Adenovirus type 36

<400> SEQUENCE: 5

Met Glu Pro Gly His Pro Thr Glu Gln Gly Leu His Pro Gly Leu Arg
1               5                   10                  15

Ser His Ala Pro Val Glu Gly Leu Asp Gln Ala Ala Gly Thr Glu Asn
            20                  25                  30

Leu Glu Leu Leu Ala Ser Thr Ala Ser Ser Gly Ser Ser Ser Ser
        35                  40                  45

Thr Gln Thr Asn Ile His Val Gly Gly Arg Asn Glu Ala Gly His Gly
    50                  55                  60

Arg Glu Pro Glu Glu Arg Pro Gly Pro Ser Val Gly Arg Gly Ala Gly
65                  70                  75                  80

Leu Asn Gln Val Ser Ser Leu Tyr Pro Glu Leu Ser Lys Val Leu Thr
                85                  90                  95

Ser Met Ala Arg Gly Val Lys Arg Glu Arg Ser Asp Gly Gly Asn Thr
            100                 105                 110

Gly Met Met Thr Glu Leu Thr Ala Ser Leu Met Asn Arg Lys Arg Pro
        115                 120                 125

Glu Arg Leu Thr Trp Tyr Glu Leu Gln Gln Glu Cys Arg Asp Glu Ile
130                 135                 140

Gly Leu Met Gln Asp Lys Tyr Gly Leu Glu Gln Ile Lys Thr His Trp
145                 150                 155                 160

Leu Asn Pro Asp Glu Asp Trp Glu Glu Ala Ile Lys Lys Tyr Ala Lys
                165                 170                 175

Ile Ala Leu Arg Pro Asp Cys Lys Tyr Ile Val Thr Lys Thr Val Asn
            180                 185                 190

Ile Arg His Ala Cys Tyr Ile Ser Gly Asn Gly Ala Glu Val Val Ile
        195                 200                 205

Asp Thr Leu Asp Lys Ala Ala Phe Arg Cys Cys Met Met Gly Met Arg
210                 215                 220

Ala Gly Val Met Asn Met Asn Ser Met Ile Phe Met Asn Ile Lys Phe
225                 230                 235                 240

Asn Gly Glu Lys Phe Asn Gly Val Leu Phe Met Ala Asn Ser His Met
                245                 250                 255

Thr Leu His Gly Cys Ser Phe Phe Gly Phe Asn Asn Met Cys Ala Glu
            260                 265                 270

Val Trp Gly Ala Ala Lys Ile Arg Gly Cys Lys Phe Tyr Gly Cys Trp
        275                 280                 285

Met Gly Val Val Gly Arg Pro Lys Ser Glu Met Ser Val Lys Gln Cys
290                 295                 300

Val Phe Glu Lys Cys Tyr Leu Gly Val Ser Thr Glu Gly Asn Ala Arg
305                 310                 315                 320

Val Arg His Cys Ser Ser Met Glu Thr Gly Cys Phe Cys Leu Val Lys
                325                 330                 335

Gly Thr Ala Ser Leu Lys His Asn Met Val Lys Gly Cys Thr Asp Glu
            340                 345                 350

Arg Met Tyr Asn Met Leu Thr Cys Asp Ser Gly Val Cys His Ile Leu
        355                 360                 365

Lys Asn Ile His Val Thr Ser His Pro Arg Lys Lys Trp Pro Val Phe
370                 375                 380

Glu Asn Asn Leu Leu Ile Lys Cys His Met His Leu Gly Ala Arg Arg
385                 390                 395                 400
```

```
Gly Thr Phe Gln Pro Tyr Gln Cys Asn Phe Ser Gln Thr Lys Leu Leu
                405                 410                 415

Leu Glu Asn Asp Ala Phe Ser Arg Val Asn Leu Asn Gly Ile Phe Asp
            420                 425                 430

Met Asp Val Ser Val Tyr Lys Ile Leu Arg Tyr Asp Glu Thr Lys Ser
        435                 440                 445

Arg Val Arg Ala Cys Glu Cys Gly Gly Arg His Thr Arg Met Gln Pro
    450                 455                 460

Val Ala Leu Asp Val Thr Glu Glu Leu Arg Pro Asp His Leu Val Met
465                 470                 475                 480

Ala Cys Thr Gly Thr Glu Phe Ser Ser Ser Gly Glu Asp Thr Asp
                485                 490                 495

<210> SEQ ID NO 6
<211> LENGTH: 134
<212> TYPE: PRT
<213> ORGANISM: Adenovirus type 36

<400> SEQUENCE: 6

Met Asn Gly Thr Gly Gly Ala Phe Glu Gly Gly Leu Phe Ser Pro Tyr
1               5                   10                  15

Leu Thr Thr Arg Leu Pro Gly Trp Ala Gly Val Arg Gln Asn Val Met
            20                  25                  30

Gly Ser Thr Val Asp Gly Arg Pro Val Leu Pro Ala Asn Ser Ser Thr
        35                  40                  45

Met Thr Tyr Ala Thr Val Gly Ser Ser Ser Leu Asp Ser Thr Ala Ala
    50                  55                  60

Ala Ala Ala Ala Ala Ala Met Thr Ala Thr Arg Leu Ala Ser Ser
65                  70                  75                  80

Tyr Met Pro Ser Ser Ser Ser Pro Ser Val Pro Ser Ser Ile Ile
                85                  90                  95

Ala Glu Glu Lys Leu Leu Ala Leu Leu Ala Glu Leu Glu Ala Leu Ser
            100                 105                 110

Arg Gln Leu Ala Ala Leu Thr Gln Gln Val Ser Glu Leu Arg Glu Gln
        115                 120                 125

Gln Gln Gln Gln Asn Lys
    130

<210> SEQ ID NO 7
<211> LENGTH: 448
<212> TYPE: PRT
<213> ORGANISM: Adenovirus type 36

<400> SEQUENCE: 7

Met Glu Thr Arg Gly Arg Arg Pro Cys Pro Phe Gln His Gln Gln Asp
1               5                   10                  15

Glu Ser Gln Ala His Pro Cys Lys Arg Pro Ala Arg Gly Pro Pro Leu
            20                  25                  30

His Arg Asp Gly Asp His Thr His Ala Asp Pro Glu Thr Leu Glu Gly
        35                  40                  45

His Asp Ala Gly Arg Ala Gly Arg Pro Ser Ser Arg Ala Leu Gln Ser
    50                  55                  60

Gln Ser Ser Gln Pro Pro Lys Arg Gly Ser Leu Leu Asp Arg Asp Ala
65                  70                  75                  80

Val Glu His Val Thr Glu Leu Trp Asp Arg Leu Glu Leu Leu Ser Gln
                85                  90                  95
```

-continued

```
Thr Leu Ala Lys Met Pro Met Ala Asp Gly Leu Lys Pro Leu Lys Asn
            100                 105                 110

Phe Ala Ser Leu Gln Glu Leu Leu Ser Leu Gly Gly Asp Arg Leu Leu
            115                 120                 125

Gly Glu Leu Val Arg Glu Asn Leu Gln Val Arg Asp Met Leu Asn Glu
130                 135                 140

Val Ala Pro Leu Leu Arg Asp Asp Gly Ser Cys Met Ser Leu Asn Tyr
145                 150                 155                 160

His Leu Gln Pro Val Ile Gly Val Ile Tyr Gly Pro Thr Gly Cys Gly
                165                 170                 175

Lys Ser Gln Leu Leu Arg Asn Leu Leu Ser Ser Gln Leu Ile Thr Pro
            180                 185                 190

Ala Pro Glu Thr Val Phe Phe Ile Ala Pro Gln Val Asp Met Ile Pro
            195                 200                 205

Pro Ser Glu Met Lys Ala Trp Glu Met Gln Ile Cys Glu Gly Asn Phe
            210                 215                 220

Ala Pro Gly Pro Glu Gly Thr Ile Val Pro Gln Ser Gly Thr Leu Arg
225                 230                 235                 240

Pro Lys Phe Ile Lys Met Ser Tyr Asp Asp Leu Thr Gln Glu His Asn
                245                 250                 255

Tyr Asp Val Ser Asp Pro Arg Asn Val Phe Ala Lys Ala Ala His
            260                 265                 270

Gly Pro Ile Ala Ile Ile Met Asp Glu Cys Met Glu Asn Leu Gly Gly
            275                 280                 285

His Lys Gly Val Ser Lys Phe His Ala Phe Pro Ser Lys Leu His
            290                 295                 300

Asp Lys Phe Pro Lys Cys Thr Gly Tyr Thr Val Leu Val Leu His
305                 310                 315                 320

Asn Met Asn Pro Arg Arg Asp Leu Gly Gly Asn Ile Ala Asn Leu Lys
                325                 330                 335

Ile Gln Ala Lys Leu His Ile Ile Ser Pro Arg Met His Pro Ser Gln
            340                 345                 350

Leu Asn Arg Phe Ala Asn Thr Tyr Thr Lys Gly Leu Pro Val Ala Ile
            355                 360                 365

Ser Leu Leu Leu Lys Asp Ile Ile Gln His Ala Gln Arg Pro Cys
370                 375                 380

Tyr Asp Trp Ile Ile Tyr Asn Thr Thr Pro Glu His Glu Ala Met Gln
385                 390                 395                 400

Trp Cys Tyr Leu His Pro Arg Asp Gly Leu Met Pro Met Tyr Leu Asn
                405                 410                 415

Ile Gln Ser His Leu Tyr Arg Val Leu Glu Lys Ile His Arg Thr Leu
            420                 425                 430

Asn Asp Arg Glu Arg Trp Thr Arg Ala Tyr Arg Ala Arg Lys Asn Lys
            435                 440                 445

<210> SEQ ID NO 8
<211> LENGTH: 1176
<212> TYPE: PRT
<213> ORGANISM: Adenovirus type 36

<400> SEQUENCE: 8

Met Ala Leu Val Gln Ser His Gly Ala Arg Gly Leu His Ala Glu Ala
1               5                   10                  15

Ala Asp Pro Gly Cys Gln Pro Pro Arg Arg Arg Ala Arg Gln Arg Ser
```

```
                    20                  25                  30
Gln Gly Ala Ala Pro Gly Pro Ala Arg Ala Pro Arg Arg Ala Ser
                35                  40                  45

Ala Ala Pro Ala Arg Gly Ala Gly Thr Ala Ala Ala Gly Ser Ala
 50                  55                  60

Ser Ala Thr Pro Leu Leu Lys Ala His Arg Gly Thr Val Val Ala Pro
 65                  70                  75                  80

Arg Ser Tyr Gly Leu Met Gln Cys Val Asp Thr Ala Thr Asn Ser Pro
                 85                  90                  95

Val Glu Ile Lys Tyr His Leu His Leu Lys His Ala Leu Thr Arg Phe
                100                 105                 110

Tyr Glu Val Asn Leu Arg Thr Leu Pro Pro Asp Leu Asp Leu Arg Asp
                115                 120                 125

Thr Met Asp Ser Ser Gln Leu Arg Ala Leu Val Phe Ala Leu Arg Pro
                130                 135                 140

Arg Arg Ala Glu Ile Trp Thr Trp Leu Pro Arg Gly Leu Val Ser Leu
145                 150                 155                 160

Ser Val Leu Glu Glu Pro Gln Gly Glu Ser His Ala Gly Glu His Glu
                165                 170                 175

Asn His Gln Pro Gly Pro Pro Leu Leu Lys Phe Leu Leu Lys Gly Arg
                180                 185                 190

Ala Val Tyr Leu Val Asp Glu Val Gln Pro Val Gln Arg Cys Glu Tyr
                195                 200                 205

Cys Gly Arg Phe Tyr Lys His Gln His Glu Cys Ser Val Arg Arg Arg
                210                 215                 220

Asp Phe Tyr Phe His His Ile Asn Ser His Ser Ser Asn Trp Trp Gln
225                 230                 235                 240

Glu Ile Gln Phe Phe Pro Ile Gly Ser His Pro Arg Thr Glu Arg Leu
                245                 250                 255

Phe Val Thr Tyr Asp Val Glu Thr Tyr Thr Trp Met Gly Ser Phe Gly
                260                 265                 270

Lys Gln Leu Val Pro Phe Met Leu Val Met Lys Phe Ser Gly Asp Pro
                275                 280                 285

Glu Leu Val Ala Leu Ala Arg Asp Leu Ala Val Arg Leu Arg Trp Asp
                290                 295                 300

Arg Trp Glu Arg Asp Pro Leu Thr Phe Tyr Cys Val Thr Pro Glu Lys
305                 310                 315                 320

Met Ala Val Gly Gln Gln Phe Arg Leu Phe Arg Asp Glu Leu Gln Thr
                325                 330                 335

Leu Met Ala Arg Glu Leu Trp Ala Ser Phe Met Gln Ala Asn Pro His
                340                 345                 350

Leu Gln Glu Trp Ala Leu Glu Gln His Gly Leu Gln Cys Pro Glu Asp
                355                 360                 365

Leu Thr Tyr Glu Glu Leu Lys Lys Leu Pro His Ile Lys Gly Arg Pro
                370                 375                 380

Arg Phe Met Glu Leu Tyr Ile Val Gly His Asn Ile Asn Gly Phe Asp
385                 390                 395                 400

Glu Ile Val Leu Ala Ala Gln Val Ile Asn Asn Arg Ala Ser Val Pro
                405                 410                 415

Gly Pro Phe Arg Ile Thr Arg Asn Phe Met Pro Arg Ala Gly Lys Ile
                420                 425                 430

Leu Phe Asn Asp Val Thr Phe Ala Leu Pro Asn Pro Leu Ser Lys Lys
                435                 440                 445
```

```
Arg Thr Asp Phe Glu Leu Trp Glu His Gly Gly Cys Asp Asp Ser Asp
    450                 455                 460

Phe Lys Tyr Gln Phe Leu Lys Val Met Val Arg Asp Thr Phe Ala Leu
465                 470                 475                 480

Thr His Thr Ser Leu Arg Lys Ala Ala Gln Ala Tyr Ala Leu Pro Val
                485                 490                 495

Glu Lys Gly Cys Cys Pro Tyr Lys Ala Val Asn His Phe Tyr Met Leu
            500                 505                 510

Gly Ser Tyr Arg Ala Asp Asp Arg Gly Phe Pro Leu Arg Glu Tyr Trp
        515                 520                 525

Lys Asp Asp Glu Glu Tyr Ala Leu Asn Arg Glu Leu Trp Glu Lys Lys
530                 535                 540

Gly Glu Ala Gly Tyr Asp Ile Ile Arg Glu Thr Leu Asp Tyr Cys Ala
545                 550                 555                 560

Met Asp Val Leu Val Thr Ala Glu Leu Val Ala Lys Leu Gln Asp Ser
                565                 570                 575

Tyr Ala His Phe Ile Arg Asp Ser Val Arg Leu Pro His Ala His Phe
                580                 585                 590

Asn Ile Phe Gln Arg Pro Thr Ile Ser Ser Asn Ser His Ala Ile Phe
            595                 600                 605

Arg Gln Ile Val Phe Arg Ala Glu Gln Pro Gln Arg Thr Asn Leu Gly
        610                 615                 620

Pro Ala Phe Leu Ala Pro Ser His Glu Leu Tyr Asp Tyr Val Arg Ala
625                 630                 635                 640

Ser Ile Arg Gly Gly Arg Cys Tyr Pro Thr Tyr Ile Gly Ile Leu Ser
                645                 650                 655

Glu Pro Ile Tyr Val Tyr Asp Ile Cys Gly Met Tyr Ala Ser Ala Leu
                660                 665                 670

Thr His Pro Met Pro Trp Gly Pro Pro Leu Asn Pro Tyr Glu Arg Ala
            675                 680                 685

Leu Ala Ala Arg Glu Trp Gln Met Ala Leu Asp Asp Ala Ser Ser Lys
        690                 695                 700

Ile Asp Tyr Phe Asp Lys Glu Leu Cys Pro Gly Ile Phe Thr Ile Asp
705                 710                 715                 720

Ala Asp Pro Pro Asp Glu His Leu Leu Asp Val Leu Pro Pro Phe Cys
                725                 730                 735

Ser Arg Lys Gly Gly Arg Leu Cys Trp Thr Asn Glu Pro Leu Arg Gly
            740                 745                 750

Glu Val Ala Thr Ser Val Asp Leu Val Thr Leu His Asn Arg Gly Trp
        755                 760                 765

Arg Val Arg Ile Val Pro Asp Glu Arg Thr Thr Val Phe Pro Glu Trp
770                 775                 780

Lys Cys Val Ala Arg Glu Tyr Val Gln Leu Asn Ile Ala Ala Lys Glu
785                 790                 795                 800

Arg Ala Asp Arg Asp Lys Asn Gln Thr Met Arg Ser Ile Ala Lys Leu
                805                 810                 815

Leu Ser Asn Ala Leu Tyr Gly Ser Phe Ala Thr Lys Leu Asp Asn Lys
            820                 825                 830

Lys Ile Val Phe Ser Asp Gln Met Asp Glu Ser Leu Leu Lys Ser Ile
        835                 840                 845

Ala Ala Gly Gln Ala Asn Ile Lys Ser Ser Phe Leu Glu Thr Asp
850                 855                 860
```

```
Asn Leu Ser Ala Glu Val Met Pro Ala Leu Glu Arg Glu Tyr Leu Pro
865                 870                 875                 880

Gln Gln Leu Ala Leu Val Asp Ser Asp Ala Glu Glu Ser Glu Asp Glu
                885                 890                 895

His Arg Pro Ala Pro Phe Tyr Thr Pro Pro Ser Gly Thr Pro Gly His
            900                 905                 910

Val Ala Tyr Thr Tyr Lys Pro Ile Thr Phe Leu Asp Ala Glu Glu Gly
        915                 920                 925

Asp Met Cys Leu His Thr Val Glu Lys Val Asp Pro Leu Val Asp Asn
    930                 935                 940

Asp Arg Tyr Pro Ser His Val Ala Ser Phe Val Leu Ala Trp Thr Arg
945                 950                 955                 960

Ala Phe Val Ser Glu Trp Ser Glu Phe Leu Tyr Glu Glu Asp Arg Gly
                965                 970                 975

Thr Ser Leu Gln Asp Arg Pro Ile Lys Ser Val Tyr Gly Asp Thr Asp
            980                 985                 990

Ser Leu Phe Val Thr Glu Arg Gly His Arg Leu Met Glu Thr Arg Gly
        995                 1000                1005

Lys Lys Arg Ile Lys Lys Asn Gly Gly Lys Leu Val Phe Asp Pro
    1010                1015                1020

Glu Gln Pro Glu Leu Thr Trp Leu Val Glu Cys Glu Thr Val Cys
    1025                1030                1035

Ala His Cys Gly Ala Asp Ala Phe Ala Pro Glu Ser Val Phe Leu
    1040                1045                1050

Ala Pro Lys Leu Tyr Ala Leu Gln Ser Leu Leu Cys Pro Ala Cys
    1055                1060                1065

Gly Arg Ser Ser Lys Gly Lys Leu Arg Ala Lys Gly His Ala Ala
    1070                1075                1080

Glu Ala Leu Asn Tyr Glu Leu Met Val Asn Cys Tyr Leu Ala Asp
    1085                1090                1095

Ala Gln Gly Glu Asp Arg Ala Arg Phe Ser Thr Ser Arg Met Ser
    1100                1105                1110

Leu Lys Arg Thr Leu Ala Ser Ala Gln Pro Gly Ala His Pro Phe
    1115                1120                1125

Thr Val Thr Glu Thr Thr Leu Thr Arg Thr Leu Arg Pro Trp Lys
    1130                1135                1140

Asp Met Thr Leu Ala Ala Leu Asp Ala His Arg Leu Val Pro Tyr
    1145                1150                1155

Ser Arg Ser Arg Pro Asn Pro Arg Asn Glu Glu Val Cys Trp Ile
    1160                1165                1170

Glu Met Pro
    1175

<210> SEQ ID NO 9
<211> LENGTH: 129
<212> TYPE: PRT
<213> ORGANISM: Adenovirus type 36

<400> SEQUENCE: 9

Met Arg Ala Asp Trp Glu Glu Leu Asp Phe Leu Pro Pro Val Gly Arg
1               5                   10                  15

Val Ala Val Asp Val Met Lys Val Glu Ile Pro Pro Ala Asn Arg Ala
            20                  25                  30

Leu Val Leu Met Leu Val Lys Ala Ser Ala Val Leu Ala Ala Leu His
        35                  40                  45
```

```
Gly Leu Tyr Leu Ile His Glu Ile His Ser Ala Ser Leu Glu Glu Glu
         50                  55                  60

Leu Gln Glu Trp Arg Pro Trp Leu Val Val Phe Met Phe Ala Cys Val
 65                  70                  75                  80

Gly Leu Thr Leu Gly Leu Leu Glu Asp Gly Glu Ala Asp Glu Pro Ala
                 85                  90                  95

Arg Glu Pro Gly Pro Asp Leu Gly Ala Ala Gly Ala Glu Ser Glu Asp
                100                 105                 110

Glu Gly Ala Gln Leu Gly Ala Val His Gly Val Ala Glu Ile Gln Gly
                115                 120                 125

Thr

<210> SEQ ID NO 10
<211> LENGTH: 635
<212> TYPE: PRT
<213> ORGANISM: Adenovirus type 36

<400> SEQUENCE: 10

Met Ala Leu Ser Val Asn Asp Cys Ala Arg Leu Thr Gly Gln Thr Val
 1               5                  10                  15

Pro Thr Met Asp Tyr Phe Leu Pro Leu Arg Asn Ile Trp Asn Arg Val
                20                  25                  30

Arg Glu Phe Pro Arg Ala Ser Thr Thr Ala Ala Gly Ile Thr Trp Met
             35                  40                  45

Ser Arg Tyr Leu Tyr Gly Tyr His Arg Leu Met Leu Glu Asp Leu Ala
         50                  55                  60

Pro Gly Ala Pro Ala Thr Gln Arg Trp Pro Leu Tyr Arg Gln Pro Pro
 65                  70                  75                  80

Pro His Phe Leu Val Gly Tyr Gln Tyr Leu Val Arg Thr Cys Asn Asp
                 85                  90                  95

Tyr Val Phe Asp Ser Arg Ala Phe Ser Arg Leu Arg Tyr Ser Glu Val
                100                 105                 110

Val Gln Pro Gly Leu Gln Thr Val Asn Trp Ser Leu Met Ala Asn Cys
            115                 120                 125

Thr Tyr Thr Ile Asn Thr Gly Ala Tyr His Arg Phe Val Asp Met Asp
        130                 135                 140

Asp Phe Gln Asp Thr Leu Thr Arg Val Gln Gln Ala Ile Leu Ala Glu
145                 150                 155                 160

Arg Val Val Ala Asp Leu Ala Leu Val Gln Pro Leu Arg Gly Val Gly
                165                 170                 175

Val Thr Arg Met Glu Asp Ser Ala Ser Ala Ser Asp Ile Glu Arg
                180                 185                 190

Leu Met His Asp Tyr Tyr Lys Asn Leu Ser Arg Cys Gln Gly Gln Ala
            195                 200                 205

Trp Gly Met Ala Glu Arg Leu Arg Ile Gln Gln Ala Gly Pro Lys Asp
        210                 215                 220

Leu Val Leu Leu Ala Thr Ile Arg Arg Leu Lys Asn Ala Tyr Phe Asn
225                 230                 235                 240

Tyr Ile Ile Ser Asn Arg Asn Ser Asn Ser Val His Arg Ala Ala Thr
                245                 250                 255

Cys Leu Ser Leu Pro Cys Asp Cys Asp Trp Leu Asp Ala Phe Leu Glu
                260                 265                 270

Arg Phe Ser Asp Pro Val Asp Leu Asp Ala Leu Thr Ser Pro Thr Pro
            275                 280                 285
```

Gln Leu Ile Arg Cys Ile Val Ser Ala Leu Ser Leu Pro Asn Gly Asp
            290                 295                 300

Pro Pro His Tyr Arg Glu Met Thr Gly Gly Val Phe Thr Leu Arg Pro
305                 310                 315                 320

Arg Glu Arg Gly Arg Ala Val Thr Glu Thr Met Arg Arg Arg Arg Gly
                325                 330                 335

Glu Met Ile Glu Arg Phe Val Asp Arg Leu Pro Val Arg Arg Arg Arg
            340                 345                 350

Arg Arg Ala Pro Pro Pro Pro Pro Glu Glu Ile Glu Glu
                355                 360                 365

Glu Val Val Met Glu Glu Glu Glu Glu Val Pro Gly Asp Phe
370                 375                 380

Glu Arg Glu Val Arg Ala Thr Ile Ala Glu Leu Ile Arg Leu Glu
385                 390                 395                 400

Asp Glu Leu Thr Val Ser Ala Arg Asn Ala Gln Phe Phe Asn Phe Ala
                405                 410                 415

Val Asp Phe Tyr Glu Ala Met Glu Arg Leu Glu Ala Ile Gly Asp Ile
            420                 425                 430

Ser Glu Met Pro Leu Arg Arg Trp Ile Met Tyr Phe Phe Val Thr Glu
            435                 440                 445

His Ile Ala Thr Thr Leu Asn Tyr Leu Phe Gln Arg Leu Arg Asn Tyr
450                 455                 460

Ala Val Phe Thr Arg His Val Glu Leu Asn Leu Ala Gln Val Val Met
465                 470                 475                 480

Arg Ala Arg Asp Ala Asp Gly Asp Val Val Tyr Ser Arg Val Trp Asn
                485                 490                 495

Glu Ser Gly Leu Gly Ala Phe Ser Gln Leu Met Gly Arg Ile Ser Asn
            500                 505                 510

Asp Leu Ala Ala Thr Val Glu Arg Ala Gly Arg Gly Asp Leu Gln Glu
            515                 520                 525

Glu Glu Ile Glu Gln Phe Met Ser Glu Ile Ala Tyr Gln Asp Asn Ser
530                 535                 540

Gly Asp Val Gln Glu Ile Leu Arg Gln Ala Ala Val Asn Asp Ala Glu
545                 550                 555                 560

Ile Asp Ser Val Glu Leu Ser Phe Arg Phe Lys Val Thr Gly Pro Val
                565                 570                 575

Val Phe Thr Gln Arg Arg Gln Ile Gln Asp Val Asn Arg Arg Val Val
            580                 585                 590

Ala His Ala Ser Ala Leu Arg Ala Gln His Arg Asp Leu Pro Glu Arg
                595                 600                 605

His Ala Asp Val Pro Leu Pro Pro Leu Pro Ala Gly Pro Glu Pro Pro
610                 615                 620

Leu Pro Pro Gly Ala Arg Pro Arg His Arg Phe
625                 630                 635

<210> SEQ ID NO 11
<211> LENGTH: 372
<212> TYPE: PRT
<213> ORGANISM: Adenovirus type 36

<400> SEQUENCE: 11

Met His Pro Val Leu Arg Gln Met Arg Pro Thr Pro Pro Ala Thr Thr
1               5                   10                  15

Ala Thr Ala Ala Val Thr Gly Ala Gly Ala Ser Gln Pro Gln Thr Glu

```
                    20                  25                  30
Met Asp Leu Glu Glu Gly Glu Gly Leu Ala Arg Leu Gly Ala Pro Ser
            35                  40                  45

Pro Glu Arg His Pro Arg Val Gln Leu Gln Lys Asp Val Arg Pro Ala
        50                  55                  60

Tyr Val Pro Ala Gln Asn Leu Phe Arg Asp Arg Ser Gly Glu Glu Pro
 65                  70                  75                  80

Glu Glu Met Arg Asp Cys Arg Phe Arg Ala Gly Arg Glu Leu Arg Glu
                85                  90                  95

Gly Leu Asp Arg Gln Arg Val Leu Arg Asp Glu Asp Phe Glu Pro Asn
            100                 105                 110

Glu Gln Thr Gly Ile Ser Pro Ala Arg Ala His Val Ala Ala Ala Asn
        115                 120                 125

Leu Val Thr Ala Tyr Glu Gln Thr Val Lys Gln Glu Arg Asn Phe Gln
130                 135                 140

Lys Ser Phe Asn Asn His Val Arg Thr Leu Ile Ala Arg Glu Glu Val
145                 150                 155                 160

Ala Leu Gly Leu Met His Leu Trp Asp Leu Ala Glu Ala Ile Val Gln
                165                 170                 175

Asn Pro Asp Ser Lys Pro Leu Thr Ala Gln Leu Phe Leu Val Val Gln
            180                 185                 190

His Ser Arg Asp Asn Glu Ala Phe Arg Glu Ala Leu Leu Asn Ile Ala
        195                 200                 205

Glu Pro Glu Gly Arg Trp Leu Leu Glu Leu Ile Asn Ile Leu Gln Ser
    210                 215                 220

Ile Val Val Gln Glu Arg Ser Leu Ser Leu Ala Glu Lys Val Ala Ala
225                 230                 235                 240

Ile Asn Tyr Ser Val Leu Ser Leu Gly Lys Phe Tyr Ala Arg Lys Ile
                245                 250                 255

Tyr Lys Thr Pro Tyr Val Pro Ile Asp Lys Glu Val Lys Ile Asp Ser
            260                 265                 270

Phe Tyr Met Arg Met Ala Leu Lys Val Leu Thr Leu Ser Asp Asp Leu
        275                 280                 285

Gly Val Tyr Arg Asn Asp Arg Ile His Lys Ala Val Ser Thr Ser Arg
    290                 295                 300

Arg Arg Glu Leu Ser Asp Arg Glu Leu Met Leu Ser Leu Arg Arg Ala
305                 310                 315                 320

Leu Val Gly Gly Ala Gly Gly Glu Glu Ser Tyr Phe Asp Met Gly
                325                 330                 335

Ala Asp Leu His Trp Gln Pro Ser Arg Arg Ala Leu Glu Ala Ala Tyr
            340                 345                 350

Gly Pro Glu Asp Leu Asp Glu Asp Glu Glu Glu Asp Ala Pro
        355                 360                 365

Val Ala Gly Tyr
    370

<210> SEQ ID NO 12
<211> LENGTH: 561
<212> TYPE: PRT
<213> ORGANISM: Adenovirus type 36

<400> SEQUENCE: 12

Met Ser Gln Gln Ala Pro Asp Pro Ala Ile Arg Ala Ala Leu Gln Ser
 1               5                  10                  15
```

```
Gln Pro Ser Gly Leu Ala Ser Asp Asp Trp Glu Ala Ala Met Gln Arg
            20                  25                  30

Ile Met Ala Leu Thr Thr Arg Asn Pro Glu Ser Phe Arg Gln Gln Pro
        35                  40                  45

Gln Ala Asn Arg Leu Ser Ala Ile Leu Glu Ala Val Val Pro Ser Arg
    50                  55                  60

Thr Asn Pro Thr His Glu Lys Val Leu Ala Ile Val Asn Ala Leu Ala
65                  70                  75                  80

Glu Asn Lys Ala Ile Arg Pro Asp Glu Ala Gly Leu Val Tyr Asn Ala
                85                  90                  95

Leu Leu Glu Arg Val Gly Arg Tyr Asn Ser Thr Asn Val Gln Ser Asn
            100                 105                 110

Leu Asp Arg Leu Val Thr Asp Val Arg Glu Ala Val Ala Gln Arg Glu
        115                 120                 125

Arg Phe Lys Asn Glu Gly Leu Gly Ser Leu Val Ala Leu Asn Ala Phe
    130                 135                 140

Leu Ala Thr Gln Pro Ala Asn Val Pro Arg Gly Gln Asp Asp Tyr Thr
145                 150                 155                 160

Asn Phe Ile Ser Ala Leu Arg Leu Met Val Thr Glu Val Pro Gln Ser
                165                 170                 175

Glu Val Tyr Gln Ser Gly Pro Asp Tyr Phe Phe Gln Thr Ser Arg Gln
            180                 185                 190

Gly Leu Gln Thr Val Asn Leu Ser Gln Ala Phe Lys Asn Leu Arg Gly
        195                 200                 205

Leu Trp Gly Val Gln Ala Pro Val Gly Asp Arg Ser Thr Val Ser Ser
    210                 215                 220

Leu Leu Thr Pro Asn Ser Arg Leu Leu Leu Leu Ile Ala Pro Phe
225                 230                 235                 240

Thr Asp Ser Gly Ser Val Asn Arg Asn Ser Tyr Leu Gly His Leu Leu
                245                 250                 255

Thr Leu Tyr Arg Glu Ala Ile Gly Gln Ala Gln Val Asp Glu Gln Thr
            260                 265                 270

Phe Gln Glu Ile Thr Ser Val Ser Arg Ala Leu Gly Gln Asn Asp Thr
        275                 280                 285

Asp Ser Leu Arg Ala Thr Leu Asn Phe Leu Leu Thr Asn Arg Gln Gln
    290                 295                 300

Lys Ile Pro Ala Gln Tyr Ala Leu Ser Ala Glu Glu Arg Ile Leu
305                 310                 315                 320

Arg Tyr Val Gln Gln Ser Val Gly Leu Phe Leu Met Gln Glu Gly Ala
                325                 330                 335

Thr Pro Ser Ala Ala Leu Asp Met Thr Ala Arg Asn Met Glu Pro Ser
            340                 345                 350

Met Tyr Ala Ala Asn Arg Pro Phe Ile Asn Lys Leu Met Asp Tyr Leu
        355                 360                 365

His Arg Ala Ala Ala Met Asn Thr Asp Tyr Phe Thr Asn Ala Ile Leu
    370                 375                 380

Asn Pro His Trp Leu Pro Pro Gly Phe Tyr Thr Gly Glu Tyr Asp
385                 390                 395                 400

Met Pro Asp Pro Asn Asp Gly Phe Leu Trp Asp Val Asp Ser Ala
                405                 410                 415

Val Phe Ser Pro Thr Phe Gln Lys Arg Gln Glu Ala Pro Pro Ser Glu
            420                 425                 430

Gly Ala Val Gly Arg Ser Pro Phe Pro Ser Leu Gly Ser Leu His Ser
```

```
                    435                 440                 445
Leu Pro Gly Ser Val Asn Ser Gly Arg Val Ser Arg Pro Arg Leu Leu
            450                 455                 460

Gly Glu Asp Glu Tyr Leu Asn Asp Ser Leu Leu Gln Pro Pro Arg Val
465                 470                 475                 480

Lys Asn Ala Met Ala Asn Asn Gly Ile Glu Ser Leu Val Asp Lys Leu
                485                 490                 495

Asn Arg Trp Lys Thr Tyr Ala Gln Asp His Arg Glu Pro Ala Pro Ala
            500                 505                 510

Pro Arg Arg Gln Arg His Asp Arg Gln Arg Gly Leu Val Trp Asp Asp
            515                 520                 525

Glu Asp Ser Ala Asp Ser Ser Val Leu Asp Leu Gly Gly Ser Gly
            530                 535                 540

Gly Ala Asn Pro Phe Ala His Leu Gln Pro Arg Leu Gly Arg Arg Met
545                 550                 555                 560

Phe

<210> SEQ ID NO 13
<211> LENGTH: 520
<212> TYPE: PRT
<213> ORGANISM: Adenovirus type 36

<400> SEQUENCE: 13

Met Arg Arg Ala Val Val Ser Ser Ser Pro Pro Ser Tyr Glu Ser
1               5                   10                  15

Val Met Ala Gln Ala Thr Leu Glu Val Pro Phe Val Pro Pro Arg Tyr
                20                  25                  30

Met Ala Pro Thr Glu Gly Arg Asn Ser Ile Arg Tyr Ser Glu Leu Ala
            35                  40                  45

Pro Gln Tyr Asp Thr Thr Arg Val Tyr Leu Val Asp Asn Lys Ser Ala
        50                  55                  60

Asp Ile Ala Ser Leu Asn Tyr Gln Asn Asp His Ser Asn Phe Leu Thr
65                  70                  75                  80

Thr Val Val Gln Asn Asn Asp Phe Thr Pro Ala Glu Ala Ser Thr Gln
                85                  90                  95

Thr Ile Asn Phe Asp Glu Arg Ser Arg Trp Gly Gly Asp Leu Lys Thr
            100                 105                 110

Ile Leu His Thr Asn Met Pro Asn Val Asn Glu Tyr Met Phe Thr Ser
        115                 120                 125

Lys Phe Lys Ala Arg Val Met Val Ala Arg Lys His Pro Lys Asp Val
130                 135                 140

Asp Ala Ser Asp Leu Ser Lys Asp Ile Leu Glu Tyr Lys Trp Phe Glu
145                 150                 155                 160

Phe Thr Leu Pro Glu Gly Asn Phe Ser Glu Thr Met Thr Ile Asp Leu
                165                 170                 175

Met Asn Asn Ala Ile Leu Glu Asn Tyr Leu Gln Val Gly Arg Gln Asn
            180                 185                 190

Gly Val Leu Glu Ser Asp Ile Gly Val Lys Phe Asp Ser Arg Asn Phe
        195                 200                 205

Arg Leu Gly Trp Asp Pro Val Thr Lys Leu Val Met Pro Gly Val Tyr
            210                 215                 220

Thr Tyr Glu Ala Phe His Pro Asp Val Leu Leu Pro Gly Cys Gly
225                 230                 235                 240

Val Asp Phe Thr Glu Ser Arg Leu Ser Asn Leu Leu Gly Ile Arg Lys
```

```
                        245                 250                 255
Lys Gln Pro Phe Gln Glu Gly Phe Arg Ile Met Tyr Glu Asp Leu Glu
                    260                 265                 270

Gly Gly Asn Ile Pro Ala Leu Leu Asp Thr Lys Lys Tyr Leu Asp Ser
                275                 280                 285

Lys Lys Glu Leu Glu Asp Ala Ala Lys Glu Ala Ala Lys Gln Gln Gly
            290                 295                 300

Asp Gly Ala Val Thr Arg Gly Asp Thr His Leu Thr Val Ala Gln Glu
305                 310                 315                 320

Lys Ala Ala Glu Lys Glu Leu Val Ile Val Pro Ile Glu Lys Asp Glu
                325                 330                 335

Ser Asn Arg Ser Tyr Asn Leu Ile Lys Asp Thr His Asp Thr Leu Tyr
                340                 345                 350

Arg Ser Trp Tyr Leu Ser Tyr Thr Tyr Gly Asp Pro Glu Lys Gly Val
                355                 360                 365

Gln Ser Trp Thr Leu Leu Thr Thr Pro Asp Val Thr Cys Gly Ala Glu
                370                 375                 380

Gln Val Tyr Trp Ser Leu Pro Asp Leu Met Gln Asp Pro Val Thr Phe
385                 390                 395                 400

Arg Ser Thr Gln Gln Val Ser Asn Tyr Pro Val Val Gly Ala Glu Leu
                405                 410                 415

Met Pro Phe Arg Ala Lys Ser Phe Tyr Asn Asp Leu Ala Val Tyr Ser
                420                 425                 430

Gln Leu Ile Arg Ser Tyr Thr Ser Leu Thr His Val Phe Asn Arg Phe
                435                 440                 445

Pro Asp Asn Gln Ile Leu Cys Arg Pro Pro Ala Pro Thr Ile Thr Thr
450                 455                 460

Val Ser Glu Asn Val Pro Ala Leu Thr Asp His Gly Thr Leu Pro Leu
465                 470                 475                 480

Arg Ser Ser Ile Arg Gly Val Gln Arg Val Thr Val Thr Asp Ala Arg
                485                 490                 495

Arg Arg Thr Cys Pro Tyr Val Tyr Lys Ala Leu Gly Ile Val Ala Pro
                500                 505                 510

Arg Val Leu Ser Ser Arg Thr Phe
                515                 520

<210> SEQ ID NO 14
<211> LENGTH: 195
<212> TYPE: PRT
<213> ORGANISM: Adenovirus type 36

<400> SEQUENCE: 14

Met Ser Ile Leu Ile Ser Pro Ser Asn Thr Gly Trp Gly Leu Thr
1               5                   10                  15

Arg Pro Ser Thr Met Tyr Gly Gly Ala Lys Lys Arg Ser Gln Gln His
                20                  25                  30

Pro Val Arg Val Arg Gly His Phe Arg Ala Pro Trp Gly Ala Tyr Lys
            35                  40                  45

Arg Gly Arg Thr Ala Thr Ala Ala Val Arg Thr Thr Val Asp Asp
        50                  55                  60

Val Ile Asp Ser Val Val Ala Asp Ala Arg Asn Tyr Thr Pro Ala Pro
65                  70                  75                  80

Ser Thr Val Asp Ala Val Ile Asp Ser Val Val Ala Asp Ala Arg Asp
                85                  90                  95
```

```
Tyr Ala Arg Arg Lys Ser Arg Arg Arg Ile Ala Arg His Arg
                100                 105                 110

Ser Thr Pro Ala Met Arg Ala Ala Arg Ala Leu Leu Arg Arg Ala Arg
            115                 120                 125

Arg Thr Gly Arg Arg Ala Met Met Arg Ala Ala Arg Arg Ala Ala Thr
        130                 135                 140

Ala Pro Pro Ala Gly Arg Thr Arg Arg Ala Ala Ala Ala Ala
145                 150                 155                 160

Ala Ala Ile Ser Ser Met Thr Arg Pro Arg Gly Asn Val Tyr Trp
                165                 170                 175

Val Arg Asp Ser Val Thr Gly Val Arg Val Pro Val Arg Thr Arg Pro
            180                 185                 190

Pro Arg Pro
        195

<210> SEQ ID NO 15
<211> LENGTH: 332
<212> TYPE: PRT
<213> ORGANISM: Adenovirus type 36

<400> SEQUENCE: 15

Met Ser Lys Arg Lys Ile Lys Glu Glu Met Leu Gln Val Val Ala Pro
1               5                   10                  15

Glu Ile Tyr Gly Pro Pro Asp Gln Lys Pro Arg Lys Ile Lys Arg Val
            20                  25                  30

Lys Lys Lys Asp Glu Val Asp Glu Gly Ala Val Glu Phe Val Arg Glu
        35                  40                  45

Phe Ala Pro Arg Arg Val Asn Trp Lys Gly Arg Arg Val Gln Arg
    50                  55                  60

Val Leu Arg Pro Gly Thr Ala Val Val Phe Thr Pro Gly Glu Arg Ser
65              70                  75                  80

Ser Val Arg Ser Lys Arg Ser Tyr Asp Glu Val Tyr Gly Asp Asp
                85                  90                  95

Ile Leu Asp Gln Ala Ala Glu Arg Ala Gly Glu Phe Ala Tyr Gly Lys
                100                 105                 110

Arg Ser Arg Glu Glu Glu Leu Ile Ser Leu Pro Leu Asp Glu Ser Asn
            115                 120                 125

Pro Thr Pro Ser Leu Lys Pro Val Thr Leu Gln Gln Val Leu Pro Gln
        130                 135                 140

Ala Val Leu Leu Pro Ser Arg Gly Val Lys Arg Glu Gly Glu Ser Met
145                 150                 155                 160

Tyr Pro Thr Met Gln Ile Met Val Pro Lys Arg Arg Val Glu Asp
                165                 170                 175

Val Leu Asp Thr Val Lys Met Asp Glu Pro Glu Val Lys Val Arg
            180                 185                 190

Pro Ile Lys Gln Val Ala Pro Gly Leu Gly Val Gln Thr Val Asp Ile
        195                 200                 205

Gln Ile Pro Thr Asp Met Asp Val Asp Lys Lys Pro Ser Thr Ser Ile
    210                 215                 220

Glu Val Gln Thr Asp Pro Trp Leu Pro Ala Ser Thr Ala Thr Val Ser
225                 230                 235                 240

Thr Phe Thr Ala Ala Thr Ala Thr Glu Pro Pro Arg Arg Arg Trp
                245                 250                 255

Gly Ala Ala Ser Arg Leu Met Pro Asn Tyr Val Leu His Pro Ser Ile
            260                 265                 270
```

```
Ile Pro Thr Pro Gly Tyr Arg Gly Thr Arg Tyr Tyr Ala Ser Arg Arg
            275                 280                 285

Arg Pro Ala Ala Lys Arg Arg Arg Thr Ala Thr Arg Arg Arg Leu
290                 295                 300

Ala Pro Ala Arg Val Arg Arg Val Thr Thr Arg Arg Gly Arg Ser Leu
305                 310                 315                 320

Val Leu Pro Thr Val Arg Tyr His Pro Ser Ile Leu
            325                 330

<210> SEQ ID NO 16
<211> LENGTH: 74
<212> TYPE: PRT
<213> ORGANISM: Adenovirus type 36

<400> SEQUENCE: 16

Met Ala Leu Thr Cys Arg Leu Arg Ile Pro Val Pro Asn Tyr Arg Gly
1               5                   10                  15

Arg Ser Arg Arg Arg Gly Met Ala Gly Ser Gly Leu Asn Arg Arg
            20                  25                  30

Arg Arg Arg Ala Met Arg Arg Arg Leu Ser Gly Gly Phe Leu Pro Ala
            35                  40                  45

Leu Ile Pro Ile Ile Ala Ala Ala Ile Gly Thr Ile Pro Gly Ile Ala
            50                  55                  60

Ser Val Ala Leu Gln Ala Ser Gln Arg Arg
65                  70

<210> SEQ ID NO 17
<211> LENGTH: 234
<212> TYPE: PRT
<213> ORGANISM: Adenovirus type 36

<400> SEQUENCE: 17

Met Glu Asp Ile Asn Phe Ala Ser Leu Ala Pro Arg His Gly Thr Arg
1               5                   10                  15

Pro Phe Met Gly Thr Trp Asn Glu Ile Gly Thr Ser Gln Leu Asn Gly
            20                  25                  30

Gly Ala Phe Asn Trp Ser Ser Val Trp Ser Gly Leu Lys Asn Phe Gly
            35                  40                  45

Ser Thr Leu Arg Thr Tyr Gly Asn Lys Ala Trp Asn Ser Ser Thr Gly
            50                  55                  60

Gln Leu Leu Arg Glu Lys Leu Lys Asp Gln Asn Phe Gln Gln Lys Val
65                  70                  75                  80

Val Asp Gly Leu Ala Ser Gly Ile Asn Gly Val Val Asp Ile Ala Asn
            85                  90                  95

Gln Ala Val Gln Arg Glu Ile Asn Ser Arg Leu Asp Pro Arg Pro Pro
            100                 105                 110

Thr Val Val Glu Met Glu Asp Ala Thr Leu Pro Pro Lys Gly Glu
            115                 120                 125

Lys Arg Pro Arg Pro Asp Ala Glu Glu Thr Ile Leu Gln Val Asp Glu
130                 135                 140

Pro Pro Ser Tyr Glu Glu Ala Val Lys Ala Gly Met Pro Thr Thr Arg
145                 150                 155                 160

Ile Ile Ala Pro Leu Ala Thr Gly Val Met Lys Pro Ala Thr Leu Asp
            165                 170                 175

Leu Pro Pro Pro Pro Thr Pro Ala Pro Pro Lys Ala Ala Pro Val Val
            180                 185                 190
```

```
Gln Ala Pro Pro Val Ala Thr Ala Val Arg Arg Val Pro Ala Arg Arg
        195                 200                 205

Gln Ala Gln Asn Trp Gln Ser Thr Leu His Ser Ile Val Gly Leu Gly
210                 215                 220

Val Lys Ser Leu Lys Arg Arg Arg Cys Tyr
225                 230
```

<210> SEQ ID NO 18
<211> LENGTH: 944
<212> TYPE: PRT
<213> ORGANISM: Adenovirus type 36

<400> SEQUENCE: 18

```
Met Ala Thr Pro Ser Met Met Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
50                  55                  60

Thr Leu Arg Phe Val Pro Val Asp Arg Glu Asp Thr Thr Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Ser Ser Gln Trp Thr Asp Lys Glu Arg Gln Asn Gly Gly
130                 135                 140

Gln Pro Pro Thr Thr Lys Asp Val Thr Lys Thr Phe Gly Val Ala Ala
145                 150                 155                 160

Arg Gly Gly Leu His Ile Thr Asp Lys Gly Leu Gln Ile Gly Glu Asp
                165                 170                 175

Glu Asn Asn Glu Asp Gly Glu Glu Ile Tyr Ala Asp Lys Thr Phe
            180                 185                 190

Gln Pro Glu Pro Gln Val Gly Glu Asn Trp Gln Asp Thr Asp Val
        195                 200                 205

Phe Tyr Gly Gly Arg Ala Leu Lys Lys Glu Thr Lys Met Lys Pro Cys
210                 215                 220

Tyr Gly Ser Phe Ala Arg Pro Thr Asn Glu Lys Gly Gly Gln Ala Lys
225                 230                 235                 240

Phe Leu Asn Gly Glu Asn Gly Gln Pro Ser Lys Asp Gln Asp Ile Thr
                245                 250                 255

Leu Ala Phe Phe Asp Leu Lys Gln Asn Asp Thr Gly Thr Thr Gln Asn
            260                 265                 270

Gln Pro Asp Val Val Met Tyr Thr Glu Asn Val Tyr Leu Glu Thr Pro
        275                 280                 285

Asp Thr His Val Val Tyr Lys Pro Gly Lys Glu Asp Thr Ser Ser Ala
290                 295                 300

Ala Asn Leu Thr Gln Gln Ser Met Pro Asn Arg Pro Asn Tyr Ile Gly
305                 310                 315                 320

Phe Arg Asp Asn Phe Val Gly Leu Met Tyr Tyr Asn Ser Thr Gly Asn
```

-continued

```
                325                 330                 335
Met Gly Val Leu Ala Gly Gln Ala Ser Gln Leu Asn Ala Val Val Asp
                340                 345                 350
Leu Gln Asp Arg Asn Thr Glu Leu Ser Tyr Gln Leu Leu Asp Ser
                355                 360                 365
Leu Gly Asp Arg Thr Arg Tyr Phe Ser Met Trp Asn Ser Ala Val Asp
            370                 375                 380
Ser Tyr Asp Pro Asp Val Arg Ile Ile Glu Asn His Gly Val Glu Asp
385                 390                 395                 400
Glu Leu Pro Asn Tyr Cys Phe Pro Leu Asp Gly Ser Gly Ser Asn Thr
                    405                 410                 415
Ala Tyr Gln Gly Val Lys Tyr Glu Asn Gly Ala Gly Asn Gly Ser Trp
                420                 425                 430
Lys Val Asp Gly Glu Val Ala Ser Gln Asn Gln Ile Ala Lys Gly Asn
                435                 440                 445
Leu Tyr Ala Met Glu Ile Asn Leu Gln Ala Asn Leu Trp Lys Ser Phe
            450                 455                 460
Leu Tyr Ser Asn Val Ala Leu Tyr Leu Pro Asp Ser Tyr Lys Tyr Thr
465                 470                 475                 480
Pro Ala Asn Ile Thr Leu Pro Thr Asn Thr Asn Thr Tyr Glu Tyr Met
                        485                 490                 495
Asn Gly Arg Val Val Ala Pro Ser Leu Val Asp Ala Tyr Val Asn Ile
                    500                 505                 510
Gly Ala Arg Trp Ser Leu Asp Pro Met Asp Asn Val Asn Pro Phe Asn
                515                 520                 525
His His Arg Asn Ala Gly Leu Arg Tyr Arg Ser Met Leu Leu Gly Asn
            530                 535                 540
Gly Arg Tyr Val Pro Phe His Ile Gln Val Pro Gln Lys Phe Phe Ala
545                 550                 555                 560
Ile Lys Asn Leu Leu Leu Pro Gly Ser Tyr Thr Tyr Glu Trp Asn
                    565                 570                 575
Phe Arg Lys Asp Val Asn Met Ile Leu Gln Ser Ser Leu Gly Asn Asp
                580                 585                 590
Leu Arg Val Asp Gly Ala Ser Val Arg Phe Asp Ser Val Asn Leu Tyr
            595                 600                 605
Ala Thr Phe Phe Pro Met Ala His Asn Thr Ala Ser Thr Leu Glu Ala
            610                 615                 620
Met Leu Arg Asn Asp Thr Asn Asp Gln Ser Phe Asn Asp Tyr Leu Ser
625                 630                 635                 640
Ala Ala Asn Met Leu Tyr Pro Ile Pro Ala Lys Ala Thr Asn Val Pro
                    645                 650                 655
Ile Ser Ile Pro Ser Arg Asn Trp Ala Ala Phe Arg Gly Trp Ser Phe
                660                 665                 670
Thr Arg Leu Lys Thr Lys Glu Thr Pro Ser Leu Gly Ser Gly Phe Asp
            675                 680                 685
Pro Tyr Phe Val Tyr Ser Gly Ser Ile Pro Tyr Leu Asp Gly Thr Phe
            690                 695                 700
Tyr Leu Asn His Thr Phe Lys Lys Val Ser Ile Met Phe Asp Ser Ser
705                 710                 715                 720
Val Ser Trp Pro Gly Asn Asp Arg Leu Leu Thr Pro Asn Glu Phe Glu
                    725                 730                 735
Ile Lys Arg Ser Val Asp Gly Glu Gly Tyr Asn Val Ala Gln Cys Asn
                740                 745                 750
```

```
Met Thr Lys Asp Trp Phe Leu Val Gln Met Leu Ser His Tyr Asn Ile
            755                 760                 765

Gly Tyr Gln Gly Phe Tyr Val Pro Glu Gly Tyr Lys Asp Arg Met Tyr
    770                 775                 780

Ser Phe Arg Asn Phe Gln Pro Met Ser Arg Gln Val Val Asp Glu
785                 790                 795                 800

Ile Asn Tyr Lys Asp Tyr Lys Ala Val Thr Leu Pro Phe Gln His Asn
                805                 810                 815

Asn Ser Gly Phe Thr Gly Tyr Leu Ala Pro Thr Met Arg Gln Gly Gln
                820                 825                 830

Pro Tyr Pro Ala Asn Phe Pro Tyr Pro Leu Ile Gly Gln Thr Ala Val
                835                 840                 845

Pro Ser Val Thr Gln Lys Lys Phe Leu Cys Asp Arg Val Met Trp Arg
                850                 855                 860

Ile Pro Phe Ser Ser Asn Phe Met Ser Met Gly Ala Leu Thr Asp Leu
865                 870                 875                 880

Gly Gln Asn Met Leu Tyr Ala Asn Ser Ala His Ala Leu Asp Met Thr
                885                 890                 895

Phe Glu Val Asp Pro Met Asp Glu Pro Thr Leu Leu Tyr Leu Leu Phe
                900                 905                 910

Glu Val Phe Asp Val Val Arg Val His Gln Pro His Arg Gly Val Ile
                915                 920                 925

Glu Ala Val Tyr Leu Arg Thr Pro Phe Ser Ala Gly Asn Ala Thr Thr
                930                 935                 940

<210> SEQ ID NO 19
<211> LENGTH: 209
<212> TYPE: PRT
<213> ORGANISM: Adenovirus type 36

<400> SEQUENCE: 19

Met Ser Gly Ser Ser Glu Arg Glu Leu Ala Ala Ile Val Arg Asp Leu
1               5                   10                  15

Gly Cys Gly Pro Tyr Phe Leu Gly Thr His Asp Lys Arg Phe Pro Gly
                20                  25                  30

Phe Leu Ala Gly Asp Lys Leu Ala Cys Ala Ile Val Asn Thr Ala Gly
            35                  40                  45

Arg Glu Thr Gly Gly Val His Trp Leu Ala Phe Gly Trp Asn Pro Arg
    50                  55                  60

Ser Arg Thr Cys Tyr Met Phe Asp Pro Phe Gly Phe Ser Asp Arg Arg
65                  70                  75                  80

Leu Lys Gln Ile Tyr Ser Phe Glu Tyr Glu Ala Met Leu Arg Arg Ser
                85                  90                  95

Ala Leu Ala Ser Ser Pro Asp Arg Cys Leu Ser Leu Glu Gln Ser Thr
                100                 105                 110

Gln Thr Val Gln Gly Pro Asp Ser Ala Ala Cys Gly Leu Phe Cys Cys
            115                 120                 125

Met Phe Leu His Ala Phe Val His Trp Pro Asp Arg Pro Met Asp Gly
130                 135                 140

Asn Pro Thr Met Asn Leu Leu Thr Gly Val Pro Asn Gly Met Leu Gln
145                 150                 155                 160

Ser Pro Gln Val Leu Pro Thr Leu Arg Arg Asn Gln Glu Glu Leu Tyr
                165                 170                 175

Arg Phe Leu Ala Arg His Ser Pro Tyr Phe Arg Ser His Arg Ala Ala
```

```
            180                 185                 190
Ile Glu His Ala Thr Ala Phe Asp Lys Met Lys Gln Leu Arg Val Ser
                195                 200                 205

Gln

<210> SEQ ID NO 20
<211> LENGTH: 489
<212> TYPE: PRT
<213> ORGANISM: Adenovirus type 36

<400> SEQUENCE: 20

Met Ala Gly Gly Ser Gln Asp Val Arg Arg Phe Met Glu Arg Glu Ala
1               5                   10                  15

Thr Pro Pro Arg Gly His Gly Ser Ala Arg Tyr Pro Pro Glu Gln Glu
                20                  25                  30

Arg Ser Pro Ser Pro Pro Pro Leu Pro Thr Lys Arg Arg Lys Tyr
            35                  40                  45

Gln Arg Val Gly Ser Gly Ser Ser Glu Glu Asp Val Pro Val Asp
        50                  55                  60

Ser Pro Pro Lys Lys Lys Gln Ala Arg Lys Thr Lys His Val Thr Lys
65                  70                  75                  80

Val Asp Pro Asp Glu Glu Met Pro Gln Glu Asp Ala Val Ile Val Gly
                85                  90                  95

Val Gly Phe Ser Gln Pro Pro Val Leu Leu Lys Glu Gly Lys Asp Gly
                100                 105                 110

Lys Arg Ile Val Glu Pro Ala Thr Pro Gly Val Leu Asn Val Arg Asn
            115                 120                 125

Pro Leu Ser Leu Pro Leu Val Ser Ser Trp Glu Lys Gly Met Asp Thr
        130                 135                 140

Met Asn Val Leu Met Glu Arg Tyr Arg Val Asp Ser Gly Leu Arg Asp
145                 150                 155                 160

Ala Tyr Lys Leu Met Pro Glu Gln Thr Glu Ile Phe Gln Lys Met Cys
                165                 170                 175

Gln Thr Trp Met Asn Glu Glu Ala Arg Gly Leu Gln Leu Thr Phe Thr
                180                 185                 190

Thr Gln Lys Ala Phe Ser Thr Val Met Gly Arg Leu Leu Gln Gly Tyr
            195                 200                 205

Ile Phe Ser His Ser Gly Ile Ala His Lys Asn Trp Glu Cys Thr Gly
        210                 215                 220

Cys Ala Leu Trp Asp His Gly Cys Thr Glu Val Glu Gly Gln Leu Lys
225                 230                 235                 240

Cys Leu His Gly Thr Val Met Ile His Lys Asp His Val Val Glu Met
                245                 250                 255

Asp Val Thr Ser Glu Asn Gly Gln Arg Ala Leu Lys Glu Gln Pro Ser
                260                 265                 270

Lys Ala Lys Val Thr Gln Asn Arg Trp Gly Arg Ser Val Val Gln Leu
            275                 280                 285

Thr Ser His Asp Ala Arg Cys Cys Val Gln Asp Ala Gly Cys Gly Asn
        290                 295                 300

Asn Gln Phe Ser Gly Lys Ser Cys Gly Leu Phe Ser Glu Gly Ala
305                 310                 315                 320

Lys Ala Gln Gln Ala Phe Lys Gln Ile Ser Ala Phe Val Lys Ala Leu
                325                 330                 335

Tyr Pro Asn Met Gln Arg Gly Ala Gly Met Met Leu Met Pro Ile His
```

```
                    340                 345                 350
Cys Glu Cys Asn His Lys Pro Gln Ser Val Pro Phe Leu Gly Arg Gln
            355                 360                 365
Leu Cys Lys Met Thr Pro Phe Gly Leu Ser Asn Ala Glu Asp Leu Asp
        370                 375                 380
Lys Asp Gln Ile Thr Asp Lys Ser Val Leu Ala Ser Val Lys Tyr Pro
385                 390                 395                 400
Ser Leu Met Val Phe Gln Cys Cys Asn Pro Val Tyr Arg Asn Ser Arg
                405                 410                 415
Ala Gln Ser Thr Gly Pro Asn Cys Asp Phe Lys Ile Ser Ala Pro Asp
            420                 425                 430
Met Leu Gly Ala Leu Gln Met Ser Arg Arg Met Trp Ser Glu Thr Phe
        435                 440                 445
Pro Glu Ile Pro Val Pro Lys Leu Val Ile Pro Glu Phe Lys Trp Leu
    450                 455                 460
Pro Lys Tyr Gln Tyr Arg Asn Val Ala Leu Pro Ser Ala Ala His Asn
465                 470                 475                 480
Asp Glu Arg Glu Asn Pro Phe Asp Phe
                485

<210> SEQ ID NO 21
<211> LENGTH: 731
<212> TYPE: PRT
<213> ORGANISM: Adenovirus type 36

<400> SEQUENCE: 21

Met Glu Glu Gln Pro Arg Lys Gln Glu Gln Glu Glu Asp Leu Thr Thr
1               5                   10                  15
His Glu Gln Pro Lys Ile Glu Gln Asp Leu Gly Phe Glu Glu Pro Ala
            20                  25                  30
Arg Leu Glu Pro Pro Gln Asp Glu Gln Glu His Glu Gln Asp Ala Gly
        35                  40                  45
Gln Glu Glu Thr Asp Ala Gly Leu Glu His Gly Tyr Leu Gly Gly Glu
    50                  55                  60
Glu Asp Val Leu Leu Lys His Leu Gln Arg Gln Ser Leu Ile Leu Arg
65                  70                  75                  80
Asp Ala Leu Ala Asp Arg Ser Glu Thr Pro Leu Ser Val Glu Glu Leu
                85                  90                  95
Cys Arg Ala Tyr Glu Leu Asn Leu Phe Ser Pro Arg Val Pro Pro Lys
            100                 105                 110
Arg Gln Pro Asn Gly Thr Cys Glu Pro Asn Pro Arg Leu Asn Phe Tyr
        115                 120                 125
Pro Val Phe Ala Val Pro Glu Ala Leu Ala Thr Tyr His Ile Phe Phe
    130                 135                 140
Lys Asn Gln Lys Ile Pro Val Ser Cys Arg Ala Asn Arg Thr Arg Ala
145                 150                 155                 160
Asp Ala Leu Leu Ala Leu Gly Pro Gly Ala Arg Ile Pro Asp Ile Ala
                165                 170                 175
Ser Leu Glu Glu Val Pro Lys Ile Phe Glu Gly Leu Gly Arg Asp Glu
            180                 185                 190
Thr Arg Ala Ala Asn Ala Leu Lys Glu Thr Ala Glu Glu Gly His
        195                 200                 205
Thr Ser Ala Leu Val Glu Leu Glu Gly Asp Asn Ala Arg Leu Val Val
    210                 215                 220
```

```
Leu Lys Arg Ser Val Glu Leu Thr His Phe Ala Tyr Pro Ala Val Asn
225                 230                 235                 240

Leu Pro Pro Lys Val Met Arg Arg Ile Met Asp Gln Leu Ile Met Pro
                245                 250                 255

His Ile Glu Ala Ile Asp Glu Thr Gln Glu Gln Arg Pro Glu Asp Ala
            260                 265                 270

Arg Pro Val Val Ser Asp Glu Met Leu Ala Arg Trp Leu Gly Thr Arg
        275                 280                 285

Asp Pro Gln Ala Leu Glu Gln Arg Arg Lys Leu Met Leu Ala Val Val
    290                 295                 300

Leu Val Thr Leu Glu Leu Glu Cys Met Arg Arg Phe Phe Cys Asp Pro
305                 310                 315                 320

Glu Thr Leu Arg Lys Val Glu Thr Leu His Tyr Thr Phe Arg His
                325                 330                 335

Gly Phe Val Arg Gln Ala Cys Lys Ile Ser Asn Val Glu Leu Thr Asn
                340                 345                 350

Leu Val Ser Cys Leu Gly Ile Leu His Glu Asn Arg Leu Gly Gln Thr
            355                 360                 365

Val Leu His Ser Thr Leu Lys Gly Glu Ala Arg Arg Asp Tyr Val Arg
370                 375                 380

Asp Cys Val Phe Leu Phe Leu Cys His Thr Trp Gln Ala Ala Met Gly
385                 390                 395                 400

Val Trp Gln Gln Cys Leu Glu Asp Glu Asn Leu Lys Glu Leu Asp Lys
                405                 410                 415

Leu Leu Ala Arg Asn Leu Lys Lys Leu Trp Thr Gly Phe Asp Glu Arg
                420                 425                 430

Thr Val Ala Ser Asp Leu Ala Glu Ile Val Phe Pro Glu Arg Leu Arg
            435                 440                 445

His Thr Leu Lys Gly Gly Leu Pro Asp Phe Met Ser Gln Ser Met Leu
        450                 455                 460

Gln Asn Tyr Arg Thr Phe Ile Leu Glu Arg Ser Gly Ile Leu Pro Ala
465                 470                 475                 480

Thr Cys Asn Ala Phe Pro Ser Asp Phe Val Pro Leu Ser Tyr Arg Glu
                485                 490                 495

Cys Pro Pro Pro Leu Trp Ser His Cys Tyr Leu Leu Gln Leu Ala Asn
            500                 505                 510

Tyr Ile Ser Tyr His Ser Asp Val Ile Glu Asp Val Ser Gly Glu Gly
            515                 520                 525

Leu Leu Glu Cys His Cys Arg Cys Asn Leu Cys Ser Pro His Arg Ser
530                 535                 540

Leu Val Cys Asn Pro Gln Leu Leu Ser Glu Thr Gln Val Ile Gly Thr
545                 550                 555                 560

Phe Glu Leu Gln Gly Pro Glu Lys Ser Thr Ala Pro Leu Lys Leu Thr
                565                 570                 575

Pro Gly Leu Trp Thr Ser Ala Tyr Leu Arg Lys Phe Val Pro Glu Asp
            580                 585                 590

Tyr His Ala His Glu Ile Lys Phe Phe Glu Asp Gln Ser Arg Pro Gln
            595                 600                 605

His Ala Asp Leu Thr Ala Cys Val Ile Thr Gln Gly Ala Ile Leu Ala
        610                 615                 620

Gln Leu His Ala Ile Gln Lys Ser Arg Gln Glu Phe Leu Leu Lys Lys
625                 630                 635                 640

Gly Arg Gly Val Tyr Leu Asp Pro Gln Thr Gly Glu Val Leu Asn Pro
```

```
                    645                 650                 655
Gly Leu Pro Gln His Ala Glu Glu Ala Gly Ala Ala Ser Gly Gly
                660                 665                 670

Asp Gly Arg Arg Met Gly Gln Pro Gly Arg Gly Gly Arg Met Gly Gly
            675                 680                 685

Gly Asp Arg Gly Gly Arg Ile Gly Arg Gly Gly Arg Gly Ala Gly Asn
        690                 695                 700

Arg Ala Ala Arg Arg Thr Ile Arg Ala Gly Ser Pro Gly Gly His
705                 710                 715                 720

Gly Tyr Asn Leu Arg Ser Gly Gln Ala Ser Ser
                725                 730
```

<210> SEQ ID NO 22
<211> LENGTH: 172
<212> TYPE: PRT
<213> ORGANISM: Adenovirus type 36

<400> SEQUENCE: 22

```
Met Pro Arg Lys Lys Gln Glu Pro Leu Val Glu Glu Met Glu Glu Glu
1               5                   10                  15

Trp Asp Ser Gln Ala Glu Glu Asp Glu Trp Glu Glu Glu Thr Glu Glu
            20                  25                  30

Glu Glu Leu Glu Glu Val Glu Glu Gln Ala Thr Glu Gln Pro Val
        35                  40                  45

Ala Ala Pro Ser Ala Pro Ala Ala Pro Ala Val Thr Asp Thr Thr Ser
    50                  55                  60

Ala Pro Val Lys Pro Pro Arg Arg Trp Asp Arg Val Lys Gly Asp Ala
65                  70                  75                  80

Lys Lys Lys Gln Val Arg Gly Val Ala Gly Gly Gly Leu Arg Ile Ala
                85                  90                  95

Ala Asn Glu Pro Ser Thr Thr Arg Glu Leu Arg Asn Arg Ile Phe Pro
            100                 105                 110

Thr Leu Tyr Ala Ile Phe Gln Gln Ser Arg Gly Gln Gln Gln Glu Leu
        115                 120                 125

Lys Val Lys Asn Arg Ser Leu Arg Ser Leu Thr Arg Ser Cys Leu Tyr
    130                 135                 140

His Lys Asn Glu Asp Gln Leu Gln Arg Thr Leu Glu Asp Ala Glu Ala
145                 150                 155                 160

Leu Phe His Lys Tyr Cys Ala Leu Thr Leu Lys Asp
                165                 170
```

<210> SEQ ID NO 23
<211> LENGTH: 136
<212> TYPE: PRT
<213> ORGANISM: Adenovirus type 36

<400> SEQUENCE: 23

```
Met Pro Arg Lys Lys Gln Glu Pro Leu Val Glu Glu Met Glu Glu Glu
1               5                   10                  15

Trp Asp Ser Gln Ala Glu Glu Asp Glu Trp Glu Glu Glu Thr Glu Glu
            20                  25                  30

Glu Glu Leu Glu Glu Val Glu Glu Gln Ala Thr Glu Gln Pro Val
        35                  40                  45

Ala Ala Pro Ser Ala Pro Ala Ala Pro Ala Val Thr Asp Thr Thr Ser
    50                  55                  60

Ala Pro Val Lys Pro Pro Arg Arg Trp Asp Arg Val Lys Gly Asp Gly
```

```
                65                  70                  75                  80
Lys His Glu Arg Gln Gly Tyr Arg Ser Trp Arg Ala His Lys Ala Ala
                    85                  90                  95

Ile Ile Ala Cys Leu Gln Asp Cys Gly Gly Asn Ile Ala Phe Ala Arg
                100                 105                 110

Arg Tyr Leu Leu Phe His Arg Gly Val Asn Ile Pro Arg Asn Val Leu
                115                 120                 125

His Tyr Tyr Arg His Leu His Ser
            130                 135

<210> SEQ ID NO 24
<211> LENGTH: 227
<212> TYPE: PRT
<213> ORGANISM: Adenovirus type 36

<400> SEQUENCE: 24

Met Ser Lys Glu Ile Pro Thr Pro Tyr Met Trp Ser Tyr Gln Pro Gln
1               5                   10                  15

Met Gly Leu Ala Ala Gly Ala Ser Gln Asp Tyr Ser Thr Arg Met Asn
                20                  25                  30

Trp Leu Ser Ala Gly Pro Ser Met Ile Ser Arg Val Asn Gly Val Arg
            35                  40                  45

Asn His Arg Asn Gln Ile Leu Leu Glu Gln Ala Ala Val Thr Ser Thr
        50                  55                  60

Pro Arg Ala Lys Leu Asn Pro Arg Asn Trp Pro Ser Thr Leu Val Tyr
65                  70                  75                  80

Gln Glu Ile Pro Gly Pro Thr Thr Val Leu Leu Pro Arg Asp Ala Leu
                85                  90                  95

Ala Glu Val Arg Met Thr Asn Ser Gly Val Gln Leu Ala Gly Gly Ala
                100                 105                 110

Ser Arg Cys Pro Leu Arg Pro Gln Ser Gly Ile Lys Thr Leu Met Ile
            115                 120                 125

Arg Gly Arg Gly Thr Gln Leu Asn Asp Glu Leu Val Ser Ser Ser Ile
        130                 135                 140

Gly Leu Arg Pro Asp Gly Val Phe Gln Leu Ala Gly Ala Gly Arg Ser
145                 150                 155                 160

Ser Phe Thr Pro Asn Gln Ala Tyr Leu Thr Leu Gln Ser Ser Ser Ser
                165                 170                 175

Glu Pro Arg Ser Gly Gly Ile Gly Thr Leu Gln Phe Val Glu Glu Phe
                180                 185                 190

Val Pro Ser Val Tyr Phe Asn Pro Phe Ser Gly Ser Pro Gly Leu Tyr
            195                 200                 205

Pro Asp Glu Phe Ile Pro Asn Phe Asp Ala Val Arg Glu Ala Val Asp
        210                 215                 220

Gly Tyr Asp
225

<210> SEQ ID NO 25
<211> LENGTH: 106
<212> TYPE: PRT
<213> ORGANISM: Adenovirus type 36

<400> SEQUENCE: 25

Met Ser His Gly Asp Ser Ala Glu Leu Ala Arg Leu Arg His Leu Asp
1               5                   10                  15

His Cys Arg Arg Leu Arg Cys Phe Ala Arg Glu Ser Cys Gly Leu Ile
```

```
                    20                  25                  30

Tyr Phe Glu Leu Pro Glu Glu His Pro Asn Gly Pro Ala His Gly Val
                35                  40                  45

Arg Ile Thr Val Glu Gly Thr Ala Glu Ser His Leu Val Arg Phe Phe
            50                  55                  60

Thr Gln Gln Pro Phe Leu Val Glu Arg Asp Arg Gly Ala Thr Thr Tyr
65                  70                  75                  80

Thr Val Tyr Cys Ile Cys Pro Thr Pro Lys Leu His Glu Asn Phe Cys
                85                  90                  95

Cys Thr Leu Cys Gly Glu Phe Asn Lys Ser
            100                 105

<210> SEQ ID NO 26
<211> LENGTH: 197
<212> TYPE: PRT
<213> ORGANISM: Adenovirus type 36

<400> SEQUENCE: 26

Met Arg Ile Phe Ala Val Leu Phe Val Val Ser Leu Ile Lys Ala Glu
1               5                   10                  15

Leu Arg Thr Tyr Phe Gly Ile Pro Cys Arg His Gln Ile His Lys Thr
                20                  25                  30

Ile Asn Phe Thr Phe Glu Glu Gln Val Asn Phe Thr Cys Lys Pro His
            35                  40                  45

Lys Lys Tyr Val Thr Trp Phe Tyr Gln Asn Thr Thr Leu Ala Val Ala
        50                  55                  60

Asn Thr Cys Ser Asn Asp Gly Val Leu Leu Pro Asn Asn Leu Thr Ser
65                  70                  75                  80

Gly Leu Thr Phe Ser Val Lys Arg Ala Lys Leu Ile Leu His Arg Pro
                85                  90                  95

Ile Val Glu Gly Thr Tyr Gln Cys Gln Ser Gly Pro Cys Phe His Ser
            100                 105                 110

Phe Thr Leu Val Asn Val Thr Gly Ser Ser Thr Val Ala Pro Glu Thr
        115                 120                 125

Asn Leu Leu Ser Asp Thr Asn Thr Pro Lys Thr Gly Gly Glu Leu Trp
    130                 135                 140

Val Pro Ser Leu Thr Glu Gly Gly Ser His Ile Glu Ala Val Gly Tyr
145                 150                 155                 160

Leu Ile Leu Gly Val Val Leu Gly Gly Cys Ile Ala Val Leu Tyr Tyr
                165                 170                 175

Leu Pro Cys Trp Val Glu Ile Arg Val Phe Ile Cys Trp Val Arg His
            180                 185                 190

Cys Gly Glu Glu Pro
        195

<210> SEQ ID NO 27
<211> LENGTH: 156
<212> TYPE: PRT
<213> ORGANISM: Adenovirus type 36

<400> SEQUENCE: 27

Met Lys Gly Leu Leu Ile Ile Leu Ser Leu Val Gly Gly Leu Leu
1               5                   10                  15

Ala Cys His Glu Gln Pro Arg Cys Asn Ile Thr Thr Gly Asn Glu Arg
                20                  25                  30

Asn Asp Cys Ser Val Val Ile Lys Cys Glu His Gln Cys Pro Leu Asn
```

```
                  35                  40                  45
Ile Thr Phe Lys Asn Lys Thr Met Gly Asn Val Trp Val Gly Phe Trp
 50                  55                  60

Gln Pro Gly Asp Glu Gln Asn Tyr Thr Val Thr Ile His Gly Ser Asp
 65                  70                  75                  80

Gly Asn His Thr Phe Gly Phe Lys Phe Ile Phe Glu Val Met Cys Asp
                     85                  90                  95

Ile Thr Leu His Val Ala Arg Leu His Gly Leu Trp Pro Pro Thr Lys
                100                 105                 110

Glu Asn Met Val Gly Phe Ser Leu Ala Phe Val Ile Met Ala Cys Ala
                115                 120                 125

Met Ser Gly Leu Leu Val Gly Ala Leu Val Trp Phe Leu Lys Arg Lys
130                 135                 140

Pro Arg Tyr Gly Asn Glu Glu Lys Glu Lys Leu Leu
145                 150                 155

<210> SEQ ID NO 28
<211> LENGTH: 418
<212> TYPE: PRT
<213> ORGANISM: Adenovirus type 36

<400> SEQUENCE: 28

Met Asn Thr Leu Thr Ser Val Val Leu Ser Leu Leu Val Ile Asn
 1               5                  10                  15

Val Glu Cys Ala Asp Pro Ile Leu Val Ser Val Asp Trp Gly Lys Asn
                 20                  25                  30

Leu Thr Leu Glu Gly Pro Lys Glu Thr Pro Val Glu Trp Trp Gly Gly
                 35                  40                  45

Arg Asn Ile Gln Gln Leu Cys Ile Gly Asn Gln Thr Lys His Lys Glu
 50                  55                  60

Leu Ser His Arg Cys Asn Val Gln Asn Ile Thr Leu Leu Phe Val Asn
 65                  70                  75                  80

Thr Ser Phe Asn Gly Asp Tyr Phe Gly Phe Lys Asn Asp Asn Ser Gly
                 85                  90                  95

Met Lys His Tyr Lys Val Thr Val Ile Pro Pro Lys Pro Ser Thr Arg
                100                 105                 110

Lys Pro Leu Ser Pro Pro His Tyr Val Asn Ala Thr Met Gly Gln Asn
                115                 120                 125

Leu Thr Leu Val Gly Pro Ala Asn Ile Pro Val Thr Trp Leu Ser Glu
                130                 135                 140

Tyr Gly Thr Leu Cys Glu Gly Lys Lys Ile Leu His Lys Glu Leu Asn
145                 150                 155                 160

His Thr Cys Asn Glu Gln Asn Leu Thr Leu Leu Phe Val Asn Met Thr
                165                 170                 175

His Asn Gly Pro Tyr Phe Gly Phe Asp Lys Tyr Asn Ile Asp Arg Glu
                180                 185                 190

Gln Tyr Glu Val Ser Ile Ile Ser Leu Phe Lys Val Gly Ala Gly Gln
                195                 200                 205

Lys Lys Ile Gly Lys Gly Gln Lys Glu Lys Thr Lys Pro Asn
210                 215                 220

Ser Ser Asp Leu Gly Gln Arg Gln Ser Arg Pro Lys Lys Asp Ile
225                 230                 235                 240

Val Glu Glu Val Gln Ile Lys Thr Gly Glu Asn Arg Thr Leu Val Gly
                245                 250                 255
```

```
Pro Pro Gly Lys Val Asp Trp Ile Lys Leu Ser Ser Gly Asn Asn Asn
            260                 265                 270

Val Leu Lys Leu Cys Asn Gly Asp Lys Tyr Ile Lys His Thr Cys Asp
            275                 280                 285

Gly Gln Asn Leu Thr Leu Ile Asn Val Thr Arg Ile Tyr Asp Gly Thr
            290                 295                 300

Tyr Tyr Gly Ser Ser Asn Asp Gly Ser Ser His Tyr Lys Val Thr Ile
305                 310                 315                 320

Tyr Glu Leu His Lys Val Asn Lys Thr Lys Ser Met Leu Lys Pro Tyr
                325                 330                 335

Thr Thr Lys Arg Thr Thr Val Asn Ala Thr Asp Asp Ser Ala His Lys
            340                 345                 350

Ile Ala Leu Gln Gln Glu Asn Asn Gly Gln Thr Glu Asn Asp Gln Glu
            355                 360                 365

Ser Lys Ile Pro Ser Ala Thr Val Ala Ile Val Val Gly Val Ile Ala
            370                 375                 380

Gly Phe Ile Thr Ile Ile Ile Val Ile Leu Cys Tyr Ile Cys Cys Arg
385                 390                 395                 400

Lys Arg Pro Arg Ala Tyr Asn Asn Met Val Asp Pro Leu Leu Ser Phe
                405                 410                 415

Ser Tyr

<210> SEQ ID NO 29
<211> LENGTH: 284
<212> TYPE: PRT
<213> ORGANISM: Adenovirus type 36

<400> SEQUENCE: 29

Met Lys Ala Phe Thr Ala Cys Val Leu Ile Ser Ile Ile Thr Leu Ser
1               5                   10                  15

Leu Ala Ala Pro Lys Pro Glu Val Tyr Thr Gln Val Asn Val Thr Arg
            20                  25                  30

Gly Gly Asn Ala Thr Leu Asp Gly Pro Phe Asn Asn Asn Thr Trp Thr
        35                  40                  45

Arg Tyr His Asp Asp Gly Arg Lys Asn Gly Trp Met Asn Ile Cys Lys
    50                  55                  60

Trp Ser Asp Pro Ser Tyr Thr Cys His Ser Asn Gly Ser Leu Ser Ile
65                  70                  75                  80

Phe Ala Phe Asn Ile Ser Ser Gly Lys Tyr Lys Val Gln Ser Tyr Thr
                85                  90                  95

Asn Ser Tyr Asn Gly Leu Asp Gly Tyr Glu Lys Leu Glu Val Lys Met
            100                 105                 110

Phe Asn Leu Thr Val Ile Glu Pro Pro Thr Thr Arg Ala Pro Thr Thr
        115                 120                 125

Val Arg Thr Thr Lys Glu Thr Thr Gln Pro Thr Thr Val Pro Thr Thr
    130                 135                 140

His Pro Thr Thr Thr Val Ser Thr Thr Ile Glu Thr Thr Thr His Thr
145                 150                 155                 160

Thr Gln Leu Asp Thr Thr Val Gln Asn Thr Thr Leu Leu Ile Glu Phe
                165                 170                 175

Leu Leu Arg Gly Asn Glu Ser Thr Thr Asp Gln Thr Glu Ala Thr Ser
            180                 185                 190

Ser Ala Phe Ser Ser Thr Ala Asn Leu Thr Ser Leu Ala Trp Thr Asn
        195                 200                 205
```

```
Glu Thr Gly Val Ser Leu Met His Gly Gln Pro Tyr Ser Gly Leu Asp
210                 215                 220

Ile Gln Ile Thr Phe Leu Val Val Cys Gly Ile Phe Ile Leu Val Val
225                 230                 235                 240

Leu Leu Tyr Phe Val Cys Cys Lys Ala Arg Glu Lys Ser Ser Arg Pro
                245                 250                 255

Ile Tyr Arg Pro Val Ile Gly Glu Pro Gln Pro Leu Gln Val Glu Gly
                260                 265                 270

Gly Leu Arg Asn Leu Leu Phe Ser Phe Ser Val Trp
            275                 280
```

<210> SEQ ID NO 30
<211> LENGTH: 91
<212> TYPE: PRT
<213> ORGANISM: Adenovirus type 36

<400> SEQUENCE: 30

```
Met Ile Pro Arg Phe Phe Leu Phe Asn Ile Leu Phe Cys Leu Phe Asn
1               5                   10                  15

Ile Cys Ala Ala Phe Ala Ala Val Ser His Ala Ser Pro Asp Cys Leu
                20                  25                  30

Gly Pro Phe Pro Thr Tyr Leu Leu Phe Ala Leu Leu Thr Cys Thr Cys
            35                  40                  45

Val Cys Ser Ile Val Cys Leu Val Val Thr Phe Leu Gln Leu Ile Asp
50                  55                  60

Trp Cys Cys Ala Arg Tyr Asn Tyr Leu His His Ser Pro Glu Tyr Arg
65                  70                  75                  80

Asp Lys Asn Val Ala Arg Ile Leu Arg Leu Ile
                85                  90
```

<210> SEQ ID NO 31
<211> LENGTH: 124
<212> TYPE: PRT
<213> ORGANISM: Adenovirus type 36

<400> SEQUENCE: 31

```
Met Gln Thr Leu Leu Ile Leu Leu Ser Leu Ser Pro Ala Leu Ala
1               5                   10                  15

Asp Cys Lys Phe Ala Asp Ile Trp Asn Phe Leu Asp Cys Tyr Gln Glu
                20                  25                  30

Lys Met Asp Met Pro Ser Tyr Tyr Leu Val Ile Val Gly Val Val Met
            35                  40                  45

Val Cys Ser Cys Thr Phe Phe Ala Ile Met Ile Tyr Pro Cys Phe Asp
50                  55                  60

Leu Gly Trp Asn Ser Val Glu Ala Phe Thr Tyr Thr Leu Glu Ser Ser
65                  70                  75                  80

Ser Leu Ala Ser Thr Pro Pro Thr Pro Pro Arg Arg Asn Gln
                85                  90                  95

Phe Pro Leu Ile Gln Tyr Leu Glu Glu Pro Pro Arg Pro Pro Ser
                100                 105                 110

Thr Val Ser Tyr Phe His Ile Thr Gly Gly Asp Asp
            115                 120
```

<210> SEQ ID NO 32
<211> LENGTH: 130
<212> TYPE: PRT
<213> ORGANISM: Adenovirus type 36

-continued

```
<400> SEQUENCE: 32

Met Thr Asp His His Leu Asp Leu Glu Met Asp Gly Gln Ala Ser Glu
1               5                   10                  15

Gln Arg Ile Leu Gln Leu Arg Val Arg Gln Gln Glu Arg Ala Ala
            20                  25                  30

Lys Glu Leu Leu Asp Ala Ile Asn Ile His Gln Cys Lys Lys Gly Ile
            35                  40                  45

Phe Cys Leu Val Lys Gln Ala Lys Ile Thr Tyr Glu Leu Val Ser Asn
    50                  55                  60

Gly Lys Gln His Arg Leu Thr Tyr Glu Met Pro Gln Gln Lys Gln Lys
65                  70                  75                  80

Phe Thr Cys Met Val Gly Val Asn Pro Ile Val Ile Thr Gln Gln Ser
                85                  90                  95

Gly Glu Thr Ser Gly Cys Ile His Cys Ser Cys Glu Ser Pro Glu Cys
            100                 105                 110

Ile Tyr Ser Leu Leu Lys Thr Leu Cys Gly Leu Arg Asp Leu Leu Pro
        115                 120                 125

Met Asn
    130

<210> SEQ ID NO 33
<211> LENGTH: 49
<212> TYPE: PRT
<213> ORGANISM: Adenovirus type 36

<400> SEQUENCE: 33

Met Lys Ile Val Asp Gln Glu Phe Asp Ile Pro Phe Lys Val Trp Arg
1               5                   10                  15

Lys Phe Ala Ala Arg Arg Gly Leu Glu Tyr Gln Ser Trp Glu Glu Gly
            20                  25                  30

Thr Glu Val Leu Leu Asn Asn Tyr Thr Arg Asp Ile Leu Ser Asp Phe
            35                  40                  45

Lys

<210> SEQ ID NO 34
<211> LENGTH: 371
<212> TYPE: PRT
<213> ORGANISM: Adenovirus type 36

<400> SEQUENCE: 34

Met Ser Lys Arg Leu Arg Val Glu Asp Asp Phe Asn Pro Val Tyr Pro
1               5                   10                  15

Tyr Gly Tyr Ala Arg Asn Gln Asn Ile Pro Phe Leu Thr Pro Pro Phe
            20                  25                  30

Val Ser Ser Asp Gly Phe Gln Asn Phe Pro Pro Gly Val Leu Ser Leu
            35                  40                  45

Lys Leu Ala Asp Pro Ile Ala Ile Ala Asn Gly Asn Val Ser Leu Lys
    50                  55                  60

Val Gly Gly Gly Leu Thr Val Glu Gln Gln Ser Gly Lys Leu Ser Val
65                  70                  75                  80

Asp Thr Lys Ala Pro Leu Gln Val Ala Asn Asp Asn Lys Leu Glu Leu
                85                  90                  95

Ser Tyr Asp Asp Pro Phe Lys Val Glu Asn Asn Lys Leu Gly Ile Lys
            100                 105                 110

Ala Gly His Gly Leu Ala Val Val Thr Lys Glu Asn Thr Ser Leu Pro
        115                 120                 125
```

```
Ser Leu Val Gly Thr Leu Val Leu Thr Gly Lys Gly Ile Gly Thr
    130                 135                 140

Gly Ser Ser Ala His Gly Gly Thr Ile Asp Val Arg Leu Gly Glu Gly
145                 150                 155                 160

Gly Gly Leu Ser Phe Asp Glu Lys Gly Asp Leu Val Ala Trp Asp Lys
                165                 170                 175

Lys Asn Asp Thr Arg Thr Leu Trp Thr Thr Pro Asp Pro Ser Pro Asn
            180                 185                 190

Cys Lys Val Glu Thr Ala Arg Asp Ser Lys Leu Thr Leu Ala Leu Thr
        195                 200                 205

Lys Cys Gly Ser Gln Ile Leu Ala Thr Val Ser Leu Leu Val Val Thr
    210                 215                 220

Gly Lys Tyr Ala Ile Ile Ser Asp Thr Val Asn Pro Lys Gln Phe Ser
225                 230                 235                 240

Ile Lys Leu Leu Phe Asn Asp Lys Gly Val Leu Leu Ser Asp Ser Asn
                245                 250                 255

Leu Asp Gly Thr Tyr Trp Asn Tyr Arg Ser Asn Asn Asn Ile Gly
            260                 265                 270

Thr Pro Tyr Lys Glu Ala Val Gly Phe Met Pro Ser Thr Thr Ala Tyr
        275                 280                 285

Pro Lys Pro Thr Asn Asn Thr Ser Thr Asp Pro Asp Lys Lys Val Ser
    290                 295                 300

Gln Gly Lys Asn Lys Ile Val Ser Asn Ile Tyr Leu Gly Gly Glu Val
305                 310                 315                 320

Tyr Gln Pro Gly Phe Ile Val Val Lys Phe Asn Gln Glu Thr Asp Ala
                325                 330                 335

Asn Cys Ala Tyr Ser Ile Thr Phe Asp Phe Gly Trp Gly Lys Val Tyr
            340                 345                 350

Lys Asp Pro Ile Pro Tyr Asp Thr Ser Ser Phe Thr Phe Ser Tyr Ile
        355                 360                 365

Ala Gln Glu
    370

<210> SEQ ID NO 35
<211> LENGTH: 130
<212> TYPE: PRT
<213> ORGANISM: Adenovirus type 36

<400> SEQUENCE: 35

Met Ser Thr Glu Glu Gln Ser Thr Ser Leu Arg His His Pro Tyr Arg
1               5                   10                  15

Arg Ala Arg Leu Pro Arg Ser Glu Glu Thr Arg Ala Ser Leu Thr
            20                  25                  30

Glu Gln His Pro Leu Leu Pro Asp Cys Asp His Ala Glu Tyr His Asn
        35                  40                  45

Thr Val Thr Leu Asp Cys Glu Ala Arg Leu Glu Asp Phe Ser Glu Asp
    50                  55                  60

Gly Phe Ile Ser Ile Thr Asp Pro Arg Leu Ala Arg Gln Glu Thr Val
65                  70                  75                  80

Trp Ile Ile Asp Thr Lys Ser Ser Ser Arg Thr Asn Gln Asn Ile Pro
                85                  90                  95

Leu Phe Lys Ala Thr Arg Ala Glu Arg Ile Val Tyr Thr Val Lys Trp
            100                 105                 110

Ala Gly Gly Gly Arg Leu Thr Thr Arg Ala Gly Val Lys Ile Asn Lys
```

<210> SEQ ID NO 36
<211> LENGTH: 292
<212> TYPE: PRT
<213> ORGANISM: Adenovirus type 36

<400> SEQUENCE: 36

```
Met Ser Thr Glu Glu Gln Ser Thr Ser Leu Arg His His Pro Tyr Arg
1               5                   10                  15
Arg Ala Arg Leu Pro Arg Ser Glu Glu Thr Arg Ala Ser Leu Thr
            20                  25                  30
Glu Gln His Pro Leu Leu Pro Asp Cys Asp His Ala Glu Tyr His Asn
        35                  40                  45
Val Ser Ser Val Arg Gly Leu Pro Cys Ala Ala Gly Phe Thr Leu Leu
    50                  55                  60
Gln Glu Phe Pro Val Pro Trp Asp Met Ile Leu Thr Pro Glu Glu Ile
65                  70                  75                  80
Lys Ile Leu Lys Arg Cys Met Ser Val Cys Leu Cys Pro Ala Thr Leu
                85                  90                  95
Asp Leu Val Arg Ala Gln Met Val Ser Gly Tyr Glu Arg Trp Ile Leu
            100                 105                 110
His Cys His Cys Ser Ser Pro Gly Ser Leu Gln Cys Arg Ala Gly Gly
        115                 120                 125
Thr Leu Leu Ala Val Trp Phe Arg Arg Val Ile Tyr Gly Cys Met Phe
    130                 135                 140
Asn Gln Arg Phe Pro Trp Tyr Arg Gln Ile Val Asn Arg Asn Met Pro
145                 150                 155                 160
Lys Glu Ile Met Tyr Met Gly Ser Val Phe Met Arg Gly Arg His Leu
                165                 170                 175
Ile Tyr Cys Arg Ile Trp Tyr Asp Gly His Val Gly Ser Ile Ile Pro
            180                 185                 190
Asn Met Ser Phe Gly Trp Ser Thr Leu Asn Tyr Gly Leu Leu Asn Asn
        195                 200                 205
Met Val Ile Met Cys Cys Thr Tyr Cys Glu Asn Met Ser Glu Ile Arg
    210                 215                 220
Met Arg Cys Cys Ala Arg Arg Thr Arg Arg Leu Met Leu Lys Ala Val
225                 230                 235                 240
Gly Ile Ile Val Arg Glu Thr Cys Asp Pro Asp Pro Ile Cys Ser Ser
                245                 250                 255
Arg Thr Glu Pro Arg Arg Gln Arg Leu Leu Arg Ala Leu Met Glu Arg
            260                 265                 270
His Arg Pro Ile Leu Phe Ser Glu Tyr Glu Ser Val Arg Ser Ser His
        275                 280                 285
Ser Thr Arg Leu
    290
```

<210> SEQ ID NO 37
<211> LENGTH: 127
<212> TYPE: PRT
<213> ORGANISM: Adenovirus type 36

<400> SEQUENCE: 37

```
Met Cys Cys Trp Leu Tyr Pro Ala Pro Arg Val Ser Ser Pro Leu Gly
```

```
1               5                   10                  15
Tyr Asp Pro Asp Pro Arg Gly Asn Lys Asn Phe Lys Lys Met Tyr Val
                20                  25                  30

Ser Val Pro Val Pro Arg Tyr Pro Gly Leu Gly Glu Ser Ser Asp Gly
            35                  40                  45

Glu Arg Val Arg Ala Leu Asp Pro Ala Leu Pro Leu Phe Val Pro Gly
        50                  55                  60

Leu Pro Ala Val Pro Gly Gly Arg His Pro Ala Gly Arg Val Val Gln
65                  70                  75                  80

Glu Ser His Leu Arg Val His Val Gln Pro Ala Leu Pro Leu Val Pro
                85                  90                  95

Pro Asp Cys Glu Gln Lys His Ala Gln Arg Asp His Val Tyr Gly Gln
            100                 105                 110

Cys Val His Glu Gly Gln Ala Pro Asp Ile Leu Pro His Leu Val
        115                 120                 125

<210> SEQ ID NO 38
<211> LENGTH: 120
<212> TYPE: PRT
<213> ORGANISM: Adenovirus type 36

<400> SEQUENCE: 38

Met Val Leu Pro Ile Leu Pro Pro Pro Leu Asn Asp Arg Gln Gly
1               5                   10                  15

Ser Ile Asn Trp Met Gly Met Ala Tyr Arg Val Leu Ala Asp Val Met
                20                  25                  30

Arg Gly Ile Arg Met Asp Gly Leu Phe Val Ser Ser Asp Ala Glu Glu
            35                  40                  45

Leu Leu Gln Asn Leu Arg Glu Trp Met Tyr Phe Ser Trp Met Thr Glu
        50                  55                  60

Arg Gln Gln Arg Lys Asp Gly Arg Arg Gly Ile Cys Cys Ser Arg
65                  70                  75                  80

Ala Thr Phe Cys Trp Gln Lys Tyr Asp Lys Val Arg Lys Arg Val His
                85                  90                  95

Tyr Asn Glu His Arg Gly Thr Ile Asp Leu Ala Pro Pro Ser Ser Ile
            100                 105                 110

Pro Gln Gly Pro Phe Thr Thr Ile
        115                 120

<210> SEQ ID NO 39
<211> LENGTH: 117
<212> TYPE: PRT
<213> ORGANISM: Adenovirus type 36

<400> SEQUENCE: 39

Met Lys Val Cys Leu Leu Met Lys Val Glu Gly Ala Leu Trp Glu Leu
1               5                   10                  15

Phe Asn Met Cys Gly Val Asp Leu His Gln Gln Phe Val Ala Ile Ile
                20                  25                  30

Gln Gly Trp Lys Asn Glu Asn Tyr Leu Gly Met Val Gln Asp Cys Asn
            35                  40                  45

Met Met Ile Glu Glu Gln Asp Gly Gly Pro Ala Phe Asn Val Leu Leu
        50                  55                  60

Phe Leu Asp Val Arg Val Glu Pro Leu Leu Glu Ala Thr Val Glu His
65                  70                  75                  80

Leu Glu Asn Arg Ile Ile Phe Asp Leu Ala Val Cys Phe His Gln Asn
```

-continued

```
                 85                  90                  95

Ser Gly Gly Glu Arg Cys His Leu Arg Asp Leu Asn Phe Ile Leu Leu
            100                 105                 110

Arg Asp Arg Leu Glu
            115

<210> SEQ ID NO 40
<211> LENGTH: 130
<212> TYPE: PRT
<213> ORGANISM: Adenovirus type 36

<400> SEQUENCE: 40

Met Leu Glu Arg Arg Gly Val Ser Tyr His Ile Val Val Pro Gly Ala
1               5                   10                  15

Leu Val Thr Tyr Leu Glu Asp Phe Ser Ile Thr Ala Met Ile Lys Glu
            20                  25                  30

His Leu Pro Arg Phe Ile Thr His Leu Leu Glu Gly Ile Thr Gly Asp
        35                  40                  45

Thr Lys Arg Ala Tyr Ser Ser Met Gln Phe Leu Gly Ala Asn Tyr Gly
    50                  55                  60

Ala Leu Arg Tyr Ser Leu Thr Leu Ala Ser Pro Thr Leu Ser Pro Gly
65                  70                  75                  80

Ser Asp Leu Ala Ser Val Val Ala Glu Asp Leu Ser Asp Phe Leu Gln
                85                  90                  95

Leu Thr Leu Arg Arg Glu Leu Arg Ala Glu Gly Arg Asn Ser Leu Asn
            100                 105                 110

Leu Val Val Leu Asn Thr Leu Gln Val Val Glu Gln Pro Asp Leu Leu
        115                 120                 125

Leu Leu
    130

<210> SEQ ID NO 41
<211> LENGTH: 125
<212> TYPE: PRT
<213> ORGANISM: Adenovirus type 36

<400> SEQUENCE: 41

Met Ala Glu Ser Leu Tyr Ala Phe Ile Asp Ser Pro Gly Gly Ile Ala
1               5                   10                  15

Pro Val Gln Glu Gly Ala Ser Asn Arg Tyr Ile Phe Phe Cys Pro Glu
            20                  25                  30

Ser Phe His Ile Pro Pro His Gly Val Ile Leu Leu His Leu Arg Val
        35                  40                  45

Ser Val Leu Val Pro Thr Gly Tyr Gln Gly Arg Phe Met Ala Leu Asn
    50                  55                  60

Asp Tyr His Ala Arg Gly Ile Leu Thr Gln Ser Asp Val Ile Phe Ala
65                  70                  75                  80

Gly Arg Arg His Asp Leu Ser Val Leu Leu Phe Asn His Thr Asp Arg
                85                  90                  95

Phe Leu Tyr Val Arg Glu Gly His Pro Val Gly Thr Leu Leu Leu Glu
            100                 105                 110

Arg Val Ile Phe Pro Ser Val Arg Ile Ala Thr Leu Val
        115                 120                 125

<210> SEQ ID NO 42
<211> LENGTH: 230
<212> TYPE: PRT
```

-continued

<213> ORGANISM: Artificial
<220> FEATURE:
<223> OTHER INFORMATION: Synthetic Polypeptide

<400> SEQUENCE: 42

```
Met Ala Asp Glu Ala Pro Val Glu Gln Gln Ser Gly Lys Leu Ser Val
1               5                   10                  15

Asp Thr Lys Ala Pro Leu Gln Val Ala Asn Asp Asn Lys Leu Glu Leu
            20                  25                  30

Ser Tyr Asp Asp Pro Phe Lys Val Glu Asn Asn Lys Leu Gly Ile Lys
        35                  40                  45

Ala Gly His Gly Leu Ala Val Val Thr Lys Glu Asn Thr Ser Leu Pro
    50                  55                  60

Ser Leu Val Gly Thr Leu Val Val Gly Ser Ser Ala His Gly Gly Thr
65                  70                  75                  80

Ile Asp Val Arg Leu Gly Glu Gly Gly Leu Ser Phe Asp Glu Lys
                85                  90                  95

Gly Thr Val Ser Leu Leu Val Val Thr Gly Lys Tyr Ala Ile Ile Ser
            100                 105                 110

Asp Thr Val Asn Pro Lys Gln Phe Ser Ile Lys Leu Leu Phe Asn Asp
        115                 120                 125

Lys Gly Val Leu Leu Ser Asp Ser Asn Leu Asp Gly Thr Tyr Trp Asn
130                 135                 140

Tyr Arg Ser Asn Asn Asn Ile Gly Thr Pro Tyr Lys Glu Ala Val
145                 150                 155                 160

Gly Phe Met Pro Ser Thr Thr Ala Tyr Pro Lys Pro Thr Asn Asn Thr
                165                 170                 175

Ser Thr Asp Pro Asp Lys Lys Val Ser Gln Gly Lys Asn Lys Ile Val
            180                 185                 190

Ser Asn Thr Asp Ala Asn Cys Ala Tyr Ser Ile Thr Phe Asp Phe Gly
        195                 200                 205

Trp Gly Lys Val Tyr Lys Asp Pro Ile Pro Tyr Asp Thr Ser Ser Phe
    210                 215                 220

His His His His His His
225                 230
```

<210> SEQ ID NO 43
<211> LENGTH: 200
<212> TYPE: PRT
<213> ORGANISM: Artificial
<220> FEATURE:
<223> OTHER INFORMATION: Synthetic Polypeptide

<400> SEQUENCE: 43

```
Met Ala Asp Glu Ala Pro Thr Asp Lys Glu Arg Gln Asn Gly Gly Gln
1               5                   10                  15

Pro Pro Thr Thr Lys Asp Val Thr Lys Thr Phe Gly Val Ala Ala Arg
            20                  25                  30

Gly Gly Leu His Ile Thr Asp Lys Gly Leu Gln Ile Gly Glu Asp Glu
        35                  40                  45

Asn Asn Glu Asp Gly Glu Glu Glu Ile Tyr Ala Asp Lys Thr Phe Gln
    50                  55                  60

Pro Glu Pro Gln Val Gly Glu Asn Trp Gln Asp Thr Asp Val Phe
65                  70                  75                  80

Tyr Gly Gly Arg Ala Leu Lys Lys Glu Glu Lys Gly Gly Gln Ala Lys
                85                  90                  95
```

```
Phe Leu Asn Gly Glu Asn Gly Gln Pro Ser Lys Asp Gln Asp Ile Thr
            100                 105                 110

Leu Ala Phe Phe Asp Leu Lys Gln Asn Asp Thr Gly Thr Thr Gln Asn
            115                 120                 125

Gln Pro Asp Val Val Met Tyr Thr Glu Asn Val Tyr Leu Gly Lys Glu
130                 135                 140

Asp Thr Ser Ser Ala Ala Asn Leu Thr Asp Gly Ser Gly Ser Asn Thr
145                 150                 155                 160

Ala Tyr Gln Gly Val Lys Tyr Glu Asn Gly Ala Gly Asn Gly Ser Trp
                165                 170                 175

Lys Val Asp Gly Glu Val Ala Ser Gln Asn Gln Ile Ala Lys Gly Asn
            180                 185                 190

Leu Tyr His His His His His His
            195                 200

<210> SEQ ID NO 44
<211> LENGTH: 955
<212> TYPE: PRT
<213> ORGANISM: Artificial
<220> FEATURE:
<223> OTHER INFORMATION: Synthetic Polypeptide

<400> SEQUENCE: 44

Met Ala Asp Glu Ala Pro Ala Thr Pro Ser Met Met Pro Gln Trp Ala
1               5                   10                  15

Tyr Met His Ile Ala Gly Gln Asp Ala Ser Glu Tyr Leu Ser Pro Gly
            20                  25                  30

Leu Val Gln Phe Ala Arg Ala Thr Asp Thr Tyr Phe Ser Leu Gly Asn
        35                  40                  45

Lys Phe Arg Asn Pro Thr Val Ala Pro Thr His Asp Val Thr Thr Asp
50                  55                  60

Arg Ser Gln Arg Leu Thr Leu Arg Phe Val Pro Val Asp Arg Glu Asp
65                  70                  75                  80

Thr Thr Tyr Ser Tyr Lys Ala Arg Phe Thr Leu Ala Val Gly Asp Asn
                85                  90                  95

Arg Val Leu Asp Met Ala Ser Thr Tyr Phe Asp Ile Arg Gly Val Leu
            100                 105                 110

Asp Arg Gly Pro Ser Phe Lys Pro Tyr Ser Gly Thr Ala Tyr Asn Ser
            115                 120                 125

Leu Ala Pro Lys Gly Ala Pro Asn Ser Ser Gln Trp Thr Asp Lys Glu
130                 135                 140

Arg Gln Asn Gly Gly Gln Pro Thr Thr Lys Asp Val Thr Lys Thr
145                 150                 155                 160

Phe Gly Val Ala Ala Arg Gly Gly Leu His Ile Thr Asp Lys Gly Leu
                165                 170                 175

Gln Ile Gly Glu Asp Glu Asn Asn Glu Asp Gly Glu Glu Ile Tyr
            180                 185                 190

Ala Asp Lys Thr Phe Gln Pro Glu Pro Gln Val Gly Glu Glu Asn Trp
            195                 200                 205

Gln Asp Thr Asp Val Phe Tyr Gly Gly Arg Ala Leu Lys Lys Glu Thr
            210                 215                 220

Lys Met Lys Pro Cys Tyr Gly Ser Phe Ala Arg Pro Thr Asn Glu Lys
225                 230                 235                 240

Gly Gly Gln Ala Lys Phe Leu Asn Gly Glu Asn Gly Gln Pro Ser Lys
                245                 250                 255
```

Asp Gln Asp Ile Thr Leu Ala Phe Phe Asp Leu Lys Gln Asn Asp Thr
                260                 265                 270

Gly Thr Thr Gln Asn Gln Pro Asp Val Val Met Tyr Thr Glu Asn Val
            275                 280                 285

Tyr Leu Glu Thr Pro Asp Thr His Val Val Tyr Lys Pro Gly Lys Glu
        290                 295                 300

Asp Thr Ser Ser Ala Ala Asn Leu Thr Gln Gln Ser Met Pro Asn Arg
305                 310                 315                 320

Pro Asn Tyr Ile Gly Phe Arg Asp Asn Phe Val Gly Leu Met Tyr Tyr
                325                 330                 335

Asn Ser Thr Gly Asn Met Gly Val Leu Ala Gly Gln Ala Ser Gln Leu
            340                 345                 350

Asn Ala Val Val Asp Leu Gln Asp Arg Asn Thr Glu Leu Ser Tyr Gln
        355                 360                 365

Leu Leu Leu Asp Ser Leu Gly Asp Arg Thr Arg Tyr Phe Ser Met Trp
370                 375                 380

Asn Ser Ala Val Asp Ser Tyr Asp Pro Asp Val Arg Ile Ile Glu Asn
385                 390                 395                 400

His Gly Val Glu Asp Glu Leu Pro Asn Tyr Cys Phe Pro Leu Asp Gly
                405                 410                 415

Ser Gly Ser Asn Thr Ala Tyr Gln Gly Val Lys Tyr Glu Asn Gly Ala
            420                 425                 430

Gly Asn Gly Ser Trp Lys Val Asp Gly Glu Val Ala Ser Gln Asn Gln
        435                 440                 445

Ile Ala Lys Gly Asn Leu Tyr Ala Met Glu Ile Asn Leu Gln Ala Asn
450                 455                 460

Leu Trp Lys Ser Phe Leu Tyr Ser Asn Val Ala Leu Tyr Leu Pro Asp
465                 470                 475                 480

Ser Tyr Lys Tyr Thr Pro Ala Asn Ile Thr Leu Pro Thr Asn Thr Asn
                485                 490                 495

Thr Tyr Glu Tyr Met Asn Gly Arg Val Val Ala Pro Ser Leu Val Asp
            500                 505                 510

Ala Tyr Val Asn Ile Gly Ala Arg Trp Ser Leu Asp Pro Met Asp Asn
        515                 520                 525

Val Asn Pro Phe Asn His His Arg Asn Ala Gly Leu Arg Tyr Arg Ser
530                 535                 540

Met Leu Leu Gly Asn Gly Arg Tyr Val Pro Phe His Ile Gln Val Pro
545                 550                 555                 560

Gln Lys Phe Phe Ala Ile Lys Asn Leu Leu Leu Pro Gly Ser Tyr
                565                 570                 575

Thr Tyr Glu Trp Asn Phe Arg Lys Asp Val Asn Met Ile Leu Gln Ser
            580                 585                 590

Ser Leu Gly Asn Asp Leu Arg Val Asp Gly Ala Ser Val Arg Phe Asp
        595                 600                 605

Ser Val Asn Leu Tyr Ala Thr Phe Phe Pro Met Ala His Asn Thr Ala
610                 615                 620

Ser Thr Leu Glu Ala Met Leu Arg Asn Asp Thr Asn Asp Gln Ser Phe
625                 630                 635                 640

Asn Asp Tyr Leu Ser Ala Ala Asn Met Leu Tyr Pro Ile Pro Ala Lys
                645                 650                 655

Ala Thr Asn Val Pro Ile Ser Ile Pro Ser Arg Asn Trp Ala Ala Phe
            660                 665                 670

Arg Gly Trp Ser Phe Thr Arg Leu Lys Thr Lys Glu Thr Pro Ser Leu 675                 680                 685
Gly Ser Gly Phe Asp Pro Tyr Phe Val Tyr Ser Gly Ser Ile Pro Tyr
            690                 695                 700

Leu Asp Gly Thr Phe Tyr Leu Asn His Thr Phe Lys Lys Val Ser Ile
705                 710                 715                 720

Met Phe Asp Ser Ser Val Ser Trp Pro Gly Asn Asp Arg Leu Leu Thr
                725                 730                 735

Pro Asn Glu Phe Glu Ile Lys Arg Ser Val Asp Gly Glu Gly Tyr Asn
            740                 745                 750

Val Ala Gln Cys Asn Met Thr Lys Asp Trp Phe Leu Val Gln Met Leu
        755                 760                 765

Ser His Tyr Asn Ile Gly Tyr Gln Gly Phe Tyr Val Pro Glu Gly Tyr
    770                 775                 780

Lys Asp Arg Met Tyr Ser Phe Phe Arg Asn Phe Gln Pro Met Ser Arg
785                 790                 795                 800

Gln Val Val Asp Glu Ile Asn Tyr Lys Asp Tyr Lys Ala Val Thr Leu
                805                 810                 815

Pro Phe Gln His Asn Asn Ser Gly Phe Thr Gly Tyr Leu Ala Pro Thr
            820                 825                 830

Met Arg Gln Gly Gln Pro Tyr Pro Ala Asn Phe Pro Tyr Pro Leu Ile
        835                 840                 845

Gly Gln Thr Ala Val Pro Ser Val Thr Gln Lys Lys Phe Leu Cys Asp
    850                 855                 860

Arg Val Met Trp Arg Ile Pro Phe Ser Ser Asn Phe Met Ser Met Gly
865                 870                 875                 880

Ala Leu Thr Asp Leu Gly Gln Asn Met Leu Tyr Ala Asn Ser Ala His
                885                 890                 895

Ala Leu Asp Met Thr Phe Glu Val Asp Pro Met Asp Glu Pro Thr Leu
            900                 905                 910

Leu Tyr Leu Leu Phe Glu Val Phe Asp Val Val Arg Val His Gln Pro
        915                 920                 925

His Arg Gly Val Ile Glu Ala Val Tyr Leu Arg Thr Pro Phe Ser Ala
    930                 935                 940

Gly Asn Ala Thr Thr His His His His His His
945                 950                 955

<210> SEQ ID NO 45
<211> LENGTH: 418
<212> TYPE: PRT
<213> ORGANISM: Artificial
<220> FEATURE:
<223> OTHER INFORMATION: Synthetic Polypeptide

<400> SEQUENCE: 45

Met Ala Asp Glu Ala Pro Val Glu Gln Gln Ser Gly Lys Leu Ser Val
1               5                   10                  15

Asp Thr Lys Ala Pro Leu Gln Val Ala Asn Asp Asn Lys Leu Glu Leu
            20                  25                  30

Ser Tyr Asp Asp Pro Phe Lys Val Glu Asn Asn Lys Leu Gly Ile Lys
        35                  40                  45

Ala Gly His Gly Leu Ala Val Val Thr Lys Glu Asn Thr Ser Leu Pro
    50                  55                  60

Ser Leu Val Gly Thr Leu Val Val Gly Ser Ser Ala His Gly Gly Thr
65                  70                  75                  80

Ile Asp Val Arg Leu Gly Glu Gly Gly Gly Leu Ser Phe Asp Glu Lys

```
                    85                  90                  95
Gly Thr Val Ser Leu Leu Val Val Thr Gly Lys Tyr Ala Ile Ile Ser
                100                 105                 110

Asp Thr Val Asn Pro Lys Gln Phe Ser Ile Lys Leu Leu Phe Asn Asp
                115                 120                 125

Lys Gly Val Leu Leu Ser Asp Ser Asn Leu Asp Gly Thr Tyr Trp Asn
            130                 135                 140

Tyr Arg Ser Asn Asn Asn Ile Gly Thr Pro Tyr Lys Glu Ala Val
145                 150                 155                 160

Gly Phe Met Pro Ser Thr Thr Ala Tyr Pro Lys Pro Thr Asn Asn Thr
                165                 170                 175

Ser Thr Asp Pro Asp Lys Lys Val Ser Gln Gly Lys Asn Lys Ile Val
                180                 185                 190

Ser Asn Thr Asp Ala Asn Cys Ala Tyr Ser Ile Thr Phe Asp Phe Gly
                195                 200                 205

Trp Gly Lys Val Tyr Lys Asp Pro Ile Pro Tyr Asp Thr Ser Ser Phe
            210                 215                 220

Thr Asp Lys Glu Arg Gln Asn Gly Gly Gln Pro Pro Thr Thr Lys Asp
225                 230                 235                 240

Val Thr Lys Thr Phe Gly Val Ala Ala Arg Gly Leu His Ile Thr
                245                 250                 255

Asp Lys Gly Leu Gln Ile Gly Glu Asp Glu Asn Asn Glu Asp Gly Glu
                260                 265                 270

Glu Glu Ile Tyr Ala Asp Lys Thr Phe Gln Pro Glu Pro Gln Val Gly
                275                 280                 285

Glu Glu Asn Trp Gln Asp Thr Asp Val Phe Tyr Gly Arg Ala Leu
                290                 295                 300

Lys Lys Glu Glu Lys Gly Gly Gln Ala Lys Phe Leu Asn Gly Glu Asn
305                 310                 315                 320

Gly Gln Pro Ser Lys Asp Gln Asp Ile Thr Leu Ala Phe Phe Asp Leu
                325                 330                 335

Lys Gln Asn Asp Thr Gly Thr Thr Gln Asn Gln Pro Asp Val Val Met
                340                 345                 350

Tyr Thr Glu Asn Val Tyr Leu Gly Lys Glu Asp Thr Ser Ser Ala Ala
                355                 360                 365

Asn Leu Thr Asp Gly Ser Gly Ser Asn Thr Ala Tyr Gln Gly Val Lys
            370                 375                 380

Tyr Glu Asn Gly Ala Gly Asn Gly Ser Trp Lys Val Asp Gly Glu Val
385                 390                 395                 400

Ala Ser Gln Asn Gln Ile Ala Lys Gly Asn Leu Tyr His His His
                405                 410                 415

His His

<210> SEQ ID NO 46
<211> LENGTH: 418
<212> TYPE: PRT
<213> ORGANISM: Artificial
<220> FEATURE:
<223> OTHER INFORMATION: Synthetic Polypeptide

<400> SEQUENCE: 46

Met Ala Asp Glu Ala Pro Thr Asp Lys Glu Arg Gln Asn Gly Gly Gln
1               5                   10                  15

Pro Pro Thr Thr Lys Asp Val Thr Lys Thr Phe Gly Val Ala Ala Arg
                20                  25                  30
```

Gly Gly Leu His Ile Thr Asp Lys Gly Leu Gln Ile Gly Glu Asp Glu
        35                  40                  45

Asn Asn Glu Asp Gly Glu Glu Ile Tyr Ala Asp Lys Thr Phe Gln
 50                  55                  60

Pro Glu Pro Gln Val Gly Glu Asn Trp Gln Asp Thr Asp Val Phe
 65                  70                  75                  80

Tyr Gly Gly Arg Ala Leu Lys Lys Glu Lys Gly Gly Gln Ala Lys
                 85                  90                  95

Phe Leu Asn Gly Glu Asn Gly Gln Pro Ser Lys Asp Gln Asp Ile Thr
             100                 105                 110

Leu Ala Phe Phe Asp Leu Lys Gln Asn Asp Thr Gly Thr Thr Gln Asn
             115                 120                 125

Gln Pro Asp Val Val Met Tyr Thr Glu Asn Val Tyr Leu Gly Lys Glu
130                 135                 140

Asp Thr Ser Ser Ala Ala Asn Leu Thr Asp Gly Ser Gly Ser Asn Thr
145                 150                 155                 160

Ala Tyr Gln Gly Val Lys Tyr Glu Asn Gly Ala Gly Asn Gly Ser Trp
                 165                 170                 175

Lys Val Asp Gly Glu Val Ala Ser Gln Asn Gln Ile Ala Lys Gly Asn
             180                 185                 190

Leu Tyr Val Glu Gln Gln Ser Gly Lys Leu Ser Val Asp Thr Lys Ala
             195                 200                 205

Pro Leu Gln Val Ala Asn Asp Asn Lys Leu Glu Leu Ser Tyr Asp Asp
             210                 215                 220

Pro Phe Lys Val Glu Asn Asn Lys Leu Gly Ile Lys Ala Gly His Gly
225                 230                 235                 240

Leu Ala Val Val Thr Lys Glu Asn Thr Ser Leu Pro Ser Leu Val Gly
                 245                 250                 255

Thr Leu Val Val Gly Ser Ser Ala His Gly Thr Ile Asp Val Arg
             260                 265                 270

Leu Gly Glu Gly Gly Gly Leu Ser Phe Asp Glu Lys Gly Thr Val Ser
             275                 280                 285

Leu Leu Val Val Thr Gly Lys Tyr Ala Ile Ile Ser Asp Thr Val Asn
             290                 295                 300

Pro Lys Gln Phe Ser Ile Lys Leu Leu Phe Asn Asp Lys Gly Val Leu
305                 310                 315                 320

Leu Ser Asp Ser Asn Leu Asp Gly Thr Tyr Trp Asn Tyr Arg Ser Asn
                 325                 330                 335

Asn Asn Asn Ile Gly Thr Pro Tyr Lys Glu Ala Val Gly Phe Met Pro
             340                 345                 350

Ser Thr Thr Ala Tyr Pro Lys Pro Thr Asn Asn Thr Ser Thr Asp Pro
             355                 360                 365

Asp Lys Lys Val Ser Gln Gly Lys Asn Lys Ile Val Ser Asn Thr Asp
370                 375                 380

Ala Asn Cys Ala Tyr Ser Ile Thr Phe Asp Phe Gly Trp Gly Lys Val
385                 390                 395                 400

Tyr Lys Asp Pro Ile Pro Tyr Asp Thr Ser Ser Phe His His His His
                 405                 410                 415

His His

<210> SEQ ID NO 47
<211> LENGTH: 166
<212> TYPE: PRT

```
<213> ORGANISM: Artificial
<220> FEATURE:
<223> OTHER INFORMATION: Synthetic Polypeptide

<400> SEQUENCE: 47

Met Ala Asp Glu Ala Pro Arg Thr Tyr Phe Gly Ile Pro Cys Arg His
1               5                   10                  15

Gln Ile His Lys Thr Ile Asn Phe Thr Phe Glu Glu Gln Val Asn Phe
            20                  25                  30

Thr Cys Lys Pro His Lys Lys Tyr Val Thr Trp Phe Tyr Gln Asn Thr
        35                  40                  45

Thr Thr Val Ala Pro Glu Thr Asn Leu Leu Ser Asp Thr Asn Thr Pro
    50                  55                  60

Lys Thr Gly Gly Glu Leu Trp Val Pro Ser Leu Thr Glu Gly Gly Ser
65                  70                  75                  80

His Ile Glu Ala Ala Pro Lys Pro Glu Val Tyr Thr Gln Val Asn Val
                85                  90                  95

Thr Arg Gly Gly Asn Ala Thr Leu Asp Gly Pro Phe Asn Asn Asn Thr
            100                 105                 110

Trp Thr Arg Tyr His Asp Asp Gly Arg Lys Asn Gly Trp Met Phe Asn
        115                 120                 125

Ile Ser Ser Gly Lys Tyr Lys Val Gln Ser Tyr Thr Asn Ser Tyr Asn
    130                 135                 140

Gly Leu Asp Gly Tyr Glu Lys Leu Glu Val Lys Met Phe Asn Leu Thr
145                 150                 155                 160

His His His His His His
                165

<210> SEQ ID NO 48
<211> LENGTH: 315
<212> TYPE: PRT
<213> ORGANISM: Artificial
<220> FEATURE:
<223> OTHER INFORMATION: Synthetic Polypeptide

<400> SEQUENCE: 48

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Thr Ser Val Glu Gln Gln Ser
                85                  90                  95

Gly Lys Leu Ser Val Asp Thr Lys Ala Pro Leu Gln Val Ala Asn Asp
            100                 105                 110

Asn Lys Leu Glu Leu Ser Tyr Asp Asp Pro Phe Lys Val Glu Asn Asn
        115                 120                 125

Lys Leu Gly Ile Lys Ala Gly His Gly Leu Ala Val Val Thr Lys Glu
    130                 135                 140

Asn Thr Ser Leu Pro Ser Leu Val Gly Thr Leu Val Val Gly Ser Ser
145                 150                 155                 160
```

```
Ala His Gly Gly Thr Ile Asp Val Arg Leu Gly Glu Gly Gly Gly Leu
            165                 170                 175

Ser Phe Asp Glu Lys Gly Thr Val Ser Leu Leu Val Val Thr Gly Lys
            180                 185                 190

Tyr Ala Ile Ile Ser Asp Thr Val Asn Pro Lys Gln Phe Ser Ile Lys
            195                 200                 205

Leu Leu Phe Asn Asp Lys Gly Val Leu Leu Ser Asp Ser Asn Leu Asp
            210                 215                 220

Gly Thr Tyr Trp Asn Tyr Arg Ser Asn Asn Asn Ile Gly Thr Pro
225                 230                 235                 240

Tyr Lys Glu Ala Val Gly Phe Met Pro Ser Thr Thr Ala Tyr Pro Lys
            245                 250                 255

Pro Thr Asn Asn Thr Ser Thr Asp Pro Asp Lys Lys Val Ser Gln Gly
            260                 265                 270

Lys Asn Lys Ile Val Ser Asn Thr Asp Ala Asn Cys Ala Tyr Ser Ile
            275                 280                 285

Thr Phe Asp Phe Gly Trp Gly Lys Val Tyr Lys Asp Pro Ile Pro Tyr
            290                 295                 300

Asp Thr Ser Ser Phe His His His His His His
305                 310                 315

<210> SEQ ID NO 49
<211> LENGTH: 218
<212> TYPE: PRT
<213> ORGANISM: Artificial
<220> FEATURE:
<223> OTHER INFORMATION: Synthetic Polypeptide

<400> SEQUENCE: 49

Val Glu Gln Gln Ser Gly Lys Leu Ser Val Asp Thr Lys Ala Pro Leu
1               5                   10                  15

Gln Val Ala Asn Asp Asn Lys Leu Glu Leu Ser Tyr Asp Asp Pro Phe
            20                  25                  30

Lys Val Glu Asn Asn Lys Leu Gly Ile Lys Ala Gly His Gly Leu Ala
            35                  40                  45

Val Val Thr Lys Glu Asn Thr Ser Leu Pro Ser Leu Val Gly Thr Leu
    50                  55                  60

Val Val Gly Ser Ser Ala His Gly Gly Thr Ile Asp Val Arg Leu Gly
65                  70                  75                  80

Glu Gly Gly Gly Leu Ser Phe Asp Glu Lys Gly Thr Val Ser Leu Leu
                85                  90                  95

Val Val Thr Gly Lys Tyr Ala Ile Ile Ser Asp Thr Val Asn Pro Lys
            100                 105                 110

Gln Phe Ser Ile Lys Leu Leu Phe Asn Asp Lys Gly Val Leu Leu Ser
            115                 120                 125

Asp Ser Asn Leu Asp Gly Thr Tyr Trp Asn Tyr Arg Ser Asn Asn Asn
            130                 135                 140

Asn Ile Gly Thr Pro Tyr Lys Glu Ala Val Gly Phe Met Pro Ser Thr
145                 150                 155                 160

Thr Ala Tyr Pro Lys Pro Thr Asn Asn Thr Ser Thr Asp Pro Asp Lys
                165                 170                 175

Lys Val Ser Gln Gly Lys Asn Lys Ile Val Ser Asn Thr Asp Ala Asn
            180                 185                 190

Cys Ala Tyr Ser Ile Thr Phe Asp Phe Gly Trp Gly Lys Val Tyr Lys
            195                 200                 205
```

```
Asp Pro Ile Pro Tyr Asp Thr Ser Ser Phe
    210                 215

<210> SEQ ID NO 50
<211> LENGTH: 285
<212> TYPE: PRT
<213> ORGANISM: Artificial
<220> FEATURE:
<223> OTHER INFORMATION: Synthetic Polypeptide

<400> SEQUENCE: 50

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Thr Ser Thr Asp Lys Glu Arg
                85                  90                  95

Gln Asn Gly Gly Gln Pro Pro Thr Thr Lys Asp Val Thr Lys Thr Phe
            100                 105                 110

Gly Val Ala Ala Arg Gly Gly Leu His Ile Thr Asp Lys Gly Leu Gln
        115                 120                 125

Ile Gly Glu Asp Glu Asn Asn Glu Asp Gly Glu Glu Ile Tyr Ala
    130                 135                 140

Asp Lys Thr Phe Gln Pro Glu Pro Gln Val Gly Glu Glu Asn Trp Gln
145                 150                 155                 160

Asp Thr Asp Val Phe Tyr Gly Arg Ala Leu Lys Lys Glu Glu Lys
                165                 170                 175

Gly Gly Gln Ala Lys Phe Leu Asn Gly Glu Asn Gly Gln Pro Ser Lys
            180                 185                 190

Asp Gln Asp Ile Thr Leu Ala Phe Phe Asp Leu Lys Asn Asp Thr
        195                 200                 205

Gly Thr Thr Gln Asn Gln Pro Asp Val Val Met Tyr Thr Glu Asn Val
    210                 215                 220

Tyr Leu Gly Lys Glu Asp Thr Ser Ser Ala Ala Asn Leu Thr Asp Gly
225                 230                 235                 240

Ser Gly Ser Asn Thr Ala Tyr Gln Gly Val Lys Tyr Glu Asn Gly Ala
                245                 250                 255

Gly Asn Gly Ser Trp Lys Val Asp Gly Glu Val Ala Ser Gln Asn Gln
            260                 265                 270

Ile Ala Lys Gly Asn Leu Tyr His His His His His
        275                 280                 285

<210> SEQ ID NO 51
<211> LENGTH: 188
<212> TYPE: PRT
<213> ORGANISM: Artificial
<220> FEATURE:
<223> OTHER INFORMATION: Synthetic Polypeptide

<400> SEQUENCE: 51

Thr Asp Lys Glu Arg Gln Asn Gly Gly Gln Pro Pro Thr Thr Lys Asp
1               5                   10                  15
```

Val Thr Lys Thr Phe Gly Val Ala Ala Arg Gly Gly Leu His Ile Thr
            20                  25                  30

Asp Lys Gly Leu Gln Ile Gly Glu Asp Glu Asn Asn Glu Asp Gly Glu
        35                  40                  45

Glu Glu Ile Tyr Ala Asp Lys Thr Phe Gln Pro Glu Pro Gln Val Gly
50                  55                  60

Glu Glu Asn Trp Gln Asp Thr Asp Val Phe Tyr Gly Gly Arg Ala Leu
65                  70                  75                  80

Lys Lys Glu Glu Lys Gly Gly Gln Ala Lys Phe Leu Asn Gly Glu Asn
                85                  90                  95

Gly Gln Pro Ser Lys Asp Gln Asp Ile Thr Leu Ala Phe Phe Asp Leu
            100                 105                 110

Lys Gln Asn Asp Thr Gly Thr Thr Gln Asn Gln Pro Asp Val Val Met
            115                 120                 125

Tyr Thr Glu Asn Val Tyr Leu Gly Lys Glu Asp Thr Ser Ala Ala
        130                 135                 140

Asn Leu Thr Asp Gly Ser Gly Ser Asn Thr Ala Tyr Gln Gly Val Lys
145                 150                 155                 160

Tyr Glu Asn Gly Ala Gly Asn Gly Ser Trp Lys Val Asp Gly Glu Val
                165                 170                 175

Ala Ser Gln Asn Gln Ile Ala Lys Gly Asn Leu Tyr
            180                 185

<210> SEQ ID NO 52
<211> LENGTH: 1040
<212> TYPE: PRT
<213> ORGANISM: Artificial
<220> FEATURE:
<223> OTHER INFORMATION: Synthetic Polypeptide

<400> SEQUENCE: 52

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Thr Ser Ala Thr Pro Ser Met
                85                  90                  95

Met Pro Gln Trp Ala Tyr Met His Ile Ala Gly Gln Asp Ala Ser Glu
            100                 105                 110

Tyr Leu Ser Pro Gly Leu Val Gln Phe Ala Arg Ala Thr Asp Thr Tyr
            115                 120                 125

Phe Ser Leu Gly Asn Lys Phe Arg Asn Pro Thr Val Ala Pro Thr His
            130                 135                 140

Asp Val Thr Thr Asp Arg Ser Gln Arg Leu Thr Leu Arg Phe Val Pro
145                 150                 155                 160

Val Asp Arg Glu Asp Thr Thr Tyr Ser Tyr Lys Ala Arg Phe Thr Leu
                165                 170                 175

Ala Val Gly Asp Asn Arg Val Leu Asp Met Ala Ser Thr Tyr Phe Asp
            180                 185                 190

```
Ile Arg Gly Val Leu Asp Arg Gly Pro Ser Phe Lys Pro Tyr Ser Gly
            195                 200                 205

Thr Ala Tyr Asn Ser Leu Ala Pro Lys Gly Ala Pro Asn Ser Ser Gln
    210                 215                 220

Trp Thr Asp Lys Glu Arg Gln Asn Gly Gly Gln Pro Pro Thr Thr Lys
225                 230                 235                 240

Asp Val Thr Lys Thr Phe Gly Val Ala Ala Arg Gly Gly Leu His Ile
                245                 250                 255

Thr Asp Lys Gly Leu Gln Ile Gly Glu Asp Glu Asn Asn Glu Asp Gly
            260                 265                 270

Glu Glu Glu Ile Tyr Ala Asp Lys Thr Phe Gln Pro Glu Pro Gln Val
            275                 280                 285

Gly Glu Glu Asn Trp Gln Asp Thr Asp Val Phe Tyr Gly Gly Arg Ala
        290                 295                 300

Leu Lys Lys Glu Thr Lys Met Lys Pro Cys Tyr Gly Ser Phe Ala Arg
305                 310                 315                 320

Pro Thr Asn Glu Lys Gly Gly Gln Ala Lys Phe Leu Asn Gly Glu Asn
                325                 330                 335

Gly Gln Pro Ser Lys Asp Gln Asp Ile Thr Leu Ala Phe Phe Asp Leu
            340                 345                 350

Lys Gln Asn Asp Thr Gly Thr Thr Gln Asn Gln Pro Asp Val Val Met
            355                 360                 365

Tyr Thr Glu Asn Val Tyr Leu Glu Thr Pro Asp Thr His Val Val Tyr
        370                 375                 380

Lys Pro Gly Lys Glu Asp Thr Ser Ser Ala Ala Asn Leu Thr Gln Gln
385                 390                 395                 400

Ser Met Pro Asn Arg Pro Asn Tyr Ile Gly Phe Arg Asp Asn Phe Val
                405                 410                 415

Gly Leu Met Tyr Tyr Asn Ser Thr Gly Asn Met Gly Val Leu Ala Gly
            420                 425                 430

Gln Ala Ser Gln Leu Asn Ala Val Val Asp Leu Gln Asp Arg Asn Thr
            435                 440                 445

Glu Leu Ser Tyr Gln Leu Leu Leu Asp Ser Leu Gly Asp Arg Thr Arg
        450                 455                 460

Tyr Phe Ser Met Trp Asn Ser Ala Val Asp Ser Tyr Asp Pro Asp Val
465                 470                 475                 480

Arg Ile Ile Glu Asn His Gly Val Glu Asp Glu Leu Pro Asn Tyr Cys
                485                 490                 495

Phe Pro Leu Asp Gly Ser Gly Ser Asn Thr Ala Tyr Gln Gly Val Lys
            500                 505                 510

Tyr Glu Asn Gly Ala Gly Asn Gly Ser Trp Lys Val Asp Gly Glu Val
            515                 520                 525

Ala Ser Gln Asn Gln Ile Ala Lys Gly Asn Leu Tyr Ala Met Glu Ile
    530                 535                 540

Asn Leu Gln Ala Asn Leu Trp Lys Ser Phe Leu Tyr Ser Asn Val Ala
545                 550                 555                 560

Leu Tyr Leu Pro Asp Ser Tyr Lys Tyr Thr Pro Ala Asn Ile Thr Leu
                565                 570                 575

Pro Thr Asn Thr Asn Thr Tyr Glu Tyr Met Asn Gly Arg Val Val Ala
            580                 585                 590

Pro Ser Leu Val Asp Ala Tyr Val Asn Ile Gly Ala Arg Trp Ser Leu
            595                 600                 605
```

Asp Pro Met Asp Asn Val Asn Pro Phe Asn His His Arg Asn Ala Gly
610             615                 620

Leu Arg Tyr Arg Ser Met Leu Leu Gly Asn Gly Arg Tyr Val Pro Phe
625                 630                 635                 640

His Ile Gln Val Pro Gln Lys Phe Phe Ala Ile Lys Asn Leu Leu Leu
                645                 650                 655

Leu Pro Gly Ser Tyr Thr Tyr Glu Trp Asn Phe Arg Lys Asp Val Asn
                660                 665                 670

Met Ile Leu Gln Ser Ser Leu Gly Asn Asp Leu Arg Val Asp Gly Ala
                675                 680                 685

Ser Val Arg Phe Asp Ser Val Asn Leu Tyr Ala Thr Phe Phe Pro Met
690                 695                 700

Ala His Asn Thr Ala Ser Thr Leu Glu Ala Met Leu Arg Asn Asp Thr
705                 710                 715                 720

Asn Asp Gln Ser Phe Asn Asp Tyr Leu Ser Ala Ala Asn Met Leu Tyr
                725                 730                 735

Pro Ile Pro Ala Lys Ala Thr Asn Val Pro Ile Ser Ile Pro Ser Arg
                740                 745                 750

Asn Trp Ala Ala Phe Arg Gly Trp Ser Phe Thr Arg Leu Lys Thr Lys
                755                 760                 765

Glu Thr Pro Ser Leu Gly Ser Gly Phe Asp Pro Tyr Phe Val Tyr Ser
770                 775                 780

Gly Ser Ile Pro Tyr Leu Asp Gly Thr Phe Tyr Leu Asn His Thr Phe
785                 790                 795                 800

Lys Lys Val Ser Ile Met Phe Asp Ser Ser Val Ser Trp Pro Gly Asn
                805                 810                 815

Asp Arg Leu Leu Thr Pro Asn Glu Phe Glu Ile Lys Arg Ser Val Asp
                820                 825                 830

Gly Glu Gly Tyr Asn Val Ala Gln Cys Asn Met Thr Lys Asp Trp Phe
                835                 840                 845

Leu Val Gln Met Leu Ser His Tyr Asn Ile Gly Tyr Gln Gly Phe Tyr
                850                 855                 860

Val Pro Glu Gly Tyr Lys Asp Arg Met Tyr Ser Phe Phe Arg Asn Phe
865                 870                 875                 880

Gln Pro Met Ser Arg Gln Val Val Asp Glu Ile Asn Tyr Lys Asp Tyr
                885                 890                 895

Lys Ala Val Thr Leu Pro Phe Gln His Asn Asn Ser Gly Phe Thr Gly
                900                 905                 910

Tyr Leu Ala Pro Thr Met Arg Gln Gly Gln Pro Tyr Pro Ala Asn Phe
                915                 920                 925

Pro Tyr Pro Leu Ile Gly Gln Thr Ala Val Pro Ser Val Thr Gln Lys
930                 935                 940

Lys Phe Leu Cys Asp Arg Val Met Trp Arg Ile Pro Phe Ser Ser Asn
945                 950                 955                 960

Phe Met Ser Met Gly Ala Leu Thr Asp Leu Gly Gln Asn Met Leu Tyr
                965                 970                 975

Ala Asn Ser Ala His Ala Leu Asp Met Thr Phe Glu Val Asp Pro Met
                980                 985                 990

Asp Glu Pro Thr Leu Leu Tyr Leu Leu Phe Glu Val Phe Asp Val Val
                995                 1000                1005

Arg Val His Gln Pro His Arg Gly Val Ile Glu Ala Val Tyr Leu
        1010                1015                1020

Arg Thr Pro Phe Ser Ala Gly Asn Ala Thr Thr His His His His

His His
    1040

<210> SEQ ID NO 53
<211> LENGTH: 943
<212> TYPE: PRT
<213> ORGANISM: Artificial
<220> FEATURE:
<223> OTHER INFORMATION: Synthetic Polypeptide

<400> SEQUENCE: 53

Ala Thr Pro Ser Met Met Pro Gln Trp Ala Tyr Met His Ile Ala Gly
1               5                   10                  15

Gln Asp Ala Ser Glu Tyr Leu Ser Pro Gly Leu Val Gln Phe Ala Arg
            20                  25                  30

Ala Thr Asp Thr Tyr Phe Ser Leu Gly Asn Lys Phe Arg Asn Pro Thr
        35                  40                  45

Val Ala Pro Thr His Asp Val Thr Thr Asp Arg Ser Gln Arg Leu Thr
    50                  55                  60

Leu Arg Phe Val Pro Val Asp Arg Glu Asp Thr Thr Tyr Ser Tyr Lys
65                  70                  75                  80

Ala Arg Phe Thr Leu Ala Val Gly Asp Asn Arg Val Leu Asp Met Ala
                85                  90                  95

Ser Thr Tyr Phe Asp Ile Arg Gly Val Leu Asp Arg Gly Pro Ser Phe
            100                 105                 110

Lys Pro Tyr Ser Gly Thr Ala Tyr Asn Ser Leu Ala Pro Lys Gly Ala
        115                 120                 125

Pro Asn Ser Ser Gln Trp Thr Asp Lys Glu Arg Gln Asn Gly Gly Gln
    130                 135                 140

Pro Pro Thr Thr Lys Asp Val Thr Lys Thr Phe Gly Val Ala Ala Arg
145                 150                 155                 160

Gly Gly Leu His Ile Thr Asp Lys Gly Leu Gln Ile Gly Glu Asp Glu
                165                 170                 175

Asn Asn Glu Asp Gly Glu Glu Ile Tyr Ala Asp Lys Thr Phe Gln
            180                 185                 190

Pro Glu Pro Gln Val Gly Glu Glu Asn Trp Gln Asp Thr Asp Val Phe
        195                 200                 205

Tyr Gly Gly Arg Ala Leu Lys Lys Glu Thr Lys Met Lys Pro Cys Tyr
    210                 215                 220

Gly Ser Phe Ala Arg Pro Thr Asn Glu Lys Gly Gly Gln Ala Lys Phe
225                 230                 235                 240

Leu Asn Gly Glu Asn Gly Gln Pro Ser Lys Asp Gln Asp Ile Thr Leu
                245                 250                 255

Ala Phe Phe Asp Leu Lys Gln Asn Asp Thr Gly Thr Thr Gln Asn Gln
            260                 265                 270

Pro Asp Val Val Met Tyr Thr Glu Asn Val Tyr Leu Glu Thr Pro Asp
        275                 280                 285

Thr His Val Val Tyr Lys Pro Gly Lys Glu Asp Thr Ser Ser Ala Ala
    290                 295                 300

Asn Leu Thr Gln Gln Ser Met Pro Asn Arg Pro Asn Tyr Ile Gly Phe
305                 310                 315                 320

Arg Asp Asn Phe Val Gly Leu Met Tyr Tyr Asn Ser Thr Gly Asn Met
                325                 330                 335

Gly Val Leu Ala Gly Gln Ala Ser Gln Leu Asn Ala Val Val Asp Leu

```
            340                 345                 350
Gln Asp Arg Asn Thr Glu Leu Ser Tyr Gln Leu Leu Asp Ser Leu
            355                 360                 365
Gly Asp Arg Thr Arg Tyr Phe Ser Met Trp Asn Ser Ala Val Asp Ser
            370                 375                 380
Tyr Asp Pro Asp Val Arg Ile Ile Glu Asn His Gly Val Glu Asp Glu
385                 390                 395                 400
Leu Pro Asn Tyr Cys Phe Pro Leu Asp Gly Ser Gly Ser Asn Thr Ala
                405                 410                 415
Tyr Gln Gly Val Lys Tyr Glu Asn Gly Ala Gly Asn Gly Ser Trp Lys
            420                 425                 430
Val Asp Gly Glu Val Ala Ser Gln Asn Gln Ile Ala Lys Gly Asn Leu
            435                 440                 445
Tyr Ala Met Glu Ile Asn Leu Gln Ala Asn Leu Trp Lys Ser Phe Leu
            450                 455                 460
Tyr Ser Asn Val Ala Leu Tyr Leu Pro Asp Ser Tyr Lys Tyr Thr Pro
465                 470                 475                 480
Ala Asn Ile Thr Leu Pro Thr Asn Thr Asn Thr Tyr Glu Tyr Met Asn
                485                 490                 495
Gly Arg Val Val Ala Pro Ser Leu Val Asp Ala Tyr Val Asn Ile Gly
                500                 505                 510
Ala Arg Trp Ser Leu Asp Pro Met Asp Asn Val Asn Pro Phe Asn His
            515                 520                 525
His Arg Asn Ala Gly Leu Arg Tyr Arg Ser Met Leu Leu Gly Asn Gly
            530                 535                 540
Arg Tyr Val Pro Phe His Ile Gln Val Pro Gln Lys Phe Phe Ala Ile
545                 550                 555                 560
Lys Asn Leu Leu Leu Pro Gly Ser Tyr Thr Tyr Glu Trp Asn Phe
                565                 570                 575
Arg Lys Asp Val Asn Met Ile Leu Gln Ser Ser Leu Gly Asn Asp Leu
            580                 585                 590
Arg Val Asp Gly Ala Ser Val Arg Phe Asp Ser Val Asn Leu Tyr Ala
            595                 600                 605
Thr Phe Phe Pro Met Ala His Asn Thr Ala Ser Thr Leu Glu Ala Met
            610                 615                 620
Leu Arg Asn Asp Thr Asn Asp Gln Ser Phe Asn Asp Tyr Leu Ser Ala
625                 630                 635                 640
Ala Asn Met Leu Tyr Pro Ile Pro Ala Lys Ala Thr Asn Val Pro Ile
                645                 650                 655
Ser Ile Pro Ser Arg Asn Trp Ala Ala Phe Arg Gly Trp Ser Phe Thr
                660                 665                 670
Arg Leu Lys Thr Lys Glu Thr Pro Ser Leu Gly Ser Gly Phe Asp Pro
            675                 680                 685
Tyr Phe Val Tyr Ser Gly Ser Ile Pro Tyr Leu Asp Gly Thr Phe Tyr
            690                 695                 700
Leu Asn His Thr Phe Lys Lys Val Ser Ile Met Phe Asp Ser Ser Val
705                 710                 715                 720
Ser Trp Pro Gly Asn Asp Arg Leu Leu Thr Pro Asn Glu Phe Glu Ile
                725                 730                 735
Lys Arg Ser Val Asp Gly Glu Gly Tyr Asn Val Ala Gln Cys Asn Met
                740                 745                 750
Thr Lys Asp Trp Phe Leu Val Gln Met Leu Ser His Tyr Asn Ile Gly
            755                 760                 765
```

Tyr Gln Gly Phe Tyr Val Pro Glu Gly Tyr Lys Asp Arg Met Tyr Ser
                770             775             780

Phe Phe Arg Asn Phe Gln Pro Met Ser Arg Gln Val Val Asp Glu Ile
785             790             795             800

Asn Tyr Lys Asp Tyr Lys Ala Val Thr Leu Pro Phe Gln His Asn Asn
            805             810             815

Ser Gly Phe Thr Gly Tyr Leu Ala Pro Thr Met Arg Gln Gly Gln Pro
            820             825             830

Tyr Pro Ala Asn Phe Pro Tyr Pro Leu Ile Gly Gln Thr Ala Val Pro
            835             840             845

Ser Val Thr Gln Lys Lys Phe Leu Cys Asp Arg Val Met Trp Arg Ile
    850             855             860

Pro Phe Ser Ser Asn Phe Met Ser Met Gly Ala Leu Thr Asp Leu Gly
865             870             875             880

Gln Asn Met Leu Tyr Ala Asn Ser Ala His Ala Leu Asp Met Thr Phe
            885             890             895

Glu Val Asp Pro Met Asp Glu Pro Thr Leu Leu Tyr Leu Leu Phe Glu
            900             905             910

Val Phe Asp Val Val Arg Val His Gln Pro His Arg Gly Val Ile Glu
            915             920             925

Ala Val Tyr Leu Arg Thr Pro Phe Ser Ala Gly Asn Ala Thr Thr
    930             935             940

<210> SEQ ID NO 54
<211> LENGTH: 251
<212> TYPE: PRT
<213> ORGANISM: Artificial
<220> FEATURE:
<223> OTHER INFORMATION: Synthetic Polypeptide

<400> SEQUENCE: 54

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Thr Ser Arg Thr Tyr Phe Gly
            85                  90                  95

Ile Pro Cys Arg His Gln Ile His Lys Thr Ile Asn Phe Thr Phe Glu
            100             105             110

Glu Gln Val Asn Phe Thr Cys Lys Pro His Lys Lys Tyr Val Thr Trp
        115             120             125

Phe Tyr Gln Asn Thr Thr Thr Val Ala Pro Glu Thr Asn Leu Leu Ser
    130             135             140

Asp Thr Asn Thr Pro Lys Thr Gly Gly Glu Leu Trp Val Pro Ser Leu
145             150             155             160

Thr Glu Gly Gly Ser His Ile Glu Ala Ala Pro Lys Pro Glu Val Tyr
            165             170             175

Thr Gln Val Asn Val Thr Arg Gly Gly Asn Ala Thr Leu Asp Gly Pro
            180             185             190

```
Phe Asn Asn Asn Thr Trp Thr Arg Tyr His Asp Asp Gly Arg Lys Asn
            195                 200                 205
Gly Trp Met Phe Asn Ile Ser Ser Gly Lys Tyr Lys Val Gln Ser Tyr
    210                 215                 220
Thr Asn Ser Tyr Asn Gly Leu Asp Gly Tyr Glu Lys Leu Glu Val Lys
225                 230                 235                 240
Met Phe Asn Leu Thr His His His His His His
            245                 250
```

<210> SEQ ID NO 55
<211> LENGTH: 154
<212> TYPE: PRT
<213> ORGANISM: Artificial
<220> FEATURE:
<223> OTHER INFORMATION: Synthetic Polypeptide

<400> SEQUENCE: 55

```
Arg Thr Tyr Phe Gly Ile Pro Cys Arg His Gln Ile His Lys Thr Ile
1               5                   10                  15
Asn Phe Thr Phe Glu Glu Gln Val Asn Phe Thr Cys Lys Pro His Lys
            20                  25                  30
Lys Tyr Val Thr Trp Phe Tyr Gln Asn Thr Thr Val Ala Pro Glu
        35                  40                  45
Thr Asn Leu Leu Ser Asp Thr Asn Thr Pro Lys Thr Gly Gly Glu Leu
    50                  55                  60
Trp Val Pro Ser Leu Thr Glu Gly Gly Ser His Ile Glu Ala Ala Pro
65                  70                  75                  80
Lys Pro Glu Val Tyr Thr Gln Val Asn Val Thr Arg Gly Gly Asn Ala
                85                  90                  95
Thr Leu Asp Gly Pro Phe Asn Asn Asn Thr Trp Thr Arg Tyr His Asp
            100                 105                 110
Asp Gly Arg Lys Asn Gly Trp Met Phe Asn Ile Ser Ser Gly Lys Tyr
        115                 120                 125
Lys Val Gln Ser Tyr Thr Asn Ser Tyr Asn Gly Leu Asp Gly Tyr Glu
    130                 135                 140
Lys Leu Glu Val Lys Met Phe Asn Leu Thr
145                 150
```

<210> SEQ ID NO 56
<211> LENGTH: 89
<212> TYPE: PRT
<213> ORGANISM: Saccharomyces cerevisiae

<400> SEQUENCE: 56

```
Met Arg Phe Pro Ser Ile Phe Thr Ala Val Leu Phe Ala Ala Ser Ser
1               5                   10                  15
Ala Ser Ala Ala Pro Val Asn Thr Thr Thr Glu Asp Glu Thr Ala Gln
            20                  25                  30
Ile Pro Ala Glu Ala Val Ile Gly Tyr Leu Asp Leu Glu Gly Asp Phe
        35                  40                  45
Asp Val Ala Val Leu Pro Phe Ser Asn Ser Thr Asn Asn Gly Leu Leu
    50                  55                  60
Phe Ile Asn Thr Thr Ile Ala Ser Ile Ala Ala Lys Glu Glu Gly Val
65                  70                  75                  80
Ser Leu Asp Lys Arg Glu Ala Glu Ala
                85
```

```
<210> SEQ ID NO 57
<211> LENGTH: 89
<212> TYPE: PRT
<213> ORGANISM: Saccharomyces cerevisiae

<400> SEQUENCE: 57

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 58
<211> LENGTH: 6
<212> TYPE: PRT
<213> ORGANISM: Artificial
<220> FEATURE:
<223> OTHER INFORMATION: Synthetic Peptide

<400> SEQUENCE: 58

Met Ala Asp Glu Ala Pro
1               5
```

COMPOSITIONS AND METHODS FOR THE TREATMENT OR PREVENTION OF HUMAN ADENOVIRUS-36 INFECTION

CROSS-REFERENCE TO RELATED APPLICATIONS

This application is a national stage application under 35 U.S.C. 371 of PCT Application No. PCT/US2011/65868, having an international filing date of Dec. 19, 2011, which designated the United States, which PCT application claims the benefit of priority under 35 U.S.C. §119(e) from U.S. Provisional Application No. 61/424,472, filed Dec. 17, 2010, the entire disclosure of which is hereby incorporated by reference.

REFERENCE TO A SEQUENCE LISTING

This application contains a Sequence Listing submitted electronically as a text file by EFS-Web. The text file, named "3923-33-PCT_ST25", has a size in bytes of 211 KB, and was recorded on 16 Dec. 2011. The information contained in the text file is incorporated herein by reference in its entirety pursuant to 37 CFR §1.52(e)(5).

FIELD OF THE INVENTION

The present invention generally relates to immunotherapeutic compositions and methods for the prevention and/or treatment of human adenovirus-36 infection, as well as the prevention and/or treatment of obesity and/or obesity-associated disorders or other sequela related to human adenovirus-36 infection.

BACKGROUND OF THE INVENTION

The terms "obesity" and "overweight" or "pre-obese" define ranges of weights that are greater than weights that are generally considered to be healthy for a person of a given height. According to a report in August 2010 by the Centers for Disease Control (CDC), "no state met the *Healthy people 2010* obesity target of 15%, and the self-reported prevalence of obesity among U.S. adults had increased 1.1 percentage points from 2007" (Sherry et al., Morbidity and Mortality Weekly Report (MMWR), 59; 1-5; Aug. 3, 2010). In children and teens, excess weight represents a very serious health issue. The 2007-2008 National Health and Nutrition Examination Survey (NHANES) estimated that 17% of individuals age 2-19 are obese (CDC). Indeed, the CDC and the WHO have referred to an "obesity epidemic" in many populations worldwide. Overweight and obese individuals have a higher likelihood of developing a variety of health problems including, but not limited to, cardiovascular diseases and associated conditions (e.g., high blood pressure, high cholesterol), type 2 diabetes, respiratory disorders, cancer, reproductive disorders, hepatic dysfunction, and osteoarthritis.

Several different factors can contribute to obesity or being overweight, and the condition can be a complex health issue for many individuals. Behavioral factors, environmental factors, genetics, illness, and/or infectious agents may play a role in the condition. Lack of sufficient physical activity and excess calorie intake in the diet, i.e., caloric imbalance, are the most apparent and common causes of being overweight or obese. However, there appear to be several genetic factors that may predispose certain individuals to weight gain, including mutations in genes related to control of feeding behavior, and various genetic mutations or correlations of genotype with obesity in individuals and populations. In addition to these factors, various illnesses and drugs can also impact an individual's weight. More recently, infectious agents have been identified as contributing to some cases of obesity.

A few infectious agents have been associated with obesity in non-human animals, and one in particular has been associated with human obesity. Human adenovirus-36 (also denoted Ad-36, Adv-36, or hAdv-36) was first described in a child with diabetes in 1980 (Wigand et al., 1980, *Arch. Viol.* 64(3):225-233). Beginning in the early 1990's, experiments by Dhurandhar and colleagues first showed that Ad-36 increased adiposity in chickens and in mice ((Dhurandhar et al., 1990, *J. Bombay Vet. College* 2:131-132; Dhurandhar et al., 1992, *Vet. Microbiol.*, 31:101-107; Dhurandhar et al., 2000, *Int J Obes Relat Metab Disord* 24:989-996; Dhurandar et al., 2001, *Int. J. Obes. Relat. Metab. Disord.* 25(7):990-996), as well as in monkeys (Dhurandhar, et al., 2002, *J. Nutr.* 132(10):3155-3160). In mice and chickens, infection with Ad-36 resulted in viremia, infection of adipose tissue, increased visceral fat, total body fat, and/or body weight, and reduced serum cholesterol and triglycerides. In monkeys, Ad-36 promoted weight gain and lowered serum cholesterol. Pasarica and colleagues have shown that human Ad-36 induces adiposity, increases insulin sensitivity, and alters hypothalamic monoamines in rats (Pasarica et al., 2006, *Obesity* 14(11):1905-1913).

In humans, Ad-36 has been shown to have a high probability of being associated with obesity, where a unique phenotype of low serum cholesterol and triglyceride levels was present in about 30% of obese humans subjects having anti-Ad-36 antibodies, whereas only 5% of the non-obese humans tested had antibodies to Ad-36 (Dhurandhar et al., 1997, *FASEB J*, 3:A230; Atkinson et al., 1998, *Int J Obes Relat Metab Disord* 22(Suppl): S57). An epidemiological study showed that 30% of obese people were infected with Ad-36 compared to only 11% of lean people in the study (Atkinson et al., 2005, *Int J Obes* (Lond), 29(3):281-286). These investigators showed that Ad-36 is associated with increased body weight and the reduction of serum lipids in humans. Additional researchers have reported an association between human Ad-36 and lipid disorders or obesity rates in children and adolescents worldwide (Na et al., 2010, *Int. J. Obes.* 34:89-93; Gabbert et al., 2010, *Pediatrics* 2010; 126:721-726; and Atkinson et al., 2010, *Int. J. Ped. Obes.* 5:157-160). Further work by Pasarica and Dhurandhar and colleagues showed that Ad-36 induces commitment, differentiation, and lipid accumulation in human adipose-derived stem cells (Pasarica et al., 2008, Stem Cells 26:969-978). Moreover, in vitro adipogenesis was shown to be accelerated by infection of preadipocytes with human Ad-36 (Vangipuram et al., 2004, Obes. Res. 12(5):770-777), and infection was also shown to increase insulin sensitivity and suppress the expression of leptin mRNA (Vangipuram et al., 2007, *Int. J. Obes.* (Lond.) 31(1):87-96. The activity of the E4 orf1 gene of Ad-36 has been suggested to be responsible for this adipogenesis (Rogers et al., 2008, *International Journal of Obesity* 32:397-406).

In 2010, Arnold and colleagues reported the complete characterization of the human Ad-36 genome (Arnold et al., 2010, Virus Res. 149:152-161). Diagnostic assays have been described for the identification of Ad-36 infection in human tissues, via identification or use of anti-Ad-36 antibodies (see, e.g., WO 98/44946, WO 2007/120362), and a diagnostic test for Ad-36 is in commercial development (Scandivir AB). However, a treatment for the viral infection, once identified, is lacking; no preventative or therapeutic treatment that directly targets Ad-36 infection is currently commercially available. Accordingly, there remains a need in the art for an effective prophylactic and/or therapeutic treatment for adenovirus-36 infection, in order to reduce or eliminate Ad-36-associated obesity and overweight conditions.

SUMMARY OF THE INVENTION

One embodiment of the invention relates to an immunotherapeutic composition comprising: (a) a yeast vehicle; and (b) an adenovirus-36 (Ad-36) antigen comprising one or more Ad-36 proteins and/or immunogenic domains of such proteins. In one aspect, the Ad-36 proteins include at least one protein selected from, but is not limited to: hexon, fiber, CR1α, and CR1γ, and/or at least one immunogenic domain of at least one of the proteins. In one aspect, the Ad-36 proteins include at least one immunogenic domain of CR1α and at least one immunogenic domain of CR1γ.

In one aspect, the Ad-36 antigen comprises Ad-36 sequences, wherein the Ad-36 sequences consist of: positions 71-136 of Ad-36 of SEQ ID NO:34 or a corresponding sequence from another Ad-36 strain; positions 145-169 of SEQ ID NO:34 or a corresponding sequence from another Ad-36 strain; positions 290-313 of SEQ ID NO:34 or a corresponding sequence from another Ad-36 strain; and positions 334-363 of Ad-36 SEQ ID NO:34 or a corresponding sequence from another Ad-36 strain. For example, such an Ad-36 antigen can include, but is not limited to, an amino acid sequence selected from the group consisting of: SEQ ID NO:42 or a corresponding sequence from another Ad-36 strain, SEQ ID NO:48 or a corresponding sequence from another Ad-36 strain and SEQ ID NO:49 or a corresponding sequence from another Ad-36 strain.

In one aspect, the Ad-36 antigen comprises Ad-36 sequences, wherein the Ad-36 sequences consist of: positions 136-218 of SEQ ID NO:18 or a corresponding sequence from another Ad-36 strain; positions 235-285 of SEQ ID NO:18 or a corresponding sequence from another Ad-36 strain; positions 297-308 of SEQ ID NO:18 or a corresponding sequence from another Ad-36 strain; and positions 410-450 of SEQ ID NO:18 or a corresponding sequence from another Ad-36 strain. For example, such an Ad-36 antigen can include, but is not limited to, SEQ ID NO:43 or a corresponding sequence from another Ad-36 strain, SEQ ID NO:50 or a corresponding sequence from another Ad-36 strain and SEQ ID NO:51 or a corresponding sequence from another Ad-36 strain.

In another aspect, the Ad-36 antigen comprises Ad-36 sequences, wherein the Ad-36 sequences consist of positions 2-944 of SEQ ID NO:18 or a corresponding sequence from another Ad-36 strain. For example, such an Ad-36 antigen can include, but is not limited to, SEQ ID NO:44 or a corresponding sequence from another Ad-36 strain, SEQ ID NO:52 or a corresponding sequence from another Ad-36 strain and SEQ ID NO:53 or a corresponding sequence from another Ad-36 strain.

In yet another aspect, the Ad-36 antigen comprises Ad-36 sequences, wherein the Ad-36 sequences consist of: positions 71-136 of SEQ ID NO:34 or a corresponding sequence from another Ad-36 strain; positions 145-169 of SEQ ID NO:34 or a corresponding sequence from another Ad-36 strain; positions 290-313 of SEQ ID NO:34 or a corresponding sequence from another Ad-36 strain; positions 334-363 of SEQ ID NO:34 or a corresponding sequence from another Ad-36 strain; positions 136-218 of SEQ ID NO:18 or a corresponding sequence from another Ad-36 strain; positions 235-285 of SEQ ID NO:18 or a corresponding sequence from another Ad-36 strain; positions 297-308 of SEQ ID NO:18 or a corresponding sequence from another Ad-36 strain; and positions 410-450 of SEQ ID NO:18 or a corresponding sequence from another Ad-36 strain. For example, such an Ad-36 antigen can include, but is not limited to, SEQ ID NO: 45 or a corresponding sequence from another Ad-36 strain, and positions 7 to 418 of SEQ ID NO:45 or a corresponding sequence from another Ad-36 strain.

In another aspect, the Ad-36 antigen comprises Ad-36 sequences, wherein the Ad-36 sequences consist of: positions 136-218 of SEQ ID NO:18 or a corresponding sequence from another Ad-36 strain; positions 235-285 of SEQ ID NO:18 or a corresponding sequence from another Ad-36 strain; positions 297-308 of SEQ ID NO:18 or a corresponding sequence from another Ad-36 strain; positions 410-450 of SEQ ID NO:18 or a corresponding sequence from another Ad-36 strain; positions 71-136 of SEQ ID NO:34 or a corresponding sequence from another Ad-36 strain; positions 145-169 of SEQ ID NO:34 or a corresponding sequence from another Ad-36 strain; positions 290-313 of SEQ ID NO:34 or a corresponding sequence from another Ad-36 strain; and positions 334-363 of SEQ ID NO:34 or a corresponding sequence from another Ad-36 strain. For example, such an Ad-36 antigen can include, but is not limited to, SEQ ID NO:46 or a corresponding sequence from another Ad-36 strain, and positions 7 to 418 of SEQ ID NO:46 or a corresponding sequence from another Ad-36 strain.

In another aspect, the Ad-36 antigen comprises Ad-36 sequences, wherein the Ad-36 sequences consist of: positions 18-60 of SEQ ID NO:26 or a corresponding sequence from another Ad-36 strain; positions 123-157 SEQ ID NO:26 or a corresponding sequence from another Ad-36 strain; positions 19-60 of SEQ ID NO:29 or a corresponding sequence from another Ad-36 strain; and positions 83-116 of SEQ ID NO:29 or a corresponding sequence from another Ad-36 strain. For example, such an Ad-36 antigen can include, but is not limited to, SEQ ID NO:47 or a corresponding sequence from another Ad-36 strain, SEQ ID NO:54 or a corresponding sequence from another Ad-36 strain, and SEQ ID NO:55 or a corresponding sequence from another Ad-36 strain.

In any of the aspects or embodiments of the invention described above or elsewhere herein, in one aspect, the Ad-36 antigen is expressed by the yeast vehicle. In one aspect, the yeast vehicle is a whole yeast. In one aspect, the yeast is killed. In one aspect, the yeast is heat-inactivated. In one aspect, the yeast vehicle is from a genus selected from: *Saccharomyces, Candida, Cryptococcus, Hansenula, Kluyveromyces, Pichia, Rhodotorula, Schizosaccharomyces* and *Yarrowia*. In one aspect, the yeast vehicle is from *Saccharomyces*. In one aspect, the yeast vehicle is from *Saccharomyces cerevisiae.*

In any of the aspects or embodiments of the invention described above or elsewhere herein, in one aspect, a composition of the invention is formulated in a pharmaceutically acceptable excipient suitable for administration to an individual.

Another embodiment of the invention relates to a fusion protein comprising two or more Ad-36 proteins and/or immunogenic domains of one or more Ad-36 proteins, wherein the Ad-36 proteins include at least one protein selected from: hexon, fiber, CR1α, and CR1γ, and/or at least one immunogenic domain of at least one of the proteins. In one aspect, the Ad-36 proteins include E4 or at least one immunogenic domain thereof. In one aspect, the Ad-36 proteins include at least one immunogenic domain of CR1α and at least one immunogenic domain of CR1γ. In one aspect, the fusion protein comprises: (a) Ad-36 sequences consisting of: positions 71-136 of Ad-36 of SEQ ID NO:34 or a corresponding sequence from another Ad-36 strain; positions 145-169 of SEQ ID NO:34 or a corresponding sequence from another Ad-36 strain; positions 290-313 of SEQ ID NO:34 or a corresponding sequence from another Ad-36 strain; and positions 334-363 of Ad-36 SEQ ID NO:34 or a corresponding sequence from another Ad-36 strain; (b) Ad-36 sequences consisting of: positions 136-218 of SEQ ID NO:18 or a corresponding sequence from another Ad-36 strain; positions 235-285 of SEQ ID NO:18 or a corresponding sequence from another Ad-36 strain; positions 297-308 of SEQ ID NO:18 or a corresponding sequence from another Ad-36 strain; and positions 410-450 of SEQ ID NO:18 or a corresponding sequence from another Ad-36 strain; (c) Ad-36 sequences consisting of: positions 2-944 of SEQ ID NO:18 or a corresponding sequence from another Ad-36 strain; (d) Ad-36 sequences consisting of: positions 71-136 of SEQ ID NO:34 or a corresponding sequence from another Ad-36 strain; positions 145-169 of SEQ ID NO:34 or a corresponding sequence from another Ad-36 strain; positions 290-313 of SEQ ID NO:34 or a corresponding sequence from another Ad-36 strain; positions 334-363 of SEQ ID NO:34 or a corresponding sequence from another Ad-36 strain; positions 136-218 of SEQ ID NO:18 or a corresponding sequence from another Ad-36 strain; positions 235-285 of SEQ ID NO:18 or a corresponding sequence from another Ad-36 strain; positions 297-308 of SEQ ID NO:18 or a corresponding sequence from another Ad-36 strain; and positions 410-450 of SEQ ID NO:18 or a corresponding sequence from another Ad-36 strain; (e) Ad-36 sequences consisting of: positions 136-218 of SEQ ID NO:18 or a corresponding sequence from another Ad-36 strain; positions 235-285 of SEQ ID NO:18 or a corresponding sequence from another Ad-36 strain; positions 297-308 of SEQ ID NO:18 or a corresponding sequence from another Ad-36 strain; positions 410-450 of SEQ ID NO:18 or a corresponding sequence from another Ad-36 strain; positions 71-136 of SEQ ID NO:34 or a corresponding sequence from another Ad-36 strain; positions 145-169 of SEQ ID NO:34 or a corresponding sequence from another Ad-36 strain; positions 290-313 of SEQ ID NO:34 or a corresponding sequence from another Ad-36 strain; and positions 334-363 of SEQ ID NO:34 or a corresponding sequence from another Ad-36 strain; or (f) Ad-36 sequences consisting of: positions 18-60 of SEQ ID NO:26 or a corresponding sequence from another Ad-36 strain; positions 123-157 SEQ ID NO:26 or a corresponding sequence from another Ad-36 strain; positions 19-60 of SEQ ID NO:29 or a corresponding sequence from another Ad-36 strain; and positions 83-116 of SEQ ID NO:29 or a corresponding sequence from another Ad-36 strain. In one aspect, the fusion protein is selected from the group of: SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, and SEQ ID NO:55.

Yet another embodiment of the invention relates to a recombinant nucleic acid molecule encoding any of the fusion proteins described above or elsewhere herein.

Another embodiment of the invention relates to an isolated cell transfected with the recombinant nucleic acid molecule above. In one aspect, the cell is a yeast cell.

Further embodiments of the invention relate to a composition comprising any of the fusion proteins, recombinant nucleic acid molecules, or isolated cells, described above or elsewhere herein. In any of these embodiments, in one aspect, the composition further comprises at least one biological response modifier.

Another embodiment of the invention relates to a method to treat adenovirus-36 (Ad-36) infection in a subject. The method includes the step of administering to a subject that has been infected with Ad-36 any of the compositions described above or elsewhere herein, wherein administration of the composition to the subject reduces Ad-36 infection in the subject. In one aspect, administration of the composition to the subject reduces Ad-36 viral load in the subject.

Yet another embodiment of the invention relates to a method to treat adenovirus-36 (Ad-36) infection in a subject. The method includes the step of administering to a subject that has been infected with Ad-36 any of the compositions described above or elsewhere herein, wherein administration of the composition to the subject reduces the rate of weight gain in the subject.

Another embodiment of the invention relates to a method to treat adenovirus-36 (Ad-36)-associated obesity or excess weight in a subject. The method includes the step of administering to a subject that has been infected with Ad-36 and has a body mass index (BMI) of at least 25, any of the compositions described above or elsewhere herein, wherein administration of the composition to the subject reduces the BMI in the subject.

Yet another embodiment of the invention relates to a method to treat adenovirus-36 (Ad-36)-associated obesity or excess weight in a subject. The method includes the step of administering to a subject that has been infected with Ad-36 and has a body mass index (BMI) of less than 25, any of the compositions described above or elsewhere herein, wherein administration of the composition to the subject reduces the BMI in the subject or reduces the rate of weight gain in the subject.

Another embodiment of the invention relates to a method to elicit an antigen-specific, T cell-mediated immune response against an Ad-36 antigen. The method includes the step of administering to a subject any of the compositions described above or elsewhere herein.

Yet another embodiment of the invention relates to a method to prevent Ad-36 infection in a subject or to reduce the rate of weight gain in a subject. The method includes the step of administering to a subject that has not been infected with Ad-36 any of the compositions described above or elsewhere herein. In one aspect, the subject has a BMI of less than 25. In one aspect, the subject has a BMI of 25 or greater. In one aspect, the subject is between age 2 and age 19. In one aspect, the subject is an adult.

Another embodiment of the invention relates to a method to immunize a population of individuals against Ad-36 infection, comprising administering to the population of individuals any of the compositions described above or elsewhere herein. In one aspect, the individuals are adults. In one aspect, the individuals are age 2 to 19. In one aspect, the individuals have a BMI of 25 or greater. In one aspect, the individuals have a BMI of less than 25.

Another embodiment of the invention relates to any of the compositions described above or elsewhere herein for use to treat Ad-36 infection.

Yet another embodiment of the invention relates to any of the compositions described above or elsewhere herein for use to prevent Ad-36 infection.

Another embodiment of the invention relates to any of the compositions described above or elsewhere herein for use to reduce the rate of weight gain in an individual infected with Ad-36.

Another embodiment of the invention relates to any of the compositions described above or elsewhere herein for use to elicit an Ad-36 immune response in an individual.

Yet another embodiment of the invention relates to the use of any of the compositions described above or elsewhere herein in the preparation of a medicament to treat Ad-36 infection.

Another embodiment of the invention relates to the use of any of the compositions described above or elsewhere herein in the preparation of a medicament to prevent Ad-36 infection.

Another embodiment of the invention relates to the use of any of the compositions described above or elsewhere herein in the preparation of a medicament for reducing the rate of weight gain in an individual infected with Ad-36.

DETAILED DESCRIPTION OF THE INVENTION

Figure 1:
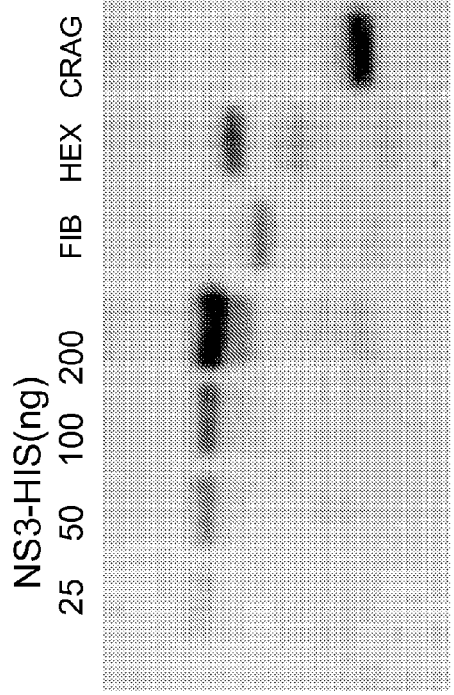
FIG. 1 is a digitized image of a western blot showing expression of: (1) a yeast-based immunotherapy composition expressing an Ad-36 fusion protein comprising fiber (FIB) (SEQ ID NO:42) under the control of a TEF2 promoter; (2) a yeast-based immunotherapy composition expressing an Ad-36 fusion protein comprising hexon (HEX) (SEQ ID NO:43) under the control of a TEF2 promoter; and (3) a yeast-based immunotherapy composition expressing an Ad-36 fusion protein comprising CR1α and CR1γ (CRAG) (SEQ ID NO:47) under the control of a TEF2 promoter.

This invention generally relates to immunotherapeutic compositions and methods for the prevention and/or treatment of adenovirus-36 (Ad-36) infection, as well as the prevention and/or treatment of obesity, obesity-associated disorders related to adenovirus-36 infection, and adipose tissue hypertrophy related to Ad-36 infection. The invention includes a yeast-based immunotherapeutic composition (also referred to as yeast-based immunotherapy) comprising a yeast vehicle and Ad-36 antigen(s) that have been designed to elicit a prophylactic and/or therapeutic immune response against Ad-36 infection in a subject. The invention includes the use of such compositions to prevent and/or treat Ad-36 infection. The invention also includes the recombinant nucleic acid molecules used in the yeast-based compositions of the invention, as well as the proteins encoded thereby, for use in any immunotherapeutic composition and/or therapeutic protocol for Ad-36 infection.

The yeast-based, Ad-36-specific immunotherapeutic compositions of the invention induce innate immune responses, as well as adaptive immune responses that specifically target Ad-36, including CD4-dependent TH17 and TH1 T cell responses and antigen-specific CD8$^+$ T cell responses, which include cytotoxic T lymphocyte (CTL) responses. In addition, yeast-based, Ad-36-specific immunotherapeutic compositions of the invention modulate regulatory T cell (Treg) numbers and/or functionality. The breadth of the immune response elicited by Ad-36-specific yeast-based immunotherapy can be modulated toward the desired type of immune response (e.g., TH1 versus TH17 versus Treg), and is well-suited to target Ad-36. In contrast to vaccines that immunize by generating neutralizing antibody responses, yeast-based immunotherapeutic compositions targeting Ad-36 elicit antigen-specific, broad-based, and potent cellular immune responses, including CD4+ T cell responses that are believed to be particularly effective in providing immunity against adenoviruses, since early adenovirus infection may inhibit MHC class I expression. The ability of yeast-based immunotherapy to enhance TH17 T cell responses is also believed to be useful, since IL-17 blocks differentiation of precursor fat cells into bonafide adipocytes and also promotes lipolysis (Shin et al., 2009).

Yeast-based immunotherapy is also highly adept at activating antigen presenting cells, and has a unique ability to cross-prime the immune response, generating CD8+ CTL responses that are typically effective against viral infections, even in the face of what may otherwise be a suppressive environment. Yeast-based immunotherapy can be designed to target regions of Ad-36 that are specific to this virus, or to target regions that are conserved among many adenovirus serotypes and/or to target a mixture of these regions, making the vaccine highly adaptable to the needs of the infected individual, and to target both protective and therapeutic immunity. Since this type of immunotherapy utilizes the natural ability of the antigen presenting cell to present relevant immunogens, it is not necessary to know the precise identity of CTL epitopes or MHC Class II epitopes to produce an effective immunotherapeutic and indeed, multiple CD4 and CD8 T cell epitopes can be targeted in a single composition. Therefore, yeast-based Ad-36 immunotherapy, by activating both the innate and the adaptive immune response, is expected to effectively target Ad-36-infected cells for non-cytopathic clearance, destruction, or both. In addition to being effective in treating excess weight or controlling the rate of weight gain, as well as in treating conditions related to excess weight or weight gain that are associated with Ad-36 infection, the yeast-based immunotherapeutic compositions of the invention are expected to be effective in cases where adipose tissue displays abnormal growth or hypertrophy that is associated with the presence of Ad-36, such as occurs in patients infected with HIV. Indeed, prior to development of full-blown AIDS, HIV-infected patients and patients experiencing Ad-36-associated abnormal adiposity that may develop in the context of reduced or impaired normal immune function, administration of the yeast-based immunotherapy described herein may be effective to treat such patients by providing a broad-based immune response sufficient to reduce Ad-36 viral load and thereby resolve the abnormal adipose tissue hypertrophy. Yeast-based immunotherapy activates multiple pathways of the immune system, and is expected to be effective where other therapeutic approaches, including other immunotherapeutic approaches, lack efficacy.

The compositions, methods and uses of the invention are directed to the prevention and/or treatment of Ad-36 infection, which may reduce or prevent one or more symptoms or conditions associated with Ad-36 infection, including but not limited to, obesity, being overweight, undesirable or abnormal weight gain, and/or abnormal adipose tissue hypertrophy. By addressing these conditions, downstream sequela of obesity and being clinically overweight, or conditions associated with obesity, excess weight, undesirable or abnormal weight gain, or abnormal adipose tissue hypertrophy, may also be reduced. Such conditions include, but are not limited to, high serum cholesterol, high triglycerides, high blood pressure, respiratory conditions, insulin resistance, and type II diabetes.

Compositions of the Invention

One embodiment of the present invention relates to a yeast-based immunotherapy composition which can be used to prevent and/or treat Ad-36 infection or to alleviate at least one symptom resulting from the Ad-36 infection, including but not limited to, obesity, being overweight, undesired or abnormal weight gain, or the propensity therefore. The composition comprises: (a) a yeast vehicle; and (b) one or more Ad-36 protein(s) and/or immunogenic domain(s) thereof (collectively, "Ad-36 antigens"). In conjunction with the yeast vehicle, the Ad-36 proteins are most typically expressed as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or much such Ad-36 proteins are loaded into a yeast vehicle or otherwise complexed with, attached to, mixed with or administered with a yeast vehicle as described herein to form a composition of the present invention. According to the present invention, reference to a "heterologous" protein or "heterologous" antigen, including a heterologous fusion protein, in connection with a yeast vehicle of the invention, means that the protein or antigen is not a protein or antigen that is naturally expressed by the yeast, although a fusion protein may include yeast sequences or proteins or portions thereof that are also naturally expressed by yeast. Ad-36 proteins are heterologous with respect to yeast. Target antigens useful in the present invention are typically Ad-36 proteins and/or immunogenic domains thereof.

Another embodiment of the invention relates to novel Ad-36 fusion proteins described herein. In one aspect, such Ad-36 fusion proteins are useful in an immunotherapeutic composition of the invention, including a yeast-based immunotherapeutic composition of the invention. Such fusion proteins, and/or the recombinant nucleic acid molecules encoding such proteins, can also be used in, in combination with, or to produce, a non-yeast-based immunotherapeutic composition, which may include, without limitation, a DNA vaccine, a protein subunit vaccine, a recombinant viral-based immunotherapeutic composition, and a killed or inactivated pathogen vaccine. In another embodiment, such fusion proteins can be used in a diagnostic assay for Ad-36 and/or to generate antibodies against Ad-36. Described herein are exemplary Ad-36 fusion proteins providing selected portions of Ad-36 which are particularly useful in yeast-based immunotherapeutic compositions of the invention.

Adenovirus-36

Adenovirus-36 (also referred to herein as Ad-36, Adv-36, hAdv-36, or HAdV-D36, or adenovirus serotype 36, all of which may be used interchangeably) is one of 52 currently known serotypes of adenoviruses that infect humans, from the Family Adenoviridae, Genus *Mastadenovirus*, Species *Human Adenovirus D* (HAdV-D). The virus was first identified in a child with diabetes and enteritis (Wigand et al., 1980, supra) and was deposited with the ATCC as ATCC® Number VR-1610$^{TH}$ by Wigand. In 2010, Arnold and colleagues sequenced the complete Ad-36 genome (Arnold et al., 2010, supra), which is deposited under GenBank® Accession No. GQ384080.1 (GI:261875889). The nucleotide sequence of this representative adenovirus-36 genomic sequence is represented herein by SEQ ID NO:1.

Ad-36 is a double-stranded DNA virus with a 35,152 bp genome, organized into 39 predicted open reading frames (ORFs). The coding sequences that are most divergent from other adenoviruses are found in the hexon, CR1β, CR1γ, and fiber coding regions. Table 1 indicates the individual protein sequences encoded by the Ad-36 genome (SEQ ID NO:1). It is noted that small variations may occur in the amino acid sequence between different viral isolates of the same protein from Ad-36. However, using the guidance provided herein and the reference to the exemplary Ad-36 sequences, one of skill in the art will readily be able to produce a variety of Ad-36-based proteins, including fusion proteins, from any Ad-36 strain (isolate) or genotype, for use in the compositions and methods of the present invention, and as such, the invention is not limited to the specific sequences disclosed herein. Reference to an Ad-36 protein or antigen anywhere in this disclosure, or to any functional, structural, or immunogenic domain thereof, can accordingly be made by reference to a particular sequence from one or more of the sequences presented in this disclosure, or by reference to the same, similar or corresponding sequence from a different Ad-36 isolate (strain). One of skill in the art will readily be able to identify the position of the corresponding sequence for each protein in Table 1 in a given Ad-36 sequence of any Ad-36 strain/isolate, given the guidance provided below, even though some amino acids may differ from those sequences in Table 1.

TABLE 1

Adenovirus-36 Protein Sequences

| Protein Name | Sequence Identifier |
| --- | --- |
| E1A 28K | SEQ ID NO: 2 |
| E1A 21K | SEQ ID NO: 3 |
| E1B 19K | SEQ ID NO: 4 |
| E1B 55K | SEQ ID NO: 5 |
| pIX | SEQ ID NO: 6 |
| IVa2 | SEQ ID NO: 7 |
| Pol protein | SEQ ID NO: 8 |
| 13.6K | SEQ ID NO: 9 |
| pTP | SEQ ID NO: 10 |
| 52K | SEQ ID NO: 11 |
| pIIIa | SEQ ID NO: 12 |
| III | SEQ ID NO: 13 |
| pVII | SEQ ID NO: 14 |
| V | SEQ ID NO: 15 |
| pX | SEQ ID NO: 16 |
| pVI | SEQ ID NO: 17 |
| Hexon | SEQ ID NO: 18 |
| Protease | SEQ ID NO: 19 |
| DBP | SEQ ID NO: 20 |
| 100K | SEQ ID NO: 21 |
| 33K | SEQ ID NO: 22 |
| 22K | SEQ ID NO: 23 |
| pVIII | SEQ ID NO: 24 |
| E3 12.5K | SEQ ID NO: 25 |
| E3 CR1α | SEQ ID NO: 26 |
| E3 18.4K | SEQ ID NO: 27 |
| E3 50K (CR1β) | SEQ ID NO: 28 |
| E3B1-2 30.8K (CR1γ) | SEQ ID NO: 29 |
| E3B2-2 10K (RIDα) | SEQ ID NO: 30 |
| E3B2-2 14.6K (RIDβ) | SEQ ID NO: 31 |
| E3B 14.7K | SEQ ID NO: 32 |
| U protein | SEQ ID NO: 33 |
| Fiber | SEQ ID NO: 34 |
| E4 ORF 6/7 | SEQ ID NO: 35 |
| E4 34K | SEQ ID NO: 36 |
| E4 17K | SEQ ID NO: 37 |
| E4 ORF4 | SEQ ID NO: 38 |
| E4 ORF3 | SEQ ID NO: 39 |
| E4 ORF2 | SEQ ID NO: 40 |
| E4 ORF1 | SEQ ID NO: 41 |

Adenovirus-36 Target Antigens and Constructs.

One embodiment of the invention relates to novel Ad-36 proteins and fusion proteins which can be used as target antigens in an immunotherapeutic composition of the invention, and recombinant nucleic acid molecules encoding these proteins or antigens. Described herein are several different novel Ad-36 proteins and fusion proteins for use as target antigens in a yeast-based immunotherapeutic composition or other composition (e.g., other immunotherapeutic or diagnostic composition) that provide one, two, or multiple (three, four, five, six, seven, eight, nine, ten, or more) proteins and/or one, two or multiple immunogenic domains from one or more proteins, all contained within the same polypeptide and encoded by the same recombinant nucleic acid construct. The proteins used in the compositions of the invention include at least one Ad-36 antigen for immunizing an animal (prophylactically or therapeutically). The composition can include, one, two, a few, several or a plurality of Ad-36 antigens, including one or more immunogenic domains of one or more Ad-36 proteins, as desired.

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, or larger, and can include multiple epitopes. As such, the size of an antigen can be as small as about 5-12 amino acids (i.e., a peptide) and as large as: a full length protein, a multimer, a fusion protein, a chimeric protein, a whole cell, a whole microorganism, or any portions thereof (e.g., lysates of whole cells or extracts of microorganisms. In addition, antigens can include carbohydrates, which can be loaded into a yeast vehicle or into a composition of the invention. It will be appreciated that in some embodiments (i.e., when the antigen is expressed by the yeast vehicle from a recombinant nucleic acid molecule), the antigen is a protein, fusion protein, chimeric protein, or fragment thereof, rather than an entire cell or microorganism.

When the antigen is to be expressed in yeast, an antigen is of a minimum size capable of being expressed recombinantly in yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or is at least 25-50 amino acids in length, at least 30-50 amino acids in length, or at least 35-50 amino acids in length, or at least 40-50 amino acids in length, or at least 45-50 amino acids in length. Smaller proteins may be expressed, and considerably larger proteins (e.g., hundreds of amino acids in length or even a few thousand amino acids in length) may be expressed. In one aspect, a full-length protein or a structural or functional domain thereof or an immunogenic domain thereof that is lacking one or more amino acids from the N- and/or the C-terminus may be expressed (e.g., lacking between about 1 and about 20 amino acids from the N- and/or the C-terminus). Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired). An "Ad-36 antigen" is an antigen derived, designed, or produced from one or more Ad-36 proteins such that targeting the antigen also targets Adenovirus-36.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, the immunogen elicits a cell-mediated immune response, including a $CD4^+$ T cell response (TH1 and/or TH17) and/or a $CD8^+$ T cell response (e.g., a CTL response).

An "immunogenic domain" of a given antigen can be any portion, fragment or epitope of an antigen (e.g., a peptide fragment or subunit or an antibody epitope or other conformational epitope) that contains at least one epitope that can act as an immunogen when administered to an animal. Therefore, an immunogenic domain is larger than a single amino acid and is at least of a size sufficient to contain at least one epitope. For example, a single protein can contain multiple different immunogenic domains. Immunogenic domains need not be linear sequences within a protein, such as in the case of a humoral immune response, where conformational domains are contemplated.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be up to 25 amino acids or longer. In addition, T cell epitopes have predicted structural characteristics depending on the specific MHC molecules bound by the epitope. Epitopes can be linear sequence epitopes or conformational epitopes (conserved binding regions). Most antibodies recognize conformational epitopes.

A "functional domain" of a given protein is a portion or functional unit of the protein that includes sequence or structure that is directly or indirectly responsible for at least one biological or chemical function associated with, ascribed to, or performed by the protein. For example, a functional domain can include an active site for enzymatic activity, a ligand binding site, a receptor binding site, a binding site for a molecule or moiety such as calcium, a phosphorylation site, or a transactivation domain.

A "structural domain" of a given protein is a portion of the protein or an element in the protein's overall structure that has an identifiable structure (e.g., it may be a primary or tertiary structure belonging to and indicative of several proteins within a class or family of proteins), is self-stabilizing and/or may fold independently of the rest of the protein. A structural domain is frequently associated with or features prominently in the biological function of the protein to which it belongs.

In some embodiments, an Ad-36 antigen useful in the present invention is a fusion protein. In one aspect of the invention, such a fusion protein can include two or more antigens. In one aspect, the fusion protein can include two or more immunogenic domains and/or two or more epitopes of one or more Ad-36 proteins. An immunotherapeutic composition containing such antigens may provide antigen-specific immunization in a broad range of patients. For example, a protein or fusion protein encompassed by the invention can include at least a portion or the full-length of any one or more Ad-36 proteins represented in Table 1 (amino acid sequences represented by SEQ ID NOs:2 through 41) and/or any one or more immunogenic domains of any one or more of these Ad-36 proteins, provided in any combination. In one embodiment, a protein useful in the present invention comprises one or more of the following Ad-36 proteins and/or one or more immunogenic domains of any one of more of the following proteins: hexon, fiber, CR1α, CR1γ, and/or E4. In one embodiment, an antigen useful in an immunotherapeutic composition of the invention is a single Ad-36 protein (full-length, near full-length, or portion thereof comprising at least, one, two, three, four or more immunogenic domains of a full-length protein). In one embodiment of the invention, an immunotherapeutic composition includes one, two, three, four, five or more individual yeast vehicles, each expressing or containing a different Ad-36 antigen.

In one embodiment of the invention, the Ad-36 antigen(s) for use in a composition or method of the invention is an Ad-36 antigen comprising or consisting of hexon, fiber, CR1α, CR1γ, and/or E4 and/or one or more domains (structural, functional or immunogenic) thereof, or any combination thereof. In one aspect, any one or more of these proteins or domains is full-length or near full-length. According to the present invention, reference to a "full-length" protein (or a full-length functional domain or full-length immunological domain) includes the full-length amino acid sequence of the protein or functional domain or immunological domain, as described herein or as otherwise known or described in a publicly available sequence. A protein or domain that is "near full-length", which is also a type of homologue of a protein, differs from a full-length protein or domain, by the addition or deletion of 1, 2, 3, 4, 5, 6, 7, 8, 9, or 10 amino acids from the N- and/or C-terminus of such a full-length protein or full-length domain. General reference to a protein or domain can include both full-length and near full-length proteins, as well as other homologues thereof. In one aspect, one or more of these proteins or domains comprise or consist of 1, 2, 3, 4, 5, 6, 7, 8, 9, or 10 or more immunogenic domains. In one aspect, any one or more of these proteins or domains comprises at least 80%, 85%, 90%, 91%, 92%, 93%, 94%, 95%, 96%, 97%, 98%, or 99% of the linear sequence of the corresponding full-length sequence or of a specified domain or portion of the full-length sequence. An N-terminal expression sequence and/or a C-terminal tag are optional for use with the Ad-36 antigens, and may be selected from several different sequences described elsewhere herein to improve expression, stability, and/or allow for identification and/or purification of the protein, or one or both of the N- or C-terminal sequences are omitted altogether. In addition, many different promoters suitable for use in yeast are known in the art. Furthermore if two or more Ad-36 proteins or domains thereof are included in an Ad-36 antigen, short intervening linker sequences (e.g., 1, 2, 3, 4, or 5, or larger, amino acid peptides) may optionally be introduced between portions of the protein or between the proteins and other elements (e.g., N-terminal peptides) for a variety of reasons, including the introduction of restriction enzyme sites to facilitate cloning and future manipulation of the constructs. Finally, as discussed elsewhere herein, the sequences described herein are exemplary, and may be modified as described above to substitute, add, or delete sequences in order to accommodate preferences for Ad-36 strain or isolate, or consensus sequences and inclusion of preferred T cell epitopes, including dominant and/or subdominant T cell epitopes.

In one aspect of the invention, the Ad-36 antigens useful in the invention are antigens that are divergent, or less conserved, with respect to other adenoviruses (e.g., have relatively low sequence homology or identity with the same or equivalent proteins from other adenovirus serotypes/genotypes). In one embodiment of the invention, a divergent region of a protein, or reference to a protein or region of a protein that is divergent with respect to other proteins of similar structure and/or function (e.g., a region of an Ad-36 protein as compared to approximately the same or similar region of the same protein or an equivalent protein from another adenovirus serotype/genotype), is defined as a protein region for which there is less than about 60% average amino acid identity between the reference sequence and at least five other sequences from other sources that are equivalent in structure and or function, determined, for example, using a BLAST algorithm (described below). Accordingly, proteins or domains or portions of proteins from Ad-36 that are not highly conserved (are relatively or very non-conserved) with other adenovirus serotypes/genotypes are included in antigens and fusion proteins useful in the invention, in one embodiment of the invention. The inclusion of Ad-36 antigens that are divergent from other adenovirus antigens (e.g., similar or equivalent antigens, with respect to structure and/or function, from other adenovirus serotypes or genotypes) has the advantage of creating an immunotherapeutic composition that is specific for Ad-36 and potentially minimizes off-target effects of the immunotherapeutic or dilution of the specificity of the immunotherapeutic. In another aspect of the invention, antigens from conserved regions of Ad-36 (e.g., regions with higher sequence homology to other similar or equivalent antigens from other adenovirus serotypes/genotypes) may be included in a fusion protein or composition of the invention, which has the advantage, for example, of providing a broad spectrum immunotherapeutic with potential applications beyond the treatment or prevention of obesity and adipose-related conditions.

In one exemplary embodiment of the invention, the Ad-36 antigen(s) for use in a composition or method of the invention is a protein comprising Ad-36 sequences, wherein the Ad-36 sequences comprise or consist of Ad-36 fiber protein and/or one or more immunogenic domains of Ad-36 fiber protein. In one aspect, the Ad-36 fiber antigen is full-length fiber protein or near full-length fiber protein. In one aspect, the Ad-36 fiber antigen comprises at least 80%, 85%, 90%, 91%, 92%, 93%, 94%, 95%, 96%, 97%, 98%, or 99% of the linear sequence of a full-length Ad-36 fiber antigen or an immunogenic domain or portion thereof. In one aspect, the Ad-36 fiber antigen is at least 80%, 85%, 90%, 91%, 92%, 93%, 94%, 95%, 96%, 97%, 98%, or 99% identical to a full-length Ad-36 fiber antigen or an immunogenic domain or portion thereof. In one embodiment, a protein useful in a composition or method of the invention comprises or consists of divergent domains or portions, i.e., relatively non-conserved domains or portions, with respect to other adenoviruses, of Ad-36 fiber protein. For example, an Ad-36 fiber protein construct according to this embodiment can be comprised of a fusion of one, two, three, four, or more different regions of Ad-36 fiber protein that are poorly conserved across human adenoviral genotypes.

Examples of such fusion proteins are described in Example 1. One Ad-36 antigen comprising fiber protein sequence described in Example 1 is a fusion protein expressed as a single polypeptide with the following sequence elements fused in frame from N- to C-terminus, represented by SEQ ID NO:42: (1) an N-terminal peptide to impart resistance to proteasomal degradation and stabilize expression (positions 1 to 6 of SEQ ID NO:42); (2) positions 71-136 of Ad-36 fiber (positions 71-136 of SEQ ID NO:34 or a corresponding sequence from another Ad-36 strain or isolate), corresponding to positions 7-72 of SEQ ID NO:42; (3) positions 145-169 of Ad-36 fiber (positions 145-169 of SEQ ID NO:34 or a corresponding sequence from another Ad-36 strain or isolate), corresponding to positions 73-97 of SEQ ID NO:42; (4) positions 290-313 of Ad-36 fiber (positions 290-313 of SEQ ID NO:34 or a corresponding sequence from another Ad-36 strain or isolate), corresponding to positions 98-194 of SEQ ID NO:42; (5) positions 334-363 of Ad-36 fiber (positions 334-363 of SEQ ID NO:34 or a corresponding sequence from another Ad-36 strain or isolate), corresponding to positions 195-224 of SEQ ID NO:42; and (6) a hexahistidine tag (positions 225-230 of SEQ ID NO:42). A nucleic acid sequence encoding the fusion protein of SEQ ID NO:42 (codon optimized for yeast expression) is also included in the present invention.

Another Ad-36 antigen comprising fiber protein sequence described in Example 1 is a fusion protein expressed as a single polypeptide with the following sequence elements fused in frame from N- to C-terminus, represented by SEQ ID NO:48: (1) an N-terminal peptide to impart resistance to proteasomal degradation and stabilize or enhance expression (SEQ ID NO:56, or positions 1 to 89 of SEQ ID NO: 48); (2) a two amino acid spacer/linker (Thr-Ser) to facilitate cloning and manipulation of the sequences (positions 90 to 91 of SEQ ID NO:48); (3) positions 71-136 of Ad-36 fiber (positions 71-136 of SEQ ID NO:34 or a corresponding sequence from another Ad-36 strain or isolate), corresponding to positions 92-157 of SEQ ID NO:48; (4) positions 145-169 of Ad-36 fiber (positions 145-169 of SEQ ID NO:34 or a corresponding sequence from another Ad-36 strain or isolate), corresponding to positions 158-182 of SEQ ID NO:48; (5) positions 290-313 of Ad-36 fiber (positions 290-313 of SEQ ID NO:34 or a corresponding sequence from another Ad-36 strain or isolate), corresponding to positions 183-279 of SEQ ID NO:48; (6) positions 334-363 of Ad-36 fiber (positions 334-363 of SEQ ID NO:34 or a corresponding sequence from another Ad-36 strain or isolate), corresponding to positions 280-309 of SEQ ID NO:48; and (7) a hexahistidine tag (positions 310-315 of SEQ ID NO:48). A nucleic acid sequence encoding the fusion protein of SEQ ID NO:48 (codon optimized for yeast expression) is also included in the present invention.

The amino acid segments used in these fusion proteins can be modified by the use of additional amino acids flanking either end of any domain; the examples provided herein are exemplary only. In addition, the N-terminal expression sequence (e.g., positions 1 to 6 of SEQ ID NO:42 or positions 1-89 of SEQ ID NO:48) and the C-terminal tag (e.g., positions 225-230 of SEQ ID NO:42 or positions 310-315 of SEQ ID NO:48) are optional, and may be selected instead from other different sequences described elsewhere herein or known in the art to improve expression, stability, and/or allow for identification and/or purification of the protein, or one or both may be omitted altogether. Furthermore, short intervening linker sequences such as that exemplified in SEQ ID NO:48 (e.g., 1, 2, 3, 4, or 5, or larger, amino acid peptides) may be introduced between portions of the fusion protein for a variety of reasons, including the introduction of restriction enzyme sites to facilitate cloning as cleavage sites for host phagosomal proteases, to accelerate protein or antigen processing, and for future manipulation of the constructs. The amino acid sequence consisting of only the Ad-36 fiber proteins in the fusion proteins described above is represented herein by SEQ ID NO:49. SEQ ID NO:49 is a fusion protein expressed as a single polypeptide: (1) positions 71-136 of Ad-36 fiber (positions 71-136 of SEQ ID NO:34 or a corresponding sequence from another Ad-36 strain or isolate), corresponding to positions 1-66 of SEQ ID NO:49; (2) positions 145-169 of Ad-36 fiber (positions 145-169 of SEQ ID NO:34 or a corresponding sequence from another Ad-36 strain or isolate), corresponding to positions 67-91 of SEQ ID NO:49; (3) positions 290-313 of Ad-36 fiber (positions 290-313 of SEQ ID NO:34 or a corresponding sequence from another Ad-36 strain or isolate), corresponding to positions 92-188 of SEQ ID NO:49; and (4) positions 334-363 of Ad-36 fiber (positions 334-363 of SEQ ID NO:34 or a corresponding sequence from another Ad-36 strain or isolate), corresponding to positions 189-218 of SEQ ID NO:49. A nucleic acid sequence encoding the fusion protein of SEQ ID NO:49 (codon optimized for yeast expression) is also included in the present invention.

In another exemplary embodiment of the invention, the Ad-36 antigen(s) for use in a composition or method of the invention is a protein comprising Ad-36 sequences, wherein the Ad-36 sequences comprise or consist of Ad-36 hexon protein and/or one or more immunogenic domains of Ad-36 hexon protein. In one aspect, the Ad-36 hexon antigen is full-length hexon protein or near full-length hexon protein (full-length and near full-length are defined above). In one aspect, the Ad-36 hexon antigen comprises at least 80%, 85%, 90%, 91%, 92%, 93%, 94%, 95%, 96%, 97%, 98%, or 99% of the linear sequence of a full-length Ad-36 hexon protein or an immunogenic domain or portion thereof. In one aspect, the Ad-36 hexon antigen is at least 80%, 85%, 90%, 91%, 92%, 93%, 94%, 95%, 96%, 97%, 98%, or 99% identical to a full-length Ad-36 hexon protein or an immunogenic domain or portion thereof. In one embodiment, a protein useful in a composition or method of the invention comprises or consists of divergent domains or portions, i.e., relatively non-conserved domains or portions, with respect to other adenoviruses, of Ad-36 hexon protein. For example, an Ad-36 hexon protein construct according to this embodiment can be comprised of a fusion of one, two, three, four, five, or more different regions of Ad-36 hexon protein that are poorly conserved across human adenoviral genotypes.

Examples of such fusion proteins comprising hexon proteins are described in Example 1. One such Ad-36 antigen comprising hexon protein sequences derived from divergent portions of Ad-36 hexon is a fusion protein expressed as a single polypeptide with the following sequence elements fused in frame from N- to C-terminus, represented by SEQ ID NO:43: (1) an N-terminal peptide to impart resistance to proteasomal degradation and stabilize expression (positions 1 to 6 of SEQ ID NO:43); (2) positions 136-218 of Ad-36 hexon (positions 136-218 of SEQ ID NO:18 or a corresponding sequence from another Ad-36 strain or isolate), corresponding to positions 7-89 of SEQ ID NO:43; (3) positions 235-285 of Ad-36 hexon (positions 235-285 of SEQ ID NO:18 or a corresponding sequence from another Ad-36 strain or isolate), corresponding to positions 90-141 of SEQ ID NO:43; (4) positions 297-308 of Ad-36 hexon (positions 297-308 of SEQ ID NO:18 or a corresponding sequence from another Ad-36 strain or isolate), corresponding to positions 142-153 of SEQ ID NO:43; (5) positions 410-450 of Ad-36 hexon (positions 410-450 of SEQ ID NO:18 or a corresponding sequence from another Ad-36 strain or isolate), corresponding to positions 154-194 of SEQ ID NO:43; and (6) a hexahistidine tag (positions 195-200 of SEQ ID NO:43). A nucleic acid sequence encoding the fusion protein of SEQ ID NO:43 (codon optimized for yeast expression) is also included in the present invention.

Another Ad-36 antigen comprising hexon protein sequence derived from divergent portions of Ad-36 sequence is a fusion protein expressed as a single polypeptide with the following sequence elements fused in frame from N- to C-terminus, represented by SEQ ID NO:50: (1) an N-terminal peptide to impart resistance to proteasomal degradation and stabilize or enhance expression (SEQ ID NO:56, or positions 1 to 89 of SEQ ID NO:50); 2) a two amino acid spacer/linker (Thr-Ser) to facilitate cloning and manipulation of the sequences (positions 90 to 91 of SEQ ID NO:50); (3) positions 136-218 of Ad-36 hexon (positions 136-218 of SEQ ID NO:18 or a corresponding sequence from another Ad-36 strain or isolate), corresponding to positions 92-174 of SEQ ID NO:50; (4) positions 235-285 of Ad-36 hexon (positions 235-285 of SEQ ID NO:18 or a corresponding sequence from another Ad-36 strain or isolate), corresponding to positions 175-226 of SEQ ID NO:50; (5) positions 297-308 of Ad-36 hexon (positions 297-308 of SEQ ID NO:18 or a corresponding sequence from another Ad-36 strain or isolate), corresponding to positions 227-238 of SEQ ID NO:50; (6) positions 410-450 of Ad-36 hexon (positions 410-450 of SEQ ID NO:18 or a corresponding sequence from another Ad-36 strain or isolate), corresponding to positions 239-279 of SEQ ID NO:50; and (7) a hexahistidine tag (positions 280-285 of SEQ ID NO:50). A nucleic acid sequence encoding the fusion protein of SEQ ID NO: 50 (codon optimized for yeast expression) is also included in the present invention.

The amino acid segments used in these hexon-based fusion proteins described above can be modified by the use of additional amino acids flanking either end of any domain; the examples provided herein are exemplary only. In addition, the N-terminal expression sequence (e.g., positions 1 to 6 of SEQ ID NO:43 or positions 1-89 of SEQ ID NO:50) and the C-terminal tag (e.g., positions 195-200 of SEQ ID NO:43 or positions 280-285 of SEQ ID NO:50) are optional, and may be selected instead from other different sequences described elsewhere herein or known in the art to improve expression, stability, and/or allow for identification and/or purification of the protein, or one or both may be omitted altogether. Furthermore, short intervening linker sequences such as that exemplified in SEQ ID NO:48 (e.g., 1, 2, 3, 4, or 5, or larger, amino acid peptides) may be introduced between portions of the fusion protein for a variety of reasons, including the introduction of restriction enzyme sites to facilitate cloning as cleavage sites for host phagosomal proteases, to accelerate protein or antigen processing, and for future manipulation of the constructs. The amino acid sequence consisting of only the Ad-36 hexon proteins in the fusion proteins described above is represented herein by SEQ ID NO:51. SEQ ID NO:51 is a fusion protein expressed as a single polypeptide: (1) positions 136-218 of Ad-36 hexon (positions 136-218 of SEQ ID NO:18 or a corresponding sequence from another Ad-36 strain or isolate), corresponding to positions 1-83 of SEQ ID NO:51; (2) positions 235-285 of Ad-36 hexon (positions 235-285 of SEQ ID NO:18 or a corresponding sequence from another Ad-36 strain or isolate), corresponding to positions 84-135 of SEQ ID NO:51; (3) positions 297-308 of Ad-36 hexon (positions 297-308 of SEQ ID NO:18 or a corresponding sequence from another Ad-36 strain or isolate), corresponding to positions 136-147 of SEQ ID NO:51;

and (4) positions 410-450 of Ad-36 hexon (positions 410-450 of SEQ ID NO:18 or a corresponding sequence from another Ad-36 strain or isolate), corresponding to positions 148-188 of SEQ ID NO:51. Any suitable N-terminal and/or C-terminal sequence may be appended to this sequence, as described above for SEQ ID NOs:43 and 50, or one or both may be omitted. A nucleic acid sequence encoding the fusion protein of SEQ ID NO:51 (codon optimized for yeast expression) is also included in the present invention.

An Ad-36 antigen comprising full-length or near full-length hexon protein sequence described in Example 1 is a fusion protein expressed as a single polypeptide with the following sequence elements fused in frame from N- to C-terminus, represented by SEQ ID NO:44: (1) an N-terminal peptide to impart resistance to proteasomal degradation and stabilize expression (positions 1 to 6 of SEQ ID NO:44); (2) positions 2-944 of Ad-36 hexon (positions 2-944 of SEQ ID NO:18 or a corresponding sequence from another Ad-36 strain or isolate), corresponding to positions 7-949 of SEQ ID NO:44; and (3) a hexahistidine tag (positions 950-955 of SEQ ID NO:44). This construct contains demonstrated or putative MHC Class I epitopes (e.g., positions 119-129 of SEQ ID NO:44; positions 319-327 of SEQ ID NO:44; positions 710-718 of SEQ ID NO:44; positions 843-851 of SEQ ID NO:44; or positions 909-915 of SEQ ID NO:44), and demonstrated or putative MHC Class II epitopes (e.g., positions 15-25 of SEQ ID NO:44; positions 31-41 of SEQ ID NO:44; 321-335 of SEQ ID NO:44; positions 373-383 of SEQ ID NO:44; positions 707-718 of SEQ ID NO:44; or positions 862-872 of SEQ ID NO:44). A nucleic acid sequence encoding the fusion protein of SEQ ID NO:44 (codon optimized for yeast expression) is also included in the present invention.

Another Ad-36 antigen comprising full-length or near full-length hexon protein sequence described in Example 1 is a fusion protein expressed as a single polypeptide with the following sequence elements fused in frame from N- to C-terminus, represented by SEQ ID NO:52: (1) an N-terminal peptide to impart resistance to proteasomal degradation and stabilize or enhance expression (SEQ ID NO:56, or positions 1 to 89 of SEQ ID NO:52); 2) a two amino acid spacer/linker (Thr-Ser) to facilitate cloning and manipulation of the sequences (positions 90 to 91 of SEQ ID NO:52); (3) positions 2-944 of Ad-36 hexon (positions 2-944 of SEQ ID NO:18 or a corresponding sequence from another Ad-36 strain or isolate), corresponding to positions 92-1034 of SEQ ID NO:52; and (3) a hexahistidine tag (positions 1035-1040 of SEQ ID NO:52). This construct contains demonstrated or putative MHC Class I epitopes (e.g., positions 204-214 of SEQ ID NO:52; positions 404-412 of SEQ ID NO:52; positions 795-803 of SEQ ID NO:52; positions 928-936 of SEQ ID NO:52; or positions 994-1000 of SEQ ID NO:52), and demonstrated or putative MHC Class II epitopes (e.g., positions 100-110 of SEQ ID NO:52; positions 116-126 of SEQ ID NO:52; 406-420 of SEQ ID NO:52; positions 458-468 of SEQ ID NO:52; positions 792-803 of SEQ ID NO:52; or positions 947-957 of SEQ ID NO:52). A nucleic acid sequence encoding the fusion protein of SEQ ID NO:52 (codon optimized for yeast expression) is also included in the present invention.

The amino acid segments used in these hexon-based fusion proteins described above can be modified by the use of additional amino acids flanking either end of any domain; the examples provided herein are exemplary only. In addition, the N-terminal expression sequence (e.g., positions 1 to 6 of SEQ ID NO:44 or positions 1-89 of SEQ ID NO:52) and the C-terminal tag (e.g., positions 950-955 of SEQ ID NO:44 or positions 1035-1040 of SEQ ID NO:52) are optional, and may be selected instead from other different sequences described elsewhere herein or known in the art to improve expression, stability, and/or allow for identification and/or purification of the protein, or one or both may be omitted altogether. Furthermore, short intervening linker sequences such as that exemplified in SEQ ID NO:48 (e.g., 1, 2, 3, 4, or 5, or larger, amino acid peptides) may be introduced between portions of the fusion protein for a variety of reasons, including the introduction of restriction enzyme sites to facilitate cloning as cleavage sites for host phagosomal proteases, to accelerate protein or antigen processing, and for future manipulation of the constructs. The amino acid sequence consisting of only the Ad-36 hexon protein in the fusion proteins described above is represented herein by SEQ ID NO:53. SEQ ID NO:53 is a fusion protein expressed as a single polypeptide and comprises positions 2-944 of Ad-36 hexon (positions 2-944 of SEQ ID NO:18 or a corresponding sequence from another Ad-36 strain or isolate), corresponding to positions 1-943 of SEQ ID NO:53. This construct contains demonstrated or putative MHC Class I epitopes (e.g., positions 113-123 of SEQ ID NO:53; positions 313-321 of SEQ ID NO:53; positions 704-712 of SEQ ID NO:53; positions 837-845 of SEQ ID NO:53; or positions 903-909 of SEQ ID NO:53), and demonstrated or putative MHC Class II epitopes (e.g., positions 9-19 of SEQ ID NO:53; positions 25-35 of SEQ ID NO:53; 315-329 of SEQ ID NO:53; positions 367-377 of SEQ ID NO:53; positions 701-712 of SEQ ID NO:53; or positions 856-866 of SEQ ID NO:53). Any suitable N-terminal and/or C-terminal sequence may be appended to this sequence, as described above for SEQ ID NOs:44 and 52, or one or both may be omitted. A nucleic acid sequence encoding the fusion protein of SEQ ID NO:53 (codon optimized for yeast expression) is also included in the present invention.

In another exemplary embodiment of the invention, the Ad-36 antigen(s) for use in a composition or method of the invention is a protein comprising Ad-36 sequences, wherein the Ad-36 sequences comprise or consist of Ad-36 hexon protein and fiber protein and/or one or more immunogenic domains of hexon protein and fiber protein. In one aspect, the Ad-36 hexon and/or the Ad-36 fiber antigen are full-length proteins or near full-length proteins (full-length and near full-length are defined above). In one aspect, the Ad-36 hexon and/or fiber antigen comprises at least 80%, 85%, 90%, 91%, 92%, 93%, 94%, 95%, 96%, 97%, 98%, or 99% of the linear sequence of a full-length Ad-36 protein or immunogenic domain or portion thereof. In one aspect, the Ad-36 hexon and/or the Ad-36 fiber antigen is at least 80%, 85%, 90%, 91%, 92%, 93%, 94%, 95%, 96%, 97%, 98%, or 99% identical to a full-length Ad-36 protein or immunogenic domain or portion thereof. In one embodiment, a protein useful in a composition or method of the invention comprises or consists of divergent domains or portions, i.e., relatively non-conserved domains or portions, with respect to other adenoviruses, of Ad-36 hexon protein and Ad-36 fiber protein. For example, an Ad-36 hexon-fiber or fiber-hexon protein construct according to this embodiment can be comprised of a fusion of one, two, three, four, five, or more different regions of Ad-36 hexon protein that are poorly conserved across human adenoviral genotypes, and one, two, three, four, five or more different regions of Ad-36 fiber protein that are poorly conserved across human adenoviral genotypes.

Examples of such fusion proteins comprising both hexon and fiber proteins are described in Example 1. One such Ad-36 antigen comprising hexon and fiber protein sequences derived from divergent portions of Ad-36 hexon and fiber is a fusion protein expressed as a single polypeptide with the following sequence elements fused in frame from N- to C-terminus, represented by SEQ ID NO:45: (1) an N-terminal peptide to impart resistance to proteasomal degradation and stabilize expression (positions 1 to 6 of SEQ ID NO:45); (2) positions 71-136 of Ad-36 fiber (positions 71-136 of SEQ ID NO:34 or a corresponding sequence from another Ad-36 strain or isolate), corresponding to positions 7-72 of SEQ ID NO:45; (3) positions 145-169 of Ad-36 fiber (positions 145-169 of SEQ ID NO:34 or a corresponding sequence from another Ad-36 strain or isolate), corresponding to positions 73-97 of SEQ ID NO:45; (4) positions 290-313 of Ad-36 fiber (positions 290-313 of SEQ ID NO:34 or a corresponding sequence from another Ad-36 strain or isolate), corresponding to positions 98-194 of SEQ ID NO:45; (5) positions 334-363 of Ad-36 fiber (positions 334-363 of SEQ ID NO:34 or a corresponding sequence from another Ad-36 strain or isolate), corresponding to positions 195-224 of SEQ ID NO:45; (6) positions 136-218 of Ad-36 hexon (positions 136-218 of SEQ ID NO:18 or a corresponding sequence from another Ad-36 strain or isolate), corresponding to positions 225-307 of SEQ ID NO:45; (7) positions 235-285 of Ad-36 hexon (positions 235-285 of SEQ ID NO:18 or a corresponding sequence from another Ad-36 strain or isolate), corresponding to positions 308-359 of SEQ ID NO:45; (8) positions 297-308 of Ad-36 hexon (positions 297-308 of SEQ ID NO:18 or a corresponding sequence from another Ad-36 strain or isolate), corresponding to positions 360-371 of SEQ ID NO:45; (9) positions 410-450 of Ad-36 hexon (positions 410-450 of SEQ ID NO:18 or a corresponding sequence from another Ad-36 strain or isolate), corresponding to positions 372-412 of SEQ ID NO:45; and (10) a hexahistidine tag (positions 413-418 of SEQ ID NO:45).

Another Ad-36 antigen comprising hexon and fiber protein sequences derived from divergent portions of Ad-36 hexon and fiber is a fusion protein expressed as a single polypeptide with the following sequence elements fused in frame from N- to C-terminus, represented by SEQ ID NO:46: (1) an N-terminal peptide to impart resistance to proteasomal degradation and stabilize expression (positions 1 to 6 of SEQ ID NO:46); (2) positions 136-218 of Ad-36 hexon (positions 136-218 of SEQ ID NO:18 or a corresponding sequence from another Ad-36 strain or isolate), corresponding to positions 7-89 of SEQ ID NO:46; (3) positions 235-285 of Ad-36 hexon (positions 235-285 of SEQ ID NO:18 or a corresponding sequence from another Ad-36 strain or isolate), corresponding to positions 90-141 of SEQ ID NO:46; (4) positions 297-308 of Ad-36 hexon (positions 297-308 of SEQ ID NO:18 or a corresponding sequence from another Ad-36 strain or isolate), corresponding to positions 142-153 of SEQ ID NO:46; (5) positions 410-450 of Ad-36 hexon (positions 410-450 of SEQ ID NO:18 or a corresponding sequence from another Ad-36 strain or isolate), corresponding to positions 154-194 of SEQ ID NO:46; (6) positions 71-136 of Ad-36 fiber (positions 71-136 of SEQ ID NO:34 or a corresponding sequence from another Ad-36 strain or isolate), corresponding to positions 195-260 of SEQ ID NO:46; (7) positions 145-169 of Ad-36 fiber (positions 145-169 of SEQ ID NO:34 or a corresponding sequence from another Ad-36 strain or isolate), corresponding to positions 261-285 of SEQ ID NO:46; (8) positions 290-313 of Ad-36 fiber (positions 290-313 of SEQ ID NO:34 or a corresponding sequence from another Ad-36 strain or isolate), corresponding to positions 286-382 of SEQ ID NO:46; (9) positions 334-363 of Ad-36 fiber (positions 334-363 of SEQ ID NO:34 or a corresponding sequence from another Ad-36 strain or isolate), corresponding to positions 383-412 of SEQ ID NO:46; and (10) a hexahistidine tag (positions 413-418 of SEQ ID NO:46). A nucleic acid sequence encoding the fusion protein of SEQ ID NO:45 or SEQ ID NO:46 (codon optimized for yeast expression) is also included in the present invention.

The amino acid segments used in any of the fusion proteins described above can be modified by the use of additional amino acids flanking either end of any domain; the examples provided herein are exemplary only. The N-terminal expression sequence (positions 1 to 6 of SEQ ID NO:45 or 46) and the C-terminal tag (positions 413-418 of SEQ ID NO:45 or 46) are optional, and may be selected instead from other different sequences described elsewhere herein or known in the art to improve expression, stability, and/or allow for identification and/or purification of the protein, or one or both may be omitted altogether. Furthermore, short intervening linker sequences such as that exemplified in SEQ ID NO:48 (e.g., 1, 2, 3, 4, or 5, or larger, amino acid peptides) may be introduced between portions of the fusion protein for a variety of reasons, including the introduction of restriction enzyme sites to facilitate cloning as cleavage sites for host phagosomal proteases, to accelerate protein or antigen processing, and for future manipulation of the constructs. For example, a fusion protein omitting both the N- and C-terminal sequences of SEQ ID NO:45 is represented by positions 7-412 of SEQ ID NO:45 and a fusion protein omitting both the N- and C-terminal sequences of SEQ ID NO:46 is represented by positions 7-412 of SEQ ID NO:46.

In yet another exemplary embodiment of the invention, the Ad-36 antigen(s) for use in a composition or method of the invention is a protein comprising Ad-36 sequences, wherein the Ad-36 sequences comprise or consist of Ad-36 CR1α protein and/or Ad-36 CR1γ and/or one or more immunogenic domains of CR1α and/or CR1γ. In one aspect, the Ad-36 CR1α and/or the Ad-36 CR1γ antigen are full-length proteins or near full-length proteins (full-length and near full-length are defined above). In one aspect, the Ad-36 CR1α and/or the Ad-36 CR1γ antigen comprises at least 80%, 85%, 90%, 91%, 92%, 93%, 94%, 95%, 96%, 97%, 98%, or 99% of the linear sequence of a full-length Ad-36 protein or immunogenic domain or portion thereof. In one aspect, the Ad-36 CR1α and/or the Ad-36 CR1γ antigen is at least 80%, 85%, 90%, 91%, 92%, 93%, 94%, 95%, 96%, 97%, 98%, or 99% identical to a full-length Ad-36 protein or immunogenic domain or portion thereof. In one embodiment, a protein useful in a composition or method of the invention comprises or consists of divergent domains or portions, i.e., relatively non-conserved domains or portions, with respect to other adenoviruses, of Ad-36 CR1α and/or CR1γ. For example, an Ad-36 CR1α and/or CR1γ protein construct according to this embodiment can be comprised of a fusion of one, two, three, four, five, or more different regions of Ad-36 CR1α and/or CR1γ protein that are poorly conserved across human adenoviral genotypes. In one embodiment, a notably hydrophobic N-terminal region is omitted from CR1α in a protein of the invention (e.g., about positions 1-17 of the mature protein) to minimize the risk of aggregation and/or insolubility when that protein is expressed in yeast. In one embodiment, a C-terminal segment of mature CR1α is omitted from proteins used in the invention because of notable hydrophobicity (positions 158-177) plus high sequence conservation with other adenovirus serotypes/genotypes (positions 158 through C-terminus). In another embodiment, the N-terminal positions 1-18 of CR1γ are omitted from proteins used in the invention as they contain both highly conserved amino acid positions with other adenovirus serotypes/genotypes, and they also contain a very hydrophobic element.

Examples of such fusion proteins comprising both CR1α and CR1γ proteins are described in Example 1. One such Ad-36 antigen comprising CR1α and CR1γ protein sequences derived from divergent and/or selected portions of Ad-36 CR1α and CR1γ is a fusion protein expressed as a single polypeptide with the following sequence elements fused in frame from N- to C-terminus, represented by SEQ ID NO:47: (1) an N-terminal peptide to impart resistance to proteasomal degradation and stabilize expression (positions 1 to 6 of SEQ ID NO:47); (2) positions 18-60 of CR1α (positions 18-60 of SEQ ID NO:26 or a corresponding sequence from another Ad-36 strain or isolate), corresponding to positions 7-49 of SEQ ID NO:47; (3) positions 123-157 of Ad-36 CR1α (positions 123-157 of SEQ ID NO:26 or a corresponding sequence from another Ad-36 strain or isolate), corresponding to positions 50-84 of SEQ ID NO:47; (4) positions 19-60 of Ad-36 CR1γ (positions 19-60 of SEQ ID NO:29 or a corresponding sequence from another Ad-36 strain or isolate), corresponding to positions 85-126 of SEQ ID NO:47; (5) positions 83-116 of Ad-36 CR1γ (positions 83-116 of SEQ ID NO:29 or a corresponding sequence from another Ad-36 strain or isolate), corresponding to positions 127-160 of SEQ ID NO:47; and (6) a hexahistidine tag (positions 161-166 of SEQ ID NO:47). The amino acid segments used in any of the fusion proteins described above can be modified by the use of additional amino acids flanking either end of any domain; the examples provided herein are exemplary only. A nucleic acid sequence encoding the fusion protein of SEQ ID NO:47 (codon optimized for yeast expression) is also included in the present invention.

Another Ad-36 antigen comprising CR1α and CR1γ protein sequences described in Example 1 is a fusion protein expressed as a single polypeptide with the following sequence elements fused in frame from N- to C-terminus, represented by SEQ ID NO:54: (1) an N-terminal peptide to impart resistance to proteasomal degradation and stabilize or enhance expression (SEQ ID NO:56, or positions 1 to 89 of SEQ ID NO:54); 2) a two amino acid spacer/linker (Thr-Ser) to facilitate cloning and manipulation of the sequences (positions 90 to 91 of SEQ ID NO:54); (3) positions 18-60 of CR1α (positions 18-60 of SEQ ID NO:26 or a corresponding sequence from another Ad-36 strain or isolate), corresponding to positions 92-134 of SEQ ID NO:54; (4) positions 123-157 of Ad-36 CR1α (positions 123-157 of SEQ ID NO:26 or a corresponding sequence from another Ad-36 strain or isolate), corresponding to positions 135-169 of SEQ ID NO:54; (5) positions 19-60 of Ad-36 CR1γ (positions 19-60 of SEQ ID NO:29 or a corresponding sequence from another Ad-36 strain or isolate), corresponding to positions 170-211 of SEQ ID NO:54; (6) positions 83-116 of Ad-36 CR1γ (positions 83-116 of SEQ ID NO:29 or a corresponding sequence from another Ad-36 strain or isolate), corresponding to positions 212-245 of SEQ ID NO:54; and (7) a hexahistidine tag (positions 246-251 of SEQ ID NO:54). A nucleic acid sequence encoding the fusion protein of SEQ ID NO:54 (codon optimized for yeast expression) is also included in the present invention.

The amino acid segments used in these CR1α and CR1γ-based fusion proteins described above can be modified by the use of additional amino acids flanking either end of any domain; the examples provided herein are exemplary only. In addition, the N-terminal expression sequence (e.g., positions 1 to 6 of SEQ ID NO:47 or positions 1-89 of SEQ ID NO:54) and the C-terminal tag (e.g., positions 161-166 of SEQ ID NO:47 or positions 246-251 of SEQ ID NO:54) are optional, and may be selected instead from other different sequences described elsewhere herein or known in the art to improve expression, stability, and/or allow for identification and/or purification of the protein, or one or both may be omitted altogether. Furthermore, short intervening linker sequences such as that exemplified in SEQ ID NO:48 (e.g., 1, 2, 3, 4, or 5, or larger, amino acid peptides) may be introduced between portions of the fusion protein for a variety of reasons, including the introduction of restriction enzyme sites to facilitate cloning as cleavage sites for host phagosomal proteases, to accelerate protein or antigen processing, and for future manipulation of the constructs. The amino acid sequence consisting of only the Ad-36 CR1α and CR1γ proteins in the fusion proteins described above is represented herein by SEQ ID NO:55. SEQ ID NO:55 is a fusion protein expressed as a single polypeptide: (1) positions 18-60 of CR1α (positions 18-60 of SEQ ID NO:26 or a corresponding sequence from another Ad-36 strain or isolate), corresponding to positions 1-43 of SEQ ID NO:55; (2) positions 123-157 of Ad-36 CR1α (positions 123-157 of SEQ ID NO:26 or a corresponding sequence from another Ad-36 strain or isolate), corresponding to positions 44-78 of SEQ ID NO:55; (3) positions 19-60 of Ad-36 CR1γ (positions 19-60 of SEQ ID NO:29 or a corresponding sequence from another Ad-36 strain or isolate), corresponding to positions 79-120 of SEQ ID NO:55; and (4) positions 83-116 of Ad-36 CR1γ (positions 83-116 of SEQ ID NO:29 or a corresponding sequence from another Ad-36 strain or isolate), corresponding to positions 121-154 of SEQ ID NO:55. Any suitable N-terminal and/or C-terminal sequence may be appended to this sequence, as described above for SEQ ID NOs:47 and 54, or one or both may be omitted. A nucleic acid sequence encoding the fusion protein of SEQ ID NO:55 (codon optimized for yeast expression) is also included in the present invention.

The invention also includes homologues of any of the above-described fusion proteins, as well as the use of homologues, variants, or mutants of the individual Ad-36 proteins or portions thereof that are part of such fusion proteins. In one aspect, the invention includes the use of fusion proteins having amino acid sequences that are at least 85%, 86%, 87%, 88%, 89%, 90%, 91%, 92%, 93%, 94%, 95%, 96%, 97%, 98%, or 99% identical to the amino acid sequence of the fusion proteins described herein over the full length of the fusion protein, or with respect to a defined protein or domain thereof (immunological domain or functional domain (domain with at least one biological activity)) that forms part of the fusion protein.

Recombinant nucleic acid molecules useful in a yeast-based composition of the invention do not include the full length genome of Ad-36, but rather include less than the full-length Ad-36 genome. Typically, recombinant nucleic acid molecules useful in a yeast-based composition of the invention include one or more full-length coding sequences and/or one or more coding sequences of domains (immunogenic or functional) for Ad-36 proteins. Proteins included in a single yeast-based composition of the invention do not include all of the proteins encoded by Ad-36. Preferably, a yeast-based composition comprises one, two, three, four, five, six, seven, eight, nine, ten or more proteins encoded by Ad-36, and/or one or more immunogenic domains of any one or more Ad-36 proteins.

Recombinant nucleic acid molecules and the proteins encoded thereby, including fusion proteins, as one embodiment of the invention, may be used in yeast-based immunotherapy compositions, or for any other suitable purpose for an Ad-36 antigen(s), including in an in vitro assay, for the production of antibodies, or in another immunotherapy composition, including another vaccine, that is not based on the yeast-based immunotherapy described herein. Expression of the proteins/antigens by yeast is one preferred embodiment, although other expression systems may be used to produce the proteins/antigens for applications other than a yeast-based immunotherapy composition.

Yeast-Based Immunotherapy Compositions. In various embodiments of the invention, the invention includes the use of at least one "yeast-based immunotherapeutic composition" (which phrase may be used interchangeably with "yeast-based immunotherapy product", "yeast-based immunotherapy composition", "yeast-based composition", "yeast-based immunotherapeutic", "yeast-based vaccine", or derivatives of these phrases). An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and can elicit or induce an immune response, such as a cellular immune response, including without limitation a T cell-mediated cellular immune response. In one aspect, a yeast-based immunotherapeutic composition useful in the invention is capable of inducing a $CD8^+$ and/or a $CD4^+$ T cell-mediated immune response and in one aspect, a $CD8^+$ and a $CD4^+$ T cell-mediated immune response. A $CD4^+$ immune response can include TH1 immune responses, TH17 immune responses, or both, as yeast-based immunotherapeutics are capable of generating both types of response. A $CD8^+$ immune response can include a cytotoxic T lymphocyte (CTL) response, as yeast-based immunotherapeutics are capable of generating such responses. In one aspect, a yeast-based immunotherapeutic composition modulates the number and/or functionality of regulatory T cells (Tregs) in a subject. Yeast-based immunotherapy can also be modified to promote one type of response over another, e.g., by the addition of cytokines, antibodies, and/or modulating the manufacturing process for the yeast. Optionally, a yeast-based immunotherapy composition is capable of eliciting a humoral immune response. A yeast-based immunotherapeutic composition useful in the present invention can, for example, elicit an immune response in an individual such that the individual is protected from Ad-36 infection and/or is treated for Ad-36 infection or for symptoms resulting from Ad-36 infection.

Yeast-based immunotherapy compositions of the invention may be either "prophylactic" or "therapeutic". When provided prophylactically, the compositions of the present invention are provided in advance of any symptom of Ad-36 infection. Such a composition could be administered at birth, in early childhood, or to adults, and can include obese, overweight, non-obese, and non-overweight subjects. The prophylactic administration of the immunotherapy compositions serves to prevent subsequent Ad-36 infection, to resolve an infection more quickly or more completely if Ad-36 infection subsequently ensues, and/or to prevent or ameliorate the symptoms of Ad-36 infection if infection subsequently ensues. When provided therapeutically, the immunotherapy compositions are provided at or after the onset of Ad-36 infection, with the goal of preventing or ameliorating at least one symptom of the infection (e.g., preventing obesity in non-obese, Ad-36-infected subjects, or reducing weight in obese, Ad-36-infected subjects) and preferably, with a goal of eliminating the infection, providing a long lasting remission of infection, and/or providing long term immunity against subsequent infections or reactivations of the virus.

Typically, a yeast-based immunotherapy composition includes a yeast vehicle and at least one antigen (e.g., an Ad-36 protein) or immunogenic domain thereof expressed by, attached to, or mixed with the yeast vehicle, wherein the antigen is heterologous to the yeast, and wherein the antigen comprises one or more Ad-36 proteins or immunogenic domains thereof. In some embodiments, the antigen or immunogenic domain thereof is provided as a fusion protein. Several Ad-36 fusion proteins suitable for use in the compositions and methods of the invention have been described above. In one aspect of the invention, fusion protein can include two or more antigens. In one aspect, the fusion protein can include two or more immunogenic domains of one or more antigens, or two or more epitopes of one or more antigens.

A TARMOGEN® is one non-limiting example of a yeast-based immunotherapy composition that is useful in the present invention. A TARMOGEN® (TARgeted MOlecular immunoGEN, GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN®s have been generally described in the art. See, e.g., U.S. Pat. No. 5,830,463.

Yeast-based immunotherapy compositions, and methods of making and generally using the same, are described in detail, for example, in U.S. Pat. No. 5,830,463, U.S. Pat. No. 7,083,787, U.S. Pat. No. 7,736,642, Stubbs et al., *Nat. Med.* 7:625-629 (2001), Lu et al., *Cancer Research* 64:5084-5088 (2004), and in Bernstein et al., *Vaccine* 2008 Jan. 24; 26(4): 509-21, each of which is incorporated herein by reference in its entirety. These yeast-based immunotherapeutic products have been shown to elicit immune responses, including cellular and humoral immune responses. Yeast-based immunotherapeutic products are capable of killing target cells expressing a variety of antigens in vivo, in a variety of animal species, and to do so via antigen-specific, $CD4^+$ and $CD8^+$ T cell-mediated immune responses. Additional studies have shown that yeast are avidly phagocytosed by and directly activate dendritic cells which then present yeast-associated proteins to $CD4^+$ and $CD8^+$ T cells in a highly efficient manner. See, e.g., Stubbs et al. *Nature Med.* 5:625-629 (2001) and U.S. Pat. No. 7,083,787.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention, or in one aspect, the yeast vehicle can be used alone or as an adjuvant. The yeast vehicle can therefore include, but is not limited to, a live intact (whole) yeast microorganism (i.e., a yeast cell having all its components including a cell wall), a killed (dead) or inactivated intact yeast microorganism, or derivatives of intact yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, non-pathogenic yeast strains are used.

Genera of yeast strains that may be used in the invention include but are not limited to *Saccharomyces, Candida* (which can be pathogenic), *Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe,* and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe. S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

In one embodiment, a yeast vehicle of the present invention is capable of fusing with the cell type to which the yeast vehicle and antigen/agent is being delivered, such as a dendritic cell or macrophage, thereby effecting particularly efficient delivery of the yeast vehicle, and in many embodiments, the antigen(s) or other agent, to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. A number of viral surface proteins (including those of immunodeficiency viruses such as HIV, influenza virus, poliovirus and adenovirus) and other fusogens (such as those involved in fusions between eggs and sperm) have been shown to be able to effect fusion between two membranes (i.e., between viral and mammalian cell membranes or between mammalian cell membranes). It is noted, however, that incorporation of a targeting moiety into the yeast vehicle, while it may be desirable under some circumstances, is not necessary. In the case of yeast vehicles that express antigens extracellularly, this can be a further advantage of the yeast vehicles of the present invention. In general, yeast vehicles useful in the present invention are readily taken up by dendritic cells (as well as other cells, such as macrophages).

In most embodiments of the invention, the yeast-based immunotherapy composition includes at least one antigen, immunogenic domain thereof, or epitope thereof. The antigens contemplated for use in this invention include any Ad-36 antigen or immunogenic domain thereof, including mutants, variants and agonists of Ad-36 proteins or domains thereof, against which it is desired to elicit an immune response for the purpose of prophylactically or therapeutically immunizing a host against Ad-36 infection.

As discussed above, the compositions of the invention include at least one Ad-36 antigen and/or at least one immunogenic domain of at least one Ad-36 antigen for immunizing a subject. In some embodiments, the antigen is a fusion protein, several examples of which have been described above.

Optionally, proteins, including fusion proteins, which are used as a component of the yeast-based immunotherapeutic composition of the invention are produced using constructs that are particularly useful for improving the expression of heterologous antigens in yeast. Typically, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, wherein either fusion partner provides improved stability of expression of the protein in the yeast and/or a prevents posttranslational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., 6×His) or any other short epitope tag. Peptides attached to the C-terminus of an antigen according to the invention can be used with or without the addition of the N-terminal peptides discussed above.

In one embodiment, a synthetic peptide useful in a fusion protein is linked to the N-terminus of the antigen, the peptide consisting of at least two amino acid positions that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid positions at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine) The synthetic peptide can be as short as two amino acids, but in one aspect, is 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents posttranslational modification of the protein in the yeast includes the sequence M-A-D-E-A-P (e.g., SEQ ID NO:58). Another exemplary synthetic sequence with the same properties is M-V. In addition to the enhanced stability of the expression product, this fusion partner does not appear to negatively impact the immune response against the immunizing antigen in the construct. In addition, the synthetic fusion peptides can be designed to provide an epitope that can be recognized by a selection agent, such as an antibody.

In one aspect of the invention, the yeast vehicle is manipulated such that the antigen is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length. Another consideration for optimizing antigen surface expression, if that is desired, is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria or the endoplasmic reticulum or the nucleus. Examples of suitable yeast protein that can be used for any of the embodiments above include, but are not limited to, TK, AF, SECT; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

In one embodiment, the Ad-36 antigen is linked at the N-terminus to a yeast protein, such as an alpha factor prepro sequence (also referred to as the alpha factor signal leader sequence, the amino acid sequence of which is exemplified herein by SEQ ID NO:56 or SEQ ID NO:57. Other sequences for yeast alpha factor prepro sequence are known in the art and are encompassed for use in the present invention. Without being bound by theory, the inventors believe that one advantage of utilizing alpha factor prepro sequence in a yeast-based fusion protein is the minimization of proteolysis of the protein, since the protein is sequestered away from cytosolic proteasomes.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen or other protein.

In one aspect, a yeast cell or yeast spheroplast used to prepare the yeast vehicle is transfected with a recombinant nucleic acid molecule encoding the antigen(s) or other protein such that the antigen or other protein is recombinantly expressed by the yeast cell or yeast spheroplast. In this aspect, the yeast cell or yeast spheroplast that recombinantly expresses the antigen(s) or other protein is used to produce a yeast vehicle comprising a yeast cytoplast, a yeast ghost, or a yeast membrane particle or yeast cell wall particle, or fraction thereof.

In general, the yeast vehicle and antigen(s) and/or other agents can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) is expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 heterologous antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SECT) and acid phosphatase (PHO5), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego).

In some aspects of the invention, the yeast are grown under neutral pH conditions, and particularly, in a media maintained at a pH level of at least 5.5, namely the pH of the culture media is not allowed to drop below pH 5.5. In other aspects, the yeast is grown at a pH level maintained at about 5.5. In other aspects, the yeast is grown at a pH level maintained at about 5.6, 5.7, 5.8 or 5.9. In another aspect, the yeast is grown at a pH level maintained at about 6. In another aspect, the yeast is grown at a pH level maintained at about 6.5. In other aspects, the yeast is grown at a pH level maintained at about 6, 6.1, 6.2, 6.3, 6.4, 6.5, 6.6, 6.7, 6.8, 6.9 or 7.0. In other aspects, the yeast is grown at a pH level maintained at about 7, 7.1, 7.2, 7.3, 7.4, 7.5, 7.6, 7.7, 7.8, 7.9, or 8.0. The pH level is important in the culturing of yeast. One of skill in the art will appreciate that the culturing process includes not only the start of the yeast culture but the maintenance of the culture as well. As yeast culturing is known to turn acidic (i.e., lowering the pH) over time, care must be taken to monitor the pH level during the culturing process. Yeast cell cultures whereby the pH level of the medium drops below 6 are still contemplated within the scope of the invention provided that the pH of the media is brought up to at least 5.5 at some point during the culturing process. As such, the longer time the yeast are grown in a medium that is at least pH 5.5 or above, the better the results will be in terms of obtaining yeast with desirable characteristics.

As used herein, the general use of the term "neutral pH" refers to a pH range between about pH 5.5 and about pH 8, and in one aspect, between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. The use of a neutral pH in culturing yeast promotes several biological effects that are desirable characteristics for using the yeast as vehicles for immunomodulation. In one aspect, culturing the yeast in neutral pH allows for good growth of the yeast without any negative effect on the cell generation time (e.g., slowing down the doubling time). The yeast can continue to grow to high densities without losing their cell wall pliability. In another aspect, the use of a neutral pH allows for the production of yeast with pliable cell walls and/or yeast that are sensitive to cell wall digesting enzymes (e.g., glucanase) at all harvest densities. This trait is desirable because yeast with flexible cell walls can induce unusual immune responses, such as by promoting the secretion of cytokines (e.g., interferon-γ (IFN-γ)) in the cells hosting the yeast. In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5). Finally, in another aspect, yeast cultured using the neutral pH methodologies, elicit increased production of at least TH1-type cytokines including, but not limited to, IFN-γ, interleukin-12 (IL-12), and IL-2, and may also elicit increased production of other cytokines, such as proinflammatory cytokines (e.g., IL-6).

In one embodiment, control of the amount of yeast glycosylation is used to control the expression of antigens by the yeast, particularly on the surface. The amount of yeast glycosylation can affect the immunogenicity and antigenicity of the antigen expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g. mnn1, och1 and mnn9 mutants), or one could eliminate by mutation the glycosylation acceptor sequences on the target antigen. Alternatively, one could use a yeast with abbreviated glycosylation patterns, e.g., *Pichia*. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein(s) are being used, one of skill in the art will select a spacer arm that effectuates appropriate spacing for the antigen or other protein on the yeast surface. In one embodiment, the spacer arm is a yeast protein of at least 450 amino acids. Spacer arms have been discussed in detail above.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment of the invention, the yeast vehicle and the antigen or other protein are both loaded intracellularly into a carrier such as a dendritic cell or macrophage to form the therapeutic composition or vaccine of the present invention. Alternatively, an antigen or other protein can be loaded into a dendritic cell in the absence of the yeast vehicle.

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention, including preparations to be administered to a subject directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a TH17 response versus a TH1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Some suitable agents include, but are not limited to, IL-1 or agonists of IL-1 or of IL-1R, anti-IL-1 or other IL-1 antagonists; IL-6 or agonists of IL-6 or of IL-6R, anti-IL-6 or other IL-6 antagonists; IL-12 or agonists of IL-12 or of IL-12R, anti-IL-12 or other IL-12 antagonists; IL-17 or agonists of IL-17 or of IL-17R, anti-IL-17 or other IL-17 antagonists; IL-21 or agonists of IL-21 or of IL-21R, anti-IL-21 or other IL-21 antagonists; IL-22 or agonists of IL-22 or of IL-22R, anti-IL-22 or other IL-22 antagonists; IL-23 or agonists of IL-23 or of IL-23R, anti-IL-23 or other IL-23 antagonists; IL-25 or agonists of IL-25 or of IL-25R, anti-IL-25 or other IL-25 antagonists; IL-27 or agonists of IL-27 or of IL-27R, anti-IL-27 or other IL-27 antagonists; type I interferon (including IFN-α) or agonists or antagonists of type I interferon or a receptor thereof; type II interferon (including IFN-γ) or agonists or antagonists of type II interferon or a receptor thereof; anti-CD40, CD40L, anti-CTLA-4 antibody (e.g., to release anergic T cells); T cell co-stimulators (e.g., anti-CD137, anti-CD28, anti-CD40); alemtuzumab (e.g., CAMPATH®), denileukin diftitox (e.g., ONTAK®); anti-CD4; anti-CD25; anti-PD-1, anti-PD-L1, anti-PD-L2; agents that block FOXP3 (e.g., to abrogate the activity/kill $CD4^+$/$CD25^+$ T regulatory cells); Flt3 ligand, imiquimod (ALDARA™), granulocyte-macrophage colony stimulating factor (GM-CSF); granulocyte-colony stimulating factor (G-CSF), sargramostim (Leukine®); hormones including without limitation prolactin and growth hormone; Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiD™s (which are structural and functional analogues of thalidomide (e.g., REVLIMID® (lenalidomide), ACTIMID® (pomalidomide)); proinflammatory agents, such as fungal or bacterial components or any proinflammatory cytokine or chemokine; immunotherapeutic vaccines including, but not limited to, virus-based vaccines, bacteria-based vaccines, or antibody-based vaccines; and any other immunomodulators, immunopotentiators, anti-inflammatory agents, and/or pro-inflammatory agents. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein.

Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

Compositions of the invention can further include or can be administered with (concurrently, sequentially, or intermittently with) any other compounds or compositions that are useful for preventing or treating Ad-36 infection or any compounds that treat or ameliorate any symptom of Ad-36 infection. In addition, compositions of the invention can be used together with other immunotherapeutic compositions, including prophylactic and/or therapeutic immunotherapy.

The invention also includes a kit comprising any of the compositions described herein, or any of the individual components of the compositions described herein. Kits may include additional reagents and written instructions or directions for using any of the compositions of the invention to prevent or treat Ad-36 infection and/or obesity or being overweight that is or may be associated with such an infection.

Methods for Administration or Use of Compositions of the Invention

Compositions of the invention, which in one embodiment, include yeast-based immunotherapeutic compositions described above, as well as Ad-36 fusion proteins described herein and recombinant nucleic acid molecules encoding such Ad-36 fusion proteins, and other compositions comprising such yeast-based compositions, fusion proteins, or recombinant molecules described herein, can be used in a variety of in vivo and in vitro methods, including, but not limited to, methods and uses to treat and/or prevent Ad-36 infection and/or obesity, excess weight (e.g., being clinically overweight), or abnormal adipose tissue hypertrophy associated with Ad-36 infection, other symptoms and conditions associated with Ad-36 infection and/or excess weight or abnormal adipose tissue hypertrophy, in diagnostic assays for Ad-36, or to produce antibodies against Ad-36.

One embodiment of the invention relates to a method to treat Ad-36 infection, and/or to prevent, ameliorate or treat at least one symptom or sequela of chronic Ad-36 infection, in an individual or population of individuals. In one aspect, the invention relates to a method to reduce or prevent obesity, excess weight, or abnormal adipose tissue hypertrophy that is associated with Ad-36 infection, by reducing, halting, or preventing, Ad-36 infection. The method includes the step of administering to an individual or a population of individuals who are, may be, or may become, infected with Ad-36, an immunotherapeutic composition of the invention. In one aspect, the composition is an immunotherapeutic composition comprising one or more Ad-36 antigens (Ad-36 proteins and/or immunogenic domains thereof), including any of the Ad-36 antigens (including any fusion protein) as described herein. In one aspect, the immunotherapeutic composition is a yeast-based immunotherapeutic composition. In one aspect, the composition includes a fusion protein comprising Ad-36 antigens as described herein, or recombinant nucleic acid molecule encoding such antigens. In one embodiment, the individual or population of individuals has Ad-36 infection (is currently infected with Ad-36 or at least has evidence of being infected). In one embodiment, the individual or population of individuals is overweight or obese, and in another embodiment, the individual or population of individuals is not overweight or is not obese. In one aspect, the individual or population of individuals is additionally treated with at least one other therapeutic compound or therapeutic protocol useful for the treatment of Ad-36 infection, or useful for the treatment of a condition associated with Ad-36 infection, including, but not limited to, obesity, being overweight, abnormal adipose tissue hypertrophy, type II diabetes, or symptoms of these conditions. Suitable additional therapeutic compounds include, but are not limited to, direct-acting antiviral drugs and/or interferons and/or other immunotherapeutic or immunomodulatory agents and/or insulin. Suitable additional therapeutic protocols include, but are not limited to, the administration of such agents, diet programs, and exercise programs.

Another embodiment of the invention relates to a method to immunize an individual or population of individuals against Ad-36 in order to prevent Ad-36 infection, prevent chronic Ad-36 infection, and/or reduce the severity of Ad-36 infection in the individual or population of individuals. The method includes the step of administering to an individual or population of individuals that is not infected with Ad-36 (or believed not to be infected with Ad-36 or not known to be or have been infected with Ad-36), a composition of the invention. In one aspect, the composition is an immunotherapeutic composition comprising one or more Ad-36 antigens as described herein, including a yeast-based immunotherapeutic composition. In one aspect, the composition includes a fusion protein comprising Ad-36 antigens as described herein, or recombinant nucleic acid molecule encoding such fusion protein.

As used herein, the phrase "treat" Ad-36 infection, or any permutation thereof (e.g., "treated for Ad-36 infection", etc.) generally refers to applying or administering a composition of the invention once the infection (acute or chronic) has occurred, with the goal of reduction or elimination of detectable viral titer, reaching seroconversion as measured by development of antibodies against Ad-36 that are reflective of an elimination of the virus, reduction in at least one symptom resulting from the infection in the individual (e.g., reduction in BMI, reduction in body weight, reduced rate of weight gain, reduced adiposity, etc.), delaying or preventing the onset and/or severity of symptoms and/or downstream sequela caused by the infection, reduction of organ or physiological system damage resulting from the infection, improvement in organ or system function that was negatively impacted by the infection, improvement of immune responses against the virus, improvement of long term memory immune responses against the virus, and/or improved general health of the individual or population of individuals. To "prevent" Ad-36 infection, or any permutation thereof (e.g., "prevention of Ad-36 infection", etc.), generally refers to applying or administering a composition of the invention before an infection with Ad-36 has occurred, with the goal of preventing infection by Ad-36, preventing chronic infection by Ad-36 (i.e., enabling an individual to clear an acute Ad-36 infection without further intervention), or at least reducing the severity, and/or length of infection and/or the physiological damage caused by the chronic infection, and/or reducing the rate of weight gain, in an individual or population of individuals should the infection later occur.

According to the present invention, body mass index, or BMI, is routinely used to determine a degree of weight excess (e.g., being overweight) and obesity, although it is not a direct measure of body fat. It is a measure of weight in relation to height of an individual and can be calculated in English or metric units. According to the Centers for Disease Control and Prevention (CDC), an adult who has a body mass index (BMI) between 25 and 29.9 is considered to be overweight. An adult who has a BMI of 30 or higher is considered to be obese. For children and teens, BMI ranges above a normal weight have different labels and take into account normal differences in body fat between boys and girls and differences in body fat at various ages. Being "overweight" in children and teens ages 2-19 years is defined as a BMI at or above the $85^{th}$ percentile and lower than the $95^{th}$ percentile for children of the same age and sex. Obesity in children and teens ages 2-19 is defined as a BMI at or above the $95^{th}$ percentile for children of the same age and sex. As used herein, the phrase "excess weight" is generally used to refer to a weight that is greater than that considered to be healthy for an individual of a given age, gender, and/or height, which is typically at least "overweight" as defined by the CDC or other public health institution and as set forth herein. Accordingly, the reference to "excess weight" can be used interchangeably with reference to "overweight" or "being overweight". BMI calculators for children and teens, as well as adults, are publicly available through the Centers for Disease Control and Prevention, for example, and can be used to determine BMI for a specific age, height, gender and weight (for children and teens, for adults, height and weight are considered), and advise the weight percentile for the individual if child or teen, and further advise whether the individual is considered to be potentially overweight or obese according to current standards for children, teens and adults.

According to the invention, reference to "abnormal adipose tissue", "hypertrophic adipose tissue" or "abnormal adipose tissue hypertrophy", refers to an increase in adipose tissue (adiposity) or adipocyte growth that is abnormal and typically presents as a benign lipoma or a deposit of adipose tissue in an unusual anatomical location. Abnormal adipose tissue is therefore distinguished from obesity, as an individual may not be clinically obese, but may have areas of abnormal adipose tissue or adipose tissue hypertrophy. Abnormal adipose tissue is, for example, a condition associated with HIV infection.

Preferably, the use of an immunotherapeutic composition of the invention results in the prevention of obesity or excess weight gain, in a reduction in weight gained or a reduced rate of weigh gain in individuals who are or become infected with Ad-36, and/or in a reduction in the likelihood of becoming obese or overweight, in an individual who is or becomes infected with the virus but is not currently overweight or obese. In an adult individual with a BMI of 30 or higher, or in a child or teen aged 2-19 years with a BMI at or above the $95^{th}$ percentile for children/teens of the same age and sex, in one aspect of the invention, the use of an immunotherapeutic composition of the invention results in a reduction of BMI in the individual to less than 30 for such adults, or less than the 95$^{th}$ percentile for such children or teens. In an adult individual with a BMI of between 25 and 29.9, or in a child or teen aged 2-19 years with a BMI at or above the 85$^{th}$ percentile for children/teens of the same age and sex, in one aspect of the invention, the use of an immunotherapeutic composition of the invention results in a reduction of BMI to below 25 for such adults, and to less than the 85$^{th}$ percentile for such children or teen.

The efficacy, or effectiveness, of an immunotherapeutic composition of the invention can also be defined as a statistically significant change, or statistical trend, toward patient benefit in any one or more measurable or detectable parameter associated with Ad-36 infection or conditions linked to such infection, in an individual receiving the immunotherapeutic composition, as compared to a control value for the parameter being evaluated. In one aspect of the invention, a clinically relevant change can be measured as a percentage change toward patient benefit as compared to a prior evaluation, and can be 1%, 2%, 3%, 4%, 5%, 6%, 7%, 8%, 9%, 10%, or greater. Benefit can also be measured as a change in the slope of a curve over time as compared to a control (e.g., a change in the slope of body weight or the rate of weight gain plotted over time before, during and after treatment).

Parameters to be evaluated for determination of effectiveness of a composition or method of the invention include, but are not limited to, viral load, viral clearance, adipose tissue hypertrophy, body weight, BMI, rate of weight gain, total body fat, serum cholesterol, triglycerides, blood pressure, glucose tolerance, insulin sensitivity, and immune responses, including Ad-36-specific T cell responses and neutralizing antibody responses. The control value can be selected from any suitable control value, including, but not limited to, one or more prior measurements of the parameter in the same individual; a measurement of the parameter as an average or mean in a population of individuals meeting similar criteria for gender, age, weight, and or other clinical status; or a reference value provided in the form of stored information regarding a previously determined baseline level for the given parameter. Such a form of stored information can include, for example, but is not limited to, a reference chart, listing or electronic file of population or individual data regarding "healthy" individuals (negative control), or obese or overweight individuals or individuals infected with Ad-36 that have not been cured or treated (positive control); a medical chart for the individual recording data from previous evaluations; or any other source of data regarding baseline levels that are useful for the evaluation of the efficacy of the treatment.

According to the invention, a "baseline level" is a control level, and in some embodiments (but not all embodiments, depending on the method), a normal level, of a given clinical endpoint or parameter against which a test level of the given clinical endpoint or parameter can be compared. The term "negative control" used in reference to a baseline level of such a clinical endpoint or parameter typically refers to a baseline level established in a sample from the patient or from a population of individuals that is believed to be normal (i.e., not infected with Ad-36, not overweight, not obese, not being abnormal with respect to the endpoint being tested). In one embodiment, a baseline level or control can be established from an individual at the onset of therapeutic or preventative treatment so that the status of the individual can be monitored over time and/or so that the efficacy of a given therapeutic or prophylactic protocol can be evaluated over time (continuously or intermittently). A "positive control" can include any control that confirms the positive detection of the parameter or clinical endpoint that is associated with Ad-36 infection and/or obesity or excess weight, or other associated endpoint.

Methods for detection of Ad-36 virus are known in the art and are described, for example, in WO 2007/120362, WO 2010 011440, WO 2007/064836, and WO 98/44946. The presence of viral DNA can be determined by conventional methods including, but not limited to, DNA sequencing, oligonucleotide hybridization, or PCR amplification. Detection of Ad-36 antibodies or proteins that bind to Ad-36 antibodies have also been described and such methods are encompassed by the invention. Binding can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

The present invention includes the delivery (administration, immunization) of an immunotherapeutic composition of the invention, including a yeast-based immunotherapy composition, to a subject. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a site of infection or target tissue, such as adipose tissue). Suitable routes of administration will be apparent to those of skill in the art, depending on the type of condition to be prevented or treated, the antigen used, and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). Other routes of administration that modulate mucosal immunity may be useful in the treatment of viral infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously. In one aspect, the immunotherapeutic composition is administered directly to adipose tissue.

With respect to the yeast-based immunotherapy compositions of the invention, in general, a suitable single dose is a dose that is capable of effectively providing a yeast vehicle and an antigen (if included) to a given cell type, tissue, or region of the patient body in an amount effective to elicit an antigen-specific immune response against one or more Ad-36 antigens or epitopes, when administered one or more times over a suitable time period. For example, in one embodiment, a single dose of a yeast vehicle of the present invention is from about $1\times10^5$ to about $5\times10^7$ yeast cell equivalents per kilogram body weight of the organism being administered the composition. In one aspect, a single dose of a yeast vehicle of the present invention is from about 0.1 Y.U. ($1\times10^6$ cells) to about 100 Y.U. ($1\times10^9$ cells) per dose (i.e., per organism), including any interim dose, in increments of $0.1\times10^6$ cells (i.e., $1.1\times10^6$, $1.2\times10^6$, $1.3\times10^6$ . . . ). In one embodiment, doses include doses between 1 Y.U and 40 Y.U. or 80 Y.U. and in one aspect, between 10 Y.U. and 40 Y.U. or 80 Y.U. In one embodiment, the doses are administered at different sites on the individual but during the same dosing period. For example, a 40 Y.U. dose may be administered via by injecting 10 Y.U. doses to four different sites on the individual during one dosing period, or a 20 Y.U. dose may be administered by injecting 5 Y.U. doses to four different sites on the individual, or by injecting 10 Y.U. doses to two different sites on the individual, during the same dosing period. The invention includes administration of an amount of the yeast-based immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose. One Yeast Unit (Y.U.) is $1\times10^7$ yeast cells.

"Boosters" or "boosts" of a therapeutic composition are administered, for example, when the immune response against the antigen has waned or as needed to provide an immune response or induce a memory response against a particular antigen or antigen(s). Boosters can be administered from about 1, 2, 3, 4, 5, 6, 7, or 8 weeks apart, to monthly, to bimonthly, to quarterly, to annually, to several years after the original administration. In one embodiment, an administration schedule is one in which from about $1\times10^5$ to about $5\times10^7$ yeast cell equivalents of a composition per kg body weight of the organism is administered at least 1, 2, 3, 4, 5, 6, 7, 8, 9, 10, or more times over a time period of from weeks, to months, to years. In one embodiment, the doses are administered weekly for 1, 2, 3, 4, 5, 6, 7, 8, 9, 10 or more doses, followed by monthly doses as needed to achieve the desired inhibition or elimination of the Ad-36 virus.

In one aspect of the invention, one or more additional therapeutic agents are administered sequentially with the yeast-based immunotherapy composition (e.g., a direct-acting antiviral, a nutraceutical composition, or the like). In another embodiment, one or more additional therapeutic agents are administered before the yeast-based immunotherapy composition is administered. In another embodiment, one or more additional therapeutic agents are administered after the yeast-based immunotherapy composition is administered. In one embodiment, one or more additional therapeutic agents are administered in alternating doses with the yeast-based immunotherapy composition, or in a protocol in which the yeast-based composition is administered at prescribed intervals in between or with one or more consecutive doses of the additional agents, or vice versa. In one embodiment, the yeast-based immunotherapy composition is administered in one or more doses over a period of time prior to commencing the administration of the additional agents. In other words, the yeast-based immunotherapy composition is administered as a monotherapy for a period of time, and then the agent administration is added, either concurrently with new doses of yeast-based immunotherapy, or in an alternating fashion with yeast-based immunotherapy. Alternatively, the agent may be administered for a period of time prior to beginning administration of the yeast-based immunotherapy composition. In one aspect, the yeast is engineered to express or carry the agent, or a different yeast is engineered or produced to express or carry the agent.

In the method of the present invention, compositions and therapeutic compositions can be administered to animal, including any vertebrate, and particularly to any member of the Vertebrate class, *Mammalia*, including, without limitation, primates, rodents, livestock and domestic pets. Livestock include mammals to be consumed or that produce useful products (e.g., sheep for wool production). Mammals to treat or protect include humans, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); Current Protocols in Molecular Biology (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and *Vaccines*, S. Plotkin, W. Orenstein, and P. Offit, eds., Fifth Edition (2008).

GENERAL DEFINITIONS

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound (including a protein or peptide) has at least one detectable activity that has an effect on the metabolic or other processes of a cell or organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA, immunoblot assays, etc.).

Reference to a protein or polypeptide used in the present invention includes full-length proteins, fusion proteins, or any fragment, domain (structural, functional, or immunogenic), conformational epitope, or homologue of such proteins. An isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have either enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule may also include portions of a gene. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

Yeast-Based Immunotherapeutic Design and Production

The following example describes the design and production of several different yeast-based immunotherapeutic compositions for the treatment or prevention of adenovirus-36 (Ad-36) infection.

In these experiments, yeast (e.g., *Saccharomyces cerevisiae*) were engineered to express various Ad-36 fusion proteins under the control of the copper-inducible promoter, CUP1, or the TEF2 promoter. Briefly, to produce each of the yeast-based immunotherapeutics constructed in this Example, DNA encoding the Ad-36 antigen as set forth for each fusion protein below was prepared, codon optimized for expression in yeast, and then digested with SpeI and NotI and inserted behind the CUP1 promoter (pGI-100) or the TEF2 promoter (pTK57-1), as indicated for each construct below, in yeast 2 μm expression vectors. The resulting plasmids were introduced into *Saccharomyces cerevisiae* W303α yeast by Lithium acetate/polyethylene glycol transfection, and primary transfectants were selected on solid minimal plates lacking Uracil (UDM; uridine dropout medium). Other yeast strains, yeast species or yeast genera can be used in yeast-based immunotherapeutics of the invention; *Saccharomyces cerevisiae* W303α is an exemplary strain. Colonies were re-streaked onto UDM or ULDM (uridine and leucine dropout medium) and allowed to grow for 3 days at 30° C. Liquid cultures lacking uridine (U2) or lacking uridine and leucine (UL2) were inoculated from plates and starter cultures were grown for 20 h at 30° C., 250 rpm. If desired, although not used for these experiments, pH buffered media containing 4.2 g/L of Bis-Tris (BT-U2; BT-UL2) can be inoculated. Primary cultures were used to inoculate final cultures of the same formulation and growth is continued until a density or 1.1 to 4.0 Y.U./mL is reached.

For TEF2 strains (constitutive expression), cells were then harvested, washed and heat killed at 56° C. for 1 h in PBS. For CUP1 strains (inducible expression), expression was induced in the same medium with 0.375 mM copper sulfate for 5 h at 30° C., 250 rpm. Cells were harvested, washed and heat killed at 56° C. for 1 h in PBS.

After heat kill of TEF2 and CUP1 cultures, cells were washed three times in PBS. Total protein expression was measured by a TCA precipitation/nitrocellulose binding assay and Ad-36 fusion protein expression was measured by western blot using an anti-his tag monoclonal antibody (see FIGS. 1 and 2). As described below, FIGS. 1 and 2 showed that the yeast-based immunotherapy composition of the invention expressed the Ad-36 fusion protein well using both promoters, and using two different N-terminal sequences in the fusion proteins (SEQ ID NO:56 or SEQ ID NO:58), and were readily identified by Western blot.

Recipe for U2 liquid medium:
 20 g/L of glucose
 6.7 g/L of Yeast nitrogen base containing ammonium sulfate
 0.04 mg/mL each of histidine, leucine, tryptophan, and adenine Recipe for UL2 liquid medium:
 20 g/L of glucose
 6.7 g/L of Yeast nitrogen base containing ammonium sulfate
 0.04 mg/mL each of histidine, tryptophan, and adenine Several different yeast-based immunotherapeutics expressing Ad-36 fusion proteins were produced in this experiment. One yeast-based immunotherapeutic, denoted in FIG. 1 as "FIB", was designed to express an Ad-36 fusion protein as a single polypeptide comprising selected portions of the Ad-36 fiber protein (the full Ad-36 fiber protein is represented by SEQ ID NO:34), fused at its N-terminus to a synthetic peptide represented by SEQ ID NO:58. *Saccharomyces cerevisiae* were engineered to express this protein under the control of the TEF2 promoter. The fusion protein has the following sequence elements fused in frame from N- to C-terminus, represented by SEQ ID NO:42: (1) an N-terminal peptide to impart resistance to proteasomal degradation and stabilize expression (positions 1 to 6 of SEQ ID NO:42); (2) positions 71-136 of Ad-36 fiber (positions 71-136 of SEQ ID NO:34 or a corresponding sequence from another Ad-36 strain or isolate), corresponding to positions 7-72 of SEQ ID NO:42; (3) positions 145-169 of Ad-36 fiber (positions 145-169 of SEQ ID NO:34 or a corresponding sequence from another Ad-36 strain or isolate), corresponding to positions 73-97 of SEQ ID NO:42; (4) positions 290-313 of Ad-36 fiber (positions 290-313 of SEQ ID NO:34 or a corresponding sequence from another Ad-36 strain or isolate), corresponding to positions 98-194 of SEQ ID NO:42; (5) positions 334-363 of Ad-36 fiber (positions 334-363 of SEQ ID NO:34 or a corresponding sequence from another Ad-36 strain or isolate), corresponding to positions 195-224 of SEQ ID NO:42; and (6) a hexahistidine tag (positions 225-230 of SEQ ID NO:42). The amino acid segments used in this fusion protein can be modified by the use of additional amino acids flanking either end of any domain. The nucleic acid sequence encoding the fusion protein of SEQ ID NO:42 was codon optimized for expression in yeast, and the yeast-based immunotherapeutic expressing this fusion protein was produced as described above.

The expression of this Ad-36 fiber fusion protein in yeast is shown in FIG. 1 (FIB). The estimated expression level of the fusion protein was 1704 ng/Y.U.

Figure 2:
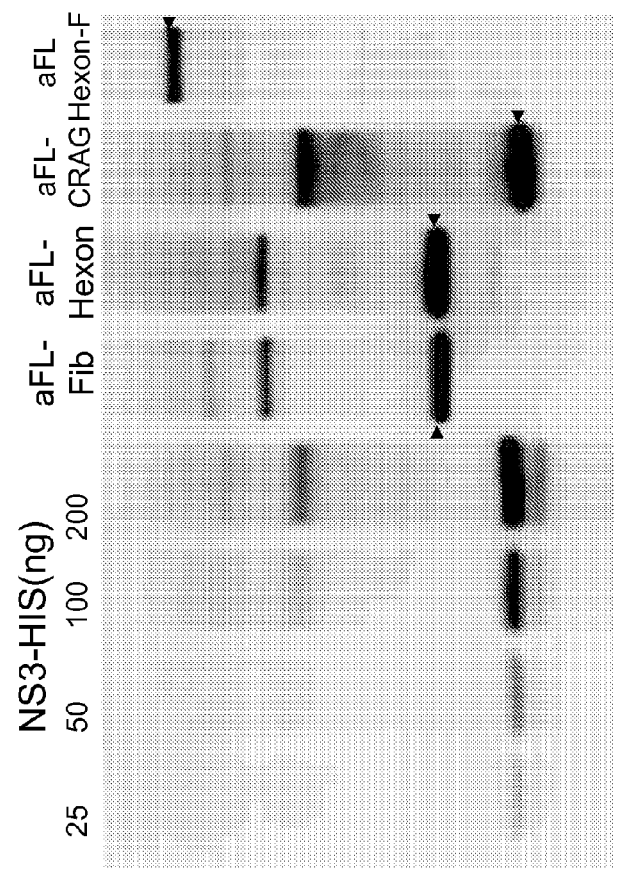
FIG. 2 is a digitized image of a western blot showing expression of: (1) a yeast-based immunotherapy composition expressing an Ad-36 fusion protein comprising fiber (Ad-aFL-FIB) (SEQ ID NO:48) under the control of a Cup1 promoter; (2) a yeast-based immunotherapy composition expressing an Ad-36 fusion protein comprising hexon (Ad-aFL-HEX) (SEQ ID NO:50) under the control of a Cup1 promoter; (3) a yeast-based immunotherapy composition expressing an Ad-36 fusion protein comprising CR1α and CR1γ (Ad-aFL-CRAG) (SEQ ID NO:54) under the control of a Cup1 promoter; and (4) a yeast-based immunotherapy composition expressing an Ad-36 fusion protein comprising full length hexon (Ad-aFL-Hexon-Full) (SEQ ID NO:52) under the control of a TEF2 promoter.

Another yeast-based immunotherapeutic, denoted in FIG. 2 as "aFL-Fib" was designed to express an Ad-36 fusion protein as a single polypeptide comprising portions of the Ad-36 fiber protein (the full Ad-36 fiber protein is represented by SEQ ID NO:34) fused at its N-terminus to a yeast alpha factor signal leader (SEQ ID NO:56). *Saccharomyces cerevisiae* were engineered to express this protein under the control of the CUP1 promoter. This fusion protein has the following sequence elements fused in frame from N- to C-terminus, represented by SEQ ID NO:48: (1) an N-terminal peptide to impart resistance to proteasomal degradation and stabilize or enhance expression (SEQ ID NO:56, or positions 1 to 89 of SEQ ID NO: 48); (2) a two amino acid spacer/linker (Thr-Ser) to facilitate cloning and manipulation of the sequences (positions 90 to 91 of SEQ ID NO:48); (3) positions 71-136 of Ad-36 fiber (positions 71-136 of SEQ ID NO:34 or a corresponding sequence from another Ad-36 strain or isolate), corresponding to positions 92-157 of SEQ ID NO:48; (4) positions 145-169 of Ad-36 fiber (positions 145-169 of SEQ ID NO:34 or a corresponding sequence from another Ad-36 strain or isolate), corresponding to positions 158-182 of SEQ ID NO:48; (5) positions 290-313 of Ad-36 fiber (positions 290-313 of SEQ ID NO:34 or a corresponding sequence from another Ad-36 strain or isolate), corresponding to positions 183-279 of SEQ ID NO:48; (6) positions 334-363 of Ad-36 fiber (positions 334-363 of SEQ ID NO:34 or a corresponding sequence from another Ad-36 strain or isolate), corresponding to positions 280-309 of SEQ ID NO:48; and (7) a hexahistidine tag (positions 310-315 of SEQ ID NO:48). The amino acid segments used in this fusion protein can be modified by the use of additional amino acids flanking either end of any domain; the example provided herein is exemplary. The nucleic acid sequence encoding the fusion protein of SEQ ID NO:48 was codon optimized for expression in yeast, and the yeast-based immunotherapeutic expressing this fusion protein was produced as described above.

The expression of this Ad-36 fiber fusion protein in yeast is shown in FIG. 2 (aFL-FIB). The estimated expression level of the fusion protein was 14,854 ng/Y.U.

Another yeast-based immunotherapeutic, denoted in FIG. 1 as "HEX", was designed to express an Ad-36 fusion protein as a single polypeptide comprising portions of the Ad-36 hexon protein (the full Ad-36 hexon protein is represented by SEQ ID NO:18) fused at its N-terminus to a synthetic peptide represented by SEQ ID NO:58. *Saccharomyces cerevisiae* were engineered to express this protein under the control of the TEF2 promoter. This fusion protein has the following sequence elements fused in frame from N- to C-terminus, represented by SEQ ID NO:43: (1) an N-terminal peptide to impart resistance to proteasomal degradation and stabilize expression (positions 1 to 6 of SEQ ID NO:43); (2) positions 136-218 of Ad-36 hexon (positions 136-218 of SEQ ID NO:18 or a corresponding sequence from another Ad-36 strain or isolate), corresponding to positions 7-89 of SEQ ID NO:43; (3) positions 235-285 of Ad-36 hexon (positions 235-285 of SEQ ID NO:18 or a corresponding sequence from another Ad-36 strain or isolate), corresponding to positions 90-141 of SEQ ID NO:43; (4) positions 297-308 of Ad-36 hexon (positions 297-308 of SEQ ID NO:18 or a corresponding sequence from another Ad-36 strain or isolate), corresponding to positions 142-153 of SEQ ID NO:43; (5) positions 410-450 of Ad-36 hexon (positions 410-450 of SEQ ID NO:18 or a corresponding sequence from another Ad-36 strain or isolate), corresponding to positions 154-194 of SEQ ID NO:43; and (6) a hexahistidine tag (positions 195-200 of SEQ ID NO:43). The amino acid segments used in this fusion protein can be modified by the use of additional amino acids flanking either end of any domain. The nucleic acid sequence encoding the fusion protein of SEQ ID NO:43 was codon optimized for expression in yeast, and the yeast-based immunotherapeutic expressing this fusion protein was produced as described above.

The expression of this Ad-36 hexon fusion protein in yeast is shown in FIG. 1 (HEX). The estimated expression level of this protein was 1981 ng/Y.U.

Another yeast-based immunotherapeutic, denoted in FIG. 2 as "aFL-Hexon" was designed to express an Ad-36 fusion protein as a single polypeptide comprising portions of the Ad-36 hexon protein (the full Ad-36 hexon protein is represented by SEQ ID NO:18) fused with yeast alpha factor leader signal sequence (SEQ ID NO:56). *Saccharomyces cerevisiae* were engineered to express this protein under the control of the CUP1 promoter. This fusion protein has the following sequence elements fused in frame from N- to C-terminus, represented by SEQ ID NO:50: (1) an N-terminal peptide to impart resistance to proteasomal degradation and stabilize or enhance expression (SEQ ID NO:56, or positions 1 to 89 of SEQ ID NO:50); 2) a two amino acid spacer/linker (Thr-Ser) to facilitate cloning and manipulation of the sequences (positions 90 to 91 of SEQ ID NO:50); (3) positions 136-218 of Ad-36 hexon (positions 136-218 of SEQ ID NO:18 or a corresponding sequence from another Ad-36 strain or isolate), corresponding to positions 92-174 of SEQ ID NO:50; (4) positions 235-285 of Ad-36 hexon (positions 235-285 of SEQ ID NO:18 or a corresponding sequence from another Ad-36 strain or isolate), corresponding to positions 175-226 of SEQ ID NO:50; (5) positions 297-308 of Ad-36 hexon (positions 297-308 of SEQ ID NO:18 or a corresponding sequence from another Ad-36 strain or isolate), corresponding to positions 227-238 of SEQ ID NO:50; (6) positions 410-450 of Ad-36 hexon (positions 410-450 of SEQ ID NO:18 or a corresponding sequence from another Ad-36 strain or isolate), corresponding to positions 239-279 of SEQ ID NO:50; and (7) a hexahistidine tag (positions 280-285 of SEQ ID NO:50). The amino acid segments used in this fusion protein can be modified by the use of additional amino acids flanking either end of any domain. The nucleic acid sequence encoding the fusion protein of SEQ ID NO:50 was codon optimized for expression in yeast, and the yeast-based immunotherapeutic expressing this fusion protein was produced as described above.

The expression of this Ad-36 hexon fusion protein in yeast is shown in FIG. 2 (aFL-Hexon). The estimated expression level of this protein was 19,695 ng/Y.U.

Another yeast-based immunotherapeutic, denoted in FIG. 2 as "aFL-Hexon-F", was designed to express an Ad-36 fusion protein as a single polypeptide comprising the full-length Ad-36 hexon protein (the full hexon protein is represented by SEQ ID NO:18), fused at its N-terminus to yeast alpha factor leader sequence (SEQ ID NO:56). *Saccharomyces cerevisiae* were engineered to express this protein under the control of the TEF2 promoter. This fusion protein has the following sequence elements fused in frame from N- to C-terminus, represented by SEQ ID NO:52: (1) an N-terminal peptide to impart resistance to proteasomal degradation and stabilize or enhance expression (SEQ ID NO:56, or positions 1 to 89 of SEQ ID NO:52); 2) a two amino acid spacer/linker (Thr-Ser) to facilitate cloning and manipulation of the sequences (positions 90 to 91 of SEQ ID NO:52); (3) positions 2-944 of Ad-36 hexon (positions 2-944 of SEQ ID NO:18 or a corresponding sequence from another Ad-36 strain or isolate), corresponding to positions 92-1034 of SEQ ID NO:52; and (3) a hexahistidine tag (positions 1035-1040 of SEQ ID NO:52). This construct contains demonstrated or putative MHC Class I epitopes (e.g., positions 204-214 of SEQ ID NO:52; positions 404-412 of SEQ ID NO:52; positions 795-803 of SEQ ID NO:52; positions 928-936 of SEQ ID NO:52; or positions 994-1000 of SEQ ID NO:52), and demonstrated or putative MHC Class II epitopes (e.g., positions 100-110 of SEQ ID NO:52; positions 116-126 of SEQ ID NO:52; 406-420 of SEQ ID NO:52; positions 458-468 of SEQ ID NO:52; positions 792-803 of SEQ ID NO:52; or positions 947-957 of SEQ ID NO:52). The amino acid segments used in this fusion protein can be modified by the use of additional amino acids flanking either end of any domain. The nucleic acid sequence encoding the fusion protein of SEQ ID NO:44 was codon optimized for expression in yeast, and the yeast-based immunotherapeutic expressing this fusion protein was produced as described above.

The expression of this Ad-36 hexon fusion protein in yeast is shown in FIG. 2 (aFL-Hexon-F). The estimated expression level of this protein was 25,315 ng/Y.U.

Another yeast-based immunotherapeutic, denoted in FIG. 1 as "CRAG", was designed to express an Ad-36 fusion protein as a single polypeptide comprising portions of the Ad-36 CR1α and CR1γ proteins (the full CR1α protein is represented by SEQ ID NO:26 and the full CR1γ protein is represented by SEQ ID NO:29), fused at its N-terminus to a synthetic peptide represented by SEQ ID NO:58. *Saccharomyces cerevisiae* were engineered to express this protein under the control of the TEF2 promoter. This fusion protein has the following sequence elements fused in frame from N- to C-terminus, represented by SEQ ID NO:47: (1) an N-terminal peptide to impart resistance to proteasomal degradation and stabilize expression (positions 1 to 6 of SEQ ID NO:47); (2) positions 18-60 of CR1α (positions 18-60 of SEQ ID NO:26 or a corresponding sequence from another Ad-36 strain or isolate), corresponding to positions 7-49 of SEQ ID NO:47; (3) positions 123-157 of Ad-36 CR1α (positions 123-157 of SEQ ID NO:26 or a corresponding sequence from another Ad-36 strain or isolate), corresponding to positions 50-84 of SEQ ID NO:47; (4) positions 19-60 of Ad-36 CR1γ (positions 19-60 of SEQ ID NO:29 or a corresponding sequence from another Ad-36 strain or isolate), corresponding to positions 85-126 of SEQ ID NO:47; (5) positions 83-116 of Ad-36 CR1γ (positions 83-116 of SEQ ID NO:29 or a corresponding sequence from another Ad-36 strain or isolate), corresponding to positions 127-160 of SEQ ID NO:47; and (6) a hexahistidine tag (positions 161-166 of SEQ ID NO:47). The amino acid segments used in this fusion protein can be modified by the use of additional amino acids flanking either end of any domain. The nucleic acid sequence encoding the fusion protein of SEQ ID NO:43 was codon optimized for expression in yeast, and the yeast-based immunotherapeutic expressing this fusion protein was produced as described above.

The expression of this Ad-36 CR1α-CR1γ fusion protein is shown in FIG. 1 (CRAG). The estimated expression level of this protein was 3341 ng/Y.U.

Another yeast-based immunotherapeutic, denoted "aFL-CRAG" in FIG. 2, was designed to express an Ad-36 fusion protein as a single polypeptide comprising portions of the Ad-36 CR1α and CR1γ proteins (the full CR1α protein is represented by SEQ ID NO:26 and the full CR1γ protein is represented by SEQ ID NO:29), fused at its N-terminus to yeast alpha factor leader sequence (SEQ ID NO:56). *Saccharomyces cerevisiae* were engineered to express this protein under the control of the CUP1 promoter. This fusion protein has the following sequence elements fused in frame from N- to C-terminus, represented by SEQ ID NO:54: (1) an N-terminal peptide to impart resistance to proteasomal degradation and stabilize or enhance expression (SEQ ID NO:56, or positions 1 to 89 of SEQ ID NO:54); 2) a two amino acid spacer/linker (Thr-Ser) to facilitate cloning and manipulation of the sequences (positions 90 to 91 of SEQ ID NO:54); (3) positions 18-60 of CR1α (positions 18-60 of SEQ ID NO:26 or a corresponding sequence from another Ad-36 strain or isolate), corresponding to positions 92-134 of SEQ ID NO:54; (4) positions 123-157 of Ad-36 CR1α (positions 123-157 of SEQ ID NO:26 or a corresponding sequence from another Ad-36 strain or isolate), corresponding to positions 135-169 of SEQ ID NO:54; (5) positions 19-60 of Ad-36 CR1γ (positions 19-60 of SEQ ID NO:29 or a corresponding sequence from another Ad-36 strain or isolate), corresponding to positions 170-211 of SEQ ID NO:54; (6) positions 83-116 of Ad-36 CR1γ (positions 83-116 of SEQ ID NO:29 or a corresponding sequence from another Ad-36 strain or isolate), corresponding to positions 212-245 of SEQ ID NO:54; and (7) a hexahistidine tag (positions 246-251 of SEQ ID NO:54). The amino acid segments used in this fusion protein can be modified by the use of additional amino acids flanking either end of any domain. The nucleic acid sequence encoding the fusion protein of SEQ ID NO:54 was codon optimized for expression in yeast, and the yeast-based immunotherapeutic expressing this fusion protein was produced as described above. The expression of this Ad-36 CR1α-CR1γ fusion protein is shown in FIG. 2 (aFL-CRAG). The estimated expression level of this protein was 16,154 ng/Y.U.

Additional yeast-based immunotherapeutic compositions have been designed by the inventors and are produced using the same protocols described above. For example, another yeast-based immunotherapeutic is designed to express an Ad-36 fusion protein as a single polypeptide comprising the full-length Ad-36 hexon protein (the full hexon protein is represented by SEQ ID NO:18), fused at its N-terminus to a synthetic peptide represented by SEQ ID NO:58. *Saccharomyces cerevisiae* are engineered to express this protein under the control of the TEF2 or CUP1 promoter. This fusion protein has the following sequence elements fused in frame from N- to C-terminus, represented by SEQ ID NO:44: (1) an N-terminal peptide to impart resistance to proteasomal degradation and stabilize expression (positions 1 to 6 of SEQ ID NO:44); (2) positions 2-944 of Ad-36 hexon (positions 2-944 of SEQ ID NO:18 or a corresponding sequence from another Ad-36 strain or isolate), corresponding to positions 7-949 of SEQ ID NO:44; and (3) a hexahistidine tag (positions 950-955 of SEQ ID NO:44). This construct contains demonstrated or putative MHC Class I epitopes (e.g., positions 119-129 of SEQ ID NO:44; positions 319-327 of SEQ ID NO:44; positions 710-718 of SEQ ID NO:44; positions 843-851 of SEQ ID NO:44; or positions 909-915 of SEQ ID NO:44), and demonstrated or putative MHC Class II epitopes (e.g., positions 15-25 of SEQ ID NO:44; positions 31-41 of SEQ ID NO:44; 321-335 of SEQ ID NO:44; positions 373-383 of SEQ ID NO:44; positions 707-718 of SEQ ID NO:44; or positions 862-872 of SEQ ID NO:44). The amino acid segments used in this fusion protein can be modified by the use of additional amino acids flanking either end of any domain; the example provided herein is exemplary. A nucleic acid sequence encoding the fusion protein of SEQ ID NO:44 is codon optimized for expression in yeast, and a yeast-based immunotherapeutic expressing this fusion protein is produced as described above.

Another yeast-based immunotherapeutic is designed to express an Ad-36 fusion protein as a single polypeptide comprising portions of the Ad-36 fiber and hexon proteins (full protein represented by SEQ ID NO:34 (fiber) and SEQ ID NO:18 (hexon)), fused at its N-terminus to a synthetic peptide represented by SEQ ID NO:58. *Saccharomyces cerevisiae* are engineered to express this protein under the control of the TEF2 or CUP1 promoter. This fusion protein has the following sequence elements fused in frame from N- to C-terminus, represented by SEQ ID NO:45: (1) an N-terminal peptide to impart resistance to proteasomal degradation and stabilize expression (positions 1 to 6 of SEQ ID NO:45); (2) positions 71-136 of Ad-36 fiber (positions 71-136 of SEQ ID NO:34 or a corresponding sequence from another Ad-36 strain or isolate), corresponding to positions 7-72 of SEQ ID NO:45; (3) positions 145-169 of Ad-36 fiber (positions 145-169 of SEQ ID NO:34 or a corresponding sequence from another Ad-36 strain or isolate), corresponding to positions 73-97 of SEQ ID NO:45; (4) positions 290-313 of Ad-36 fiber (positions 290-313 of SEQ ID NO:34 or a corresponding sequence from another Ad-36 strain or isolate), corresponding to positions 98-194 of SEQ ID NO:45; (5) positions 334-363 of Ad-36 fiber (positions 334-363 of SEQ ID NO:34 or a corresponding sequence from another Ad-36 strain or isolate), corresponding to positions 195-224 of SEQ ID NO:45; (6) positions 136-218 of Ad-36 hexon (positions 136-218 of SEQ ID NO:18 or a corresponding sequence from another Ad-36 strain or isolate), corresponding to positions 225-307 of SEQ ID NO:45; (7) positions 235-285 of Ad-36 hexon (positions 235-285 of SEQ ID NO:18 or a corresponding sequence from another Ad-36 strain or isolate), corresponding to positions 308-359 of SEQ ID NO:45; (8) positions 297-308 of Ad-36 hexon (positions 297-308 of SEQ ID NO:18 or a corresponding sequence from another Ad-36 strain or isolate), corresponding to positions 360-371 of SEQ ID NO:45; (9) positions 410-450 of Ad-36 hexon (positions 410-450 of SEQ ID NO:18 or a corresponding sequence from another Ad-36 strain or isolate), corresponding to positions 372-412 of SEQ ID NO:45; and (10) a hexahistidine tag (positions 413-418 of SEQ ID NO:45). The amino acid segments used in this fusion protein can be modified by the use of additional amino acids flanking either end of any domain; the example provided herein is exemplary. A nucleic acid sequence encoding the fusion protein of SEQ ID NO:45 is codon optimized for expression in yeast, and the yeast-based immunotherapeutic expressing this fusion protein is produced as described above.

Yet another yeast-based immunotherapeutic is designed to express an Ad-36 fusion protein as a single polypeptide comprising portions of the Ad-36 hexon and fiber proteins (full protein represented by SEQ ID NO:18 (hexon) and SEQ ID NO:34 (fiber)) fused at its N-terminus to a synthetic peptide represented by SEQ ID NO:58. *Saccharomyces cerevisiae* are engineered to express this protein under the control of the TEF2 or CUP1 promoter. This fusion protein has the following sequence elements fused in frame from N- to C-terminus, represented by SEQ ID NO:46: (1) an N-terminal peptide to impart resistance to proteasomal degradation and stabilize expression (positions 1 to 6 of SEQ ID NO:46); (2) positions 136-218 of Ad-36 hexon (positions 136-218 of SEQ ID NO:18 or a corresponding sequence from another Ad-36 strain or isolate), corresponding to positions 7-89 of SEQ ID NO:46; (3) positions 235-285 of Ad-36 hexon (positions 235-285 of SEQ ID NO:18 or a corresponding sequence from another Ad-36 strain or isolate), corresponding to positions 90-141 of SEQ ID NO:46; (4) positions 297-308 of Ad-36 hexon (positions 297-308 of SEQ ID NO:18 or a corresponding sequence from another Ad-36 strain or isolate), corresponding to positions 142-153 of SEQ ID NO:46; (5) positions 410-450 of Ad-36 hexon (positions 410-450 of SEQ ID NO:18 or a corresponding sequence from another Ad-36 strain or isolate), corresponding to positions 154-194 of SEQ ID NO:46; (6) positions 71-136 of Ad-36 fiber (positions 71-136 of SEQ ID NO:34 or a corresponding sequence from another Ad-36 strain or isolate), corresponding to positions 195-260 of SEQ ID NO:46; (7) positions 145-169 of Ad-36 fiber (positions 145-169 of SEQ ID NO:34 or a corresponding sequence from another Ad-36 strain or isolate), corresponding to positions 261-285 of SEQ ID NO:46; (8) positions 290-313 of Ad-36 fiber (positions 290-313 of SEQ ID NO:34 or a corresponding sequence from another Ad-36 strain or isolate), corresponding to positions 286-382 of SEQ ID NO:46; (9) positions 334-363 of Ad-36 fiber (positions 334-363 of SEQ ID NO:34 or a corresponding sequence from another Ad-36 strain or isolate), corresponding to positions 383-412 of SEQ ID NO:46; and (10) a hexahistidine tag (positions 413-418 of SEQ ID NO:46). The amino acid segments used in this fusion protein can be modified by the use of additional amino acids flanking either end of any domain; the example provided herein is exemplary. A nucleic acid sequence encoding the fusion protein of SEQ ID NO:46 is codon optimized for expression in yeast, and the yeast-based immunotherapeutic expressing this fusion protein is produced as described above.

Example 2

Infection/Replication of Ad-36 in Rat Stem Cells and A549 Cells

The following example describes the ability of Ad-36 to infect primary preadipocytes and A549 cells. This experiment demonstrates that viral stock that is intended for use in in vivo experiments described in the examples below is biologically active and can infect target cells of relevance in vitro. Ad-36 is a DNA virus and lacks mRNA. Transcription of Ad-36 genes into mRNA does not occur unless the virus has infected a mammalian host cell. The presence of Ad-36 mRNAs in the target cells is therefore direct evidence of viral infection and replication.

Figure 3:
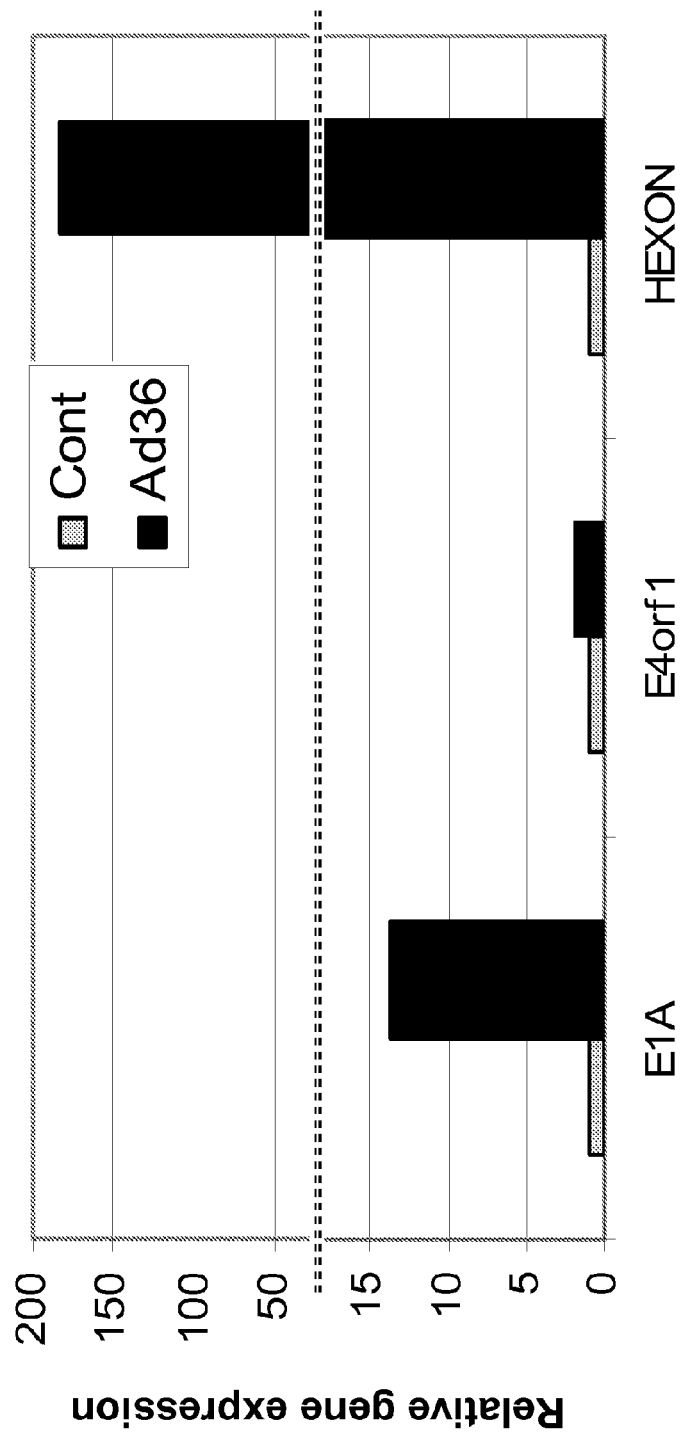
FIG. 3 is a bar graph showing the expression of genes encoding Ad-36 E1A, Ad-36 E4orf1, and Ad-36 hexon in rat adipose-derived stem cells (ADS) 15 hours after Ad-36 infection in vitro.
Figure 4:
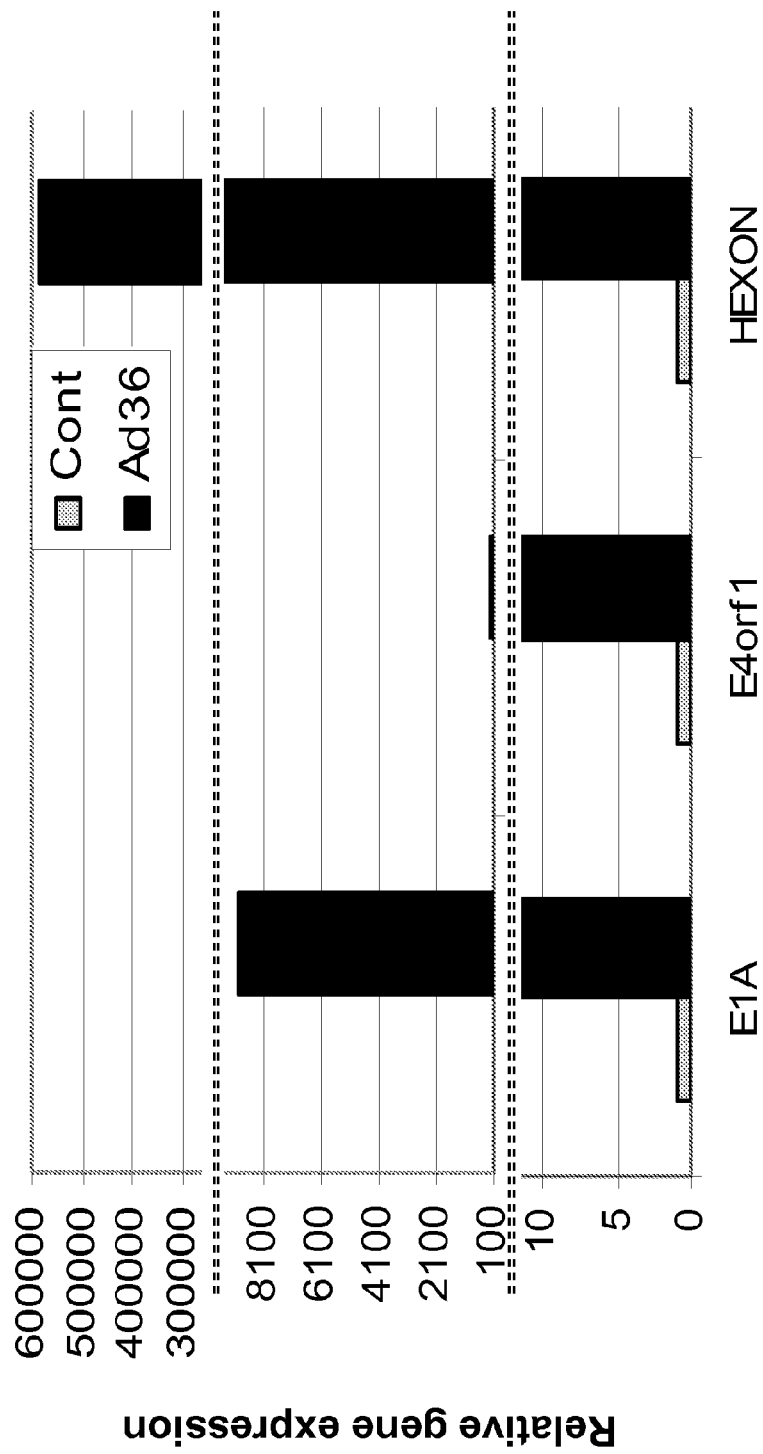
FIG. 4 is a bar graph showing the expression of genes encoding Ad-36 E1A, Ad-36 E4orf1 and Ad-36 hexon in A549 cells (natural host cell for human adenoviruses) 15 hours after Ad-36 infection in vitro.

Purified Ad-36 viral stock was added to rat adipose derived stem cells (ASC) and to A549 cells (human lung carcinoma line that is a natural host cell for human adenoviruses) in culture at a multiplicity of infection (MOI) of 5. Fifteen hours post-viral addition, total RNA was isolated from the target cells and was subjected to real-time reverse transcription PCR (RT-PCR) with fluorescent SYBR green designed to specifically measure the rate of PCR amplification of E1A, E4 orf1, and Hexon mRNAs. The relative expression of these genes was determined for mock-infected or Ad-36 infected targets. The results, shown in FIG. 3 (ASC) and FIG. 4 (A549) show the E1A and Hexon genes were expressed in both cellular targets and that the E4 Orf1 was expressed specifically in A549 cells. Gene expression required the addition of Ad-36, since mock infected cells showed only background levels of signal in all reactions.

Example 3

Rat Pilot Study-Ad36 Kinetics, and Infection of Visceral Fat Tissues

The following example describes the ability of the Ad-36 stock to infect rats in vivo and evaluates: i) the optimal dose of Ad-36 giving rise to successful viral inoculation, otherwise known as 'viral take'; ii) the kinetics of the blood viremic phase of infection; iii) the ability of the virus to infect the visceral adipose tissue.

Prior to the present invention, to the inventors' knowledge, there were no kinetic or dosing experiments or fat localization studies available that were robust enough or sufficient to establish an optimal animal model of Ad-36 infection that would be useful to evaluate prophylactic and therapeutic vaccine efficacy. Accordingly, the following experiments were designed to provide this information and to establish a relevant and useful model for studying Ad-36 infection (acute and chronic). Briefly, rats were injected intraperitoneally with PBS only or purified Ad-36 viral particles at 3 doses ($10^7$, $10^8$ or $10^9$ plaque forming units (PFU)), according to the protocol shown in Table 2. Blood samples were taken from rats at days 0 (pre-challenge) and days 1 post challenge (20 h), and at days 2 and 4 post-challenge. Virus DNA was prepared from 100 µl plasma using the QIAAMP® MINELUTE® Virus Kit (Qiagen), and the level of viral DNA was estimated by real time quantitative PCR (qPCR) featuring an Ad-36 hexon-DNA specific probe. Estimates of viral copy number were obtained by interpolation against a standard curve produced with purified hexon plasmid of known copy number. At two weeks post-challenge, rats were euthanized, the visceral fat was dissected and total DNA was isolated from the fat tissue using a proteinase K/isopropanol precipitation method. The DNA was subjected to nested two-round PCR featuring hexon DNA-specific PCR primers.

TABLE 2

| Group | # Rats | Ad36 Dose (PFU) | Total V.P. injected | Route | Blood Draws (days post-challenge) | | | | Fat Tissue Dissection |
|---|---|---|---|---|---|---|---|---|---|
| A | 2 | 0 | 0 | i.p. | d0 | d1 | d2 | d4 | d14 |
| B | 2 | $10^7$ | $2.3 \times 10^9$ | i.p. | d0 | d1 | d2 | d4 | d14 |
| C | 2 | $10^8$ | $2.3 \times 10^{10}$ | i.p. | d0 | d1 | d2 | d4 | d14 |
| D | 2 | $10^9$ | $2.3 \times 10^{11}$ | i.p. | d0 | d1 | d2 | d4 | d14 |

Figure 5:
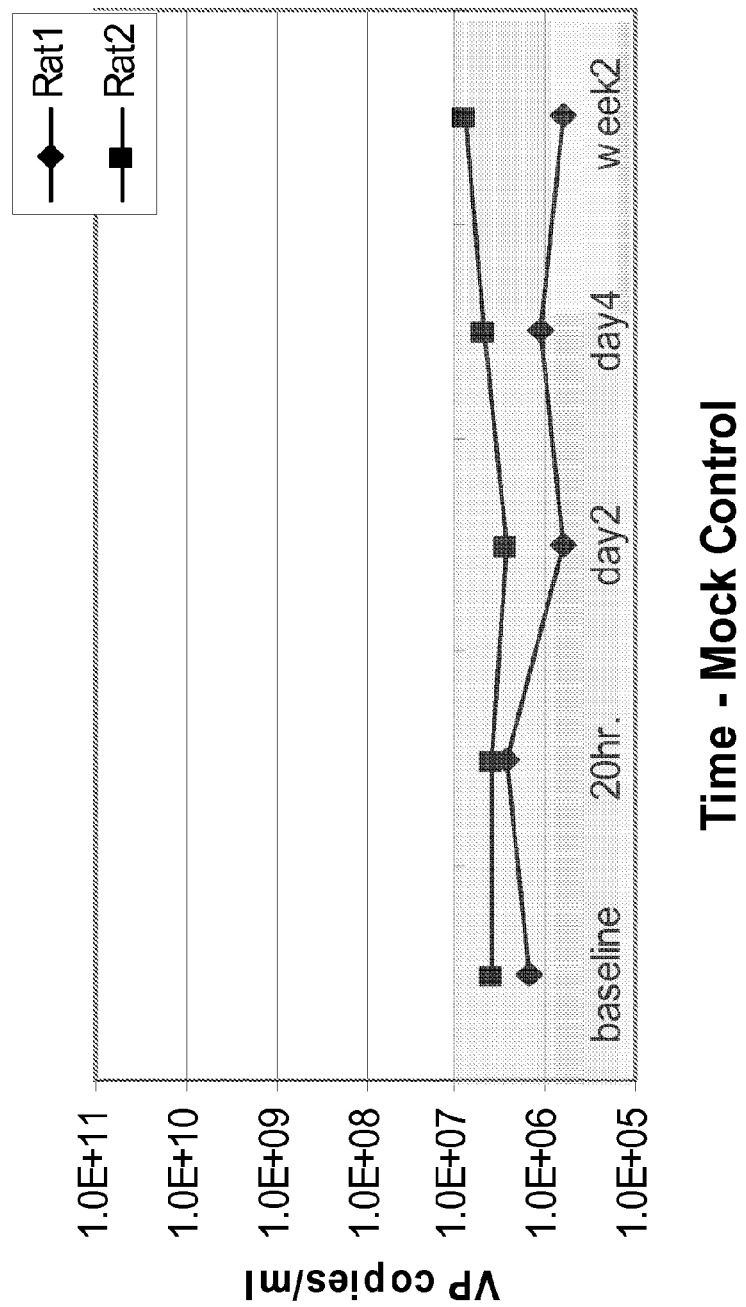
FIG. 5 is a graph showing the mock control for the early virus particles (V.P.) kinetics study.
Figure 6:
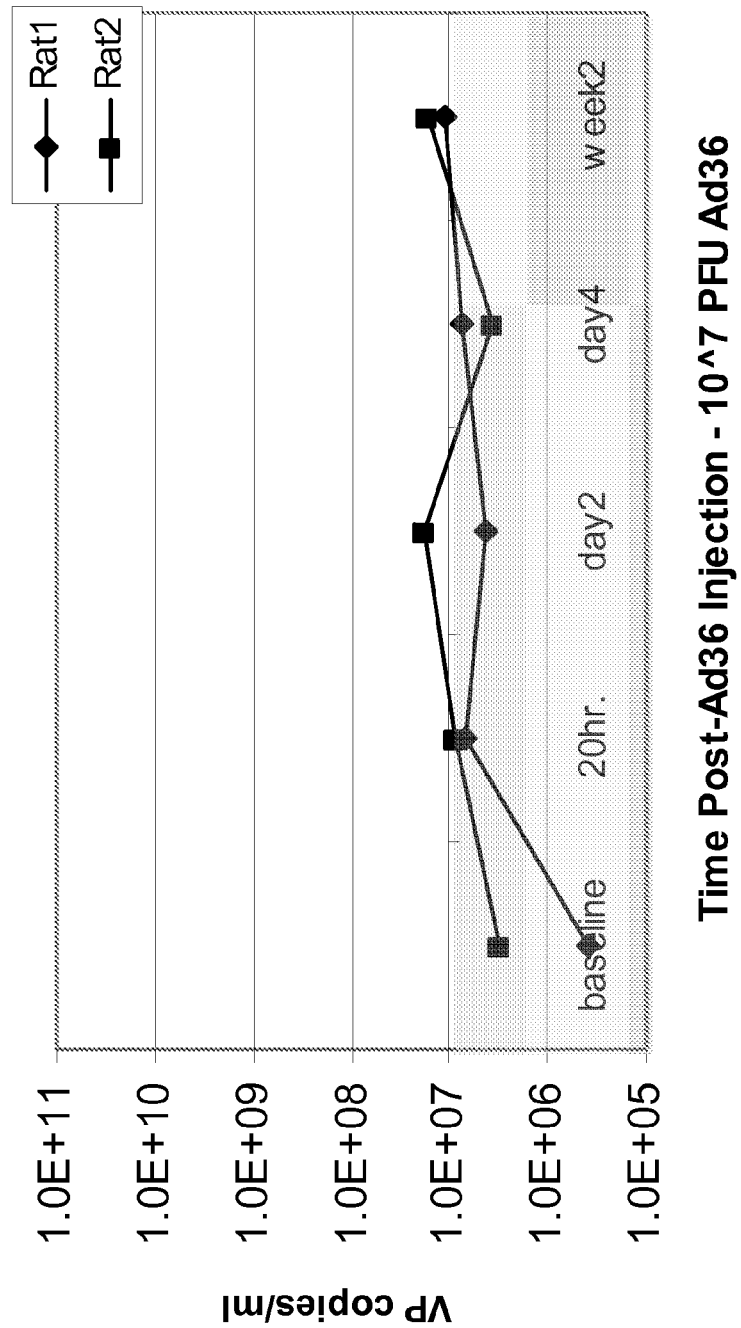
FIG. 6 is a graph showing early virus particles (V.P.) kinetics after $10^7$ PFU Ad-36 challenge.
Figure 7:
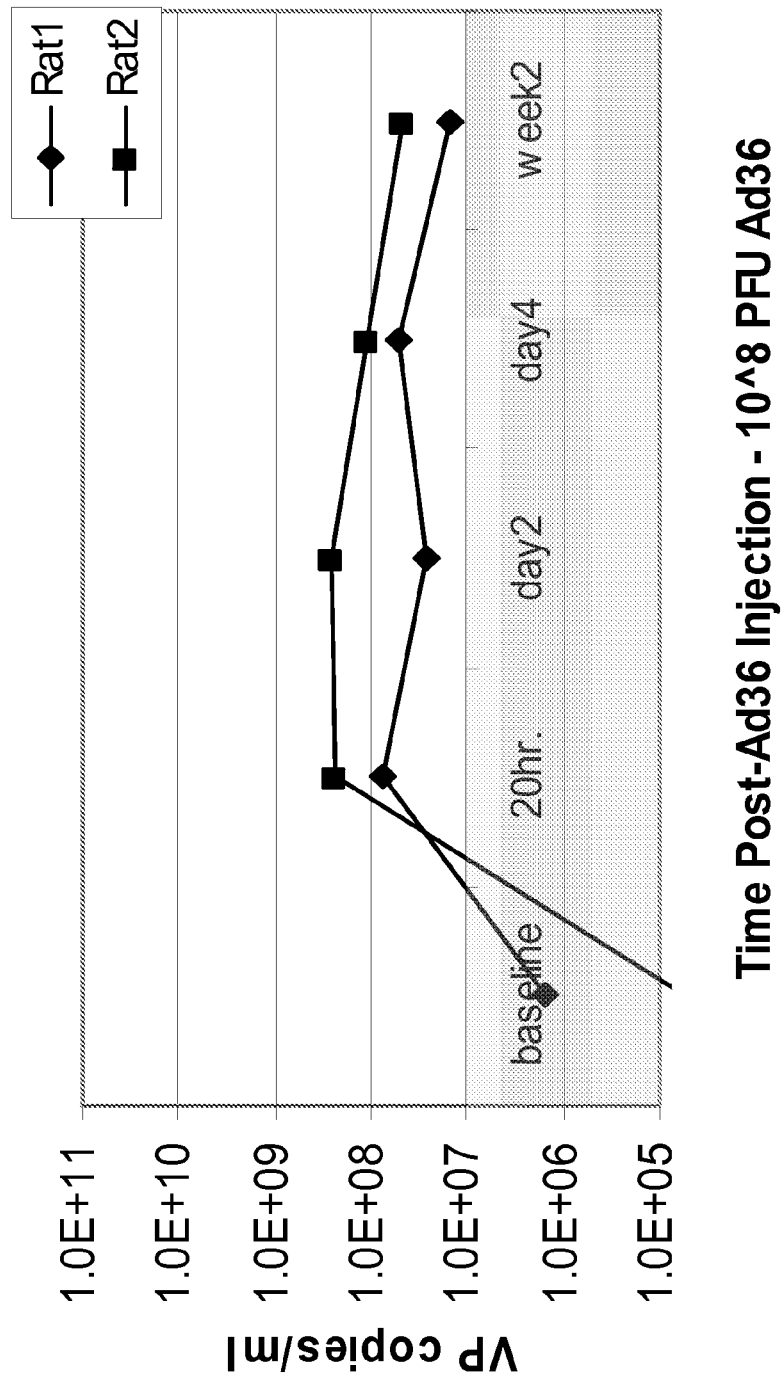
FIG. 7 is a graph showing early virus particles (V.P.) kinetics after $10^8$ PFU Ad-36 challenge.
Figure 8:
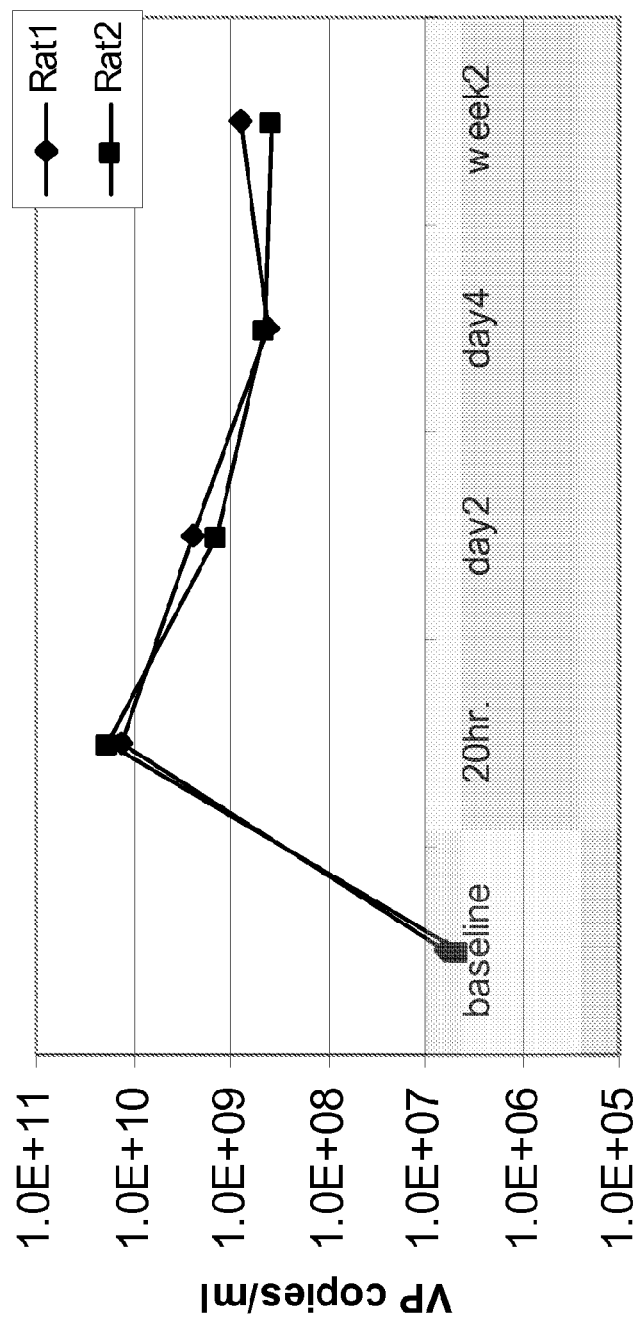
FIG. 8 is a graph showing early virus particles (V.P.) kinetics after $10^9$ PFU Ad-36 challenge.
Figure 9:
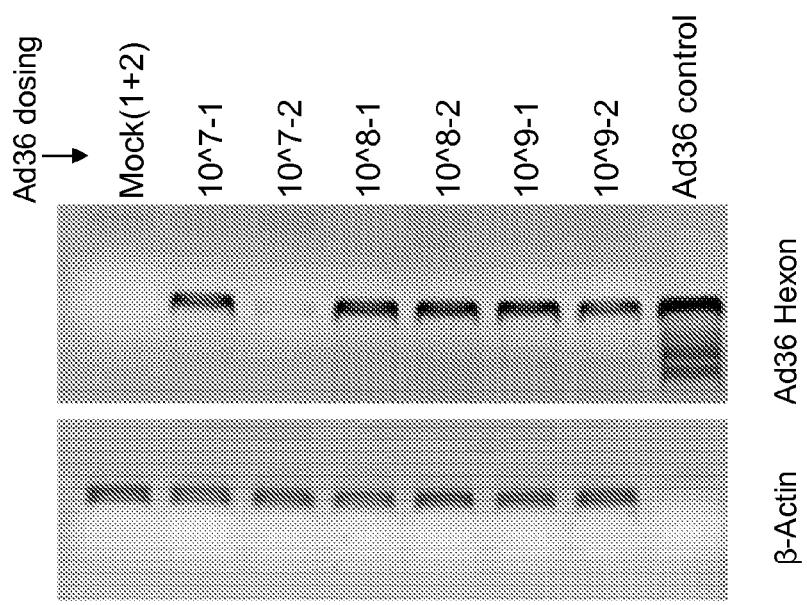
FIG. 9 is a digitized image of nested PCR detecting Ad-36 DNA in visceral adipose tissue from rats two weeks after infection with various doses of the virus in vivo.

Results showing the virus particle (V.P.) copies per ml blood at each level of viral infection are provided in FIG. 5 (Group A; mock control); FIG. 6 (Group B; $10^7$ PFU Ad-36); FIG. 7 (Group C; $10^8$ PFU Ad-36); and FIG. 8 (Group D; $10^9$ PFU Ad-36). FIG. 9 shows the results of PCR to detect Ad-36 hexon in visceral fat. Taken together, the results of these experiments demonstrate that: 1) the level of Ad-36 virus in the blood as determined by hexon qPCR is maximal at the $10^9$ PFU dose, and at 20 h post challenge; and 2) the Ad-36 virus is present in the visceral adipose tissue of all rats by 2 weeks post challenge at the $10^8$ and $10^9$ PFU doses, whereas at the $10^7$ PFU dose, virus was robustly detectable in the adipose tissue of only one of the two rats. These data show that the purified Ad-36 stock that was shown to infect primary preadipocytes in culture in Example 2 are also infective in vivo, and confirm published reports (e.g., Pasarica et al, 2008) that Ad-36 infects visceral adipose tissues. Since the maximal levels of viremia occurred with injection of $10^9$ PFU (see FIG. 8), this dose was selected for challenge of rats in the yeast-based immunotherapy vaccination experiments described in the following examples. Accordingly, these data were used to establish an optimized rat model system of Ad-36 infection for the testing of prophylactic and therapeutic vaccines (immunotherapy).

Example 4

Effect of Prophylactic Administration of Ad-36 Tarmogens in the Rat Model of Ad-36 Infection The following example describes the use of yeast-based adenovirus-36 (Ad-36) immunotherapeutics in rat prophylactic model of adenovirus-related obesity.

A rat model has been studied in the literature (Dhurandhar et al, Obesity 11:1905, 2006) in which Ad36-infected rats attained significantly greater body weight and fat pad weight by 30 weeks post-inoculation than mock infected control rats. Epididymal-inguinal, retroperitoneal, and visceral fat pad weights of the infected group were greater than PBS control rats by 60%, 46%, and 86%, respectively (p<0.00001). The present inventors have improved this rat model for the purposes of evaluating prophylactic and therapeutic vaccines, as described above in Example 3.

The following experiment describes a study to determine if prophylactic administration of the yeast-based immunotherapeutic compositions described in Example 1 prevent or reduce the extent of or rate of Ad-36-induced weight gain.

Cohorts of rats (n=18/group) were immunized subcutaneously (s.c.) with yeast-based Ad-36 immunotherapeutic compositions (vaccines), administered at four different sites with 20 million yeast cells (2 Y.U.) in 0.1 ml per site. In these experiments, two different yeast-based immunotherapeutic compositions were used. "Ad-aFL-CRAG" is the yeast-based immunotherapeutic described in Example 1 above that expresses an Ad-36 fusion protein comprising Ad-36 CR1α and CR1γ antigens, these antigens having an amino acid sequence of SEQ ID NO:55, which are linked at the N-terminus to an alpha factor leader sequence, to form a complete fusion protein having the amino acid sequence of SEQ ID NO:54. "Ad-aFL-HEX-Full" is the yeast-based immunotherapeutic described in Example 1 above that expresses an Ad-36 fusion protein comprising a near full-length hexon antigen, the antigen having an amino acid sequence of SEQ ID NO:53, which is linked at its N-terminus to an alpha factor leader sequence, to form a complete fusion protein having the amino acid sequence of SEQ ID NO:52. Dosing was once per week for 3 weeks and then, after a two week rest, rats were challenged intraperitoneally with Ad-36 ($10^9$ PFU), which was established in Example 3 to be the optimal viral dose for evaluating Ad-36 infection. Immunization was then conducted once per month for up to 30 weeks post-challenge. The experimental cohorts are shown in Table 3. Additional control groups include a group of rats receiving PBS only (naïve or "PBS"), and a group of rats immunized with control yeast compositions ("empty vector" yeast or "YVEC", which are yeast transfected with a vector that does not contain an antigen insert; i.e., these yeast do not express an Ad-36 antigen(s)).

TABLE 3

| Group | Pre-challenge Immunization | Challenge | Post-challenge Immunization |
|---|---|---|---|
| A | PBS | PBS | PBS |
| B | PBS | Ad-36 | PBS |
| C | YVEC | Ad-36 | YVEC |
| D | Yeast-Ad-aFL-CRAG | Ad-36 | Ad-aFL-CRAG |
| E | Yeast-Ad-aFL-HEX-Full | Ad-36 | Ad-aFL-HEX-Full |

Animals were weighed pre-immunization, pre-viral challenge and then biweekly for approximately 30 weeks following inoculation with virus. Food and water consumption were monitored throughout the study. Blood was collected at baseline, before viral challenge, and monthly following viral challenge to monitor for Ad-36 DNA, cholesterol, triglyceride levels, corticosterone, neutralizing antibodies to Ad-36, and other parameters (see Example 5). Glucose tolerance testing is performed at selected intervals and urine glucose levels are also measured. Blood (500 μl per timepoint) was obtained under isofluroane anaesthesia from the tail vein. At the end of the study, animals are euthanized and adipose tissue is harvested to measure viral levels by polymerase chain reaction (PCR). PCR may also be performed on biopsies obtained during the course of the study.

This experiment was performed in outbred Wistar rats. If, as expected, weight gain is prevented or reduced (or the rate of weight gain is reduced) in rats immunized with yeast-based Ad-36 immunotherapy as compared to control rats, inbred Wistar Furth rats will be evaluated according to the same or similar protocol, as this rat is expected to be more amenable to evaluation of T cell immunity. Additional experiments can also be conducted to determine the effect of diet or other factors in conjunction with immunotherapy (e.g., by administering a high fat diet versus a normal diet).

Immunization with a yeast-based Ad-36 immunotherapy composition is deemed active in this study if it causes, as compared with empty vector yeast or PBS controls, notable trends towards normalization of or beneficial outcome (more healthy, less characteristic of obesity or being or becoming overweight) in any one or more of the following parameters for Ad-36 infected rats: i) body weight or rate of body weight gain; ii) percent body fat or body mass index); iii) frequency or titer of neutralizing antibodies; iv) cholesterol levels; v) serum triglycerides vi) serum corticosterone; vii) blood and/or urine glucose levels; viii) glucose tolerance; ix) blood Ad-36 viral titer. Certain of these parameters have already been observed as positive indicators of the effectiveness of Ad-36-targeted yeast-based immunotherapy in immunized rats (see following discussion) at 18 weeks post-challenge, and are believed to show that yeast-based immunotherapy targeting Ad-36 is effective for reducing the rate of weight gain in an antigen-specific manner. It is expected that by the end of the study at 30 weeks when the Ad-36 induced phenotype fully emerges, the results will demonstrate that immunization with a yeast-based Ad-36 immunotherapy composition is effective for reducing and/or preventing weight gain, reducing rate of weight gain, and/or reducing or preventing adiposity in rats infected with Ad-36 in an antigen-specific or Ad-36-specific manner, and this may be accompanied by changes in the biochemical parameters mentioned, given their known association with the obesity phenotype.

Figure 10:
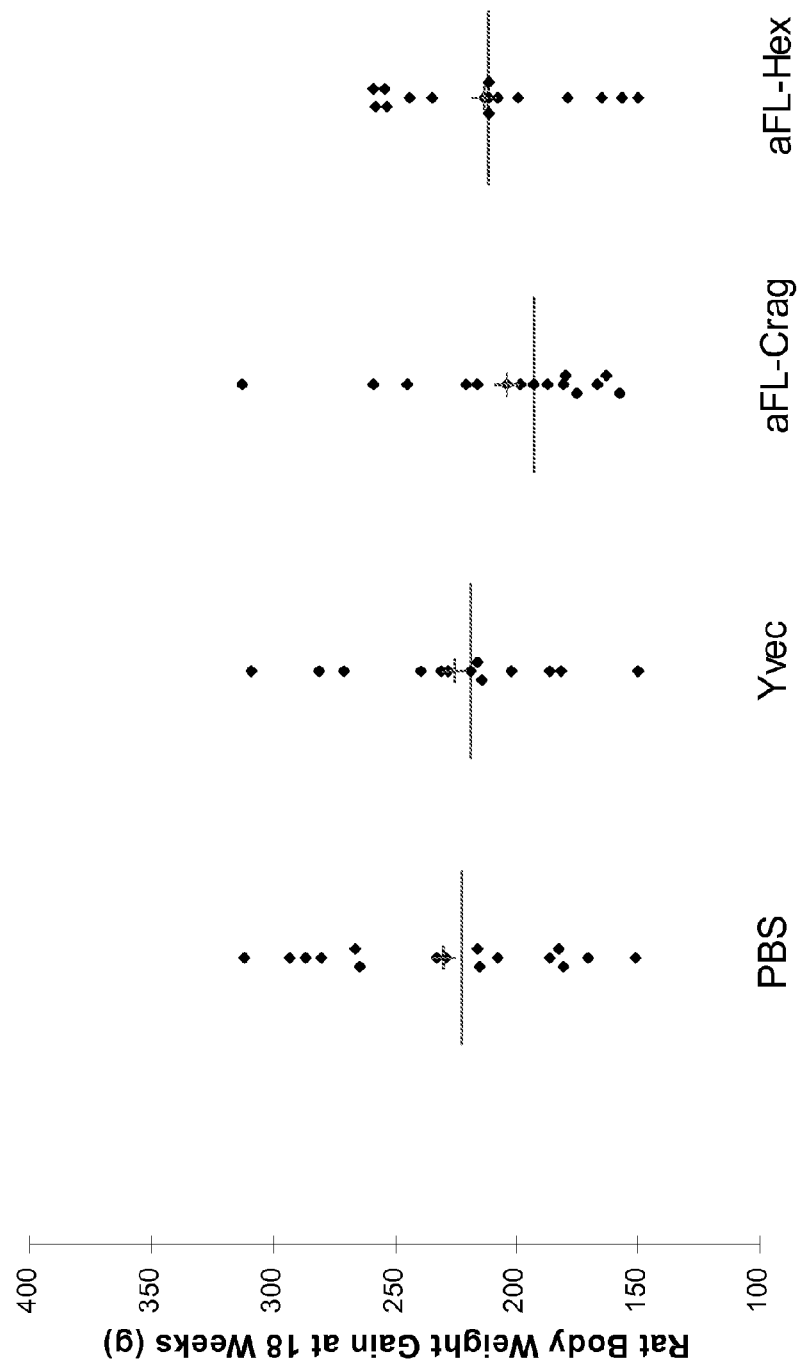
FIG. 10 is a scatter graph showing body weight gain 18 weeks after Ad-36 infection in rats which were injected with PBS (PBS), control yeast (YVEC), a yeast-based immunotherapy composition expressing a fusion protein comprising Ad-36 CR1α and Ad-36 CR1γ (aFL-Crag), and a yeast-based immunotherapy composition expressing a fusion protein comprising Ad-36 hexon (aFL-Hex).
Figure 11:
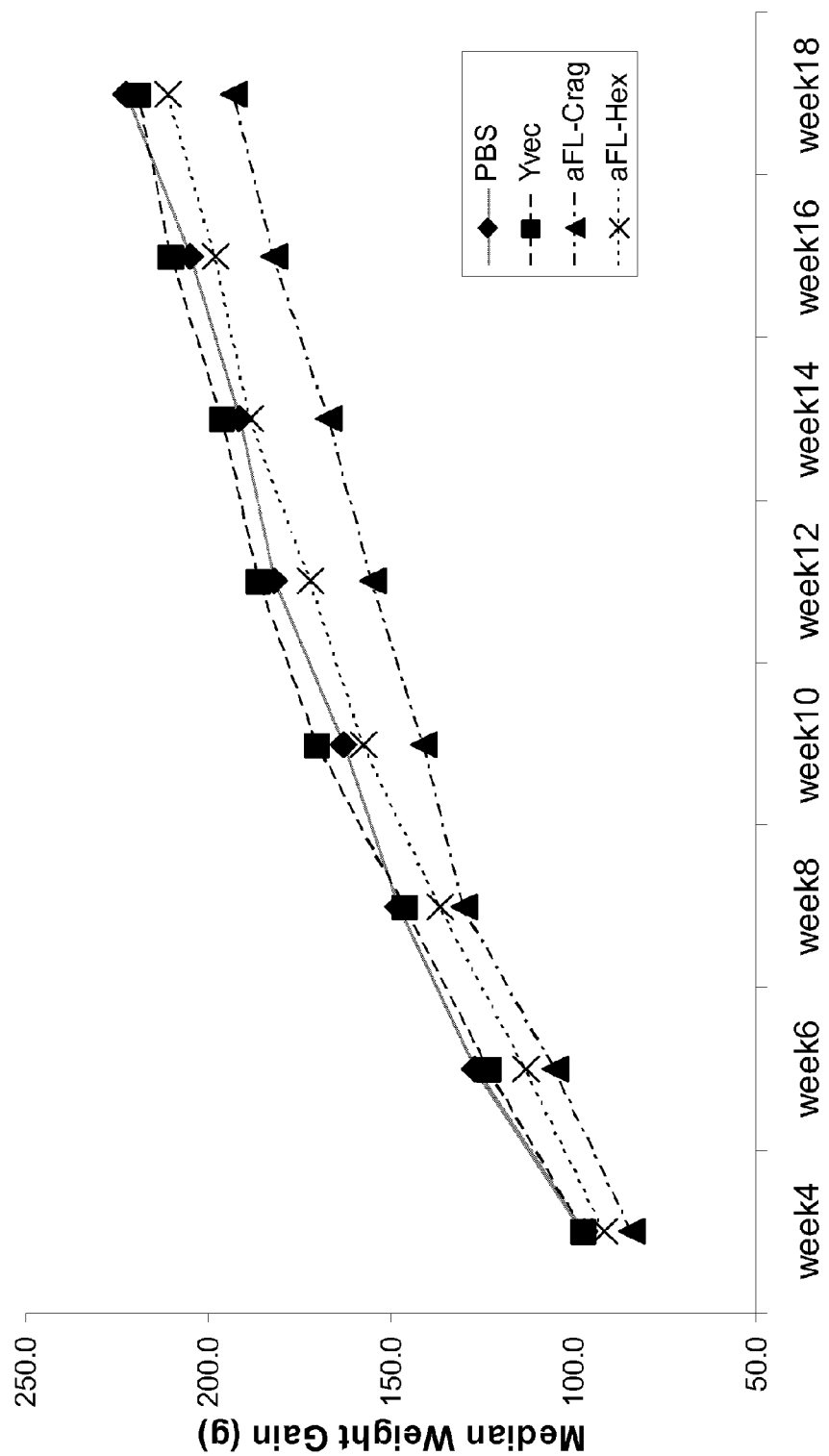
FIG. 11 is a line graph plotting the time course of median body weight gain over baseline in Ad-36 infected rats which were injected with PBS (PBS), control yeast (YVEC), a yeast-based immunotherapy composition expressing a fusion protein comprising Ad-36 CR1α and Ad-36 CR1γ (aFL-Crag), and a yeast-based immunotherapy composition expressing a fusion protein comprising Ad-36 hexon (aFL-Hex).
Figure 12:
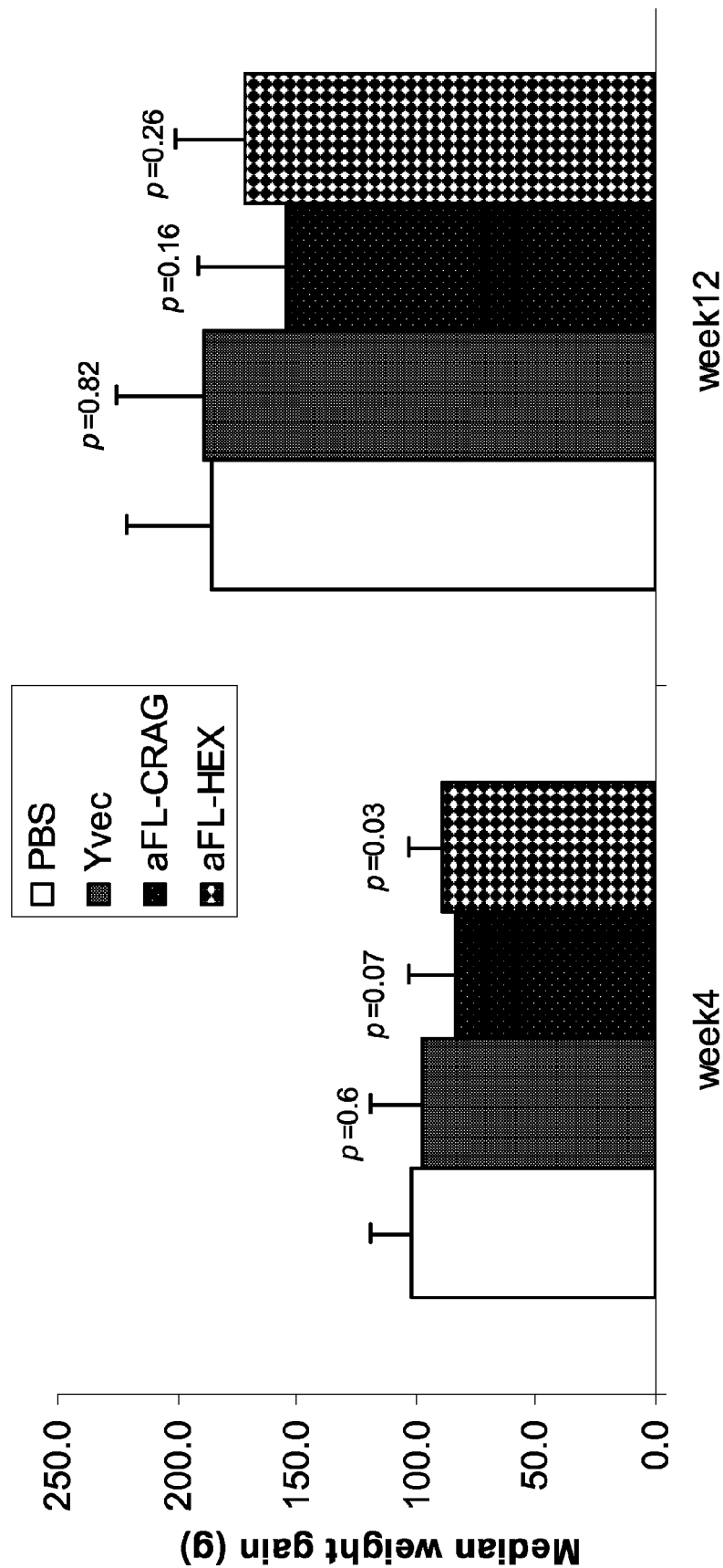
FIG. 12 is a bar graph comparing the median body weight gain at week 4 and week 12 after Ad-36 infection in rats which were injected with PBS (PBS, white bars), control yeast (YVEC, gray bars), a yeast-based immunotherapy composition expressing a fusion protein comprising Ad-36 CR1α and Ad-36 CR1γ (aFL-CRAG, black bars), and a yeast-based immunotherapy composition expressing a fusion protein comprising Ad-36 hexon (aFL-HEX, checkered bars).

As discussed above, the present study is currently at week 18 post-viral challenge. Virus-induced weight gain in control rats is not anticipated to be measurable at this early time-point based on work by Dhurandhar (Dhurandhar et al 2006). Consistent with this expectation, the weight gain data through week 18 show that Ad-36 challenge has not yet caused weight gain above PBS injected control rats. However, the aFL-CRAG Tarmogen immunization group already has a lower overall weight gain than rats in the other groups, as shown in FIGS. 10, 11 and 12. Specifically, FIG. 10 is a scatter plot showing individual rats in each of the immunization groups, and revealing a clear trend in the yeast-based immunotherapy groups, and particularly in the rats immunized with a yeast-based immunotherapeutic expressing Ad-36 CR1α and CR1γ, toward a lower rate of weight gain as compared to rats immunized with PBS only (PBS) or with the "empty vector" yeast control (YVEC). FIG. 11 shows the median weight gain for each group of animals over time. Again, the reduced rate of weight gain as compared to controls in the rats immunized with yeast-based immunotherapeutic expressing Ad-36 CR1α and CR1γ is clear. FIG. 12 illustrates two individual time points (4 weeks post-viral challenge and 12 weeks post-viral challenge) and again, the reduced rate of weight gain in rats immunized with yeast-Ad-36 immunotherapy as compared to the PBS control is evident (p values are relative to the PBS control). Error bars in FIG. 12 are generated based on comparison to the PBS-immunized, virus-challenged control group and statistical significance is measured also as compared to this group.

Taken together, these data demonstrate an Ad-36-specific, and particularly, an Ad-36 CR1α-CR1γ-antigen specific effect, of the yeast-based immunotherapeutic on body weight gain, and one that has emerged before an Ad-36 emergent obesity phenotype is even apparent. A plot of the body weight at weeks 4 and 12 shows that this the weight gain of aFL-CRAG immunized rats is statistically significantly lower than the weight gain of YVEC (control yeast) or Naive rats (PBS) at these time-points (FIG. 12). The rats immunized with the yeast expressing a hexon-based fusion protein show a trend toward a similar phenotype, although at this time point, the difference from controls is not as substantial as for the yeast expressing the CR1α-CR1γ-antigen. Therefore, yeast-based immunotherapy targeting Ad-36 reduces the rate of weight gain in an animal model of chronic Ad-36 infection, and is expected to show reduced weight gain and additional benefits, as compared to the controls, with respect to the other parameters discussed above by 30 weeks post-challenge.

Example 5

Viral Kinetics in the Prophylactic Ad-36 Yeast-Based Immunotherapy Study (Rat)

The following experiment demonstrates the use of the method described in Example 4 to test Ad-36 viral kinetics in the bloodstream after Ad-36 viral challenge.

Figure 13:
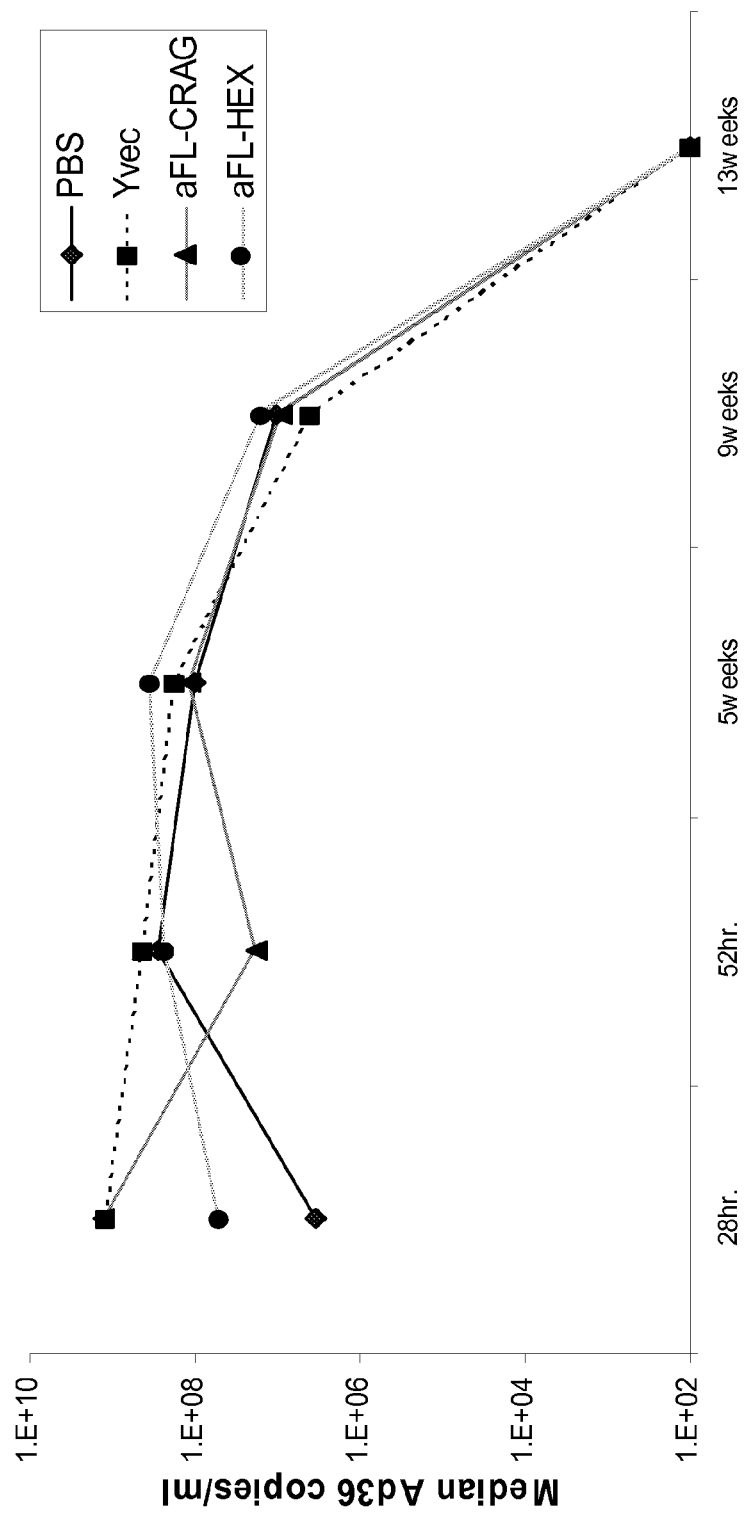
FIG. 13 is a line graph showing the Ad-36 viral kinetics in the blood for rats that were infected with Ad-36 and injected with PBS (PBS), control yeast (YVEC), a yeast-based immunotherapy composition expressing a fusion protein comprising Ad-36 CR1α and Ad-36 CR1γ (aFL-Crag), and a yeast-based immunotherapy composition expressing a fusion protein comprising Ad-36 hexon (aFL-Hex).

Briefly, blood genomic DNA was extracted from 100 μl of rat blood using Qiagen's QIAamp Kit. Ad-36 DNA was detected by quantitative polymerase chain reaction (qPCR), featuring a unique Hexon-gene specific probe designed by the inventors. The results, illustrated in FIG. 13, show that Ad-36 DNA is present at $10^6$ to $10^9$ copies per mL for up to 9 weeks post-challenge, and was cleared from the blood completely by 13 weeks post-challenge. Interestingly, the inter-rat variability of viral DNA load decreases over time, reaching a minimum just before clearance. Without being bound by theory, the inventors believe that these data could reflect the natural immune response to the virus, the yeast-based immunotherapy-induced immune response to the virus, or some combination of these effects.

Example 6

Rat Therapeutic Experiment

The following example describes the use of yeast-based Ad-36 immunotherapeutics in a rat therapeutic model of adenovirus-related obesity.

In the following experiment, yeast-based Ad-36 immunotherapeutic compositions (vaccines) were evaluated to determine whether immunization against this virus using yeast-based immunotherapy can reverse obesity or at least reduce weight gain or the rate of weight gain and adiposity in rats when immunization with yeast-based Ad-36 compositions is initiated after Ad-36 infection and subsequent weight gain.

Rats were infected with Ad-36 (approximately $1 \times 10^9$ PFU in 1 ml) by intraperitoneal administration, as described in the prophylactic study in Example 4. After an Ad-36 emergent obesity phenotype has been established, groups of rats are immunized subcutaneously (s.c.) with one of the two yeast-based Ad-36 immunotherapeutic compositions (vaccines)

described in Example 4 above and in Table 4 below, administered at four different sites, with 20 million cells (2.0 Y.U.) s.c. in 0.1 ml per site. Vaccinations are performed once per week for 2 weeks after challenge, and then monthly for as long as 30 weeks. Additional control groups include a group of rats immunized with control yeast compositions ("empty vector" yeast, or YVEC, that do not express the Ad-36 antigen(s)), and a group of rats receiving PBS only (naïve or PBS). In the present example the control group (B) is PBS.

TABLE 4

| Group | challenge | Post-challenge Immunization |
|---|---|---|
| B | Ad-36 | PBS |
| F | Ad-36 | Ad-aFL-CRAG |
| H | Ad-36 | Ad-aFL-HEX-Full |

Animals are weighed pre-viral infection and then up to biweekly for the up to 30 weeks duration of the study. In addition, food and water consumption are monitored. Blood is collected pre-viral infection and biweekly to monitor for serum viral load, cholesterol, triglyceride levels, corticosterone, neutralizing antibodies, and the other biochemical parameters as described in Example 5. Glucose tolerance testing is performed and glucose levels are measured in the urine. Blood (500 μl per timepoint) is obtained under isofluroane anaesthesia from the tail vein.

At the end of the study, animals are euthanized and adipose tissue is harvested to measure viral levels by polymerase chain reaction (PCR). PCR may also be performed on biopsies obtained during the course of the study.

This experiment was performed in outbred Wistar rats. If, as expected, additional weight gain is prevented or reduced in rats immunized with yeast-based Ad-36 immunotherapy as compared to control rats, inbred Wistar Furth rats will be evaluated according to the same or similar protocol, as these inbred rats are expected to be more amenable to evaluation of T cell immunity. Additional experiments may also determine the effect of diet or other factors in conjunction with immunotherapy (e.g., by administering a high fat diet versus a normal diet).

Immunization with a yeast-based Ad-36 immunotherapy composition is deemed active if it causes, as compared with empty vector yeast or PBS controls, notable trends towards normalization of any of the following parameters for Ad-36 infected rats: i) body weight or a reduced rate of body weight gain; ii) percent body fat or body mass index; iii) frequency or titer of neutralizing antibodies; iv) cholesterol levels; v) serum corticosterone; vi) serum triglycerides; vii) blood and/or urine glucose levels; viii) glucose tolerance; ix) blood Ad-36 viral titer. In summary, it is expected that immunization with a yeast-based Ad-36 immunotherapy composition will be effective for reducing or preventing weight gain and adiposity in rats and this may be accompanied by changes in the biochemical parameters mentioned, given their known association with the obesity phenotype.

Example 7

Effect of Yeast Vector on Rat Appetite and Body Weight Gain

The following example describes an experiment designed to determine if immunization of rats with yeast-based immunotherapeutic compositions of the invention affects the rate of weight gain of naive uninfected (not infected with Ad-36) rats. This experiment was designed to identify whether there is a yeast vector-based effect of Tarmogen vaccination on appetite or body weight gain that is independent of Ad-36 exposure. Such effects on appetite or body weight, if observed, would not be considered to be antigen-specific, since there is no viral antigen in the host, and would be important to determine prior to interpreting the effect of Ad-36 Tarmogen immunization on Ad-36-induced weight gain.

Figure 14:
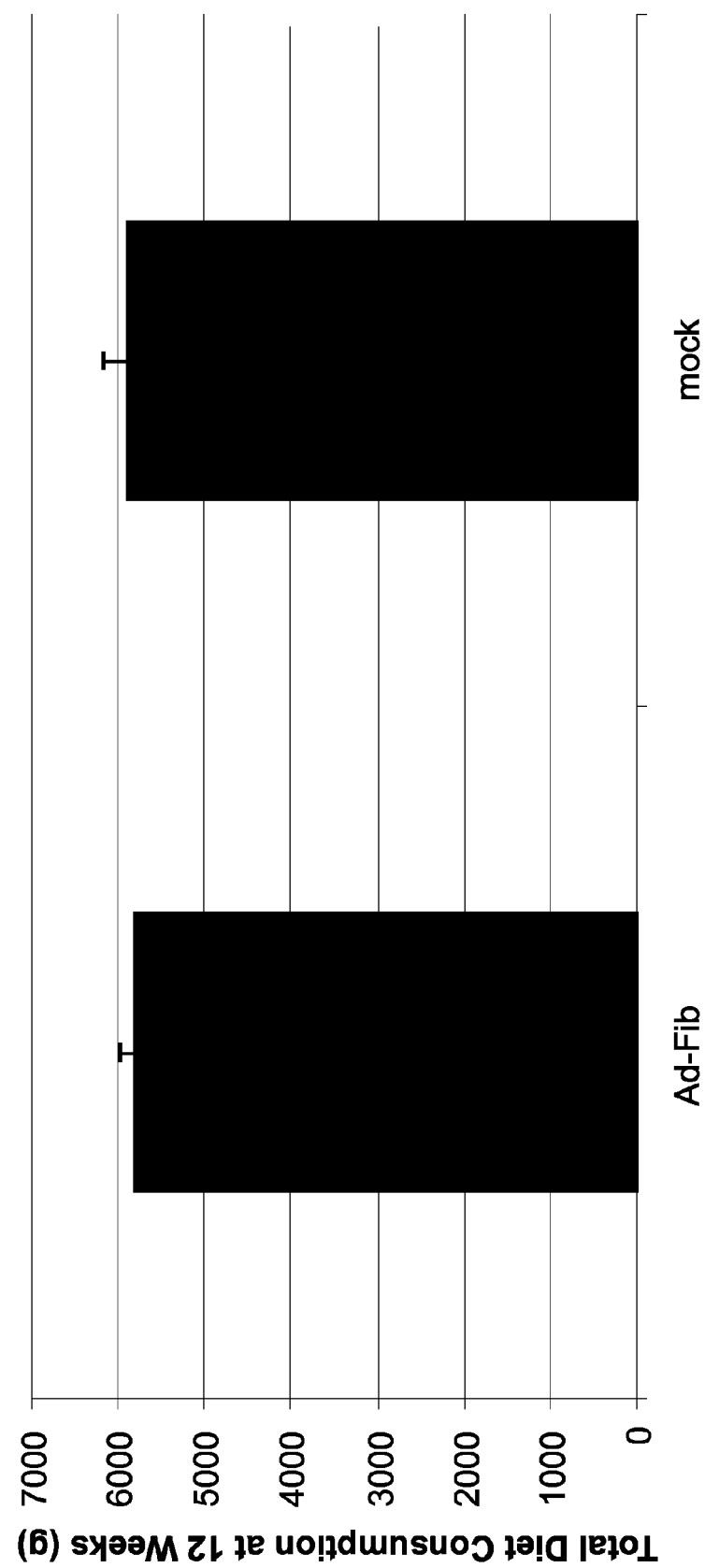
FIG. 14 is a bar graph comparing the total diet consumption (by weight) over 12 weeks of non-Ad-36-infected rats injected with a yeast-based immunotherapeutic expressing an Ad-36 fiber protein and rats which were mock-injected (no immunotherapeutic).
Figure 15:
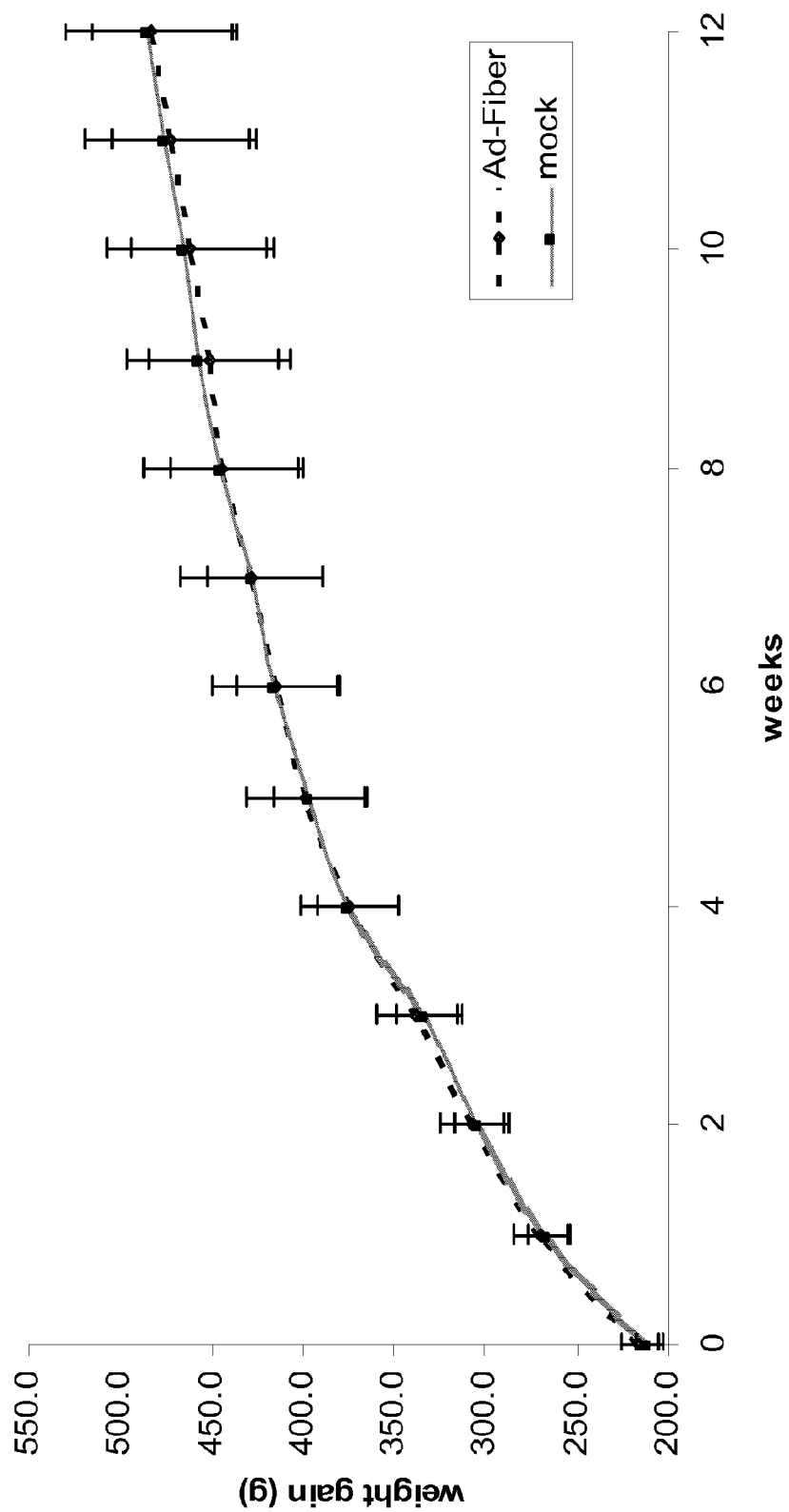
FIG. 15 is a line graph comparing the weight gain over 12 weeks of non-Ad-36-infected rats injected with a yeast-based immunotherapeutic expressing an Ad-36 fiber protein and rats which were mock-injected (no immunotherapeutic).

Rats were immunized with one of the yeast-based immunotherapy compositions described in Example 1 (Ad-Fib, the fusion protein of which is represented by SEQ ID NO:42) once per week, on weeks 1, 2, 7, 9, and 11. Vaccination was at 4 s.c sites with 2 Y.U. per site. The animals were weighed pre-immunization and biweekly following vaccination. The diet consumption and body weight of the rats was monitored during this period. The results, shown in FIG. 14, show that there was no difference in food consumption between the yeast-immunized group and control group. Also, Ad-Fiber yeast vaccination did not change the rate of body weight gain as compared to naive control rats, as shown in FIG. 15. These data demonstrate that yeast based immunotherapy vaccinations per se (in the absence of the target antigen) do not alter the appetite or body weight gain of rats. These results are consistent with the observation that the effects of Ad-36 yeast-based immunotherapy on body weight, when observed in the Ad-36 challenge experiments described above, are not believed to be attributable to a generalized effect of the yeast or yeast vector on rat appetite or metabolism.

Example 8

Organ Distribution of Ad-36 after Intraperitoneal Inoculation

The following experiment demonstrates the Ad36 distribution in major organs and tissues after the virus infection.

Figure 16:
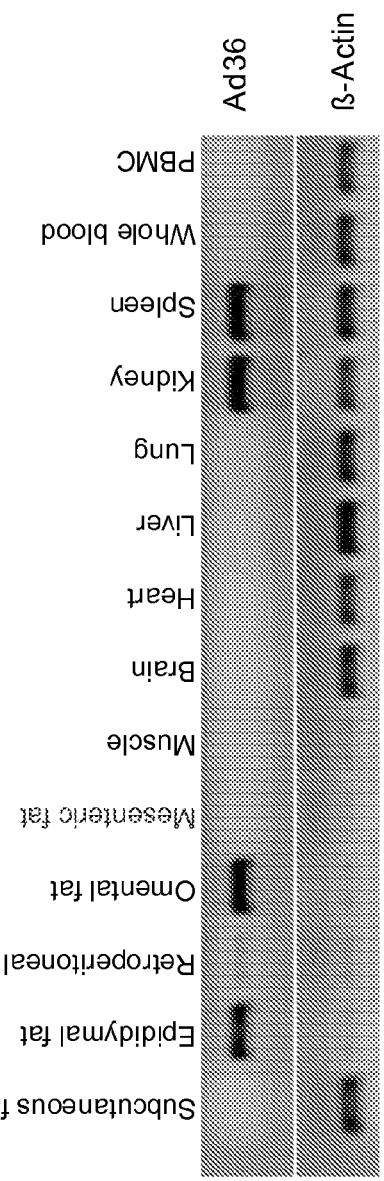
FIG. 16 is a digitized image of PCR showing Ad-36 DNA in organs and tissues of a rat 15 weeks after intraperitoneal inoculation with the Ad-36 virus.

This experiment is of relevance to the specificity/tropism of the virus and to the best of the inventors' knowledge, such analyses have not been conducted in any study this late after viral challenge. Therefore, the following experiments were designed to confirm that Ad-36 resides in fat compartments after the virus is no longer detectable in the blood, and to further indicate tissues or organs where yeast-based immunotherapy may be active. In one published study (Pasaricia et al, 2008), conducted at 4 days post challenge, Ad-36 was found in nearly all tissues tested including the central nervous system (CNS), heart, lung, liver, spleen, kidney, visceral fat, and other organs. In the present study, the organ/body-wide distribution of Ad-36 was evaluated at 15 weeks virus post-challenge in a non-immunized rat. Briefly, major organs and tissues (include blood and peripheral blood mononuclear cells (PBMC)) were removed and isolated. Organ and tissue genomic DNA was extracted from all samples using the QIAamp Kit, and Ad-36 DNA was detected with a very sensitive nested polymerase chain reaction (PCR) assay. The results, shown in FIG. 16, indicated that 15 weeks after virus inoculation, Ad-36 DNA is detectable in the epididymal, retroperitoneal, omental visceral adipose tissues, and also in the spleen and kidney. However, Ad36 DNA was absent from heart, liver, lung, brain, and subcutaneous fat, as well as the other organs/tissues tested. These results, taken together with the prior results of Pasarica et al., show that Ad-36, although widely distributed in most major organs early after challenge, becomes more localized to fat compartments, as well as kidney and spleen, by 15 weeks post viral challenge.

Example 9

Mouse Model-Prophylactic

The following example describes the use of yeast-based adenovirus-36 (Ad-36) immunotherapeutics in an animal model of adenovirus-related obesity.

A mouse model has been described in the literature whereby infection of animals with human Ad-36 has caused weight gain and increase in adiposity (Dhurandhar et al. Int. J. Obesity 24:989, 2000). In those studies, a statistically significant increase in body fat weight (p<0.02) was elicited in Ad36-infected mice compared to the control group. Additionally, 60% of Ad-36 injected mice vs. 22% of controls were considered obese when obesity was defined as >85th percentile of the control group.

In the following experiment, yeast-based Ad-36 immunotherapeutic compositions (vaccines) are evaluated to determine whether immunization against this virus using yeast-based immunotherapy can prevent obesity or at least reduce weight gain and adiposity associated with Ad-36 infection.

Groups of mice are immunized subcutaneously (s.c.) with a yeast-based Ad-36 immunotherapeutic composition (vaccine) administered at two to four different sites (1 to 20 million cells (or 0.1-2.0 Y.U.) s.c. in 0.1 ml per site), between three and six times at weekly intervals. After the final administration, mice are challenged with Ad-36 (approximately $2\times10^7$ PFU in 0.1-0.2 ml) by intraperitoneal administration. Experimental groups of mice (10-20 mice per group) are immunized with a yeast-based Ad-36 immunotherapeutic composition, e.g., one of the yeast-based immunotherapy compositions described in Example 1. Additional control groups include a group of mice immunized with control yeast compositions ("empty vector" yeast that do not express the Ad-36 antigen(s)), and a group of mice receiving PBS only (naïve).

Animals are weighed pre-treatment, pre-viral challenge and then up to twice weekly for approximately 22 weeks following inoculation with virus. In addition, food and water consumption are monitored. Blood is collected at baseline, pre-viral challenge and biweekly following challenge to monitor for cholesterol, triglyceride levels and for neutralizing antibodies to Ad36 in the serum. Glucose tolerance testing is performed and glucose levels are measured in the urine. Blood (200 μl per timepoint) is obtained under isofluroane anaesthesia from the retro-orbital plexus. At the end of the study, animals are euthanized and adipose tissue is harvested to measure viral levels by polymerase chain reaction (PCR). PCR may also be performed on biopsies obtained during the course of the study.

The experiment is initially performed in outbred mice (e.g., ICR or CD-1® mice). If, as expected, weight gain is prevented or reduced in mice immunized with yeast-based Ad-36 immunotherapy as compared to control mice, inbred strain(s) are further evaluated according to the same or similar protocol (e.g., C57BL/6, BALB/c or C3H), as these mice are expected to be more amenable to evaluation of T cell immunity. Additional experiments may also determine the effect of diet or other factors in conjunction with immunotherapy (e.g., by administering a high fat diet versus a normal diet).

Immunization with a yeast-based Ad-36 immunotherapy composition is effective if immunization results in a statistically significant difference in body weight or body weight gain between yeast-Ad-36 immunized mice and control mice (empty vector yeast or PBS-immunized), and/or at least a two-fold difference in neutralizing antibody levels, and/or a greater than 5% reduction in percent body fat, cholesterol, triglycerides, reduction in glucose in the urine or reduced glucose levels by glucose tolerance test and/or reduction in Ad-36 viral titers, between the experimental and either control group (empty vector yeast or PBS-immunized). It is expected that immunization with a yeast-based Ad-36 immunotherapy composition will be effective for reducing or preventing weight gain and adiposity in mice.

Example 10

Mouse Model-Therapeutic

The following example describes the use of yeast-based Ad-36 immunotherapeutics in an animal model of adenovirus-related obesity.

In the following experiment, yeast-based Ad-36 immunotherapeutic compositions (vaccines) are evaluated to determine whether immunization against this virus using yeast-based immunotherapy can reverse obesity or at least reduce weight gain and adiposity in mice when immunization with yeast based Ad-36 compositions is initiated after Ad-36 infection and subsequent weight gain.

Mice are infected with Ad-36 (approximately $2\times10^7$ PFU in 0.1-0.2 ml) by intraperitoneal administration. Once weight gain has been established, groups of mice will be immunized subcutaneously (s.c.) with a yeast-based Ad-36 immunotherapeutic composition (vaccine) administered at two to four different sites (1 to 20 million cells (0.1 to 2.0 Y.U.) s.c. in 0.1 ml per site), between three and six times at weekly intervals. Additional control groups include a group of mice immunized with control yeast compositions ("empty vector" yeast that do not express the Ad-36 antigen(s)), and a group of mice receiving PBS only (naïve).

Animals are weighed pre-viral infection and then up to twice weekly for the duration of the study. In addition, food and water consumption are monitored. Blood is collected pre-viral infection and biweekly to monitor for cholesterol, triglyceride levels and for neutralizing antibodies to Ad36 in the serum. Glucose tolerance testing is performed and glucose levels are measured in the urine. Blood (200 μl per timepoint) is obtained under isofluroane anaesthesia from the retro-orbital plexus.

At the end of the study, animals are euthanized and adipose tissue is harvested to measure viral levels by polymerase chain reaction (PCR). PCR may also be performed on biopsies obtained during the course of the study.

The experiment is initially performed in outbred mice (e.g., ICR or CD-1® mice). If, as expected, additional weight gain is prevented or reduced in mice immunized with yeast-based Ad-36 immunotherapy as compared to control mice, inbred strain(s) are further evaluated according to the same or similar protocol (e.g., C57BL/6, BALB/c or C3H), as these mice are expected to be more amenable to evaluation of T cell immunity. Additional experiments may also determine the effect of diet or other factors in conjunction with immunotherapy (e.g., by administering a high fat diet versus a normal diet).

Immunization with a yeast-based Ad-36 immunotherapy composition is effective if immunization results in a statistically significant difference in body weight or body weight gain between yeast-Ad-36 immunized mice and control mice (empty vector yeast or PBS-immunized), and/or at least a two-fold difference in neutralizing antibody levels, and/or a greater than 5% reduction in percent body fat, cholesterol, triglycerides in glucose in the urine or reduced glucose levels by glucose tolerance test and/or reduction in Ad-36 viral titers between the experimental and either control group (empty vector yeast or PBS-immunized). It is expected that immunization with a yeast-based Ad-36 immunotherapy composition will be effective for reducing or preventing additional weight gain and adiposity in mice.

Example 11

Treatment of Ad-36 Infection in Humans

The following example describes a clinical trial for the treatment of Ad-36 infection in human adult subjects.

A randomized phase 1 clinical trial in adult patients and/or in obese pediatric patients testing positive for adenovirus-36 infection and having a BMI of at least 25 (or pediatric patients with analogous/equivalent BMI) will be conducted. Additional groups or trials include non-obese and/or non-overweight adults and/or pediatric patients testing positive for adenovirus infection. Subjects will be randomized into two arms. Arm 1 patients will receive at least 12 weeks of yeast-based Ad-36 immunotherapy (any composition as described in Example 1) and will follow a prescribed diet and exercise regimen. Arm 2 patients will receive a placebo (PBS control injection or empty yeast) and will follow the same prescribed diet and exercise program. One primary endpoint is reduction in Ad-36 viral titer. Another endpoint is immune seroconversion determined by measurement of the presence of Ad-36 antibodies. Another endpoint is Ad-36-specific cellular immune responses (which may include T cell proliferation, induction of $CD4^+$ Th1 and/or Th17 cells, induction of $CD8^+$ T cells as measure by CTL assay or cytokine assay, and/or modulation in regulatory T cell (Treg) numbers or function). Additional secondary endpoints include a reduction in BMI, as well as relative weight loss and absolute weight loss during treatment and during longitudinal follow-up after completion of therapy.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. An immunotherapeutic composition comprising: a) a yeast vehicle; and b) a fusion protein comprising an adenovirus-36 (Ad-36) antigen, wherein the Ad-36 antigen comprises the amino acid sequence SEQ ID NO:55.

2. The immunotherapeutic composition of claim 1, wherein the yeast vehicle is a whole yeast.

3. The immunotherapeutic composition of claim 1, wherein the yeast vehicle is from *Saccharomyces cerevisiae*.

4. A fusion protein, wherein the fusion protein comprises an amino acid sequence that is at least 95% identical to SEQ ID NO:47, SEQ ID NO:54, or SEQ ID NO:55.

5. An immunotherapeutic composition comprising:
a) a yeast vehicle; and
b) a fusion protein comprising an adenovirus-36 (Ad-36) antigen, wherein the fusion protein comprises an amino acid sequence that is at least 95% identical to SEQ ID NO:54 or SEQ ID NO:47.

6. An immunotherapeutic composition comprising:
a) a yeast vehicle; and
b) a fusion protein comprising an adenovirus-36 (Ad-36) antigen, wherein the Ad-36 antigen comprises an amino acid sequence that is at least 95% identical to SEQ ID NO:55.

7. The immunotherapeutic composition of claim 6, wherein the Ad-36 antigen comprises the amino acid sequence SEQ ID NO:55.

8. The immunotherapeutic composition of claim 2, wherein the Ad-36 antigen is expressed by the whole yeast.

9. The immunotherapeutic composition of claim 2, wherein the whole yeast is heat-inactivated.

10. The immunotherapeutic composition of claim 1, wherein the composition is formulated in a pharmaceutically acceptable excipient suitable for administration to an individual.

11. The immunotherapeutic composition of claim 1, further comprising at least one biological response modifier.

12. The immunotherapeutic composition of claim 6, wherein the Ad-36 antigen comprises an amino acid sequence that is at least 97% identical to SEQ ID NO:55.

13. The immunotherapeutic composition of claim 6, wherein the Ad-36 antigen comprises an amino acid sequence that is at least 99% identical to SEQ ID NO:55.

14. The immunotherapeutic composition of claim 5, wherein the fusion protein comprises the amino acid sequence SEQ ID NO:47 or SEQ ID NO:54.

15. The fusion protein of claim 4, wherein the fusion protein comprises an amino acid sequence that is 95% identical to SEQ ID NO:55.

16. The fusion protein of claim 4, wherein the fusion protein comprises an amino acid sequence that is 99% identical to SEQ ID NO:55.

17. The fusion protein of claim 4, wherein the fusion protein comprises the amino acid sequence SEQ ID NO:55.

18. The fusion protein of claim 4, wherein the fusion protein comprises the amino acid sequence SEQ ID NO:47 or SEQ ID NO:54.

19. The immunotherapeutic composition of claim 6, wherein the yeast vehicle is a whole yeast.

20. The immunotherapeutic composition of claim 6, wherein the yeast vehicle is from *Saccharomyces cerevisiae*.

* * * * *